US009367061B2

(12) United States Patent
Miller et al.

(10) Patent No.: US 9,367,061 B2
(45) Date of Patent: Jun. 14, 2016

(54) MEDICAL CART FOR DISPENSING MEDICATION

(71) Applicant: ENOVATE MEDICAL, LLC, Murfreesboro, TN (US)

(72) Inventors: David R. Miller, Murfreesboro, TN (US); Kou Yang, Canton, MI (US); Kurt Ruppenthal, Canton, MI (US)

(73) Assignee: Enovate Medical, LLC, Murfreesboro, TN (US)

( * ) Notice: Subject to any disclaimer, the term of this patent is extended or adjusted under 35 U.S.C. 154(b) by 169 days.

(21) Appl. No.: 14/175,785

(22) Filed: Feb. 7, 2014

(65) Prior Publication Data

US 2015/0227127 A1  Aug. 13, 2015

(51) Int. Cl.
| | |
|---|---|
| *G05B 19/042* | (2006.01) |
| *G06F 19/00* | (2011.01) |
| *B62B 3/00* | (2006.01) |
| *A61G 12/00* | (2006.01) |
| *A61J 1/03* | (2006.01) |

(Continued)

(52) U.S. Cl.
CPC ............ *G05B 19/042* (2013.01); *A61G 12/001* (2013.01); *B62B 3/00* (2013.01); *G06F 19/3462* (2013.01); *A61G 2203/20* (2013.01); *A61G 2203/36* (2013.01); *A61G 2203/44* (2013.01); *A61G 2205/20* (2013.01); *A61J 1/03* (2013.01); *A61J 7/0084* (2013.01); *A61J 2200/74* (2013.01); *A61J 2205/60* (2013.01); *G05B 2219/26* (2013.01); *G10K 11/178* (2013.01)

(58) Field of Classification Search
CPC ............. G05B 19/042; G05B 2219/26; A61G 12/001; G07F 7/08

USPC ................................................... 700/231–244
See application file for complete search history.

(56) References Cited

U.S. PATENT DOCUMENTS

| | | | | |
|---|---|---|---|---|
| 7,175,081 | B2 * | 2/2007 | Andreasson et al. | 235/385 |
| 7,654,261 | B1 * | 2/2010 | Rockhold | 128/204.18 |
| 8,180,485 | B2 * | 5/2012 | Reckelhoff | 700/242 |

(Continued)

FOREIGN PATENT DOCUMENTS

WO    2012/078676 A1    6/2012

OTHER PUBLICATIONS

International Search Report and Written Opinion mailed on Apr. 9, 2015, application No. PCT/US2015/014387.

*Primary Examiner* — Patrick Cicchino
(74) *Attorney, Agent, or Firm* — Nathan J. Bailey; Waller Lansden Dortch & Davis, LLP

(57) ABSTRACT

Technology for dispensing medication from a wheeled medical cart is disclosed. A method comprises placing the medication in a medication storage compartment of a storage container of the wheeled medical cart. A method can further comprise entering medication data into a computing device operating on the wheeled medical cart. A method can further comprise electronically securing the medication stored in the medication storage compartment. A method further comprises repositioning the wheeled medical cart a patient location The method can further comprise electronically identifying at least one predetermined user of the wheeled medical cart at the patient location to enable the predetermined user to gain access to the medication in the medication storage compartment for a patient to enable the predetermined user to provide medication from the wheeled medical cart to the patient.

19 Claims, 83 Drawing Sheets

(51) Int. Cl.
 *A61J 7/00* (2006.01)
 *G10K 11/178* (2006.01)

(56) References Cited

U.S. PATENT DOCUMENTS

| | | | |
|---|---|---|---|
| 8,773,270 B2* | 7/2014 | Paydar et al. | 340/585 |
| 2005/0055244 A1* | 3/2005 | Mullan et al. | 705/2 |
| 2006/0079994 A1* | 4/2006 | Chu et al. | 700/231 |
| 2007/0228680 A1* | 10/2007 | Reppert et al. | 280/47.35 |
| 2008/0316045 A1* | 12/2008 | Sriharto et al. | 340/825.49 |
| 2010/0114367 A1* | 5/2010 | Barrett et al. | 700/236 |
| 2010/0114369 A1* | 5/2010 | Higham | 700/237 |
| 2010/0283601 A1* | 11/2010 | Tai et al. | 340/539.12 |
| 2011/0160948 A1* | 6/2011 | Bailey et al. | 701/23 |
| 2012/0203377 A1* | 8/2012 | Paydar et al. | 700/232 |
| 2013/0006415 A1* | 1/2013 | Paydar et al. | 700/235 |
| 2014/0246964 A1* | 9/2014 | Boyd | 312/209 |

* cited by examiner

| Cart angle | Tilted angle | AR | BR | AL | BL | SRX | SRY | SLX | SLY | Sum X | Sum Y |
|---|---|---|---|---|---|---|---|---|---|---|---|
| 0 | 0 | 45 | 0 | 10 | 0 | 5 | 5 | 5 | 5 | 10 | 10 |
| 45 | 90 | -7.07107 | 7.071068 | 7.071068 | 7.071068 | 7.071068 | 0 | 7.071068 | 0 | 14.14214 | 0 |
| 90 | 135 | 0 | -10 | 0 | 10 | 5 | -5 | 5 | 5 | 10 | -10 |
| 135 | 180 | -7.07107 | -7.07107 | 7.071068 | -7.07107 | 0 | -7.07107 | 0 | -7.07107 | 0 | -14.1421 |
| 180 | 225 | 0 | 0 | -10 | 0 | -5 | -5 | -5 | -5 | -10 | -10 |
| 225 | 270 | 7.071068 | -7.07107 | -7.07107 | -7.07107 | -7.07107 | 0 | -7.07107 | 0 | -14.1421 | 0 |
| 270 | 315 | 10 | 0 | 0 | 0 | -5 | 5 | -5 | 5 | -10 | 10 |
| 315 | 360 | 7.071068 | 7.071068 | -7.07107 | 7.071068 | 0 | 7.071068 | 0 | 7.071068 | 0 | 14.14214 |
| 360 | 45 | 0 | 0 | 0 | 10 | 5 | 5 | 5 | 5 | 10 | 10 |

| Cart angle | Tilted angle | Desired | | | | Rotation | Calculated | | |
|---|---|---|---|---|---|---|---|---|---|
| | | WR | WL | WC | | -45 | WR | WL | WC |
| | | | | | | -0.7854 | | | |
| 0 | 0 | 0 | 10 | 10 | | | 10.00 | 10.00 | 0.00 |
| 45 | 45 | 7.071068 | 7.071068 | 7.071068 | | | 7.07 | 7.07 | 7.07 |
| 90 | 90 | 0 | 0 | 10 | | | 0.00 | 0.00 | 10.00 |
| 135 | 135 | -7.07107 | -7.07107 | 7.071068 | | | -7.07 | -7.07 | 7.07 |
| 180 | 180 | -10 | -10 | 0 | | | -10.00 | -10.00 | 0.00 |
| 225 | 225 | -7.07107 | -7.07107 | -7.07107 | | | -7.07 | -7.07 | -7.07 |
| 270 | 270 | 0 | 0 | -10 | | | 0.00 | 0.00 | -10.00 |
| 315 | 315 | 7.071068 | 7.071068 | -7.07107 | | | 7.07 | 7.07 | -7.07 |
| 360 | 360 | 10 | 10 | 0 | | | 10.00 | 10.00 | 0.00 |
| | 45 | | | | | | | | |

FIG. 61

MEDICAL CART FOR DISPENSING MEDICATION

BACKGROUND

Traditionally medical carts have played a minor role in the medical care environment, serving as a movable surface on which to place medical instruments or medication. Additionally, medical carts are traditionally used for a particular medical procedure. In the event of an emergency, for example, the medical cart may be a crash cart with emergency care equipment or medication. Recently, medical carts have played a growing role in patient care by providing increased functionality for a caregiver. As the functionality of medical carts continues to increase and additional devices and features are added to the carts, it has become increasingly difficult for medical care personnel to use the medical carts in changing medical care environments.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure; and, wherein:

FIG. 61 provides an exemplary table of strain gauge values converted to signals for a power assist drive system in accordance with an example;

FIG. 73 illustrates a wheeled medical cart for the dispensing of medication in accordance with an example; and FIG. 74 illustrates a storage container of a wheeled medical cart in accordance with an example.

Figure 1:
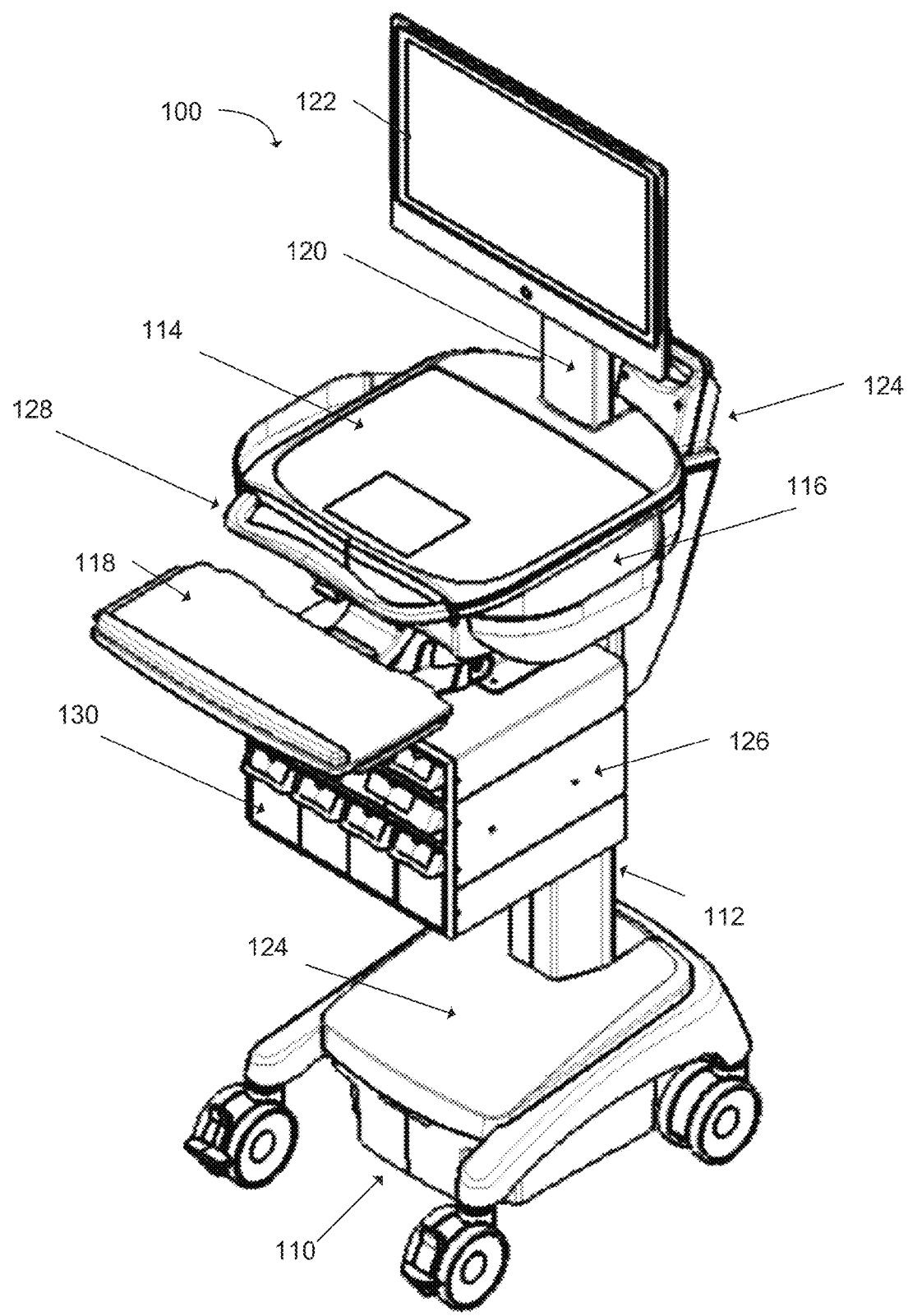
FIG. 1 illustrates one embodiment of a smart medical cart in accordance with an example.

Reference will now be made to the exemplary embodiments illustrated, and specific language will be used herein to describe the same. It will nevertheless be understood that no limitation of the scope of the invention is thereby intended.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular examples only and is not intended to be limiting. The same reference numerals in different drawings represent the same element. Numbers provided in flow charts and processes are provided for clarity in illustrating steps and operations and do not necessarily indicate a particular order or sequence.

Smart medical carts can play an important role in patient care by providing a caregiver with a mobile platform that can have multiple applications, such as collecting medical information from a patient, tracking patient status, dispensing medication, incorporating medical devices and instrumentation, and so forth. Additionally, a smart medical cart can adapt to numerous and changing environments that the smart medical cart is used in to alleviate many of the difficulties faced by caregivers using traditional medical carts. For example, a smart medical cart can adapt to situations including environments with tight quarters, areas containing numerous obstacles, uneven or changing surfaces, inclining or declining surfaces, and so forth.

FIG. 1 illustrates one embodiment of a smart medical cart 100. The smart medical cart 100 is a mobile cart that can be moved around in a medical care environment, such as within a room or from room to room. The smart medical cart can include a wheeled pedestal 110 attached to one end of a first vertical support 112. The first vertical support 112 can be attached to a first work platform 114 at the other end of the vertical support 112. In one embodiment, a frame 116, such as an open or substantially enclosed frame, can attach to the first work platform 114 on the bottom side of the first work platform 114. In one embodiment, the open or enclosed frame 116 enables the storage of objects, such as a computing device, display screen, power socket, universal serial bus (USB) hub, and so forth. In one embodiment, a second work platform 118 can be attached to the first work platform 114, the first vertical support 112, or the frame 116. In another embodiment, a bottom end of a second vertical support 120 can be attached to the first work platform 114. A computing device 122, such as a touch screen computing device or a display screen, can be attached to a top end of the second vertical support 120.

The height of the first work platform 114 can be adjusted vertically and/or laterally. In one embodiment, the height of the first work platform 114 can be adjusted using a height adjusting mechanism. The height adjusting mechanism can adjust the height of the first work platform 114 relative to the wheeled pedestal 110.

Figure 2A:
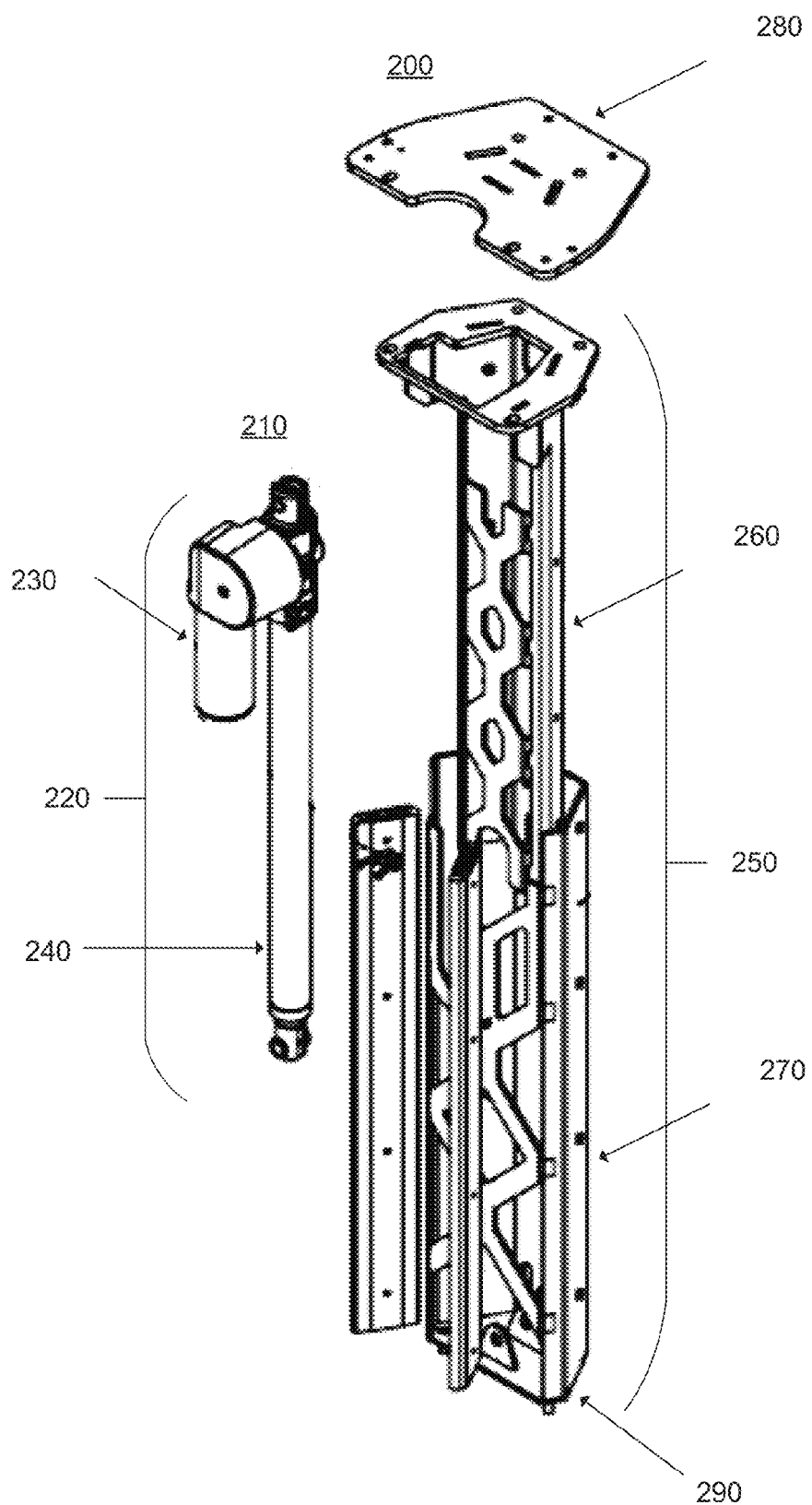
FIG. 2a shows an exposed view of a first vertical support and a height adjusting mechanism of a first vertical support in accordance with an example.

FIG. 2*a* shows an exposed view of the first vertical support 200 and the height adjusting mechanism 210 of the first vertical support 200. In one embodiment, the first vertical support 200 can be adjustable in height. In one embodiment, the height adjusting mechanism 210 can attach to the first vertical support 200 and adjust the height of the first vertical support 200 using a driver 220, such as an electric motor 230 and a pneumatic arm 240. In one embodiment, the driver 230 can include a gas driven piston to adjust the height of the first vertical support 200. In another embodiment, the driver 230 can include linear actuators used in conjunction with a motor to vertically or laterally adjust the height of the first work platform. The first vertical support 200 can include a telescoping structure 250, where the telescoping structure 250 has two members, a telescoping inner casing 260 and a telescoping outer casing 270, that can be slidably adjusted up and down. The telescoping inner casing 260 can be attached to the first work platform 114, as shown in FIG. 1, such as by using the mounting plate 280. The telescoping outer casing 270 can be a fixed outer casing that is attached to wheeled pedestal 110, as shown in FIG. 1, such as by using the mounting plate 290. The driver 220 can raise or lower the height of the first work platform 114 by slidably moving the telescoping inner casing 260 upward or downward along the interior of the telescoping outer casing 270. One of ordinary skill in the art would readily recognize that the telescoping structure 250 can be adjusted using methodologies other than slidably adjusting the telescoping structure 250. In one embodiment, the height adjusting mechanism 210 can include an elevation or height sensor or monitor to determine the height of the first work platform 114, as shown in FIG. 1, or the first vertical support 200. One advantage of the elevation or height sensor or monitor is that it can enable the adjustment of the height of the first work platform 114, as shown in FIG. 1, or the first vertical support 200 based on the location of the smart medical cart, user preferences, environmental preferences, and so forth as discussed in the proceeding paragraphs.

Figure 2B:
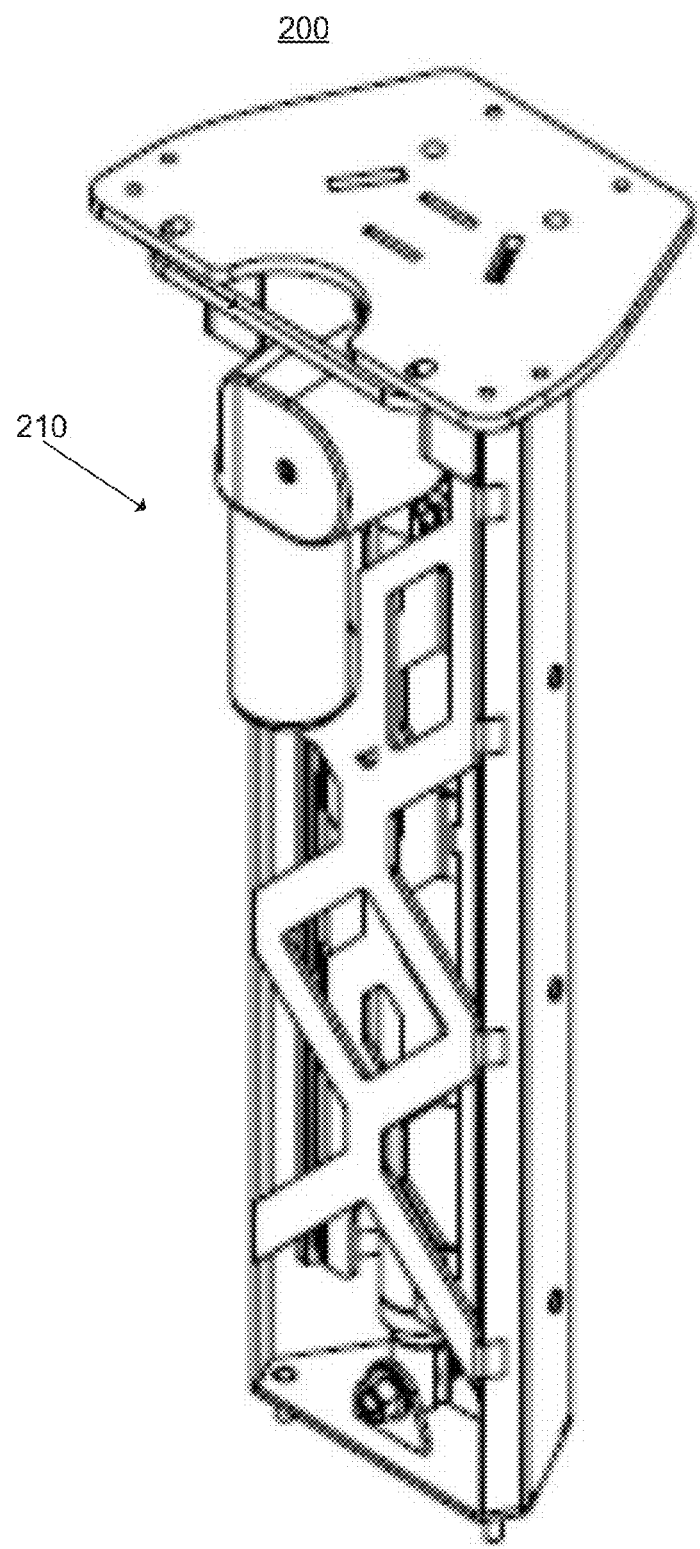
FIG. 2b shows an assembled view of a first vertical support with a height adjusting mechanism in accordance with an example.

FIG. 2b shows an assembled view of a first vertical support 200 with a height adjusting mechanism 210. FIG. 2b shows the first vertical support 200 with the height adjusting mechanism 210 that is substantially similar to the first vertical support 200 described in FIG. 2a.

Figure 3A:
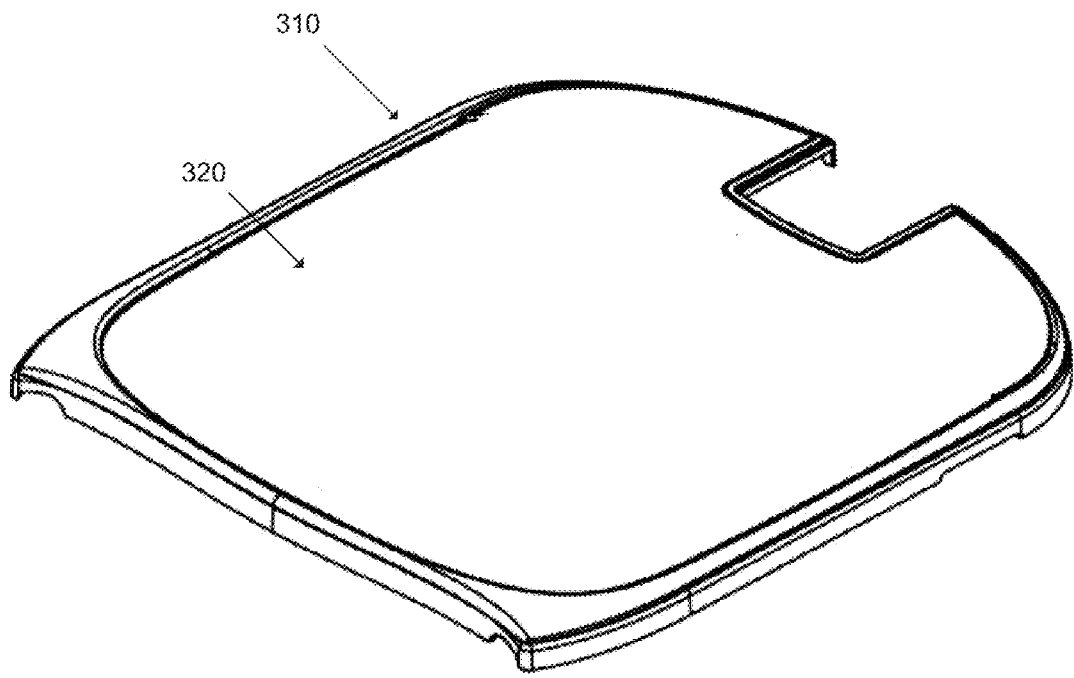
FIG. 3a shows a first work platform in accordance with an example.

FIG. 3a shows a first work platform 310 that can comprise a work surface 320. In one embodiment, the work surface 320 can be a clear or substantially transparent surface. In one embodiment, the work surface 320 can be a tempered or hardened transparent surface, such as a tempered glass, plastic, acrylic, and so forth.

Figure 3B:
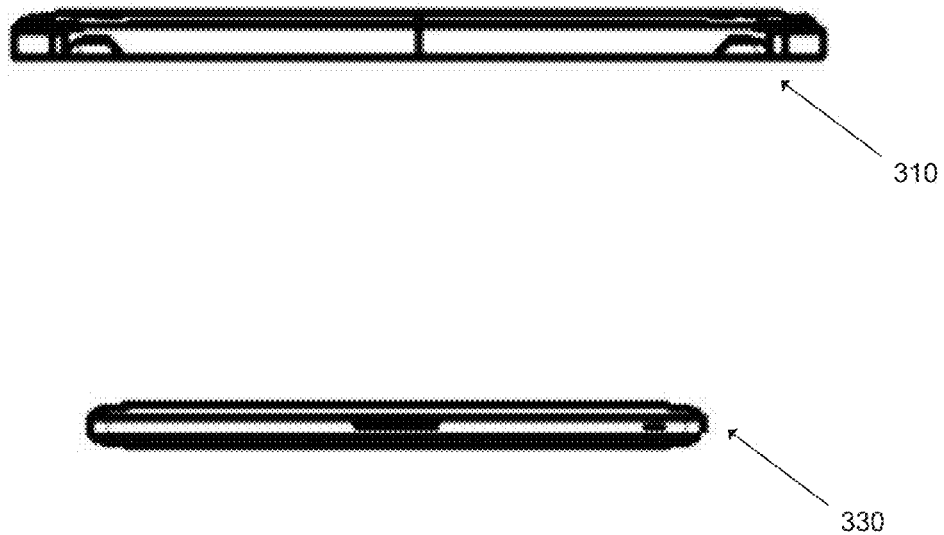
FIG. 3b shows a computing device located below the first work platform in accordance with an example.

FIG. 3b shows a computing device 330, such as a display screen, touch screen computing device, or a tablet, located below the first work platform 310. In one embodiment, the first work platform 310 and/or the work surface 320 of the first work platform 310 include an anti-bacterial material or an anti-pathogen to reduce the growth or adherence of bacterial or other pathogens on the first work platform and/or the work surface 320. One advantage to using an anti-bacterial material or anti-pathogen material is to reduce the retransmission or spreading of pathogens, such as bacterium, viruses, prion, or fungus, in a medical environment. For example, when the smart medical cart is located in an area of a medical facility, such as one patient's room, and is moved to another area of the medical facility, such as another patient's room, pathogens traditionally adhere to a surface such as a medical cart. An anti-bacterial material can reduce to eliminate the adherence of pathogens, such as bacterium, viruses, prion, or fungus, on the surface of the smart medical cart.

Figure 4A:
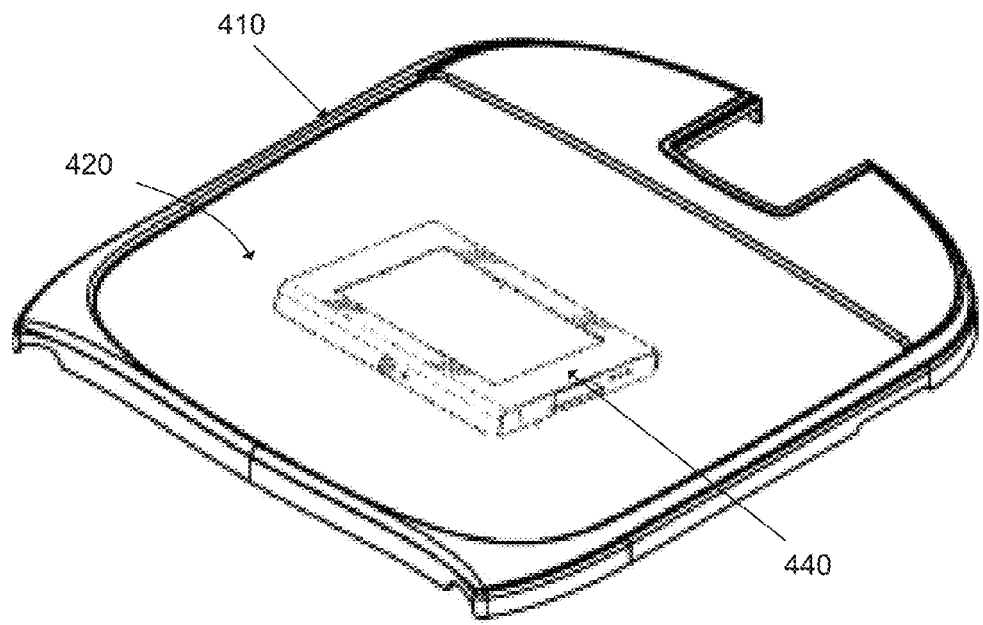
FIG. 4a shows a work surface with a portion of the work surface that includes a computing device in accordance with an example.

FIG. 4a further shows a first work platform 410 that can comprise a work surface 420, wherein a portion of the work surface 420 includes a computing device 440, such as a touch screen computing device. In one embodiment, the computing device 440 can be integrated into the work surface 440 of the first work platform 410 and can be substantially flush or level with the work surface 420 of the first work platform 410. In another embodiment the second work platform, as shown in FIG. 1, can include an integrated computing device. In one embodiment, information can be displayed on a computing device 440. The computing device 440 can have a touch screen and/or other attached input devices to enable a user to input information into the computing device 440. The computing device 440 and the remainder of the work surface 420 can form a substantially seamless first work platform 410. The substantially seamless first work platform 410 can also form a fluid proof or fluid resistant surface and/or an anti-bacterial surface. The substantially seamless first work platform can reduce the locations where pathogens may reside, enabling the surface to be more easily cleaned.

In one embodiment, the computing device and/or display screen can be a desktop computer, a laptop computer, a tablet, a smartphone, a personal digital assistant (PDA), a touch screen device, or another type of computing device. The computing device can include input and output (I/O) ports, such as a power port, one or more Ethernet ports, a keyboard port, and standardized ports such as a universal serial bus (USB), a Firewire port, a high definition media input (HDMI) port, or other desired port.

In one embodiment, the computing device can communicate with peripherals, such as medical equipment, a keyboard, a mouse, a display screen, etc. via a wired connection between the peripheral and one or more of the I/O ports at the computing device. In another embodiment, the computing device can be configured to wirelessly communicate with peripherals, other computing devices, computer servers, and so forth. The computing device can wirelessly communicate with other devices using an optical connection such as an infrared connection or fiber optic connection, or via a radio frequency connection, such as a wireless fidelity (WiFi) network, WiFi direct, a Bluetooth connection, a cellular communications system such as a third generation partnership project (3GPP) long term evolution (LTE) connection, device to device (D2D) communication, a machine type communication, or via another type of proprietary wireless connection. The cellular communications system can comprise one or more cellular network nodes and one or more Institute of Electrical and Electronics Engineers (IEEE) 802.11-2012 configured access points. In one embodiment, the one or more cellular networks may be 3rd generation partnership project (3GPP) long term evolution (LTE) Rel. 8, 9, 10, or 11 networks and/or IEEE 802.16p, 802.16n, 802.16m-2011, 802.16h-2010, 802.16j-2009, 802.16-2009 networks.

Figure 4B:
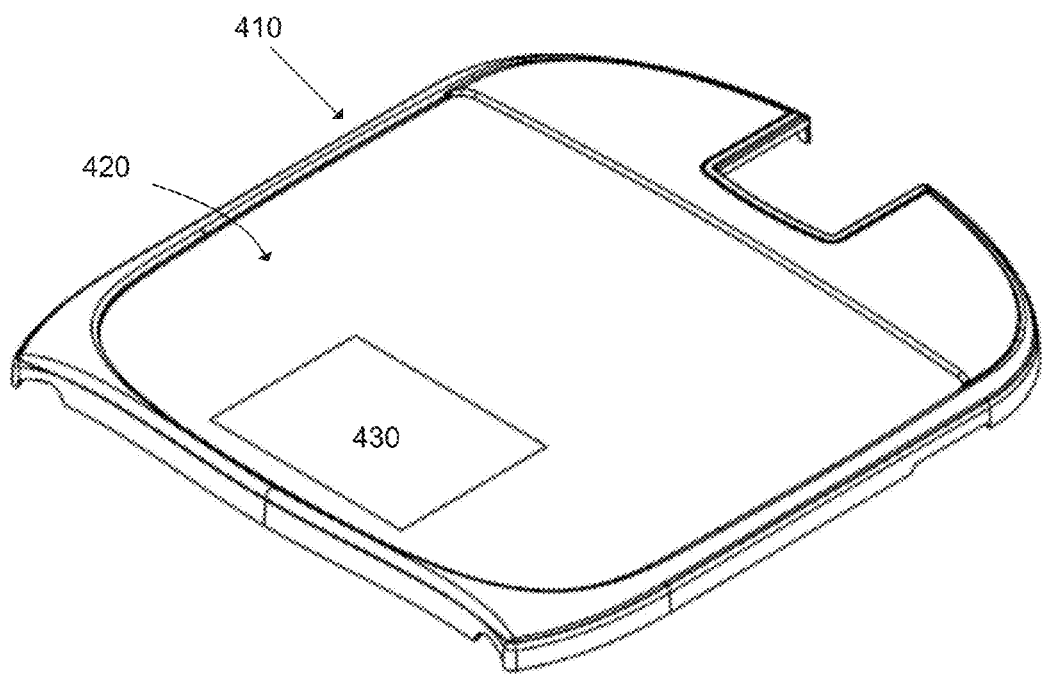
FIG. 4b further shows a work surface with a portion of the work surface that includes a transparent conductive surface in accordance with an example.

FIG. 4b further shows a first work platform 410 that can comprise a work surface 420, wherein a portion of the work surface 420 includes a transparent conductive surface 430. In one embodiment, the transparent conductive surface 430 can be integrated into the work surface 420 of the first work platform 410 and can be substantially flush or level with the work surface 420 of the first work platform 410.

Figure 5A:
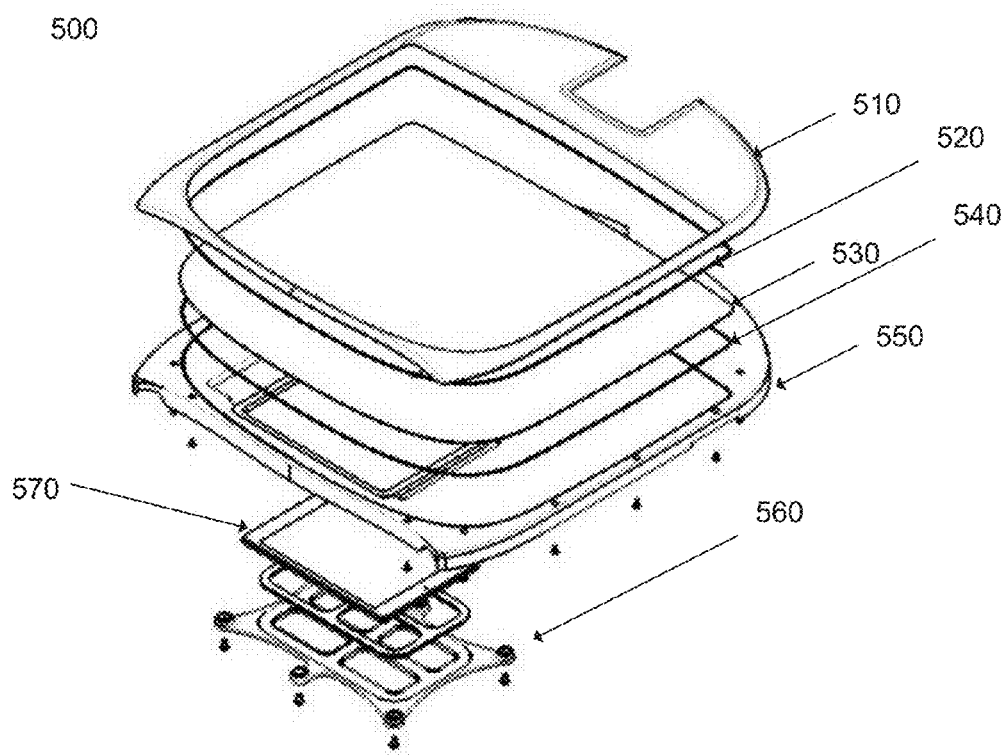
FIG. 5a shows a first work platform including an upper trim piece, an upper sealing layer, work surface, a lower sealing layer, and a lower trim piece in accordance with an example.

FIG. 5a shows the first work platform 500 including an upper trim piece 510, an upper sealing layer 520, work surface 530, a lower sealing layer 540, a lower trim piece 550. In one embodiment, the work surface 530 can be a transparent conductive surface. The first work platform 500 can include a mounting bracket 560 that can attach to a bottom surface of the first work platform 500. In one embodiment, the mounting bracket 560 can be used to attach a computing device 570 to the bottom surface of the first work surface 530. In another embodiment, the mounting bracket can be used to enable the computing device 570 to be located below the work surface 530 and in substantial proximity to the work surface 530.

Figure 5B:
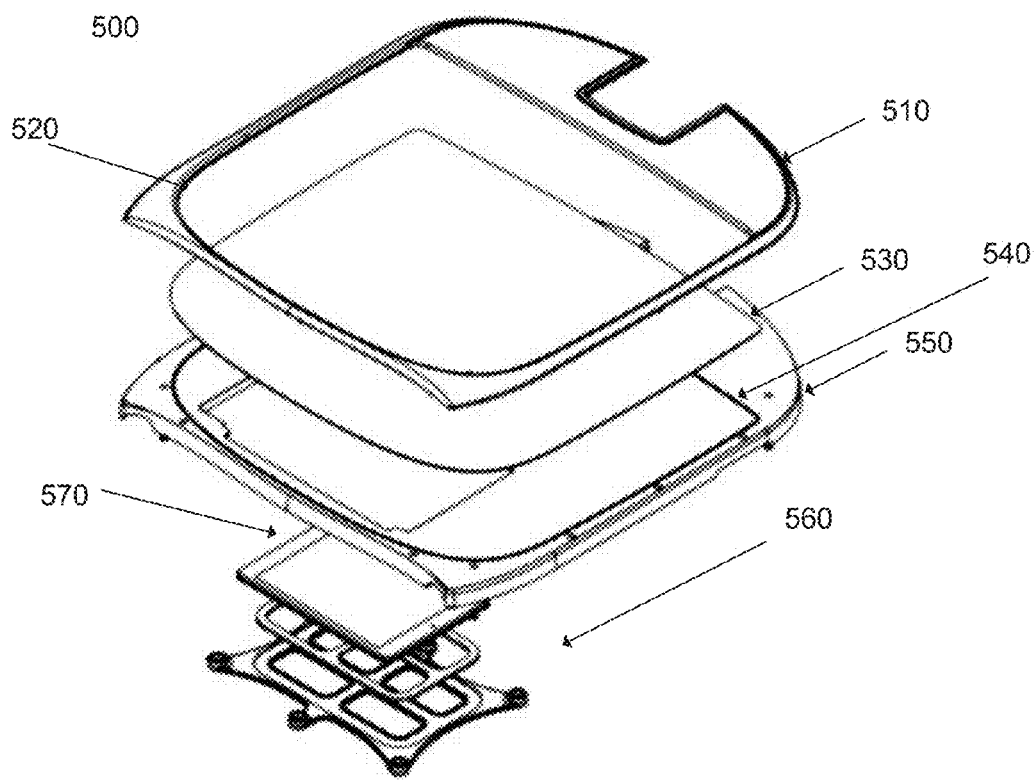
FIG. 5b shows a first work platform with an upper sealing layer incorporated into the upper trim piece and a lower sealing layer incorporated into a lower trim piece in accordance with an example.

FIG. 5b shows a first work platform 500 substantially similar to the first work platform described in FIG. 5a. In addition to the first work platform 500 illustrated in FIG. 5a, FIG. 5b shows the first work platform 500 wherein the upper sealing layer 520 is incorporated into the upper trim piece 510 and the lower sealing layer 540 is incorporated into the lower trim piece 550. The structure of the first work platform 500 in FIG. 5b can be substantially similar to the structure as previously described with respect to the first work platform 500 in FIG. 5a in other regards.

Figure 6:
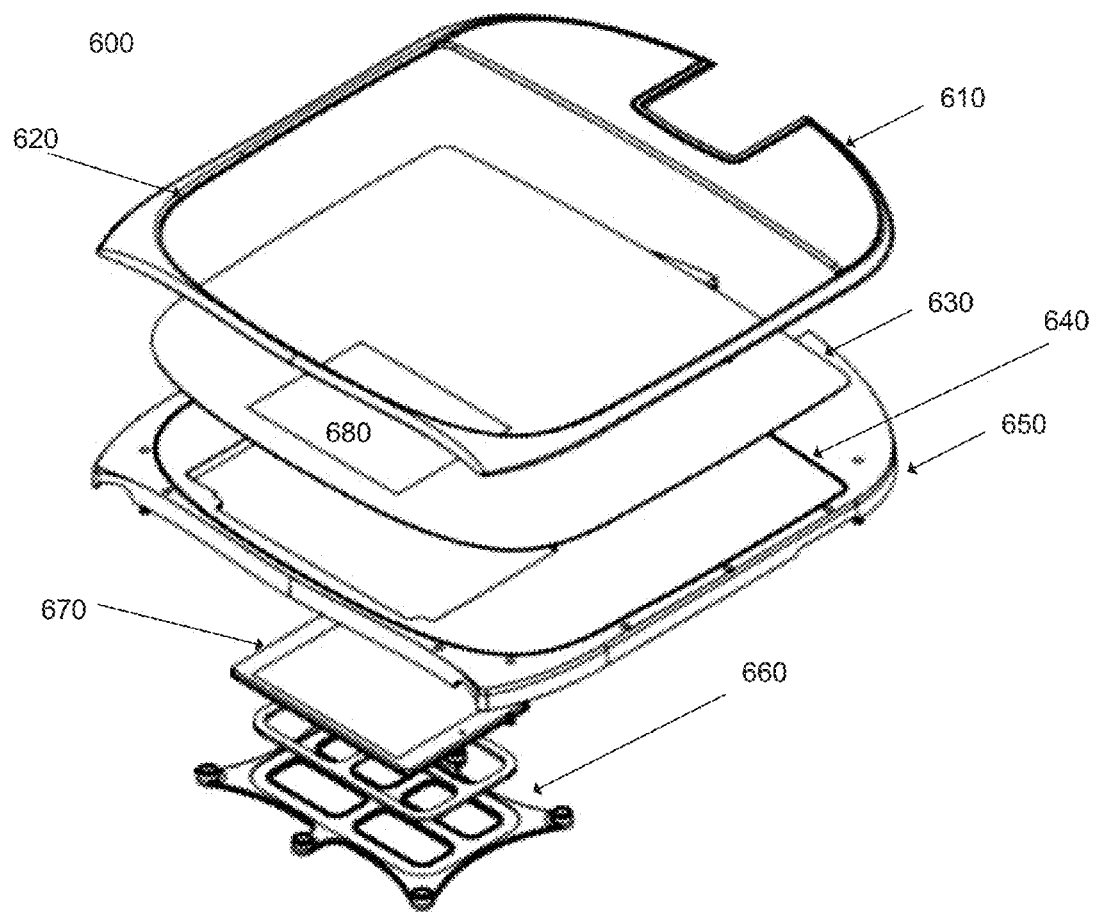
FIG. 6 shows the first work platform with a portion of the work surface that includes a transparent conductive surface in accordance with an example.

FIG. 6 shows a first work platform 600 substantially similar to the first work platform 500 described in FIG. 5b. In addition to the first work platform 500 illustrated in FIG. 5b, FIG. 6 shows the first work platform 600 wherein a portion of the work surface 630 includes a transparent conductive surface 680. In one embodiment, the transparent conductive surface 680 can be integrated into the work surface 630 of the first work platform 600 and can be substantially flush or level with the work surface 630 of the first work platform 600. The structure of the first work platform 600 in FIG. 6 can be substantially similar to the structure as previously described with respect to the first work platform 500 in FIG. 5b in other regards.

Figure 7:
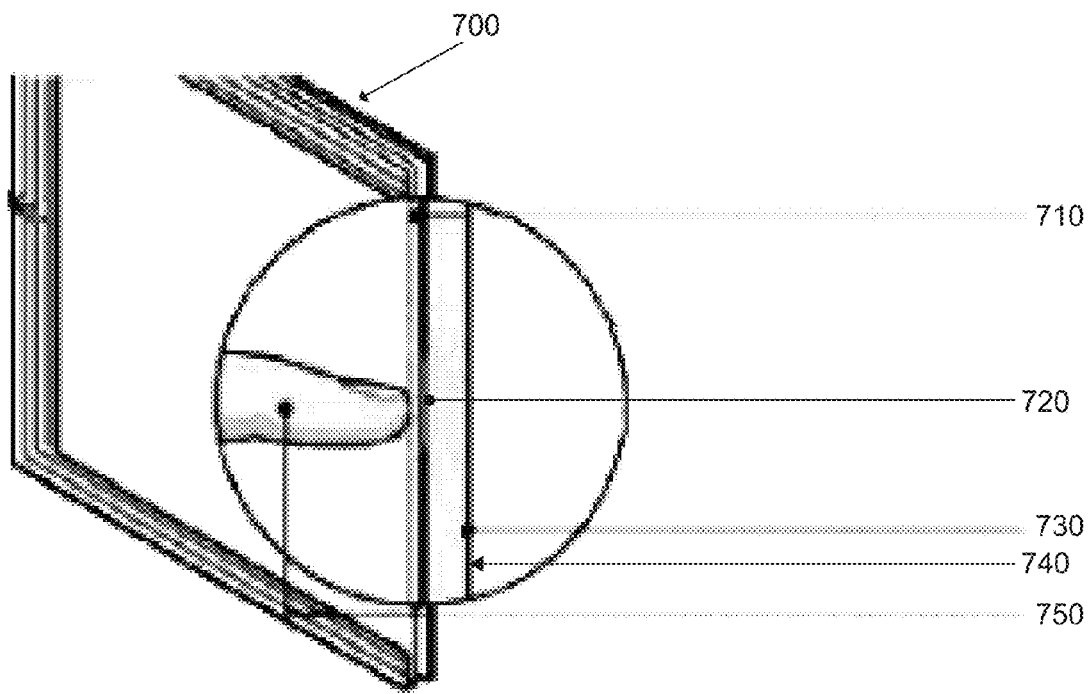
FIG. 7 depicts a capacitive transparent conductive surface in accordance with an example.

In one embodiment, the transparent conductive surface in FIGS. 5a, 5b, and 6 can have a plurality of sublayers of material to form a capacitive transparent conductive surface. FIG. 7 depicts a capacitive transparent conductive surface 700, including: a top capacitive sublayer 710, such as polyester sublayer coated with a transparent metallic conductive coating on at least one side of the polyester; a spacer sublayer 720, wherein the spacer sublayer can include an adhesive material; a bottom capacitive sublayer 730, such as a glass sublayer coated with a transparent metallic conductive coating on at least one side of the glass sublayer; and an adhesive sublayer 740 on the bottom side of the bottom capacitive sublayer 730, such as for mounting the bottom of the capacitive transparent conductive surface 700 to another object. Each of the plurality of sublayers of material can be distributed cross the lateral plane of the capacitive transparent conductive surface 700. A controlling device 750, such as a finger or stylus, can be used to change the conductance of the top capacitive sublayer 710. In one embodiment, the change in conductance can be transferred to another device located below the bottom capacitive sublayer 730, such as a touch screen computing device, to control the other device.

Figure 8:
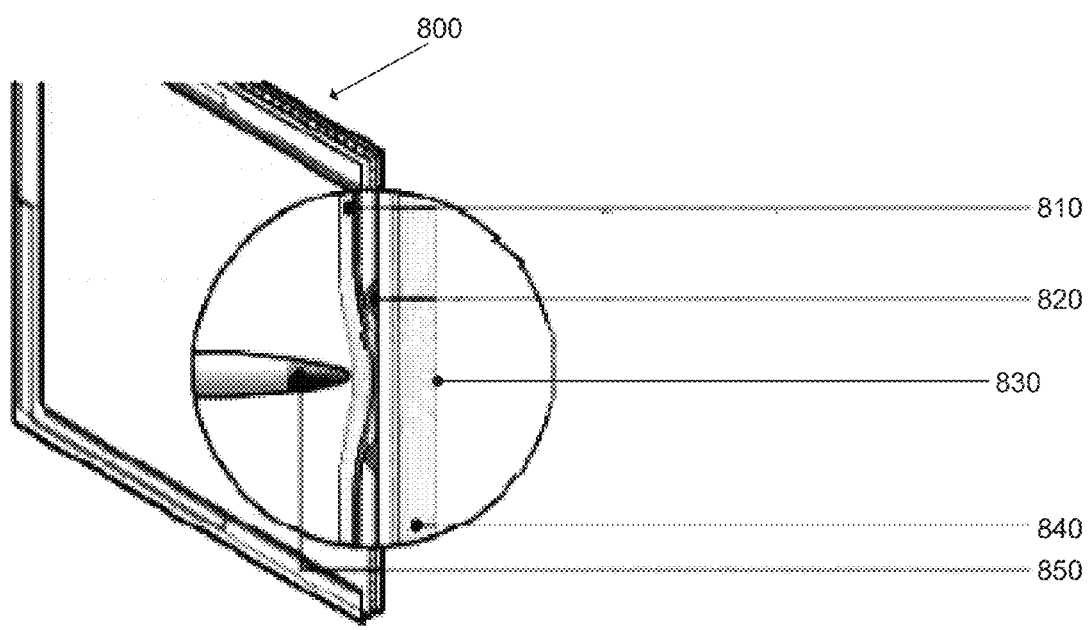
FIG. 8 depicts a resistive transparent conductive surface in accordance with an example.

In another embodiment, the transparent conductive surface in FIGS. 5a, 5b, and 6 can have a plurality of sublayers of material to form a resistive transparent conductive surface. FIG. 8 depicts a resistive transparent conductive surface 800, including: a top resistive sublayer 810, such as a polyester film; a separating sublayer 820, such as a gap or transparent spacer dots; a bottom resistive sublayer 840, such as a polyester film; and an adhesive sublayer 830 on the bottom side of the bottom resistive sublayer 840, such as for mounting the bottom of the resistive transparent conductive surface 800 to another object. The top resistive layer 810 can comprise a conductive material and the bottom resistive sublayer 840 can comprise a resistive material. A voltage can be applied across the top resistive layer. A controlling device, such as a finger or stylus, can be used to apply pressure against the top resistive layer 810 to activate the top resistive layer 810. When ample touch pressure is applied to the top resistive layer 810, the top resistive layer 810 can flex inward and can contact the bottom resistive sublayer 840, providing for a voltage drop. The pressure from the controlling device can cause the top resistive layer 810 and the bottom resistive sublayer 840 of the resistive transparent conductive surface 800 to touch each other, changing the resistance of the resistive transparent conductive surface 800. The voltage change can be transferred from the bottom resistive sublayer 840 to a computing device below the bottom resistive sublayer 840. In one embodiment, the voltage can alternate between the top resistive layer 810 and the bottom resistive sublayer 840, and x and y coordinates of the controlling device can be transferred to the computing device.

In one embodiment, the transparent conductive surface can be a transparent or substantially transparent material that provides the transfer of light through the transparent material. The transfer of light through the transparent material can enable an individual, such as a caregiver, to view an object below the transparent defending layer, such as a display screen or computing device.

Figure 9:
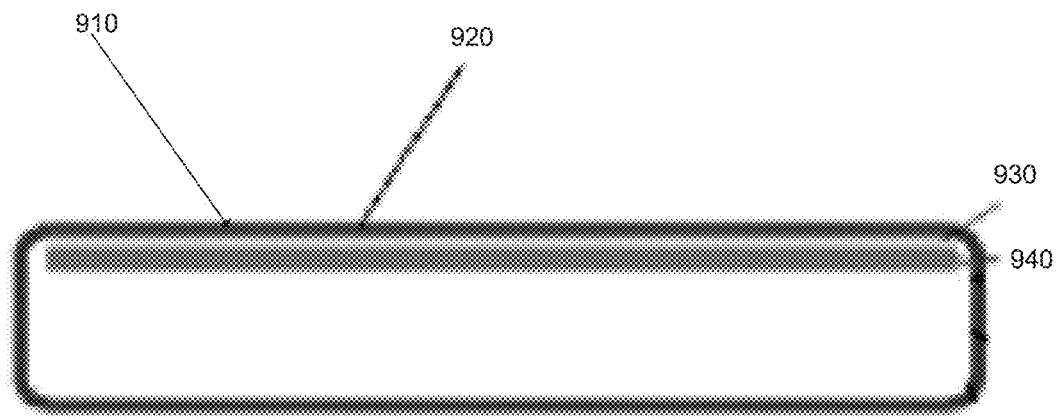
FIG. 9 illustrates a transparent conductive surface that includes a touch surface and a transfer surface in accordance with an example.

The transparent conductive surface can enable the use of a touch screen of a computing device that is located below the transparent conductive surface. FIG. 9 illustrates that the transparent conductive surface 910 can include a touch surface 920 and a transfer surface 930. In one embodiment, the touch surface 920 of the transparent conductive surface 910 can provide a surface for a controlling device, such as the finger of the caregiver or a stylus, to contact or come in close proximity to the touch surface 920 and conduct an electrical signal from the touch surface 920 to the transfer surface 930. In another embodiment, the touch surface 920 of the transparent conductive surface 910 can provide a surface for a controlling device, such as the finger of the caregiver or a stylus, to contact or come in close proximity to the touch surface 920 and convey a change in conductance from the touch surface 920 to the transfer surface 930.

In one embodiment, the transfer surface 930 can transfer an electrical signal or change in conductance to the surface of another device 940, such as the surface of a touch screen computing device. For example, the transparent conductive surface 910 can receive a change in conductance from the controlling device at the touch surface 920 of the transparent conductive surface 910, convey the change in conductance to the transfer surface 930, and transfer the change in conductance to another device 940, such as a touch screen computing device. In one embodiment, the other device 940 can be substantially in contact with the transfer surface 930. In another embodiment, a minimal gap can be between the transfer surface 930 and the other device 940.

The transparent conductive surface 910 can include a conductive material to enable the conductance of an electrical signal or a change in conductance. In one embodiment, the touch surface 920 of the transparent conductive surface 910 can receive the electrical signal or change in conductance from a controlling device above the touch surface 920. In another embodiment, the touch surface 920 of the transparent conductive surface 910 can receive the electrical signal or change in conductance from a controlling device in contact with the touch surface 920. For example, the transparent conductive surface 910 can convey a change in conductance from a controller device, such as a finger of a caregiver or a stylus, at or above the touch surface 920 of the transparent conductive surface 910 to the transfer surface 930 of the transparent conductive surface 910. The change in conductance can be transferred from the transfer surface 930 of the transparent conductive surface 910 to the top surface, or touch screen, of a computing device, such as a tablet, located below the transparent conductive surface 910. In one embodiment, the transparent conductive surface 910 can temporarily, or for a brief period of time, hold an electrical charge. In another embodiment, the transparent conductive surface 910 can block or reflect selected frequency waves, such as selected light frequency waves or sound frequency ways.

Returning to FIG. 6, in one embodiment, the transparent conductive surface 680 and the remainder of the work surface 630 can form a substantially seamless first work platform 600. The substantially seamless first work platform 600 can also form a fluid proof or fluid resistant surface and/or an anti-bacterial surface. Similarly in FIG. 5, the work surface 530 can form a substantially seamless first work platform 500.

The substantially seamless first work platform in FIGS. 5 and 6 can enable the user, such as a caregiver, to engage the touch screen of a computing device such as a tablet, by engaging with the transparent conductive surface. The substantially seamless first work platform can provide a shield between the computing device and the user. In one embodiment, the substantially seamless first work platform can provide a protective barrier to shield the interior of the frame 116, as shown in FIG. 1, the transfer surface, and/or a computing device located in the interior of the frame 116 or attached to the transfer surface from fluids that may be spilled on the first work platform. For example, if the caregiver is taking a fluid sample of a patient and the fluid spills, the substantially seamless first work platform guards against the fluid coming in contact with the computing device or other electronics located below the substantially seamless first work platform. Another advantage of the substantially seamless first work platform is that it can be used to prevent dust from entering an enclosed frame 116, as shown in FIG. 1, below the first work platform where the computing device resides, thereby lengthening the life of the computing device.

Another advantage of the substantially seamless first work platform can be to minimize the spread of disease. The substantially seamless first work platform can enable the caregiver to efficiently and effectively clean the work surface, such as the transparent conductive surface, after using the smart medical cart in one patient's room and before using the smart medical cart in another patient's room. For example, returning to FIG. 4, where first work platform 410 has a portion of the work surface 420 that includes a transparent conductive surface 430, the transparent conductive surface 430 and the remainder of the work surface 420 can form a substantially seamless first work platform 410, pathogens, such as bacterium, viruses, prion, fungus, or other disease causing agents are not trapped, nor do they adhere to channels of the substantially seamless first work platform 410. The substantially seamless first work platform 410 can also be substantially smooth, thereby reducing or eliminating areas in which pathogens can reside. Wiping down the smooth substantially seamless first work platform 410 to substantially remove pathogens can be much easier than removing pathogens from irregular surfaces, such as keyboards. A substantially seamless transparent conductive surface 430 and remaining work surface 420 can enable the caregiver to use the computing device beneath the protective surface while still enabling effective sanitation of the entire work surface to minimize and/or eliminate the transfer of pathogens and fluid leakage.

In one embodiment, the transparent conductive surface 430 can be incorporated into other work platforms, such as a second work platform. Returning to FIG. 3, the location of the computing device 330, such as a display screen, touch screen computing device, or a tablet, is not limited to a location below the first work surface 310. In one embodiment, the computing device 330 can be located at other locations on the smart medical cart, such as a second vertical support as described in the proceeding paragraphs. In another embodiment, the computing device 330 can be attached to one or more selected locations on the smart medical cart, such as by using a mounting bracket attachment.

Figure 10A:
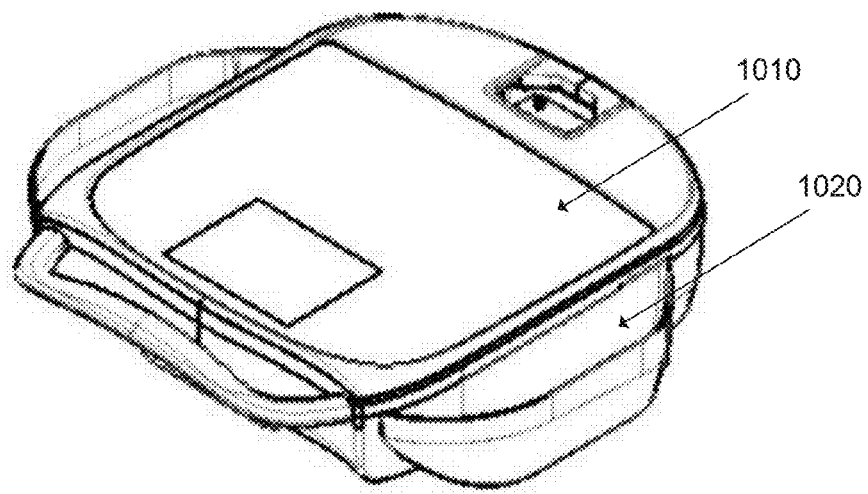
FIG. 10a depicts a perspective view of a first work platform with an attached enclosed frame in accordance with an example.
Figure 10B:
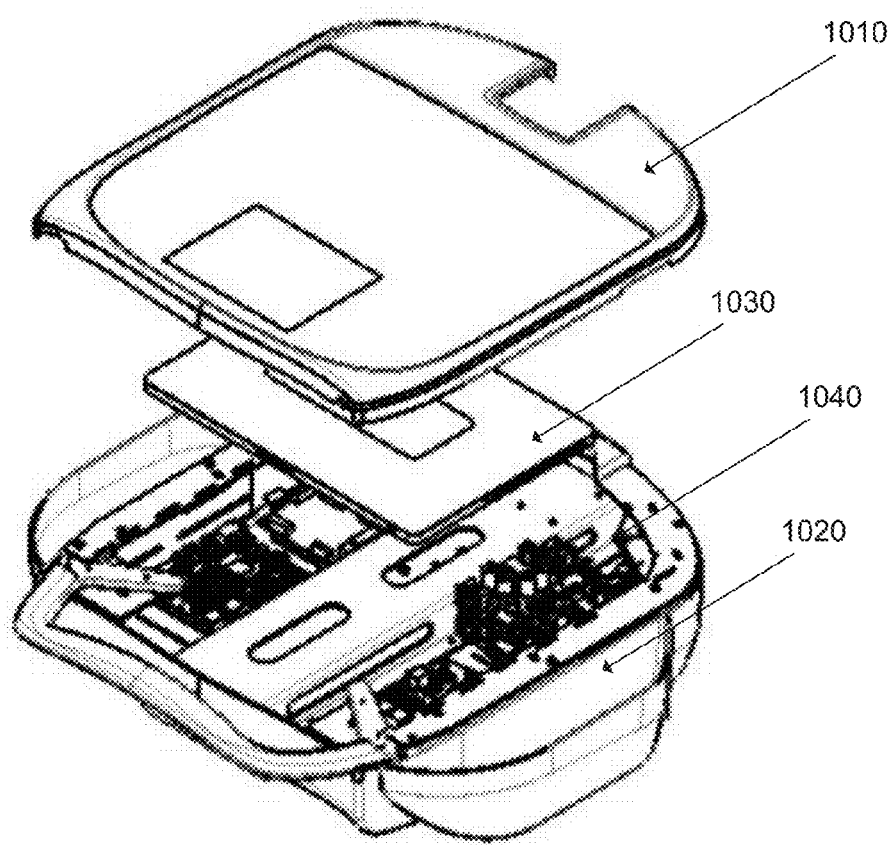
FIG. 10b depicts an exploded view of a first work platform with the attached enclosed frame in accordance with an example.

FIGS. 10a and 10b depict the first work platform 1010 with an attached enclosed frame 1020, as shown in the exemplary embodiment in FIG. 1. FIG. 10a depicts a perspective view of the first work platform 1010 with the attached enclosed frame 1020. FIG. 10b depicts an exploded view of the first work platform 1010 with the attached enclosed frame 1020. FIG. 10b depicts that the first work platform 1010 can be attached to the enclosed frame 1020 using a mounting bracket 1030. In one embodiment, the top surface of the mounting bracket 1030 can be attached to a bottom surface of the first work platform 1010, such as the bottom surface of the first work platform 1010 being mounted to the mounting plate 1030 using bolts or snapping the first work platform 1010 onto the top surface of the mounting plate 1030. The bottom surface of the mounting bracket 1030 can be attached to the top surface of the enclosed frame 1020, such as the top surface of the enclosed frame 1020 being mounted to the bottom surface of the mounting plate 1030 using a bolt or snapping the top surface of the enclosed frame 1020 onto the bottom surface of the mounting plate 1030. In another embodiment, the first work platform 1010 can be attached directly to the enclosed frame 1020, such as the first work platform 1010 being bolted or snapped on to the top surface of the mounting plate 1030. One of ordinary skill in the art would readily recognize that the first work platform 1010 can be attached to the enclosed frame 1020 using methodologies other than bolting or snapping together the first work platform 1010 and the enclosed frame 1020.

FIG. 10b shows that the enclosed frame can have an interior cavity 1040. The interior cavity 1040 can provide room to store objects, such as a computing device, universal serial bus (USB) hub, computer circuitry, a display screen, and other objects. In one embodiment, the first work platform 1010 and the enclosed frame 1020 can be attached to form an enclosed or substantially enclosed interior cavity 1040. In one embodiment, the enclosed interior cavity 1040 can be used to prevent dust or fluid from entering the enclosed frame interior cavity 1040.

Figure 11A:
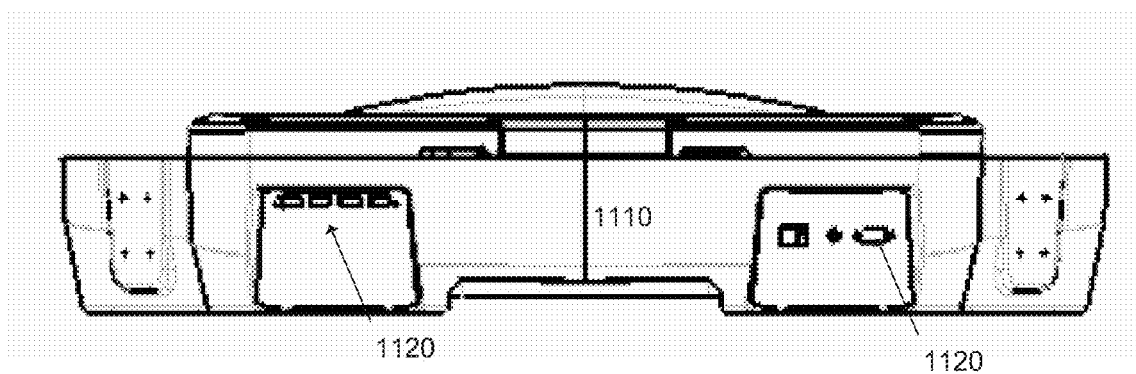
FIG. 11a shows a rear view of an enclosed frame in accordance with an example.
Figure 11B:
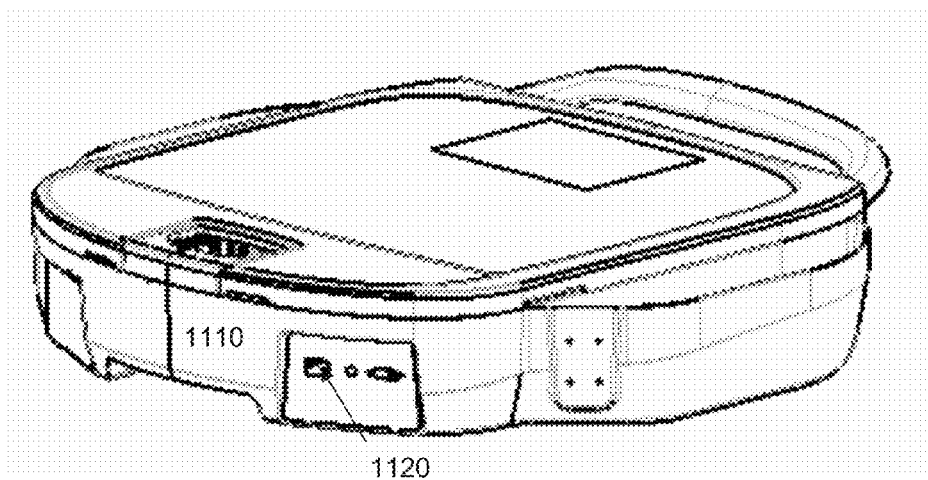
FIG. 11b shows a rear perspective view of an enclosed frame in accordance with an example.
Figure 11C:
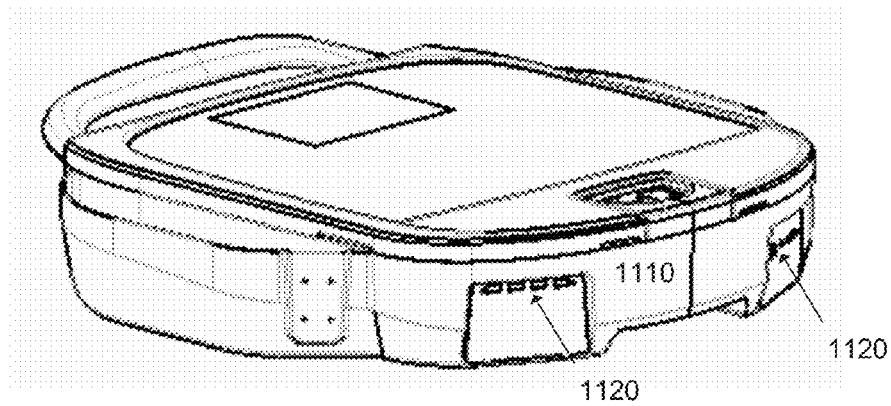
FIG. 11c shows another rear perspective view of the enclosed frame in accordance with an example.

FIGS. 11a, 11b, and 11c depict rear views of an enclosed frame 1110, as shown in the exemplary embodiment in FIGS. 10a and 10b. FIG. 11a shows a rear view of the enclosed frame 1110. FIG. 11b shows a rear perspective view of the enclosed frame 1110. FIG. 11c shows another rear perspective view of the enclosed frame 1110. FIGS. 11a, 11b, 11c depict one exemplary embodiment where one or more ports are located in the rear of the enclosed frame 1110. The one or more ports 1120 can include integrated input and output ports, such as a universal serial bus (USB) port, a high-definition multimedia interface (HDMI) port, a video graphic array (VGA) port, a printer port, a keyboard port, a mouse port, or other types of computer and electronic input output (I/O) interfaces. In another embodiment, the enclosed frame 1110 can have one or more ports integrated into one or more surfaces, e.g. a side, front, back, top, and/or bottom surface, of the enclosed frame 1110. The ports 1120 can provide a connection between an object located at the interior of the enclosed frame 1110 and an object at a different location, such as an object attached at a different location on the smart medical cart or an object located separate from the smart medical cart. In one embodiment, the connection can enable the transfer of power or information, such as video, audio, or data, between the object located at the interior of the enclosed frame 1110 and an object at a different location.

Figure 12A:
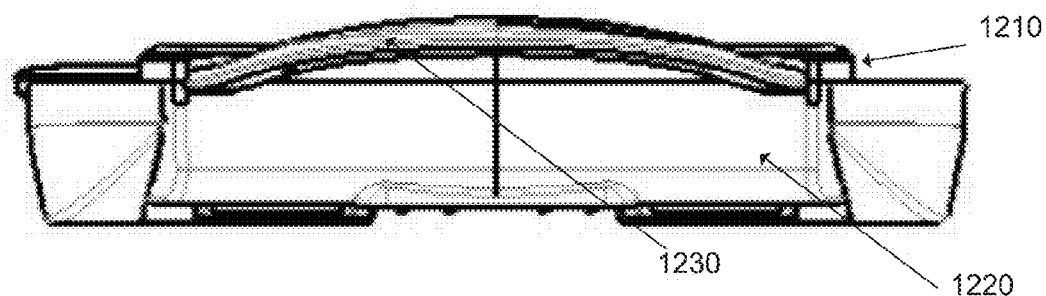
FIG. 12a shows a front view of the first work surface and the enclosed frame in accordance with an example.
Figure 12B:
FIG. 12b shows an exploded view of the first work surface and an enclosed frame in accordance with an example.
Figure 12B:
Figure 12B:
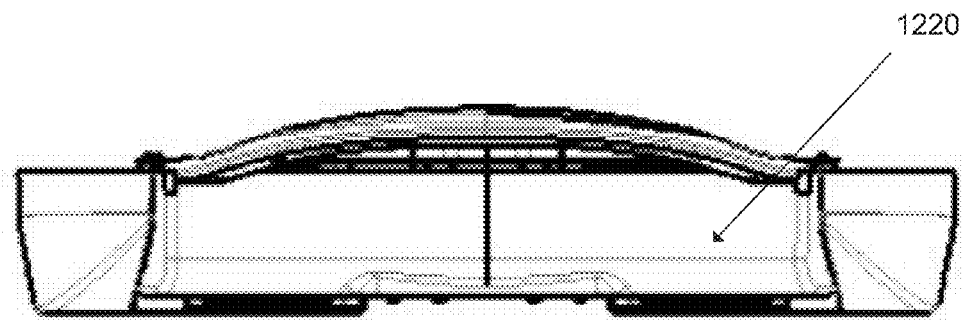
Figure 13A:
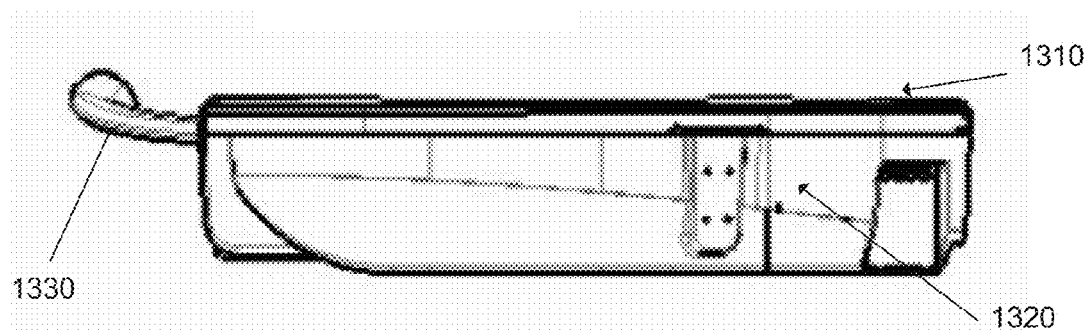
FIG. 13a illustrates a side view of a first work surface, an enclosed frame, and a handle in accordance with an example.
Figure 13B:
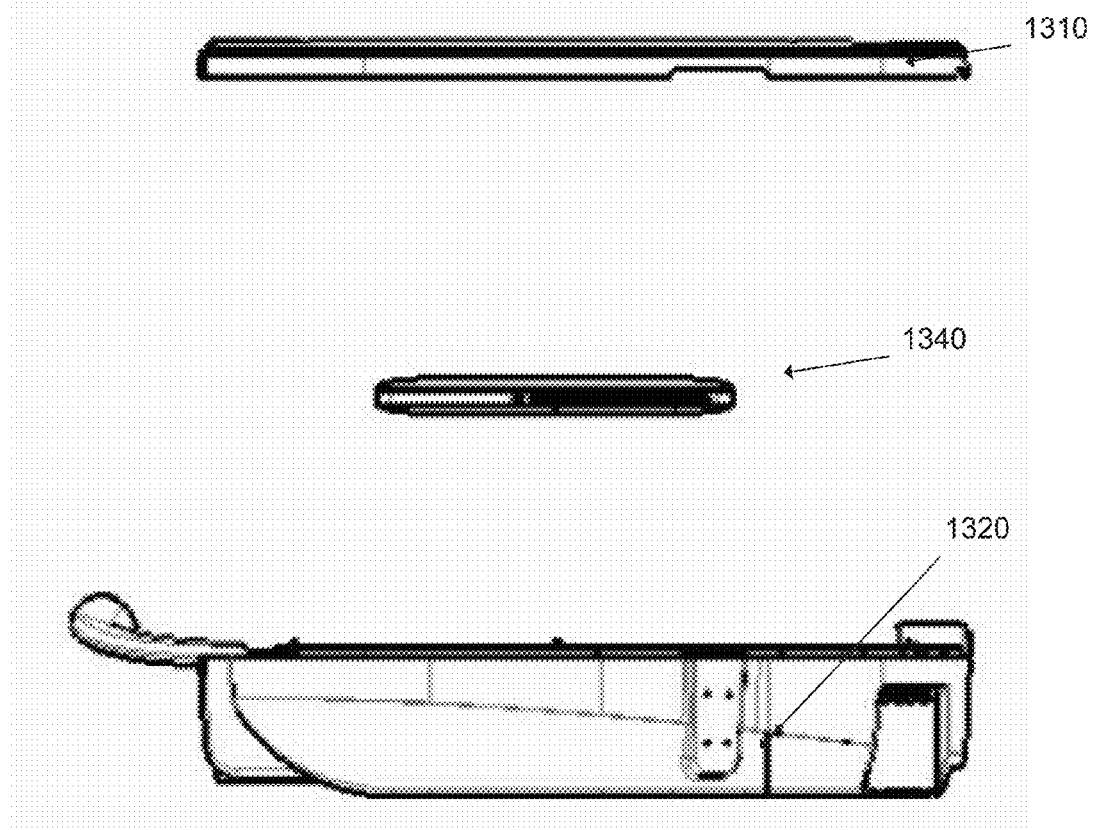
FIG. 13b illustrates a side view of a first work surface, an enclosed frame, and a computing device in accordance with an example.

FIGS. 12a and 12b show a front view of the first work surface 1210 and the enclosed frame 1220, as shown in the exemplary embodiment in FIGS. 10a and 10b. FIG. 12a shows that the handle 1230 can be attached to the first work surface 1210, such as by using bolts to attach the handle 1230 or by snapping the handle onto the first work surface 1210. In another embodiment, the handle 1230 can connect to the first work surface 1210. FIG. 12*b* shows an exploded view of the first work surface 1210 and the enclosed frame 1220, wherein a computing device 1240, such as a tablet, can be located in an interior cavity of the enclosed frame 1220. FIG. 13*a* illustrates a side view of the first work surface 1310, the enclosed frame 1320, and the handle 1330, substantially similar to FIG. 12*a*. FIG. 13*b* illustrates a side view of the first work surface 1310, the enclosed frame 1320, and the computing device 1340, substantially similar to FIG. 12*b*.

Figure 14A:
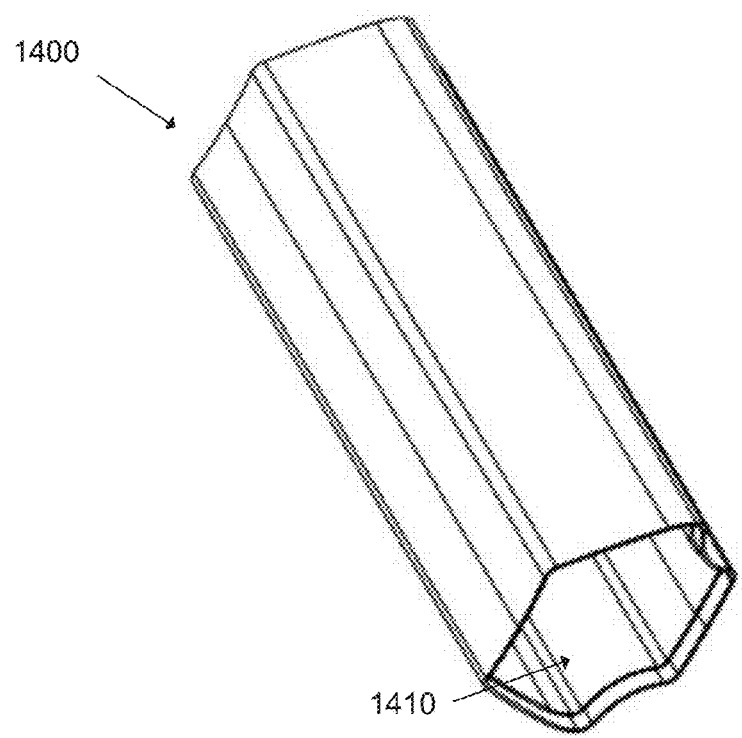
FIG. 14a illustrates a perspective view of a first vertical support in accordance with an example.
Figure 14B:
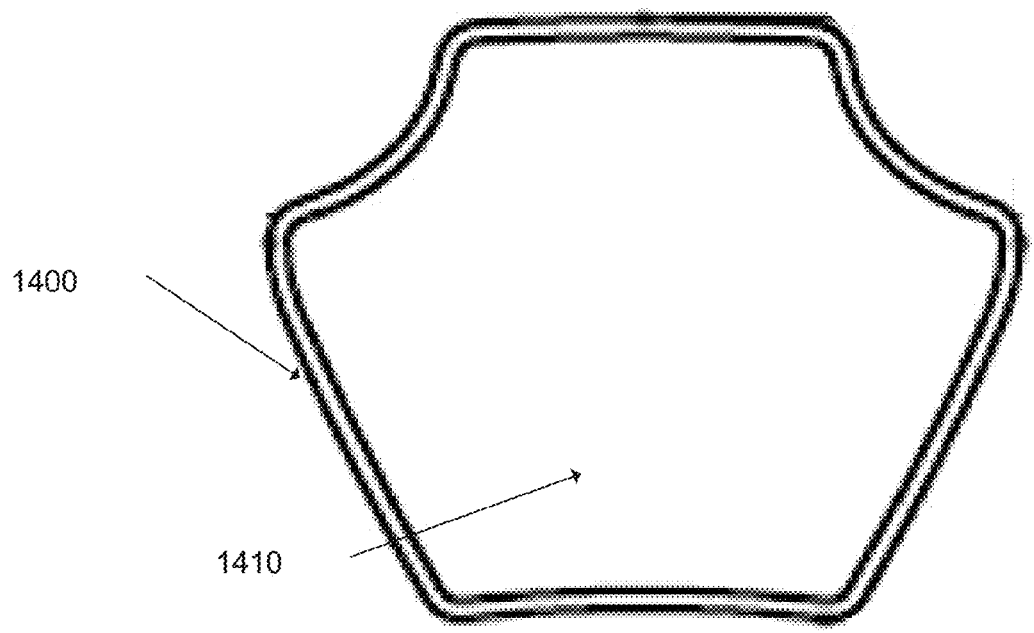
FIG. 14b illustrates a top view of a first vertical support in accordance with an example.

FIGS. 14*a* and 14*b* illustrate that a first vertical support 1400, as shown in FIG. 1, can have a hollow interior 1410. FIG. 14*a* illustrates a perspective view of the first vertical support 1400. FIG. 14*b* illustrates a top view of the first vertical support 1400. The first hollow interior 1410 can be used for a number of purposes. For example, the hollow interior 1410 can be configured to provide an area to: route wires, such as power lines and cables; connect a power source to a computing device and/or display screen; and/or connect a power source to medical equipment or devices. For example, the power source can be connected to the computing device, the display screen, an input device, and/or medical equipment using the hollow interior 1410 of the first vertical support 1400 in which to run power cords from one or more power sources to the devices. In one embodiment, the second vertical support, described in the proceeding paragraphs, can have a hollow interior similar to the first vertical support 1400.

Figure 15A:
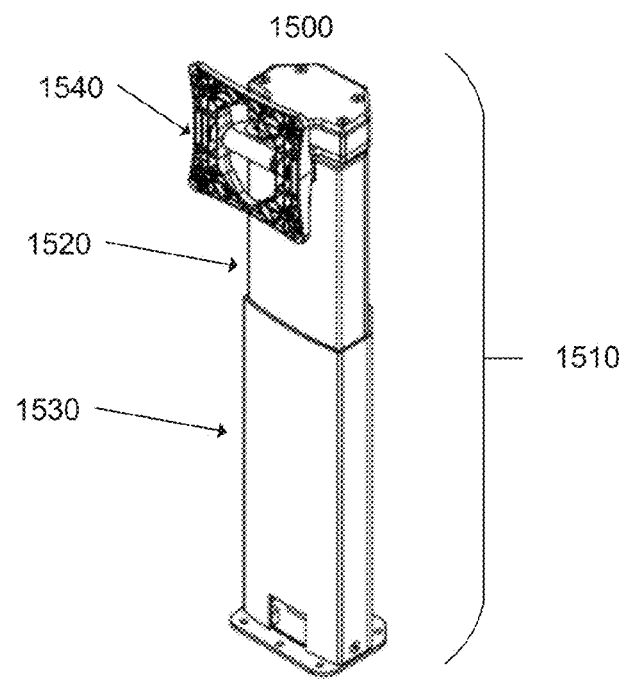
FIG. 15a shows a perspective view of a second vertical support in accordance with an example.
Figure 15B:
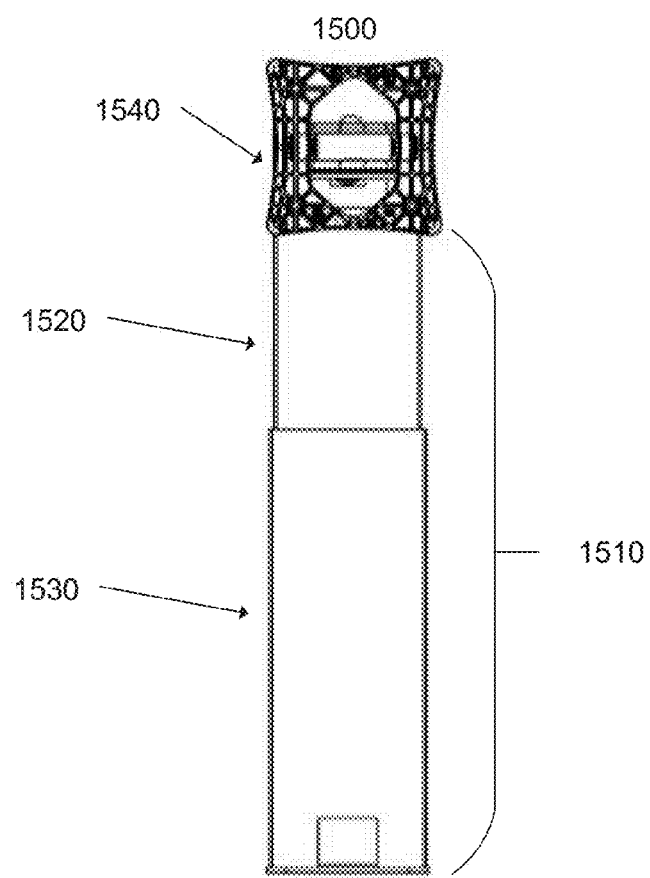
FIG. 15b shows a front view of a second vertical support in accordance with an example.

FIGS. 15*a* and 15*b* show a second vertical support 1500, as shown in FIG. 1. FIG. 15*a* shows a perspective view of the second vertical support 1500. FIG. 15*b* shows a front view of the second vertical support 1500. The second vertical support 1500 can include a telescoping structure 1510, where the telescoping structure 1510 has two members, a telescoping inner casing 1520 and a telescoping outer casing 1530, that can be slidably adjusted up and down. A driver can raise or lower the height of a computing device. The computing device can be attached to a mounting bracket 1540. The height of the computing device can be adjusted by slidably moving the telescoping inner casing 1520 upward or downward along an interior of the telescoping outer casing 1530. One of ordinary skill in the art would readily recognize that the telescoping structure 1510 can be adjusted using methodologies other than slidably adjusting the telescoping structure 1510.

Figure 16A:
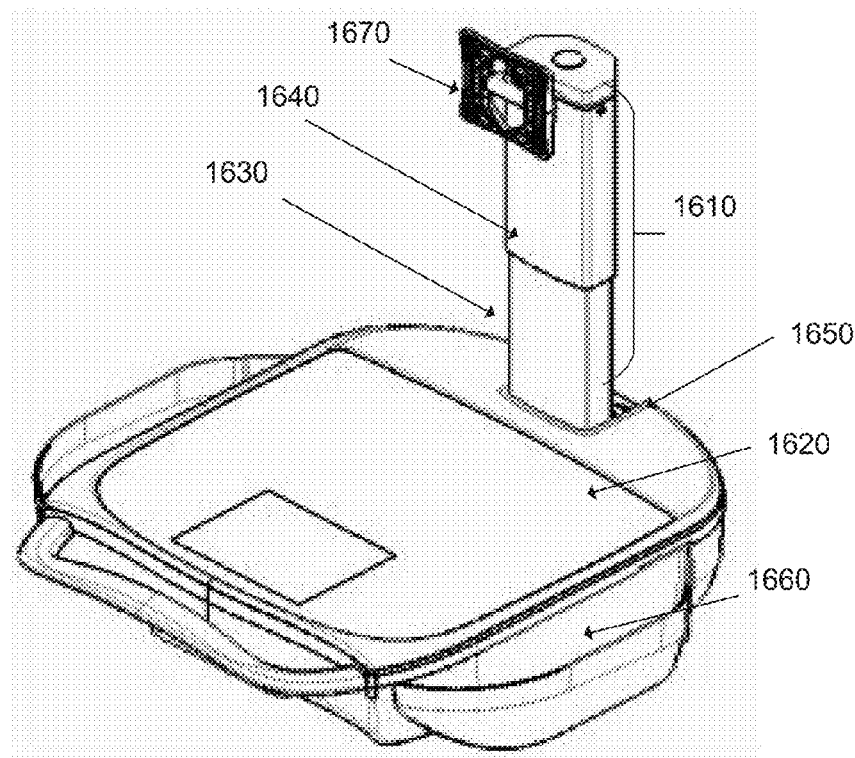
FIG. 16a shows a perspective view of a second vertical support and the first work platform in accordance with an example.
Figure 16B:
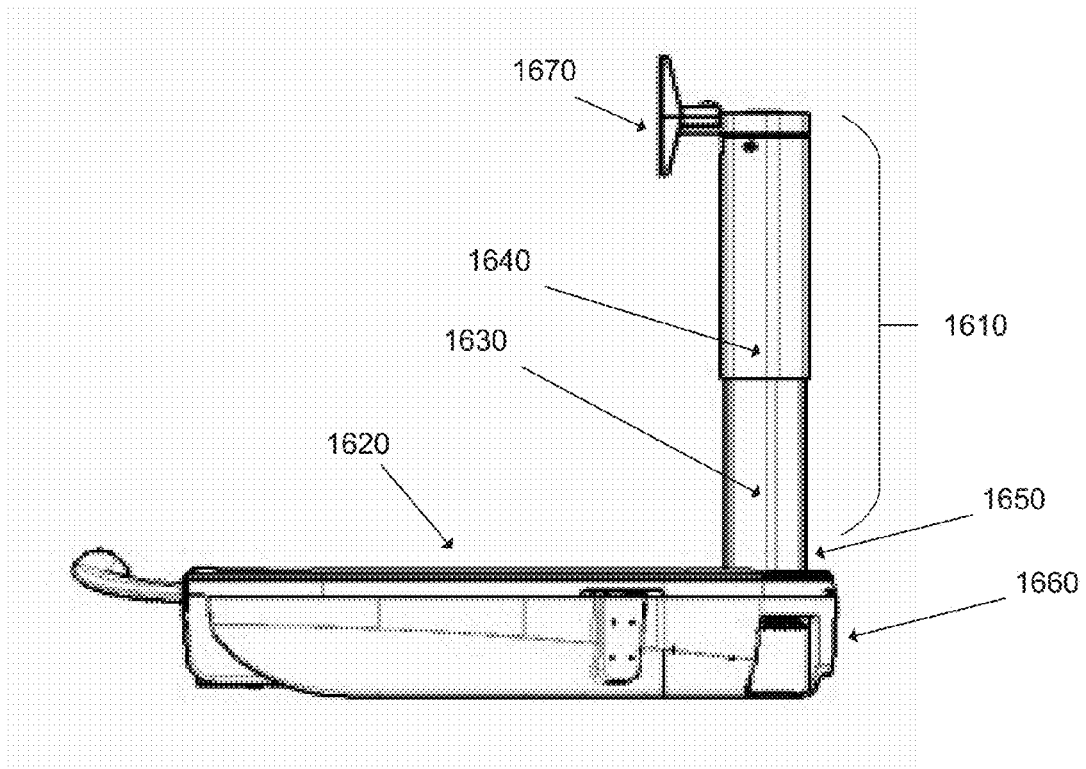
FIG. 16b shows a side view of the second vertical support and the first work platform in accordance with an example.

FIGS. 16*a* and 16*b* show that the second vertical support 1610, as shown in FIGS. 15*a* and 15*b*, can be attached to the first work platform 1620. FIG. 16*a* shows a perspective view of the second vertical support 1610 and the first work platform 1620. FIG. 16*b* shows a side view of the second vertical support 1610 and the first work platform 1620. The telescoping inner casing 1630 can be a fixed inner casing that is attached to first work platform 1620. The first work platform 1620 can include a hole or opening 1650 to enable the second vertical support 1610 to pass all of the way through the hole or opening 1650 in order to attach to the frame 1660, as shown in FIGS. 10*a* and 10*b*. In another embodiment, the second vertical support 1610 can pass all of the way through the hole or opening 1650 in order to attach to the first vertical support. In another embodiment, the second vertical support 1610 can pass partially through the hole or opening 1650 in order to attach to the first work platform 1620.

In one embodiment, the height of the second vertical support 1610 can be adjusted using a motorized linear actuator or gas shocks to raise or lower the second vertical support 1610 relative to the first work platform 1620. In one embodiment, the length of the second vertical support 1610 can be lengthened or shortened to raise and lower the height a computing device attached to a mounting bracket 1670. In another embodiment, one end of another motorized linear actuator or gas shock can be attached to the second vertical support 1610 and an opposite end of the actuator or shock can be attached to the first work platform 1620 or the frame 1660. The length of the motorized linear actuator or gas shock can be increased or decreased in order to raise or lower the height of the second vertical support 1610 and/or the computing device attached to the mounting bracket 1670.

In one embodiment, the height of the second vertical support 1610 can be adjusted using a same or substantially similar height adjustment mechanism as described in the preceding paragraphs for the height adjustment mechanism of the first vertical support.

Figure 17A:
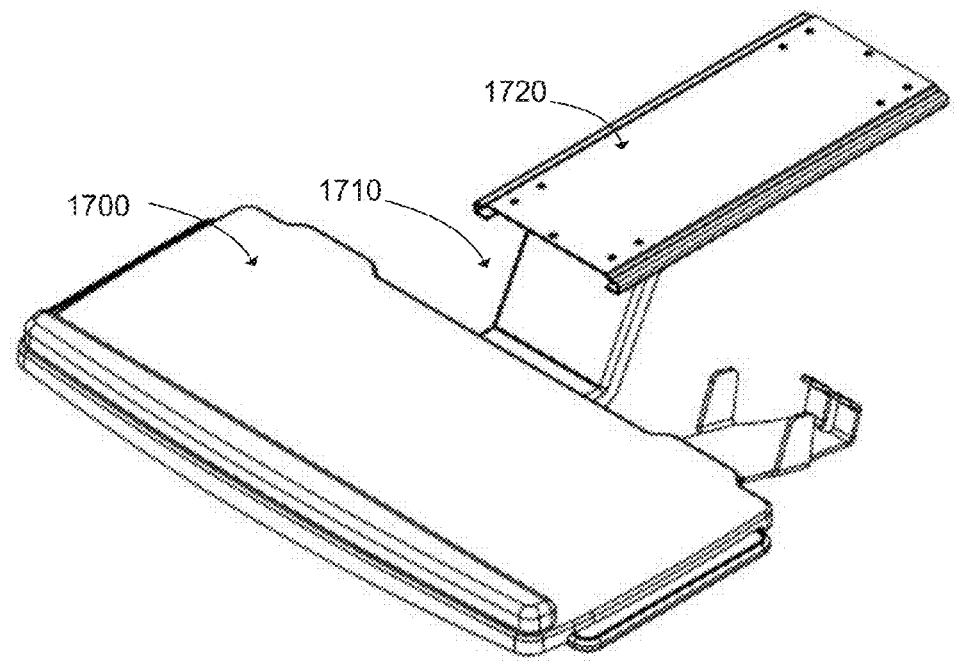
FIG. 17a shows a top perspective view of the second work platform in accordance with an example.
Figure 17B:
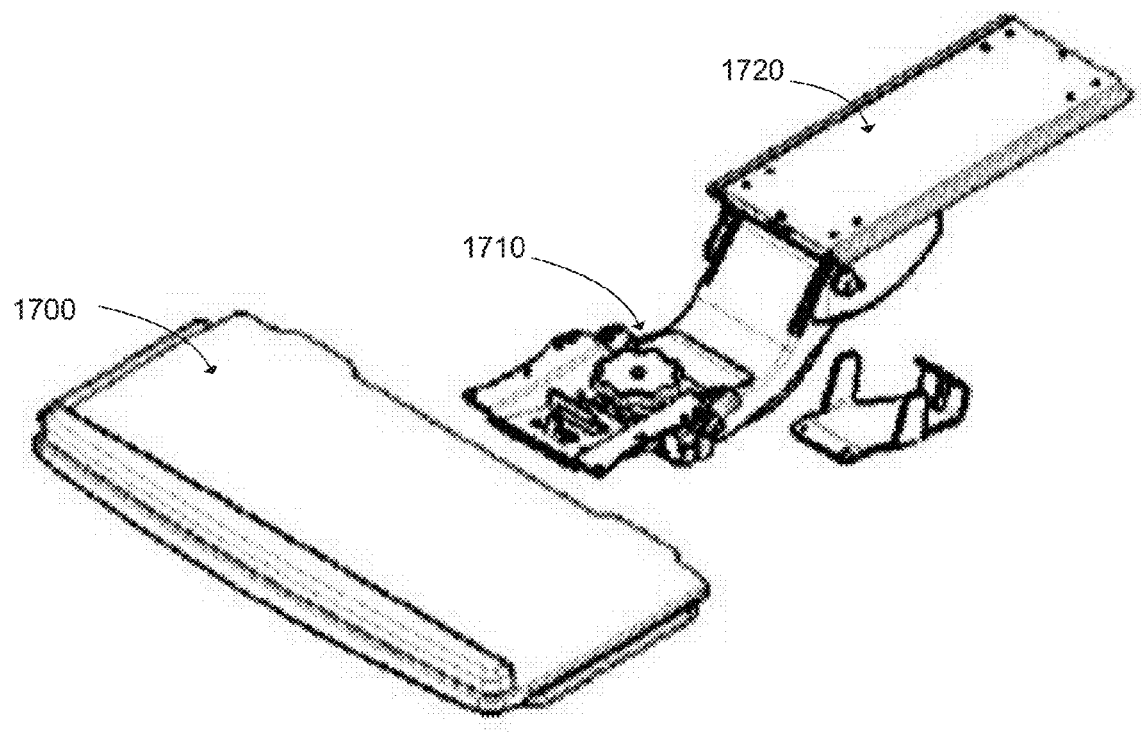
FIG. 17b shows an exploded top perspective view of the second work platform in accordance with an example.
Figure 17C:
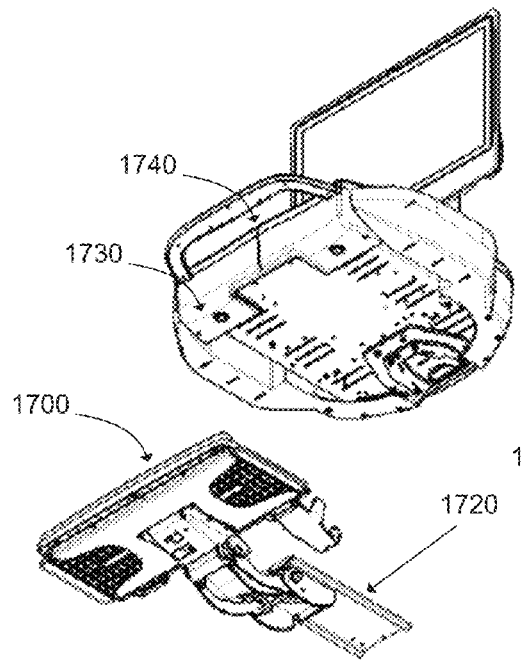
FIG. 17c shows an exploded view of a second work platform, a mounting bracket, a frame, and a first work platform in accordance with an example.
Figure 17D:
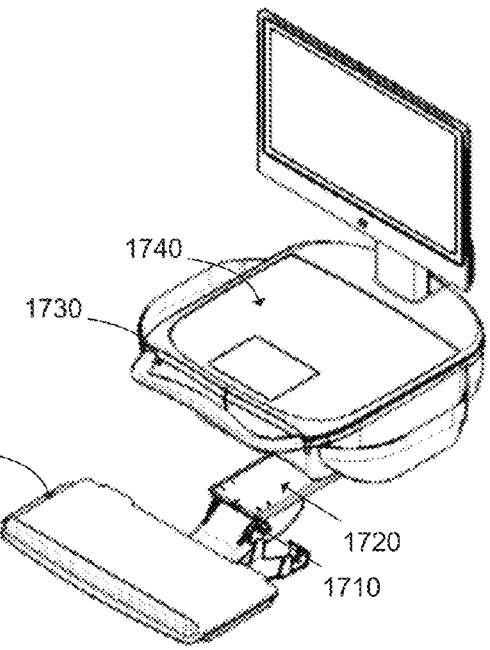
FIG. 17d depicts a top perspective view of the second work platform in accordance with an example.
Figure 17E:
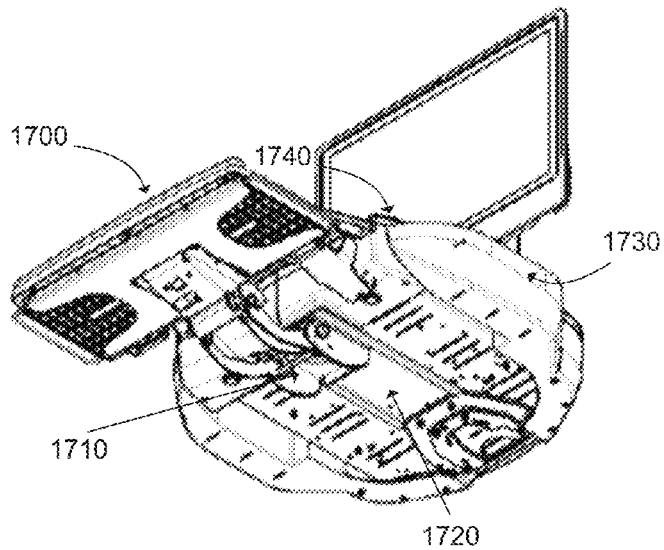
FIG. 17e depicts a bottom perspective view of a second work platform in accordance with an example.

FIGS. 17*a* and 17*b* illustrate one embodiment of the second work platform 1700, as shown in FIG. 1. FIG. 17*a* shows a top perspective view of the second work platform. FIG. 17*b* shows an exploded top perspective view of the second work platform. FIGS. 17*a* and 17*b* show that the second work platform 1700 can provide a location or platform to place peripherals, such as a keyboard and/or computer mouse. FIGS. 17*a* and 17*b* further show that the location of the second work platform 1700 can be adjusted to be raised or lowered using a location adjustment mechanism 1710. The second work platform can be attached to a plurality of locations on a smart medical cart. FIGS. 17*c*, 17*d*, and 17*e* show that the second work platform 1700 can attach to a frame 1730 of the first work platform 1740, as shown in FIG. 1, using a mounting bracket 1720. FIG. 17*c* shows an exploded view of the second work platform 1700, the mounting bracket 1720, the frame 1730, and the first work platform 1740. FIG. 17*d* depicts a top perspective view of the second work platform 1700, where the location of the second work platform 1700 can be adjusted or shifted using adjustment mechanism 1710. In another embodiment, the location adjustment mechanism 1710 can adjust the horizontal or lateral distance of the second work platform 1700 relative to the first work platform 1740. FIG. 17*e* depicts a bottom perspective view of the second work platform 1700. FIG. 17*e* further shows the mounting plate 1720 mounted to the bottom side of the frame 1730 of the first work platform 1740. FIG. 17*e* shows that the location adjustment mechanism 1710 can adjust the horizontal or lateral distance of the second work platform 1700 relative to the frame 1730. In one embodiment, the location adjustment mechanism 1710 can slide forward and backward along the mounting bracket 1720. For example, the user can move the second work platform 1700 forward or backward on a horizontal plane relative to the front of a smart medical cart. A height of the second work platform 1700 can be adjusted to make it comfortable for the user to interact with a computer controller, such as a keyboard, mouse, track pad, touch screen, or other type of controller that is in communication with the computing device to enable the user to control the computing device.

Figure 17F:
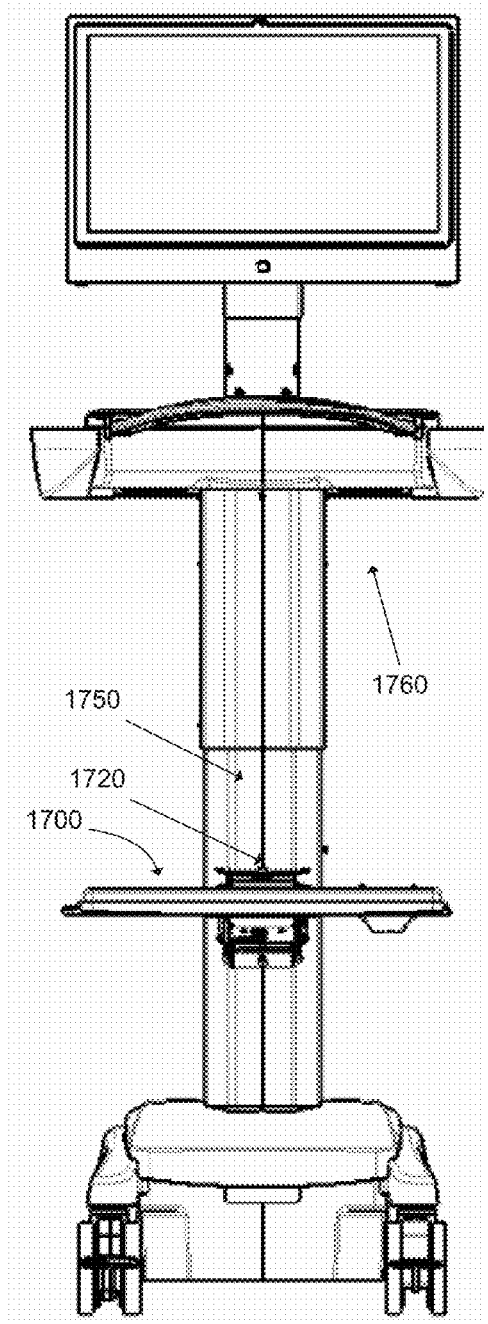
FIG. 17f depicts a front view of the second work platform attached to the first vertical support in accordance with an example.
Figure 17G:
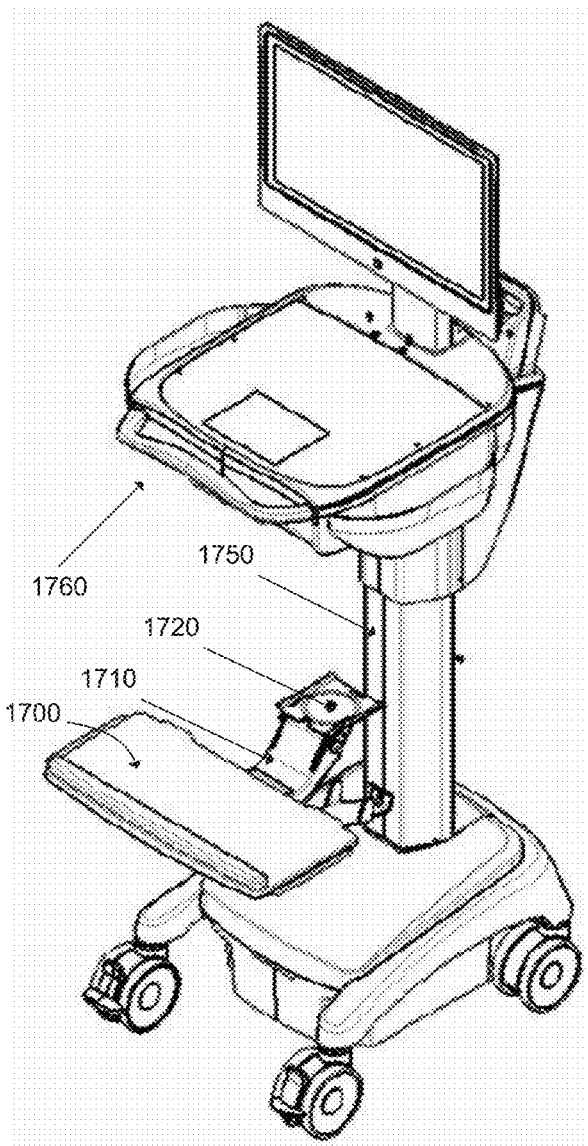
FIG. 17g depicts a perspective view of the second work platform attached to the first vertical support using the mounting bracket in accordance with an example.

FIGS. 17*f* and 17*g* illustrate that a second work platform 1700 can attach to a first vertical support 1750 of a smart medical cart 1760 using a mounting bracket 1720. FIG. 17*f* depicts a front view of the second work platform 1700 attaching to the first vertical support 1750 of the smart medical cart 1760. FIG. 17*g* shows a perspective view of the second work platform 1700 attaching to the first vertical support 1750 of the smart medical cart 1760 using the mounting bracket 1720. In one embodiment, the second work platform 1700 can be moved forward or backward on a horizontal plane parallel relative to the vertical support 1750 and relative to the front of the smart medical cart. In another embodiment, the location adjustment mechanism 1710 can adjust the horizontal distance and the height of the second work platform 1700 relative to the first vertical support.

Figure 18:
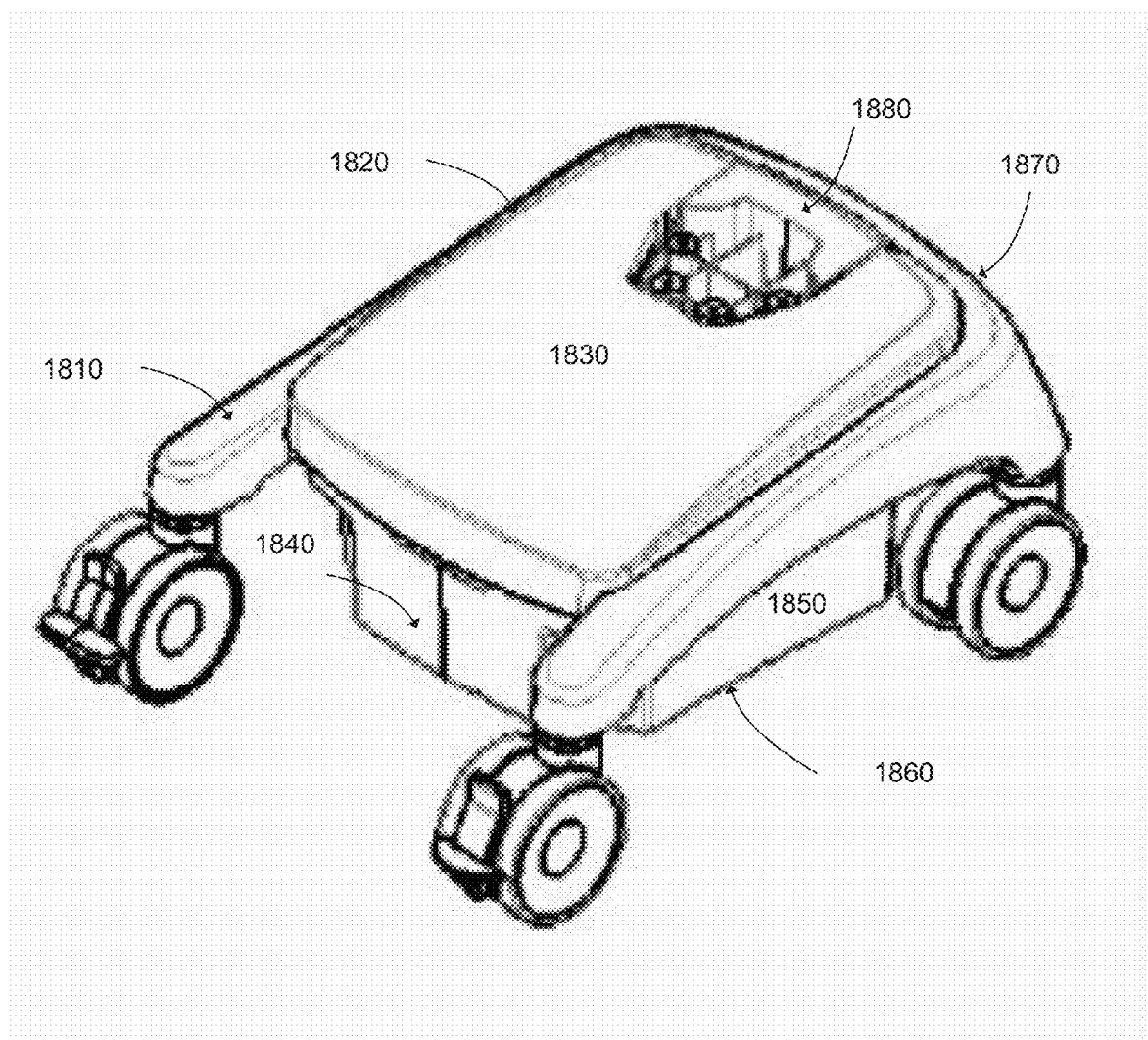
FIG. 18 depicts a perspective view of a covering of a smart medical cart in accordance with an example.

Returning back to FIG. 1, the smart medical cart 100 can include a covering 124 that can attach or connect to the wheeled pedestal 110. FIG. 18 further depicts a perspective view of the covering 1820 of the smart medical cart.

FIG. 18 depicts one exemplary embodiment where the covering 1820 can be assembled by connecting a front piece 1840, a back piece 1870, two side pieces 1850, a top piece 1830, and/or a bottom piece 1860 and can be mounted onto or around the wheeled pedestal 1810. In another embodiment, the cover 1820 can be a single molded covering. In one embodiment, the top piece 1830 of the covering 1820 can include a hole or opening 1880 to enable the first vertical support, as shown in FIG. 1, to pass all of the way through the hole or opening in order to attach to the wheeled pedestal 110. In another embodiment, the top piece 1830 of the covering 1820 can include a hole or opening 1880 to enable the first vertical support, as shown in FIG. 1, to partially pass through the hole or opening in order to attach to the covering 1820. The covering 1820 can form a shell or casing around the wheeled pedestal.

Figure 19A:
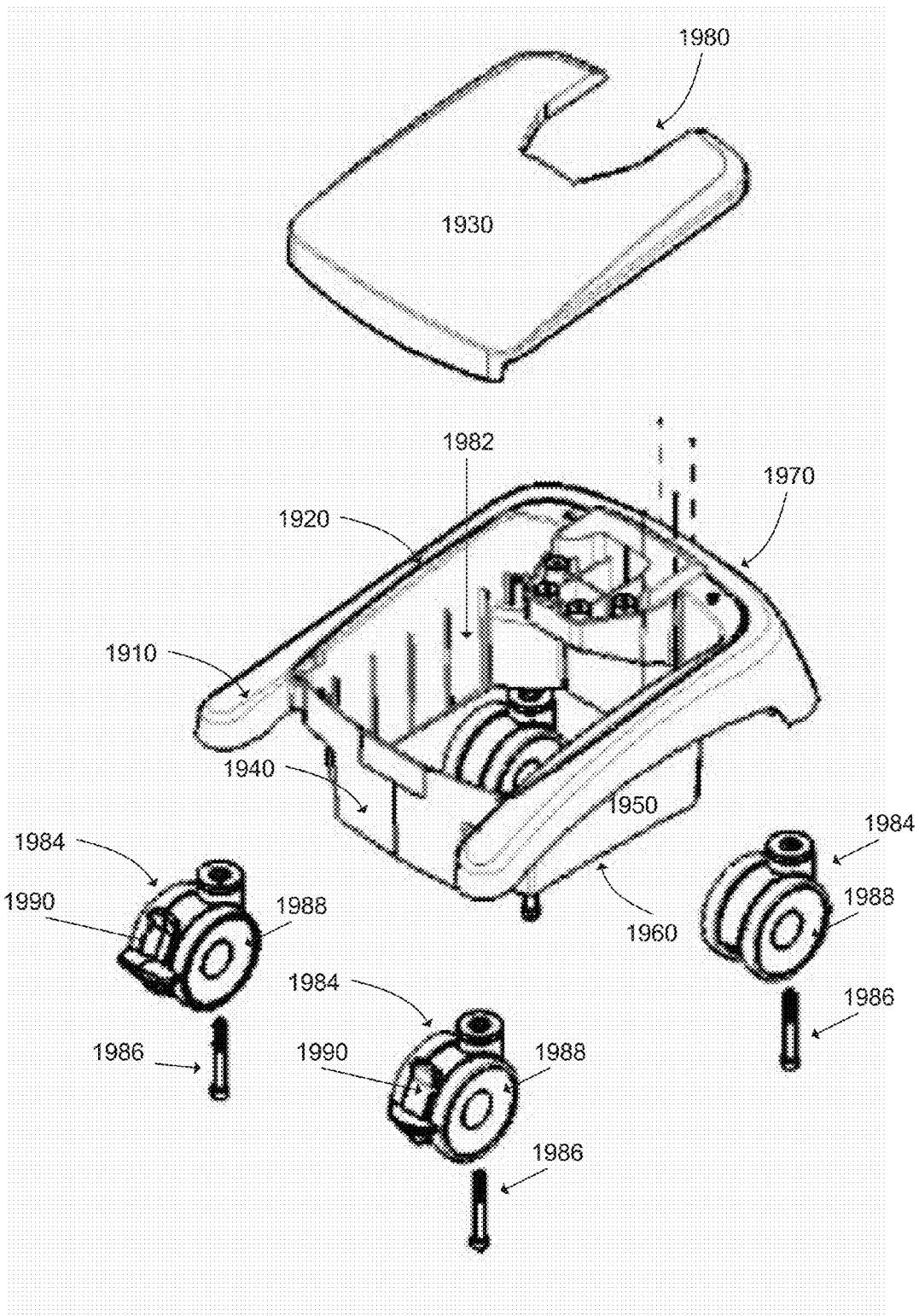
FIG. 19a depicts an exploded view of the covering in accordance with an example.

FIG. 19a depicts an exploded view of the covering 1920, as shown in FIG. 18. The structure of the covering 1920 and wheeled pedestal 1910 is substantially similar to the covering and wheeled pedestal in FIG. 18 and discussed in the preceding paragraphs. The covering 1920 can include an interior area or a storage area 1982. The storage area 1982 can be a hollow cavity and provide an area to store equipment or devices, such as a battery, computing device, power source, recharging module, etc. In one embodiment, the top 1930, the front 1940, the back 1970, the bottom 1960, and/or the side pieces 1950 can be removed or repositioned to enable access to the cavity of the storage area 1982 of the cover 1920. In one embodiment, the top 1930, the front 1940, the back 1970, the bottom 1960, and/or the side pieces 1950 can be hingedly connected to at least one other piece of the cover 1920. In another embodiment, the top 1930, the front 1940, the back 1970, the bottom 1960, and/or the side pieces 1950 can be connected to at least one other piece of the cover 1920 using sliding panels or rotating panels. In another embodiment, the top 1930, the front 1940, the back 1970, the bottom 1960, and/or the side pieces 1950 can be connected to at least one other piece of the cover 1920 using a quick connect fitting, a fastener, a magnet, screws, or another desired type of connecting device. In one embodiment, the wheeled pedestal 1910 and/or the vertical support can be die cast pieces and the cover 1920 can be a plastic covering that is formed around the die cast pieces.

In one embodiment, the storage area 1982 of the cover 1920 can be accessed from the top 1930, the front 1940, the back 1970, the bottom 1960, and/or the side pieces 1950 by moving, repositioning, or removing one or more of the cover pieces. In one embodiment, the storage area 1982 can be accessed to swap or change out a power supply such as a battery. One advantage of accessing the storage compartment from the top 1930, the front 1940, the back 1970, and/or the side pieces 1950, can be to swap out or change a power supply, such as a battery, located in the storage area while the cart can remain in the upright position. In one embodiment, a power source connection module can be installed at an opening or hole in one of the pieces of the covering. The power source connection module can be connected to an external power source, such as an alternative current (AC) outlet or other type of power source for recharging of the power source. For example, the AC outlet can be used to charge a rechargeable battery. Another advantage of accessing the storage compartment from the top 1930, the front 1940, the back 1970, and/or the side pieces 1950 can be to provide access to the cavity of the storage area 1982 without having to lay the smart medical cart on its side or turn the smart medical cart upside down to access the storage area 1982 from the bottom 1960 of the covering 1920 or the wheeled pedestal 1910. Accessing the storage compartment from the top 1930, the front 1940, the back 1970, and/or the side pieces 1950 can provide easier or more efficient access to the storage area 1982 in order to perform maintenance on the smart medical cart, clean the storage area 1982 or a power assist drive system, perform upgrades on parts or systems located in the storage area 1982, and so forth.

FIG. 19a, further illustrates that the wheeled pedestal 1910 of the smart medical cart, as shown in FIG. 1, can include a plurality of casters 1984 attached to the wheeled pedestal 1910. One or more wheels 1988 can be attached to each caster 1984. Each caster 1984 may be separated or spaced at selected distances from a center of the wheeled pedestal 1910 and/or from other casters 1984. The separation or spacing of the casters 1984 can be optimized to selected distances from the center of the wheeled pedestal 1910 and/or from other casters 1984 to provide a stable support for the smart medical cart and minimize an encroachment by the wheeled pedestal 1910 into work areas with limited space. The optimized separation or spacing of the casters 1984 can also enable movement of the smart medical cart in tight quarters or locations with multiple obstacles, such as a patient's room or a medical operating room.

FIG. 19a illustrates one embodiment of a wheeled pedestal 1910 with four casters 1984. A bottom side of the casters 1984 can be attached to wheels 1988 and the top side of the casters 1984 can be attached to the wheeled pedestal 1910. The four casters 1984 can be arranged in a square, a rectangle, or another desired configuration. In another embodiment, the wheeled pedestal 1910 can include a plurality of wheeled casters 1984, each caster having one or more attached wheels 1988. The plurality of casters 1984 can be arranged in a triangle configuration, a circular configuration, a star configuration, or another desired configuration. A desired configuration can be a configuration that enables the smart medical cart to be relatively stable and steady.

In one embodiment, the casters 1984 can each freely turn in any desired direction. In another embodiment, one or more casters 1984 can be locked in a desire direction using a locking mechanism 1990 to resist or stop the free turning of the wheel 1988 or the caster 1984. In one embodiment, the locking mechanism 1990 can be locked to stop the wheels 1988 from rotating or moving, e.g. a brake. In another embodiment, the wheels 1988 on the casters 1984 are relatively large and/or wide to enable the wheels to move across uneven floors, cracks, or holes. The wheeled pedestal 1910 can be easily maneuvered by a user and can remain relatively stable on a variety of types of floor surfaces.

Figure 19B:
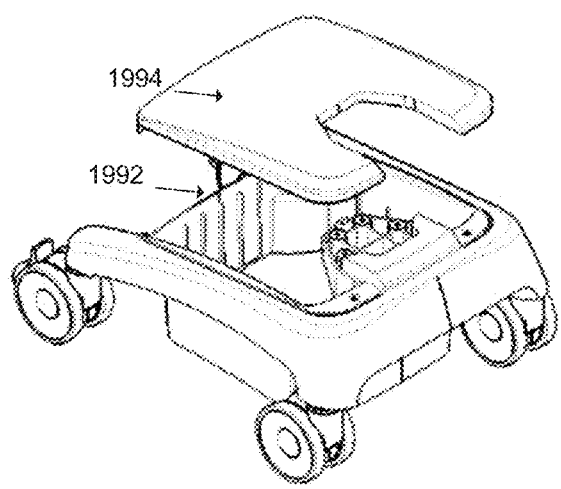
FIG. 19b shows a top perspective view of a top piece of a cover removed from a remaining portion of the cover in accordance with an example.
Figure 19C:
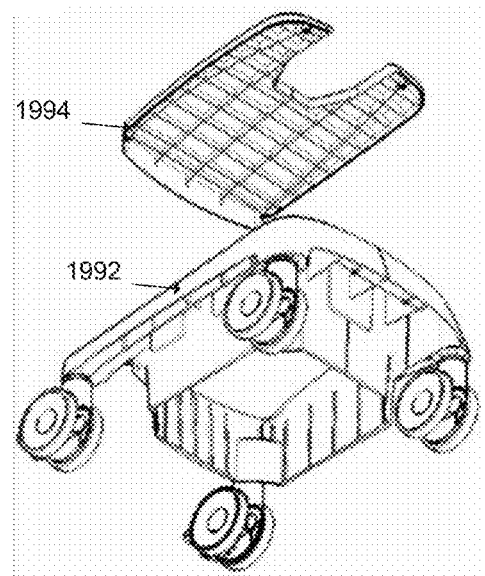
FIG. 19c shows a bottom perspective view of a top piece of a cover removed from a remaining portion of the cover in accordance with an example.
Figure 19D:
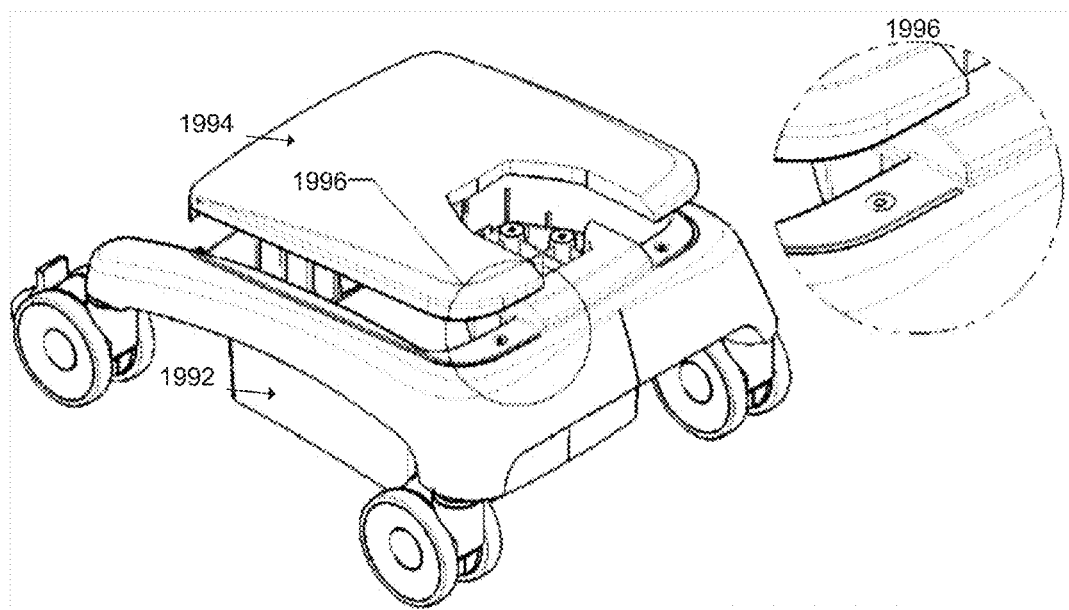
FIG. 19d shows a top piece being attached to the remaining portion of a covering in accordance with an example.

FIG. 19b shows one exemplary embodiment of a top perspective view of a top piece 1994 of the cover removed from a remaining portion of the cover 1992. FIG. 19c shows one exemplary embodiment bottom perspective view of a top piece 1994 of the cover removed from a remaining portion of the cover 1992. FIG. 19d shows one exemplary embodiment of a top piece 1994 being attached to the remaining portion of the covering 1992. In one embodiment, the top piece 1994 can be attached to the remaining portion of the covering 1992 using a snap connector or a quick connect fastener 1996. One of ordinary skill in the art would readily recognize that the top piece 1994 can be attached to the remaining portion of the covering 1992 using methodologies other than a snap connector or a quick connect fastener 1996.

Figure 20A:
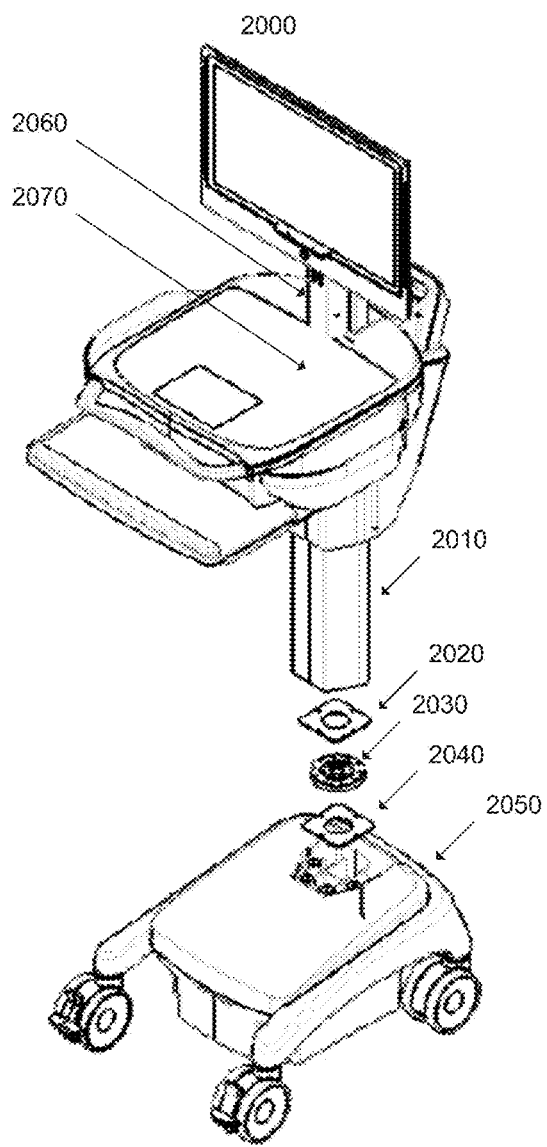
FIG. 20a shows a front perspective view of a smart medical cart in accordance with an example.
Figure 20B:
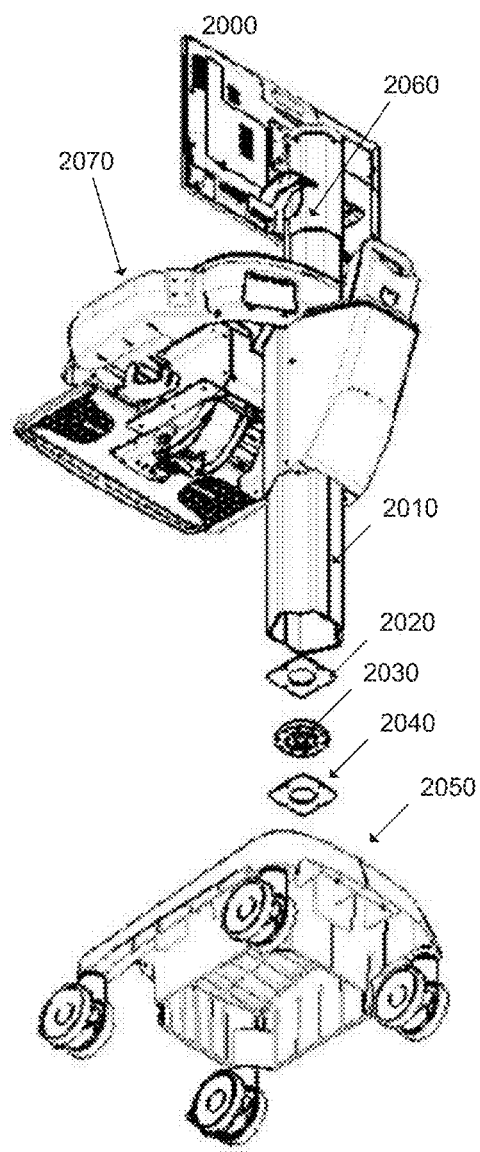
FIG. 20b shows a back perspective view of a smart medical cart in accordance with an example.

FIGS. 20a and 20b depict the wheeled pedestal 2050 can be attached to the first vertical support 2010 of the smart medical cart 2000, as shown in FIG. 1. FIG. 20a shows a front perspective view of the smart medical cart 2000. FIG. 20b shows a back perspective view of the smart medical cart 2000. The vertical support 2010 can be attached to the wheeled pedestal 2050 using one or more mounting brackets 2020 and 2040. In one embodiment, the top side of the mounting bracket 2020 or 2040 can be attached to the first vertical support 2010 and the bottom side of the mounting bracket can be attached to the wheeled pedestal 2050.

In another embodiment, the smart medical cart 2000 can swivel or pivot along a z axis. The smart medical cart 2000 can swivel or pivot along a z axis using rotating discs or plates 2030. In one embodiment, the first vertical support 2010 can be attached to a top side of the mounting bracket 2020. The bottom side of the mounting bracket 2020 can be attached to a top side of the rotating discs or plates 2030. The bottom side of the rotating discs or plates 2030 can be attached to a top side of another mounting plate 2040. A bottom side of the other mounting plate 2040 can be attached to a top side of the wheeled pedestal 2050. The first vertical support 2010, the mounting plates 2020 and 2040, rotating discs or plates 2030, and the wheeled pedestal 2050 can each be attached using a fastener, such as a bolt or a screw.

One advantage of the smart medical cart 2000 swiveling or rotating on the z axis is to enable an operator of the smart medical cart 2000 to rotate part of the smart medical cart 2000, such as the first work surface, second work surface, and/or display screen, while the wheeled pedestal remains stationary. The rotating of a part of the smart medical cart 2000 can enable the operator of the smart medical cart 2000 to more easily or efficiently use and/or maneuver the smart medical cart 2000 in areas that may be crowded or in tight quarter areas. In another embodiment, the second vertical support 2060 can attach to the first work platform 2070, as shown in FIGS. 16a and 16b, in using substantially the same structure of mounting brackets and rotating discs or plates as described in the preceding paragraph for the first vertical support 2010 attaching to the wheeled pedestal 2050.

Figure 21A:
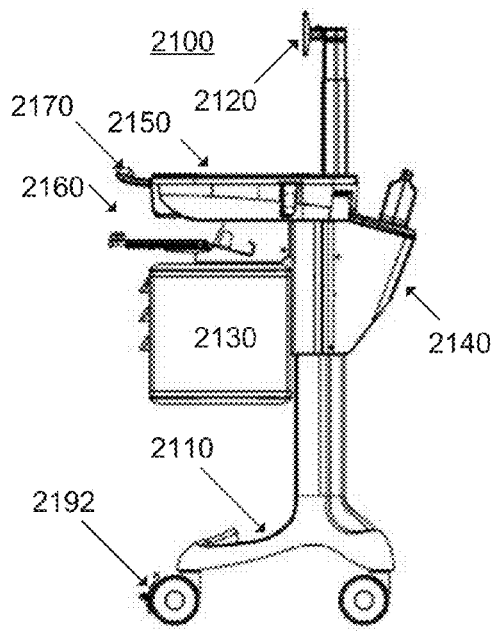
FIG. 21a shows a side view of a smart medical cart in accordance with an example.
Figure 21B:
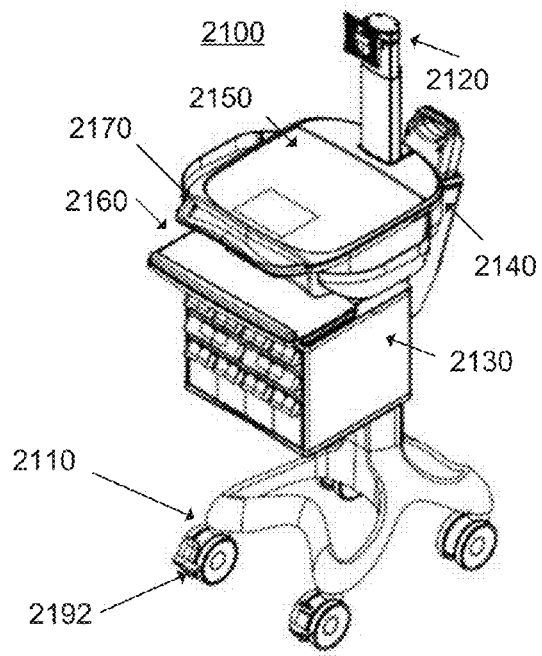
FIG. 21b shows a perspective view of a smart medical cart in accordance with an example.
Figure 21C:
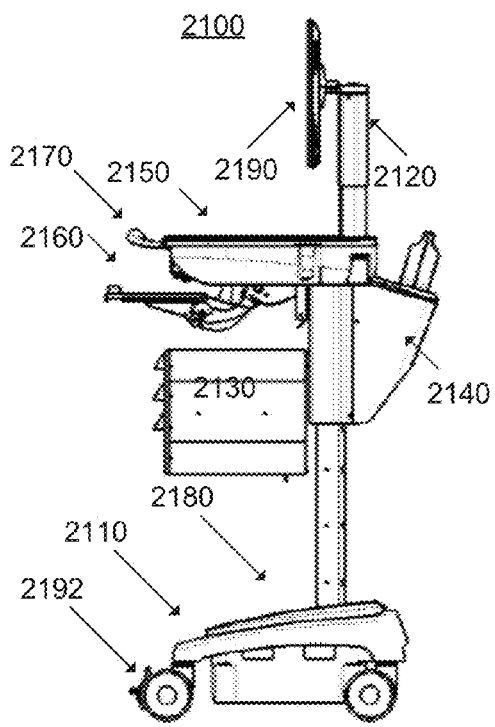
FIG. 21c shows a side view of a smart medical cart in accordance with an example.
Figure 21D:
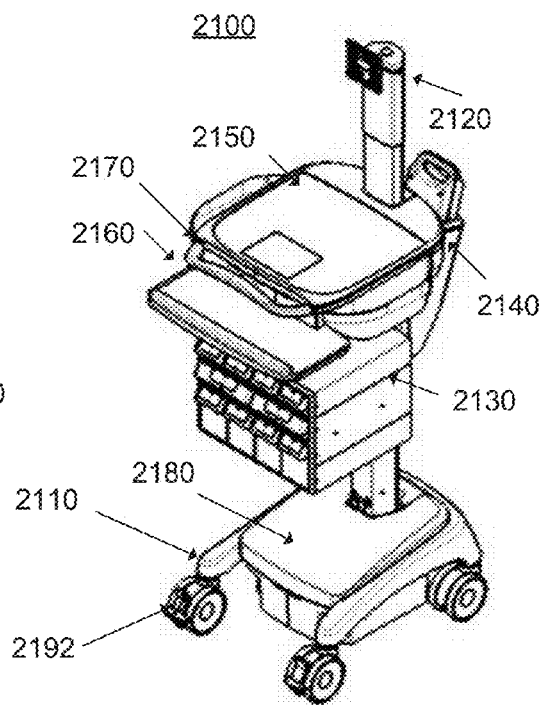
FIG. 21d shows a perspective view of a smart medical cart with a second vertical support without a computing device attached in accordance with an example.

In one embodiment, the smart medical cart can have multiple attachments, such as devices, equipment, systems, subsystems, modules, containers, power sources, and so forth that can be attached at various locations on the smart medical cart. Returning to FIG. 1, the multiple attachments on the smart medical cart 100 can include the computing device 122, an external battery 124, a medication storage container 126, a handle 128, and so forth. FIGS. 21a-21e illustrate the smart medical cart 2100 with different attachments and from different perspectives. FIG. 21a shows a side view of the smart medical cart 2100 with an open wheeled pedestal 2110, e.g. no covering, a second vertical support 2120 without a computing device attached, a larger medication storage container 2130, an external battery 2140, a first work platform 2150, a second work platform 2160, and a handle 2170. FIG. 21b shows a perspective view of the smart medical cart 2100 with substantially the same configuration and attachments as shown in FIG. 21a. FIG. 21c shows a side view the smart medical cart 2100 with a wheeled pedestal 2110, a covering 2180, a second vertical support 2120 with a computing device 2190 attached, and a smaller medication storage container 2130, an external battery 2140, a first work platform 2150, a second work platform 2160, and a handle 2170. FIG. 21d shows a perspective view of the smart medical cart 2100 with a second vertical support 2120 without a computing device attached. FIG. 21d shows the smart medical cart 2100 with substantially the same configuration and attachments as shown in FIG. 21c.

As the number of attachments connected to the smart medical cart 2100 increases, the mass and location of the attachments on the smart medical cart can affect the center of gravity of the cart. When the smart medical cart is maneuvered over uneven or slanted surfaces, the location of the center of gravity can cause the smart medical cart to become unstable or tip over. In one embodiment, to compensate for various different centers of gravity, depending on the attachments and locations of the attachments the wheeled pedestal 2110 and/or the covering 2180 can be configured to be relatively heavy. In addition, one or more casters 2192 attached to the wheeled pedestal 2110 can be spaced to compensate for the various centers of gravity of the cart. In one embodiment, the smart medical cart can be adapted or adjusted to lower the center of gravity for the smart medical cart. One advantage of a lower center of gravity is to enhance the stability of the cart and reduce the likelihood of the cart tipping over. Additional detail regarding adapting or adjusted the center of gravity of the smart medical cart is provided in the proceeding paragraphs.

Returning to FIG. 1, in one embodiment, the computing device 122, such as a display screen, can be a heads-up display (HUD). A HUD can be a transparent display that presents data without requiring a user to look away from their usual viewpoints. In another embodiment, the computing device 122 can be positioned in a plane that is substantially parallel or horizontal relative to the first work platform 114. In another embodiment, the computing device 122 can be embedded in the first work platform 114 to minimize the ability of others to view data shown on the display. The computing device 122 can be attached to the first vertical support 112, wheeled pedestal 110, the first work platform 114, the second work platform 118, a second vertical support 120, or at other desirable locations. In on embodiment, the computing device can be contained in the storage area or cavity of a cover 124 of the wheeled pedestal 110.

The smart medical cart 100 can include a medication storage container 126. In one embodiment, the medication storage container 126 can be attached to the first vertical support 112 of the smart medical cart 100. In another embodiment, the medication storage container 126 can be attached to the first work platform 114, the second work platform 118, or the wheeled pedestal 110 of the smart medical cart 100. In one embodiment, the medication storage container 126 can include compartments or drawers 130 used to store medication, medical supplies, medical devices, medical instrumentation, etc.

Figure 22A:
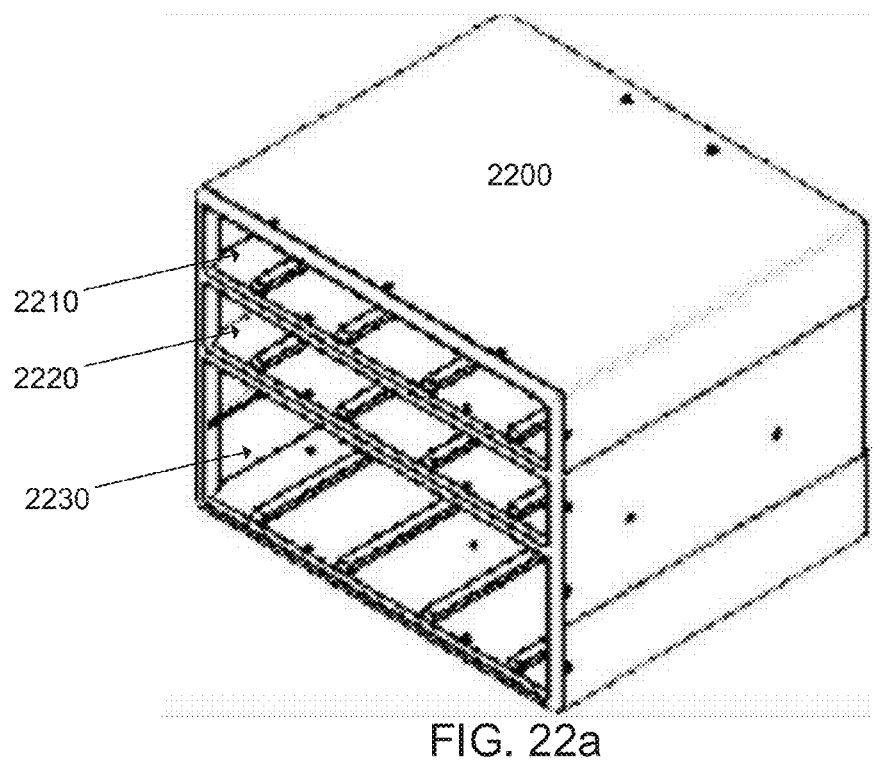
FIG. 22a shows a perspective view of a medication storage container in accordance with an example.
Figure 22B:
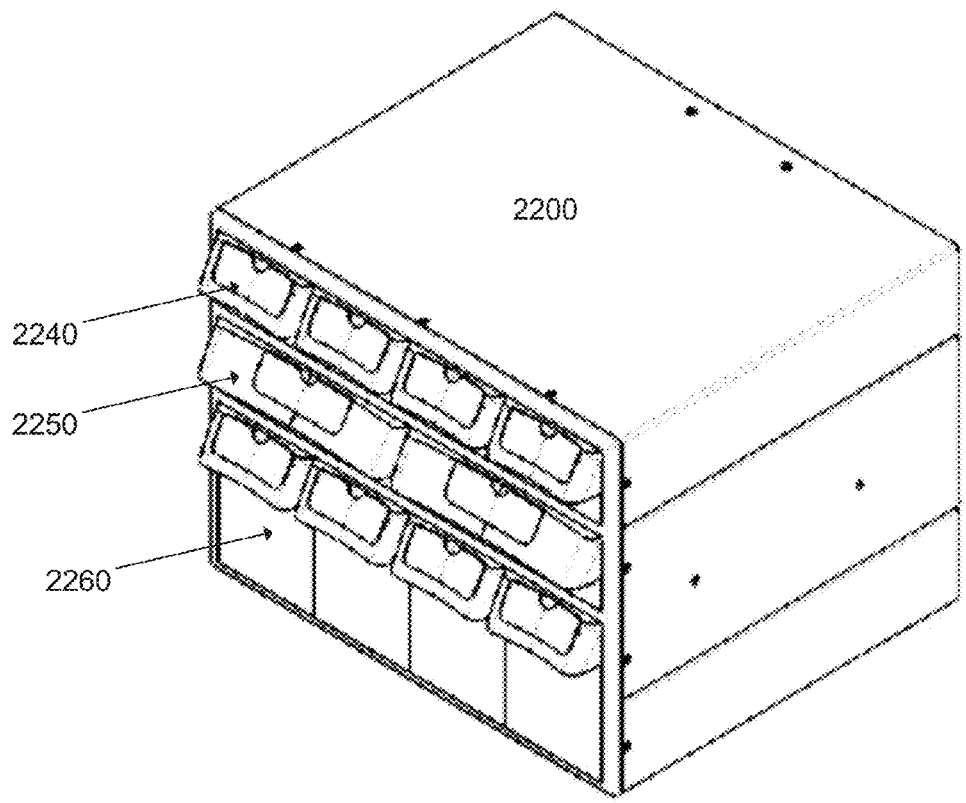
FIG. 22b shows a perspective view of a medication storage container with medication drawer in accordance with an example.

FIGS. 22a and 22b show an exemplary embodiment of the medication storage container 2200, as show in FIG. 1. FIG. 22a shows a perspective view of the medication storage container 2200 with slots or channels 2210-2230 to receive medication drawers. In one embodiment, the slots or channels 2210-2230 can receive medication drawers of various sizes. For example, channel 2210 can receive a small drawer, channel 2220 can receive a horizontally long drawer, and channel 2210 can receive a vertically long drawer.

FIG. 22b shows a perspective view of the medication storage container 2200 with medication drawers 2240-2260 attached to the medication storage container 2200, such as by attaching in medication drawers 2240-2260 to the medication storage container 2200 using the slots or channels 2210-2230 of FIG. 22a. FIG. 22b shows that the medication drawers 2240-2260 can be of various sizes and shapes, wherein medication drawer 2240 is a small drawer, medication drawer 2250 is a horizontally long drawer, and medication drawer 2260 is a vertically long drawer. In one embodiment the medication drawers 2240-2260 can be categorized to receive different types or amounts of medication. For example, medication drawer 2240 can be categorized to contain narcotics or restricted medications, medication drawer 2250 can be categorized to contain antibiotics, and medication drawer 2260 can be categorized to contain medical supplies and/or devices. In one embodiment, an operator of the smart medical cart can be restricted to have access to selected medication drawers. For example, the operator of the smart medical cart can be restricted to accessing antibiotics drawer 2250 and medical supplies and/or devices 2260 and prohibited from accessing narcotics medication drawer 2240.

Figure 23A:
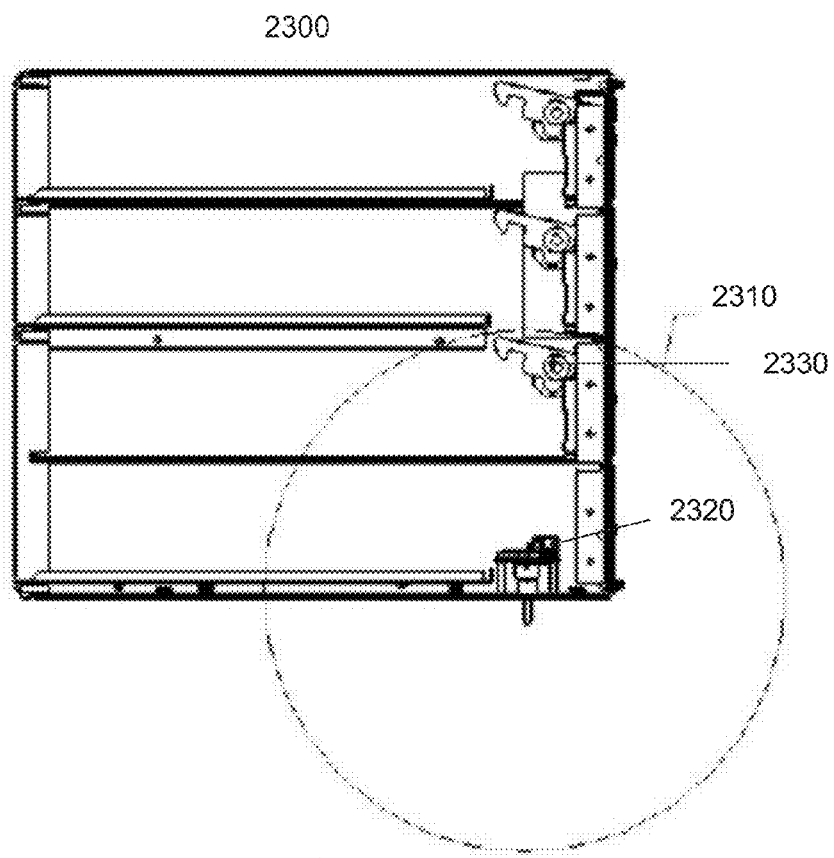
FIG. 23a shows a side view of a medication storage container in accordance with an example.
Figure 23B:
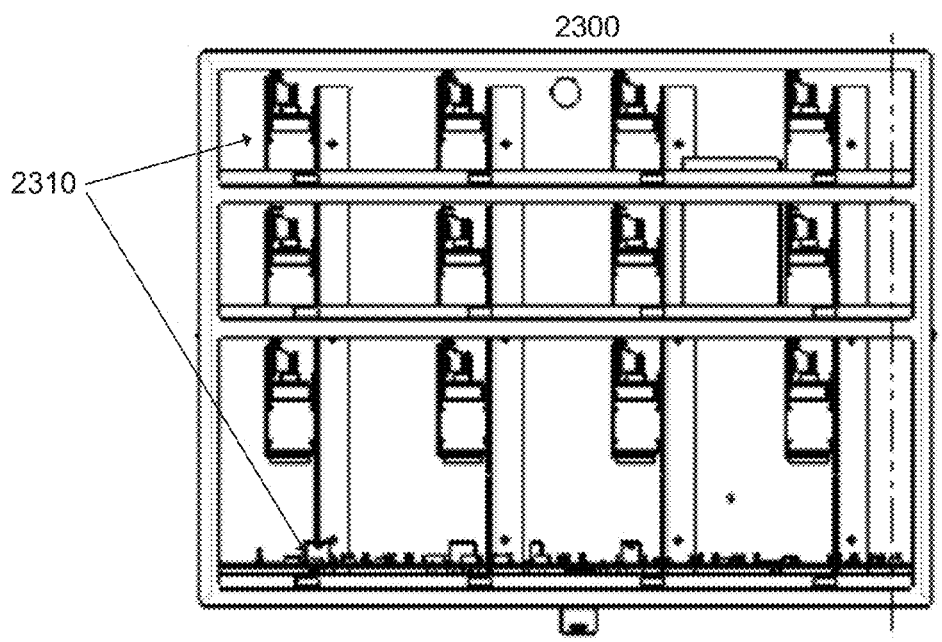
FIG. 23b shows a front view of the medication storage container with a locking mechanism in accordance with an example.

FIG. 23a shows a side view of a medication storage container 2300, as shown in FIGS. 22a and 22b, that includes a locking mechanism 2310 to secure one or more medication drawers. In one embodiment, the locking mechanism 2310 of the medication storage container 2300 can be a solenoid locking mechanism. The solenoid locking mechanism can include an electronic solenoid 2320 and a latch or bolt 2330. When the electronic solenoid 2320 is activated to enter a locking mode, the electronic solenoid 2320 can activate or actuate solenoid to throw the bolt or latch 2330 to lock or close medication drawers of the medication storage container 2300. When the electronic solenoid 2320 is activated to enter an unlocking mode, the electronic solenoid 2320 can activate or actuate solenoid and unlock or release the bolt or latch 2330 to enable one or more medication drawers of the medication storage container 2300 to be opened. In one embodiment, the locking mechanism 2310 can lock one or more medication drawers while unlocking one or more other medication drawers. FIG. 23b shows a front view of the medication storage container 2300 with the locking mechanism 2310.

Figure 23C:
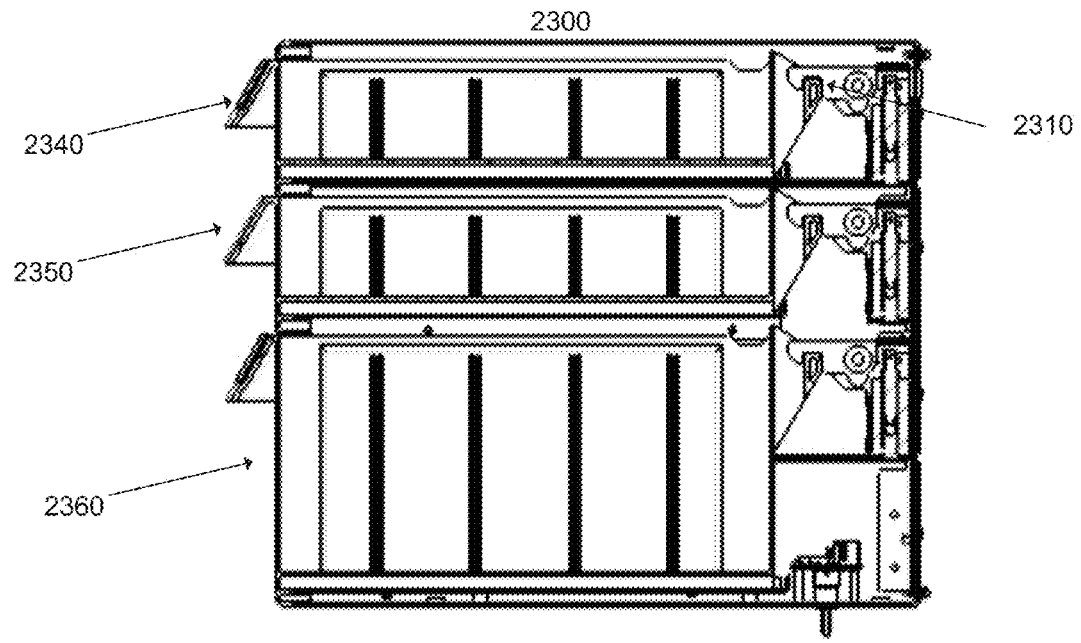
FIG. 23c depicts a locking mechanism of a medication storage container in a locked position in accordance with an example.
Figure 23D:
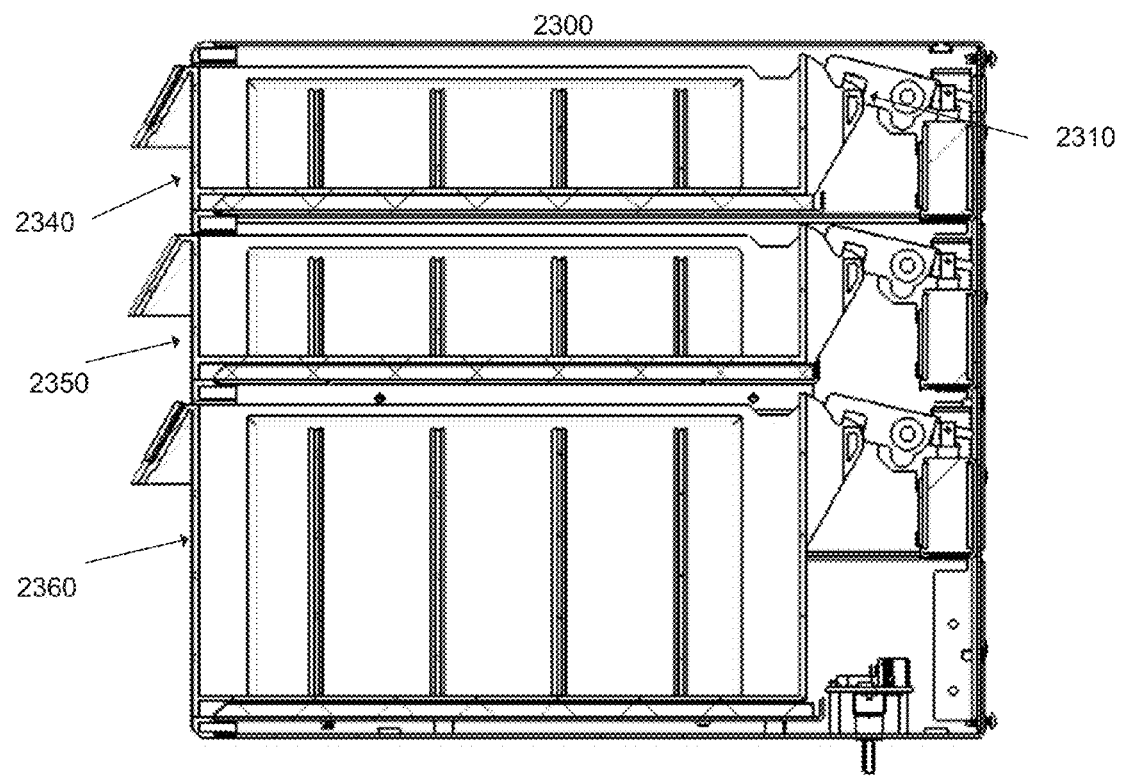
FIG. 23d depicts a locking mechanism of a medication storage container in an unlocked position in accordance with an example.

FIG. 23c depicts the locking mechanism 2310 of the medication storage container 2300 in a locked position, where the medication drawers 2340-2360 are secured in the closed position. FIG. 23d depicts the locking mechanism 2310 of the medication storage container 2300 in an unlocked position, where the medication drawers 2340-2360 are not secured in the closed position and can be accessed or opened.

Returning to FIG. 1, in one embodiment, the smart medical cart can include a power source 124, such as a power source separate from the smart medical cart, an attached external power source, and/or an integrated power source. In one embodiment, the power source 124 can be a battery that can be attached to the wheeled pedestal 110, storage area of the covering 124, the first vertical support 112, the first work platform 114, the second work platform 118, the medication storage container 126, the second vertical support 124, and/or another desired location on the smart medical cart. The power source 124 can provide power to a display screen, a computing device, medical equipment, peripherals, and other electronic equipment on the smart medical cart 100 for a predetermined period of time. In one embodiment, the integrated power source can be integrated in to the wheeled pedestal 110, storage area of the covering 124, the first vertical support 112, the first work platform 114, the second work platform 118, the medication storage container 126, the second vertical support 124, and/or another desired location on the smart medical cart.

Figure 24A:
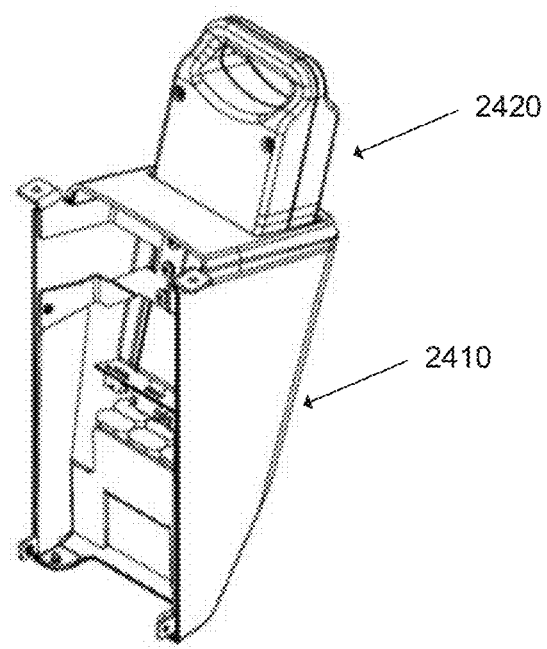
FIG. 24a shows a power source and a power source receptacle structure in accordance with an example.
Figure 24B:
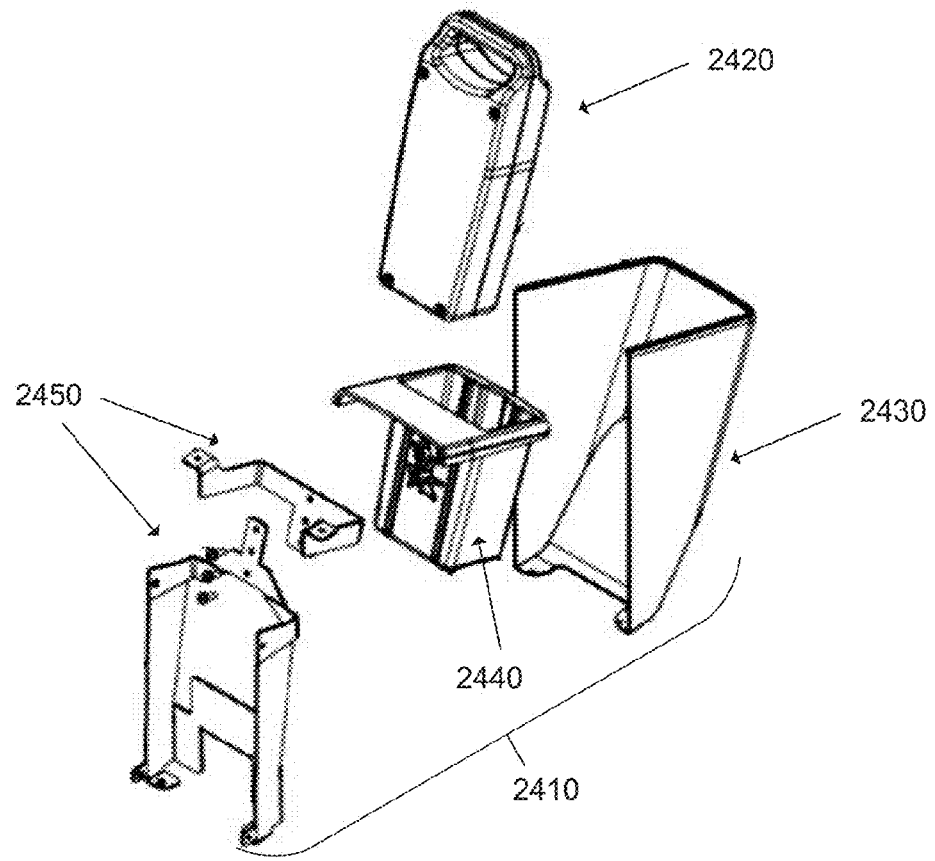
FIG. 24b illustrates an exploded view of the power source receptacle structure in accordance with an example.

FIGS. 24a and 24b show perspective views of a power source receptacle structure 2410 to attach the power source, as in FIG. 1, to a selected location on the smart medical cart. FIG. 24a shows that a power source 2420 can be attached or partially located in the power source receptacle structure 2410. FIG. 24b illustrates an exploded view of the power source receptacle structure 2410. The power source receptacle structure 2410 can include a covering 2430, a power source receptacle 2440, and a mounting bracket structure 2450. The power source receptacle 2440 can receive the power source 2420 at the power source receptacle 2440. The mounting bracket structure 2450 can be used to attach the power source receptacle structure 2410 to the smart medical cart, as in FIG. 1. The mounting bracket structure 2450 can be attached to the smart medical cart using a fastener, such as a bolt or a snap. In one embodiment the power source receptacle structure 2410 can include electrical connections between the power source 2420 and the smart medical cart to transfer power between the power source 2420 and the smart medical cart.

In one embodiment, the power source receptacle structure 2410 can be attached to the vertical support 120 and/or the work surface 130, as in FIG. 1. In another embodiment, the power source 2420 can include one or more removable or interchangeable external batteries. FIGS. 24a and 24b show an exemplary embodiment of a power source 2420 that can be removable, such as a removable rechargeable battery. In another embodiment, other types of removable power source can be used, such as a fuel cell. The power source 2420 can be configured to operate with an integrated power source to power the electronic devices on the cart. This will be discussed more fully in the proceeding paragraphs.

Figure 25:
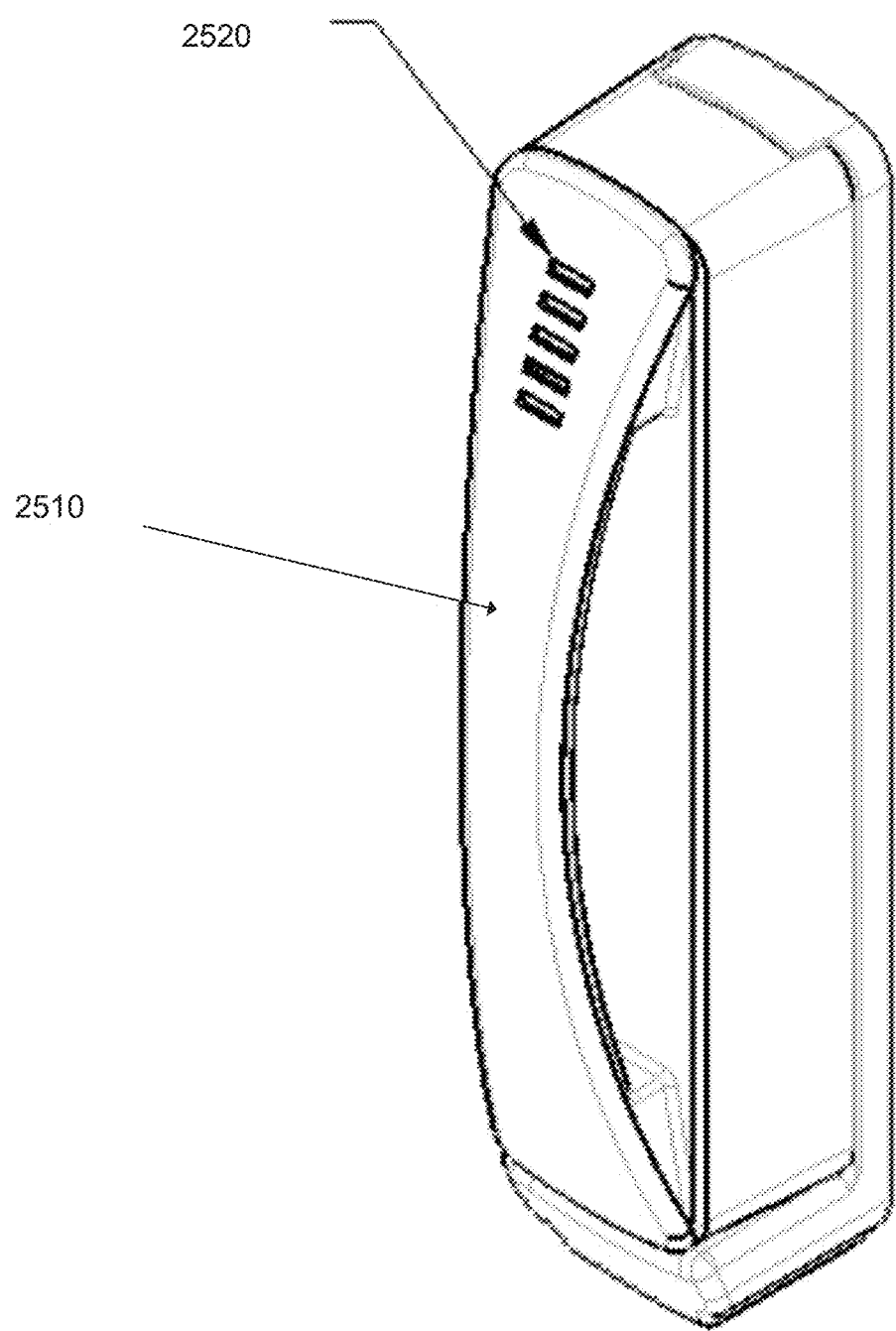
FIG. 25 shows a battery handle with a power level indicator in accordance with an example.

One or more of the external batteries can include a handle attached to the external battery or an external casing of the external battery. FIG. 25 shows that in one exemplary embodiment the battery handle 2510 can include a power level indicator 2520 to indicate the power level of the external battery the handle is attached to. The power level indicator 2520 can indicate the power level of the external battery in selected increments, such as 5 percent power level increments. In one embodiment, the power level indicator 2520 can include light emitting diodes (LEDs) that can be integrated into the battery handle 2510 to indicate the power level of the external battery. For example, the power level indicator 2520 can have 20 LEDs integrated into the handle 2520 of each external battery that can provide 5 percent power level increment indicators. When the external battery is at a full power level, the 20 LEDs integrated into the power level indicator 2520 of the battery handle 2510 can each be illuminated. As the power level of the external battery decreases, the 20 LEDs integrated into the power level indicator 2520 will sequentially stop illuminating in 5 percent increments.

Figure 26:
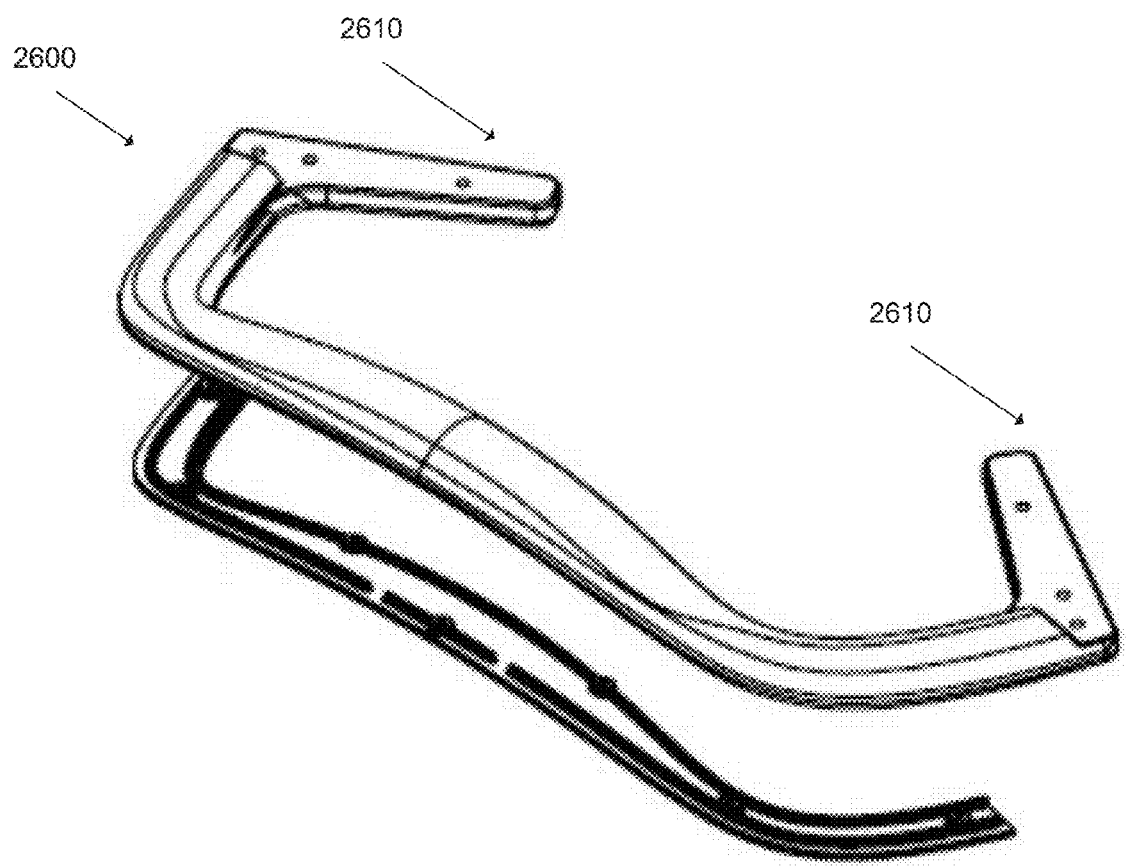
FIG. 26 illustrates a handle that can attach to the smart medical cart in accordance with an example.

One attachment of the smart medical cart, as in FIG. 1, can be a handle to steer or control the smart medical cart. FIG. 26 illustrates a handle 2600 that can attach to the smart medical cart. The handle 2600 can be connected to the first work platform, the second work platform, or the vertical support. In one embodiment, the handle can be configured to wrap around a front of the first work platform, as shown in FIG. 1. Each handle end 2610 of the handle 2600 can attach at approximately each end of the front of the first work platform or the second work platform to enable the user to hold on to the smart medical cart and/or move the smart medical cart.

In one example embodiment, a user, such as a doctor or nurse, can use the smart medical cart to input medical information into the hospital record system, update the status of the patient, or record medication prescribed to the patient. In one embodiment, the smart medical cart can have medical equipment and/or medical supplies which are integrated into or attached to the smart medical cart. A caregiver can use the equipment or supplies in connection with monitoring, screening, diagnosing, and/or treating a patient. For example, the cart may be used for monitoring the vital signs of a patient.

The information or measurements obtained using the equipment or supplies can be stored or processed by the computing device and/or displayed on the computing device or display screen of the smart medical cart to the caregiver or a third party for analysis. In one embodiment, the obtained information or measurements can be communicated from the computing device to another smart medical cart, another computer device, and/or a computer server for storage or analysis. The information can be communicated using, for example, a non-transitory computer readable medium (such as a USB memory stick), a wired communication, and/or a wireless communication, as previously discussed.

One of the difficulties faced by many caregivers is maneuvering medical carts. As additional devices and increased functionalities can be added to medical carts, such as medical equipment, instrumentation, computing devices, medication drawers, and monitoring devices, the weight and/or size the medical cart can increase. Medical carts are often used in areas that have limited room to maneuver the medical cart. For example, when a medical cart is used in a patient's room, the room may include multiple patient beds, furniture, medical equipment, medical supplies, caregivers, visiting family members, and other types of obstacles. In addition to the tight quarters, the increased weight and/or size of the medical cart can further increase the difficulty of maneuvering the potentially heavy medical cart. In one embodiment of the smart medical cart, to assist a caregiver in maneuvering the smart medical cart, a power system and a power-assisted drive system may be used.

The smart medical cart can include a power system to provide power to the systems and subsystems of the smart medical cart. The power system can include a power management module to direct power to systems and subsystems of the smart medical cart. The power system can include a power source to provide power to a power management module, as discussed in proceeding paragraphs. In one embodiment, the power source can be an alternating current (AC) power source, such as a wall power outlet. In another embodiment, the power source can be a mobile power source, such as a battery.

The mobile power source can be integrated into the smart medical cart, such as an integrated battery, and/or external to the smart medical cart, such as an attached external battery than can be removed and/or replaced. In one embodiment, the mobile power source can include a combination of batteries, such as one or more internal batteries and one or more external batteries. In one embodiment, the mobile power source can include one internal backup battery, a first external battery, and a second external battery. The first external battery and the second external battery can be configured to provide power to the power management module in sequence, such as first providing power from the first external battery and then providing power from the second external battery.

The power management module can switch between a plurality of power sources to provide power to the electrical systems and subsystems of the smart medical cart. A switch to a different power source can occur at a selected time, or based on a current level or voltage level of a power source, such as when the power from a selected power source decreases below a defined power threshold. For example, the power management module can initially receive power from the first external battery. When a power level of the first external battery decreases below a selected power threshold, the power management module can switch to receiving power from the second external battery. In one embodiment, when a power level of the second external battery decreases below a selected threshold, the power management module can receive power from both the first external battery and the second external battery simultaneously. When the power level of the first external battery and the second external battery in combination decreases below a selected threshold, the power management module can switch to using the internal backup battery. Alternatively, the power management module can be configured to switch connections with the power sources to enable the first external battery, second external battery, and internal battery to be used in series to provide a maximum amount of current to the electrical systems on the smart medical cart until a power source is replaced with a recharged battery or a different source of power.

Figure 27:
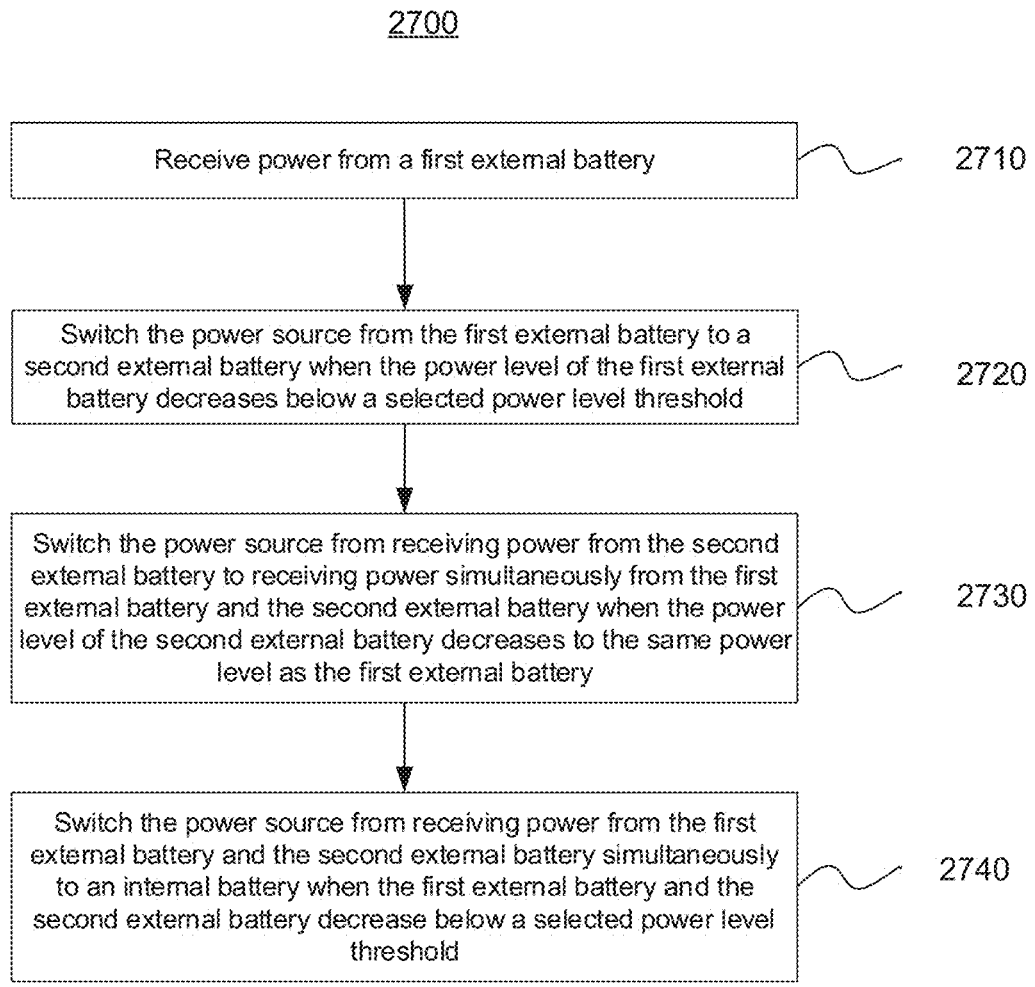
FIG. 27 depicts the functionality of computer circuitry of a power management module operable to receive power from a power source for a smart medical cart in accordance with an example.

FIG. 27 provides a flow chart 2700 to illustrate the functionality of one embodiment of a power management module with computer circuitry operable to receive power from a power source for a smart medical cart. The functionality can be implemented as a method or the functionality can be executed as instructions on a machine, where the instructions are included on at least one computer readable medium or one non-transitory machine readable storage medium. The computer circuitry can be configured to receive power from a first external battery, as in block 2710. The computer circuitry can be further configured to switch the power source from the first external battery to a second external battery when the power level of the first external battery decreases below a selected power level threshold, as in block 2720. The computer circuitry can also be configured to switch the power source from receiving power from the second external battery to receiving power simultaneously from the first external battery and the second external battery when the power level of the second external battery decreases to the same power level as the first external battery, as in block 2730. The computer circuitry can also be configured to switch the power source from receiving power from the first external battery and the second external battery simultaneously to an internal battery of the smart medical cart when the first external battery and the second external battery decrease below a selected power level threshold, as in block 2740.

One advantage of the power management module receiving power from the first external battery and the second external battery in sequence is to enable the first external battery to be switched out while the second external battery provides power to the power management module. Another advantage of the power management module receiving power from the first external battery and the second external battery simultaneously, when the power level of the first external battery and the second external battery each decrease below a selected threshold, can be an increased amount of voltage or current power to the power management module for an extended period.

When the power level of the first external battery or the second external battery individually decrease below a select level, the voltage can be too low or insufficient to power the power management module and/or the electrical systems of the smart medical cart 100. By receiving power from the first external battery and the second external battery in combination the voltage level of the combination of the first external battery and the second external battery connected in series can be sufficient to provide power to the power management module and electrical systems for an additional period of time, e.g. until the power level of the first external battery and the second external battery in combination decreases below a selected threshold.

In one embodiment, when the power management module receives power from the first external battery and the second external battery simultaneously, the first external battery and the second external battery can each be at substantially the same power level. This can be accomplished by configuring the power management module to use the first and/or second external batteries until they are both at substantially the same voltage level. The first external battery and the second external battery can each be at the same power level to provide a consistent voltage level during the period that the power management module receives power from the first external battery and the second external battery simultaneously. One advantage of the first external battery and the second external battery each being at substantially the same power level is that a constant or consistent voltage level can be maintained during the period that the first external battery and the second external battery simultaneously provide power to the power management module.

The external battery and/or internal batteries can each provide power at a selected voltage, such as 24 volts for each battery. In one embodiment, the selected voltage provided by the external batteries and the selected voltage provided by the internal batteries can be different. For example, the first external battery and the second external battery can be 24 volt batteries and the internal backup battery can be a 12 volt battery. Alternatively, each of the batteries can be configured to operate at substantially the same voltage level. The voltage of the internal batteries and/or external batteries can be selected to optimize the power provided by the batteries, the size of the batteries, the form or shape of the batteries, the capacity of the batteries, and so forth.

In one embodiment, the power management module can enable an administrative user to lock in the voltages or voltage operational ranges for selected devices, systems, and/or subsystems. In one embodiment, the power management module can include an isolation transformer to reduce or eliminate the power from one device, system, and/or subsystem of the smart medical cart interfering with other devices, systems, and/or subsystems of the smart medical device and/or other adjacent medical devices or equipment. The power management module can include a load protection module to protect against electrical shorts. In one embodiment, the power management module can automatically change voltages provided to selected systems and subsystems. The voltage changes can occur without having to shut down the power management subsystem or other selected electrical systems and subsystems. The power management module can connect the plurality of power sources to the electrical systems and subsystems using one or more direct current (DC) to DC converters to enable the selected power sources to provide power at a desired voltage level to each electrical component on the smart medical cart.

When the smart medical cart switches from receiving power from the first external battery and the second external battery to the internal backup battery, the smart medical cart can be configured to reduce the power provided to selected systems and/or subsystems. For example, the computing device or power management module of the smart medical cart can monitor the power level and/or when the first external battery and the second external battery or the internal backup battery supply power to selected systems and/or subsystems, such as by using a computer software application or a separate device in communication with the computing device to indicate the power level indication or indicate a source of the power. When the computing device receives a selected power level indication or indication of a switching of the power source, the computing device and/or power management module can send signals to selected systems, subsystems, modules, or components of the smart medical cart instructing them to shut down or reduce their power consumption.

The selected systems and subsystems that are selected to continue to receive power while the power management module uses the internal backup battery can be critical or essential devices, systems, and/or subsystems of the smart medical cart. In one example, the critical or essential devices, systems, and/or subsystems of the smart medical cart can include a computing device, a medical device, a display screen, a communication system, and so forth. For example, the computing device can continue to receive power from the power management module during the period that the power management module is using the internal backup battery while the other systems and subsystems of the smart medical cart can receive reduced power or no power until a new or recharged power source is provided.

In one embodiment, the power source of the smart medical cart can be removable and rechargeable using an external device, such as a battery recharger. In another embodiment, the power management module can include a recharging module to receive power from an alternating current (AC) power source, such as a wall power outlet, and recharge the first external battery, the second external battery, and/or the internal backup battery. In another embodiment, the recharging module can receive power from a wireless power source. The wireless power source can be a resonance wireless power source and/or induction wireless power source and can be configured to wirelessly recharge the external batteries and/or the internal battery(ies) of the smart medical cart.

In one embodiment, the power management module can indicate the amount of power that the smart medical cart is receiving from a wireless power source. The recharging module can recharge the external batteries and/or internal batteries of the smart medical cart to a selected power level. In one embodiment, the recharging module can recharge the external batteries and/or internal batteries of the smart medical cart to a 90 percent power level. One advantage of charging the external batteries and/or internal batteries of the smart medical cart to a 90 percent power level is to extend the battery life of the batteries.

The power management module can adjust or change the cycle period of the external batteries and/or internal batteries of the smart medical cart to maintain optimal battery performance, battery health, and/or battery life. For example, the first external battery, the second external battery, and/or the internal battery can include one or more power cells. In this example, each of the one or more power cells can provide a maximum voltage, such as 4.2 volts. The power management module can adjust the cycle period of the first external battery, the second external battery, and/or the internal backup battery so that each cell of the batteries provides power at a voltage level below the maximum voltage, such as 4.1 volts. One advantage of adjusting the cycle period of each battery or one or more cells of each battery is to extend the life of each battery. The example voltage is not intended to be limiting. The voltage range of each cell can be selected to provide a desired maximum voltage level and a predetermined number of watt hours. The actual voltage of each cell may range from millivolts to tens or hundreds of volts, depending on the type of device the battery will operate.

In one embodiment, the power management module can use a buck boost converter to regulate the power received from the external batteries and/or internal batteries of the smart medical cart. A buck boost converter is a DC-to-DC converter that can step-up the voltage provided from the batteries of the power management module, e.g. boost the voltage, or step-down the voltage provided from the batteries of the power management module, e.g. buck the voltage. The buck-boost converter can regulate the voltage provided to the devices, systems, and/or subsystems of the smart medical cart at a selected voltage level to enable each device, system, or subsystem of the smart medical cart to receive an optimal voltage for operating the device, system, or subsystem.

In another embodiment, the power management module can use a Ćuk converter, such as an isolated Ćuk converter. A Ćuk converter is a DC-DC converter that has an output voltage magnitude that can be adjusted to be greater than or less than the input voltage magnitude. In one embodiment, the Ćuk converter can have a hysteric voltage mode control. One advantage of using a Ćuk converter with a hysteric voltage mode control can be to have continuous current at both the input and the output of the Ćuk converter.

The smart medical cart can include an external battery receptacle to receive and/or hold each external battery, as discussed in the preceding paragraphs. The external battery receptacle can include a receptacle locking subsystem to lock each external battery into place after the external battery has been placed into the external battery receptacle. The receptacle locking subsystem and/or the power management subsystem can provide an indication to the caregiver showing which power source the smart medical cart is using to power the systems and/or subsystems of the smart medical cart. In one embodiment, the receptacle locking subsystem can be a latch, clasp, clip, or other locking mechanism that secures one or more of the external batteries into position. In one embodiment, the locking mechanism of the receptacle locking subsystem can be electronically released or disengaged, such as by entering a security code into a touch pad or computing device to disengage the locking mechanism. In another embodiment, the locking mechanism of the receptacle locking subsystem can be mechanically or manually released or disengaged, such as by using a key to disengage the locking mechanism.

In one embodiment, when the smart medical cart is using an external battery as the power source for the smart medical cart, the receptacle locking subsystem cannot be disengaged. In another embodiment, when the smart medical cart is using an external battery as the power source for the smart medical cart, the smart medical cart can provide an indication to the caregiver that the smart medical cart is using the external battery as the power source for the smart medical cart, before the caregiver removes the external battery. In another embodiment, when the smart medical cart is using an external battery as the power source for the smart medical cart, the receptacle locking subsystem can switch to receiving power from another power source, such as another external battery, before allowing the caregiver to remove the external battery. In another embodiment, when the smart medical cart is using an external battery as the power source for the smart medical cart, the power management module can automatically switch to another power source when the external battery currently powering the smart medical cart is removed. The power management module can have a buffer power subsystem that can store and/or provide temporary power to the devices, systems, and/or subsystem of the smart medical cart when a power source is removed and/or the power management module switches to another power source.

The power management system can provide power information to the smart medical cart. The power information can include a power management system temperature, power management efficiency, battery temperature, battery voltage, battery capacity, battery health, and so forth. In one embodiment, the power management system can include an indicator showing which of the systems and/or subsystems of the smart medical cart are receiving power. The power information can be accessed at the smart medical cart via one or more computing devices. For example, the power information may be accessed via a tablet computing device. The information can be used by a user to determine when a battery is operating properly and when it may need to be replaced. The power information can also be communicated from the computing device to an external location, such as a central computer or server to enable the power information of a plurality of carts to be accessed remotely. The ability to remotely access the power information enables the external battery power levels to be monitored and replaced even when a smart medical cart is not actively being used.

The smart medical cart can include a power safety module to manage the safety of power source. When the smart medical cart uses external batteries and/or internal batteries for the power source, the external batteries and/or internal batteries can dissipate heat as a byproduct of providing power. In one embodiment, the power safety module can monitor the heat dissipated by the external batteries and/or internal batteries and determine when the external batteries and/or internal batteries are operating within a selected temperature threshold. In one embodiment, when the heat dissipated by the external batteries and/or internal batteries exceeds the selected temperature threshold, the smart medical cart can shut down or reduce power to selected system and/or subsystems of the smart medical cart. In another embodiment, when the heat dissipated by the external batteries and/or internal batteries exceeds the selected temperature threshold, the smart medical cart can indicate to the caregiver or communicate to the external location that there is an error or problem with part of the power source, such as an error showing that the smart medical cart is operating at a temperature that exceeds the selected threshold.

In one embodiment, to prevent a catastrophic failure of the external batteries and/or internal batteries, each cell of the external batteries and/or internal batteries can be placed in a separate cavity within the external batteries and/or internal batteries, respectively. The separate cavity can be shielded with phase changing material to contain an exothermic reaction associated with a catastrophic failure of a cell of certain types of batteries. One advantage of placing each cell of the external batteries and/or internal batteries in separate cavities with phase changing material can be to protect each cell from a catastrophic failure of another cell. For example, if one cell of an external battery and/or internal battery catastrophically fails, the phase changing materials in the cavity can naturally absorb heat when changing phase from a solid to a liquid to stop the failing cell from beginning a chain reaction that can cause many of the cells in the battery to catastrophically fail.

The smart medical cart can be used in a variety of different environments. The smart medical cart can include a wireless power subsystem. A wireless power subsystem can be used to provide power to the power management module of the smart medical cart and/or recharge the power source or the smart medical cart in the variety of environments.

In one embodiment, the wireless power subsystem can include a wireless induction charging module. The wireless induction charging module can use an electromagnetic field to transfer energy between two objects without any direct contact between the two objects. A wireless charging system can include at least one transmitting induction coil and at least one receiving induction coil.

The transmitting induction coil can transfer energy wirelessly from the transmitting induction coil to the receiving induction coil using inductive coupling. Inductive coupling occurs when the transmitting induction coil uses an induction coil to create an alternating electromagnetic field using an energy source. A current is induced in the receiving induction coil from the alternating electromagnetic field, thereby enabling the receiving induction coil to receive power from the alternating electromagnetic field. The current can then be used to power a subsystem or system on the smart medical cart. Alternatively, the current may be stored in one or more of the power sources on the smart medical cart, such as an external battery or the embedded battery. When the transmitting induction coil and the receiving induction coil are in proximity the transmitting induction coil and the receiving induction coil combine to form an electrical transformer. The transmitting coil can be connected to an energy source, such as an alternating current (AC) power outlet, a direct current (DC) battery, and so forth.

In another embodiment, the wireless power subsystem can comprise a wireless resonant charging module. Wireless resonant charging is the resonant transmission of electrical energy between at least one transmitting resonant coil and at least one receiving resonant coil. The at least one transmitting resonant coil and at least one receiving resonant coil are tuned to resonate at the same frequency. Resonant transmission of electromagnetic waves oscillating at a selected frequency can use a transmission coil ring of the transmitting resonant coil with an oscillating current. The oscillating current of the transmission coil can generate an oscillating magnetic field. A receiving resonant coil can be brought approximate to the oscillating magnetic field and the receiving resonant coil can receive energy or power from the oscillating magnetic field. In one embodiment, the oscillating magnetic field can be a relatively non-radiative or a near field.

The use of a near field can significantly reduce the amount of power that is radiated or leaks from the resonant coils. Energy in a magnetic field falls off as the inverse cube of distance ($1/d^3$). This allows relatively high power levels to be transferred between a resonant transmission coil and a resonant receiving coil without transmitting significant power away from the resonant coils. This enables the wireless resonant charging module to be used in areas close to humans or other biological entities without significant affects.

The wireless power subsystem may include one or more transmission coils or receiving coils of the wireless induction charging module and/or the wireless resonant charging module. In one embodiment, the wireless power subsystem can include one or more repeater coils. In one embodiment, the repeater coil can enhance the wireless transmitted power of a transmission coil. In another embodiment, the repeater coil can receive the wireless power signal from the transmission coil and relay or retransmit the received power to another repeater coil or a receiver coil.

Figure 28:
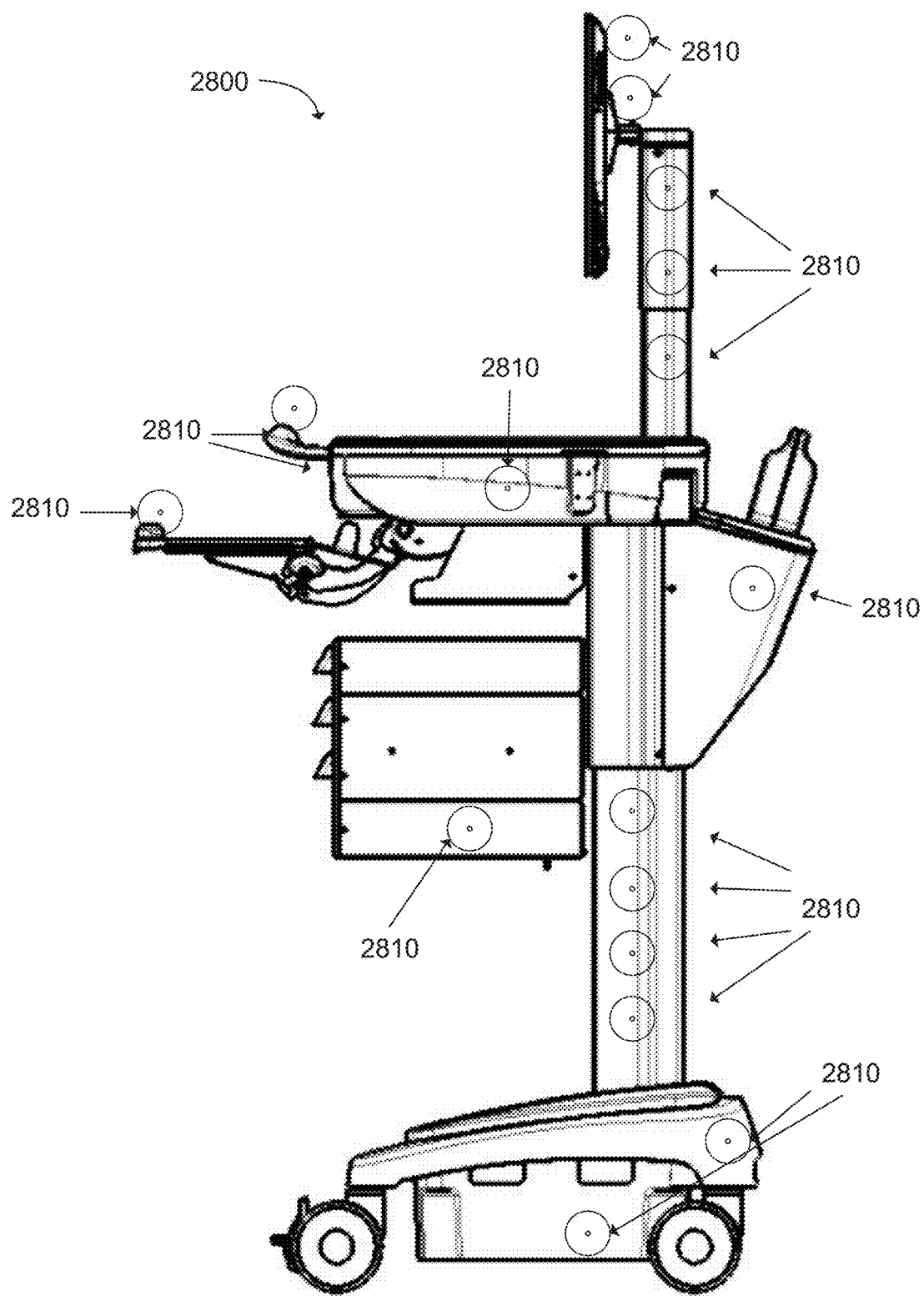
FIG. 28 shows coils attached to a smart medical cart at various locations in accordance with an example.

FIG. 28 shows that one or more coils 2810, such as transmission coils, receiving coils, and or repeater coils, can be attached to a smart medical cart 2800. The coils can be attached to locations including: the handle, the first work platform, the second work platform, the frame, the first vertical support, the second vertical support, the wheeled pedestal, the covering, the wheels, the mounting bracket of the second vertical support, the computing device, the power source, the medication storage container, and other desirable locations on the smart medical cart.

Figure 29:
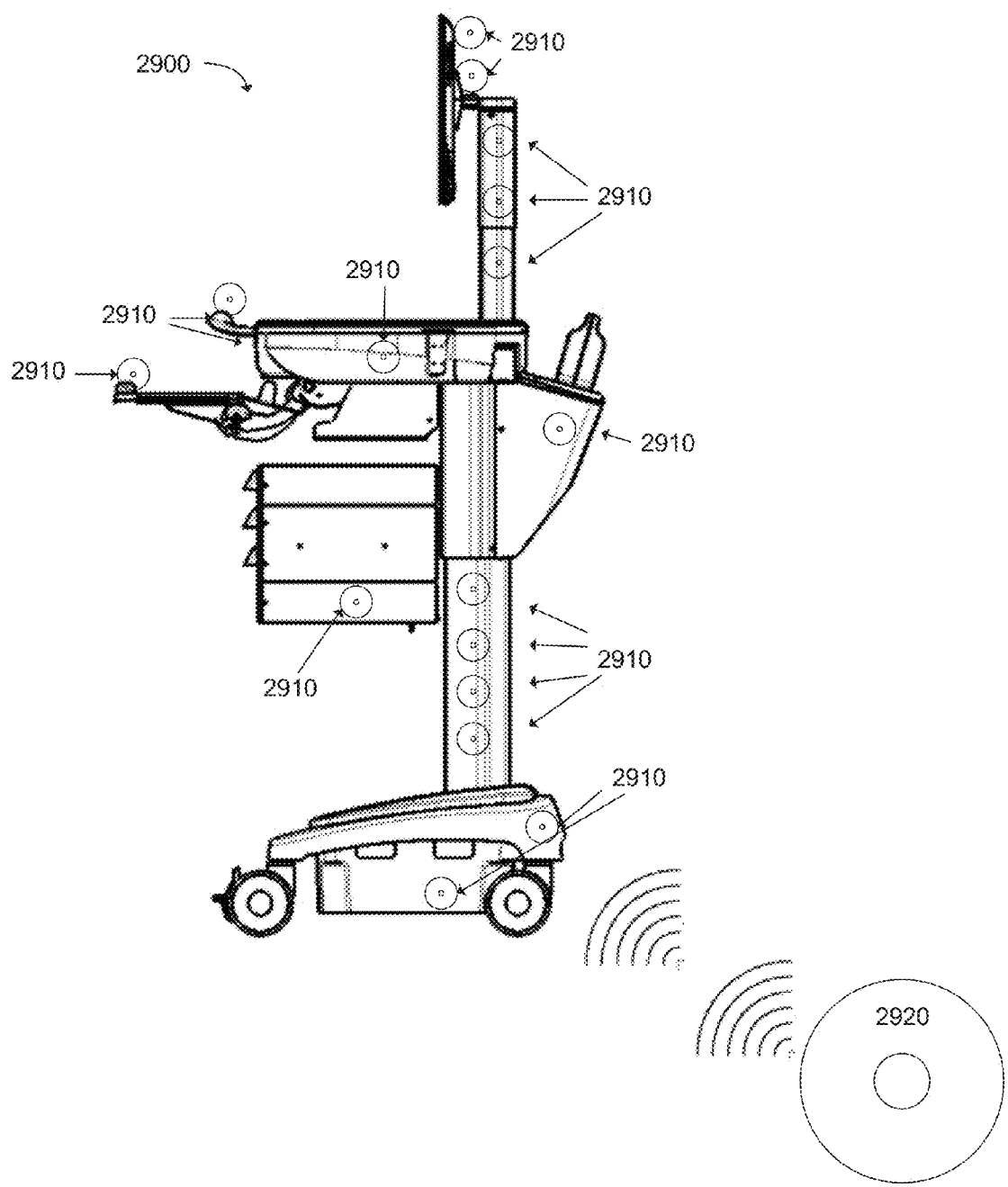
FIG. 29 illustrates a smart medical cart coil attached to a smart medical cart receiving wireless power from an external coil in accordance with an example.

FIG. 29 illustrates an exemplary embodiment of a smart medical cart coil 2910, such as a receiving coil, attached to a smart medical cart 2900, such as at the wheeled pedestal or the storage area of the covering, receiving wireless power from an external coil 2920, such as a transmission coil or a repeater coil, that is not located on the smart medical cart 2900. In one embodiment, the external coil 2920 that is not located on the smart medical cart 2900 can be a charging pad containing a transmission coil that is located on the floor surface. The smart medical cart coil 2910 can receive power from the external coil 2920 and use the received power to power the smart medical cart 2900 or recharge a power source of the smart medical cart 2900.

In another embodiment, the receiving coil located on the smart medical cart at the wheeled pedestal or the storage area of the covering can receive power from a transmission coil or a repeater coil located at another location on the smart medical cart, such as the first work platform. For example, a first repeater coil can be located at the wheeled pedestal of the smart medical cart. The first repeater coil can receive transmitted wireless power from a transmission coil located at a charging pad on the floor surface. A plurality of other repeater coils can be attached along the interior of the vertical support and relay the wireless power signal to a receiver coil attached at the first work platform. The receiver coil can receive the wireless power signal from one of the other repeater coils, convert the wireless power signal into an electrical current, and send the electrical current to the power management module, an external battery or internal battery, a computing device or display device, a selected device or equipment, and so forth.

In another embodiment, a receiving coil can be located at the first work platform and/or the second work platform of the smart medical cart. The receiving coil can receive wireless power from a transmission coil or repeater coil and use the received power to power a computing device, a display screen, a medical device, a medical instrument, and so forth.

In one embodiment, digital or analog information can be communicated via the transmission coil, repeater coil, and/or receiving coil. For example, the transmission coil can be connected to a wired or wireless communication system. Data can be communicated to the transmission coil. The data can then be modulated onto the magnetic field created by the alternating current in the transmission coil. The data can be received at the receive coil. The data can then be converted to baseband and communicated to one or more computing devices or electronic devices operating on the smart medical cart. The wireless power subsystem can be used to communicate information to and from smart medical carts.

One advantage of a smart medical cart having a wireless power subsystem is to reduce or eliminate the use of wires to transmit power or data from one location on the smart medical cart to another location. For example, typically, cables are used to transmit power from an alternating current source or a direct current source, such as the batteries, to the electrical systems, subsystems, and devices operating on the smart medical cart. In addition, data connections between various components typically use wired connections, such as connections between computer controlled equipment and the computing device(s) operating on the smart medical cart. These power and data cables may be routed within a hollow column, such as the vertical support 1410 of FIGS. 14a and 14b.

When the height of the first work platform or of the second work platform of the smart medical cart is adjusted, the wires routed inside the vertical support 410 can be stretched or wound as the height of the first work platform or the second work platform increases or decreases. When a wireless power subsystem is used, the wires routed to distribute power inside the vertical support can be eliminated or reduced to enable a more efficient and less complicated design of the smart medical cart. The elimination or reduction of cables can prevent wires from getting tangled, worn, and/or damaged as selected adjustments in height are made to the smart medical cart.

In one embodiment, the wireless power subsystem can have a current induced at a receiving resonant coil that is induced from an external transmitting resonant coil and use the current to trickle charge the power source of the smart medical cart. Trickle charging typically involves supplying a low rate of energy or electrical charge on a continuous, semi-continuous, or periodic basis. In one embodiment, wireless transmitters can be placed at various locations where the smart medical carts are used, such as medical facilities. Within each medical facility, transmitting resonant coils can be placed in various or selected locations, such as in patients' rooms, in hallways, and at specialized charging stations for the smart medical carts.

As the caregiver uses the smart medical cart at the various locations near or approximate to transmission coil and/or repeater coil locations, a receiver coil and/or a repeater coil located at the smart medical cart can receive the transmitted wireless power and convert the received wireless power into an electrical current used for trickle charging by the smart medical cart, as previously discussed. In one embodiment, the trickle charge can be used to power systems, subsystems, and/or devices on the smart medical cart, such as the computing device, power assistance drive system, medical devices, and so forth. In another embodiment, the trickle charge can be used to recharge the power source of the smart medical cart, such as an external battery or an internal battery.

The smart medical cart can include a power distribution module to manage the use and distribution of power from the power source to selected devices, systems, and subsystems of the smart medical cart. The power distribution module can reduce the overall energy consumption of the smart medical cart, prolong battery life for the smart medical cart, maintain the temperature of selected systems and subsystems to operate in selected temperature ranges, enable cooling of selected systems and subsystems, reduce noise, and so forth.

The power distribution module can lower the power consumption of the smart medical cart. In one embodiment, the power distribution module can lower the power consumption of the smart medical cart by monitoring the usage of devices, systems, and/or subsystems of the smart medical cart that are being used and/or not used by the caregiver. When a device, system, and/or subsystem remains idle for a selected period of time, the power distribution module can turn off the device, system, and/or subsystem or reduce the power distributed to the device, system, and/or subsystem by the power distribution module.

Figure 30:
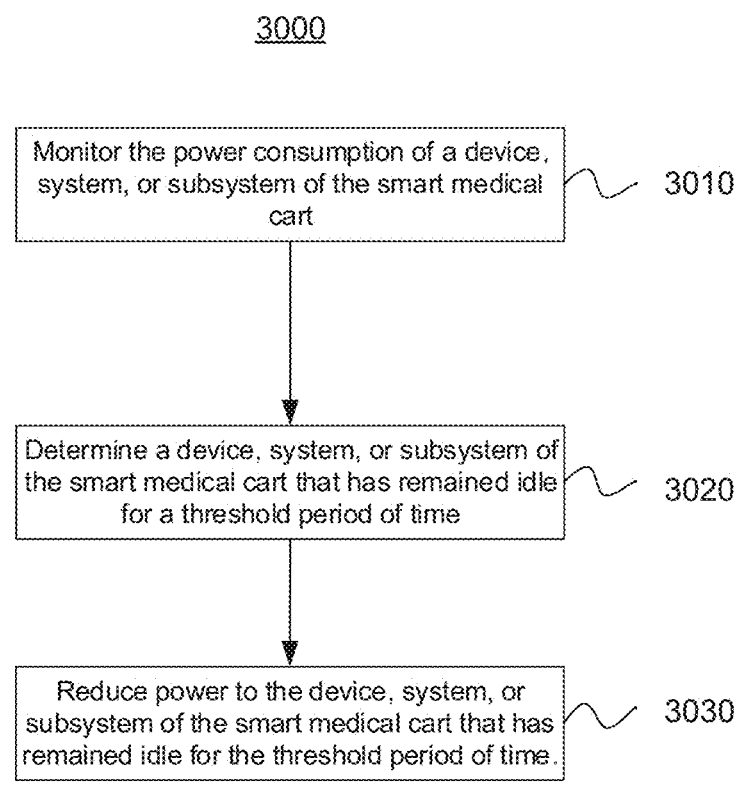
FIG. 30 depicts the functionality of computer circuitry of a user equipment operable to control power provided to one or more systems, subsystems, or device attached to a smart medical cart in accordance with an example.

FIG. 30 provides a flow chart 3000 to illustrate the functionality of one embodiment of a user equipment, such as a computing device, with computer circuitry operable to control power provided to one or more systems, subsystems, or device attached to a smart medical cart. The functionality can be implemented as a method or the functionality can be executed as instructions on a machine, where the instructions are included on at least one computer readable medium or one non-transitory machine readable storage medium. The computer circuitry can be configured to monitor the power consumption of a device, system, or subsystem of the smart medical cart, as in block 3010. The computer circuitry can be further configured to determine a device, system, or subsystem of the smart medical cart that has remained idle for a threshold period of time, as in block 3020. The computer circuitry can also be configured to reduce power to the device, system, or subsystem of the smart medical cart that has remained idle for the threshold period of time, as in block 3030.

In one embodiment, the power distribution module can lower the power consumption of the smart medical cart by monitoring where a device, system, and/or subsystem of the smart medical cart is function properly or malfunctioning. When a device, system, and/or subsystem malfunctions or is not functioning properly, the power distribution module can reduce or eliminate the power distributed to the malfunctioning device, system, and/or subsystem. Advantages of reduced power consumption can include: lower heat dissipation, which increases system stability; and less energy use, which can prolong the power source life.

Figure 31:
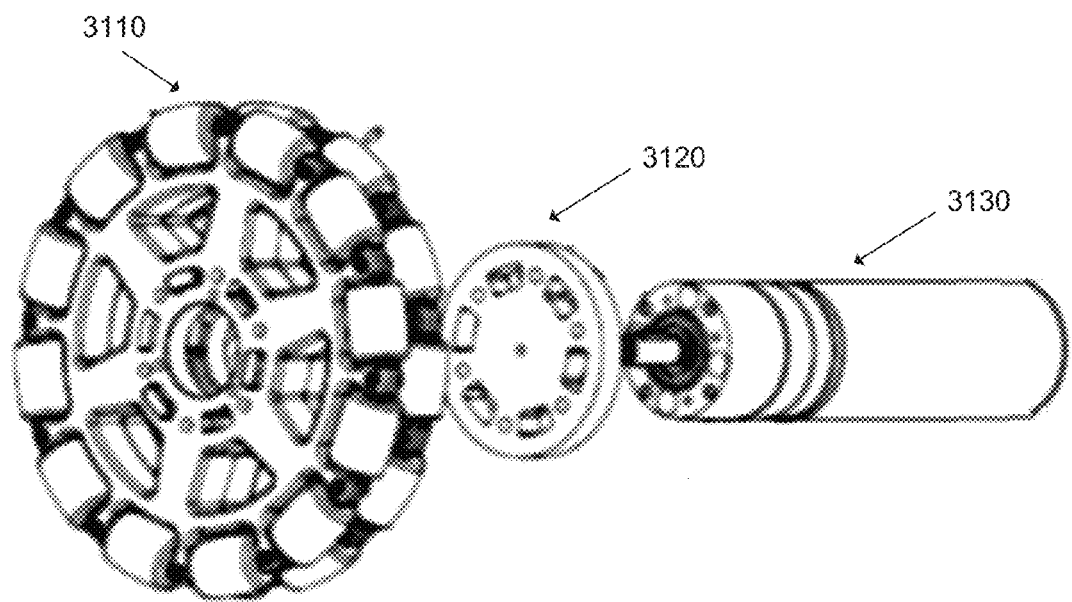
FIG. 31 shows a motor attached to a wheel using a mounting plate in accordance with an example.

The power assisted drive system of the smart medical cart can provide a caregiver with assistance in moving or maneuvering the smart medical cart. The power assisted drive system can receive power from the power sources via the power management system. The power assist drive system can comprise at least one motor or engine, such as an electric motor or combustion powered engine. The motor or engine of the power assist drive system can be connected to a wheel subsystem, where the wheel subsystem includes at least one wheel. FIG. 31 shows one embodiment of the motor 3130 connecting to a wheel 3110 using a mounting plate 3120. A first side of the mounting plate 3120 can attach to the wheel 3110, such as by bolted on or snapped on the wheel 3110 to the mounting plate 3120. A second side of the mounting plate can attach to the motor 3130, such as by bolted on or snapped on the motor 3130 to the mounting plate 3120. In another embodiment, the at least one wheel of the wheel subsystem can be attached to the motor a hub, axle, or center area of the wheel. The at least one wheel of the wheel subsystem can be powered by the motor or engine to drive or power the assisted movement of the smart medical cart.

Figure 32:
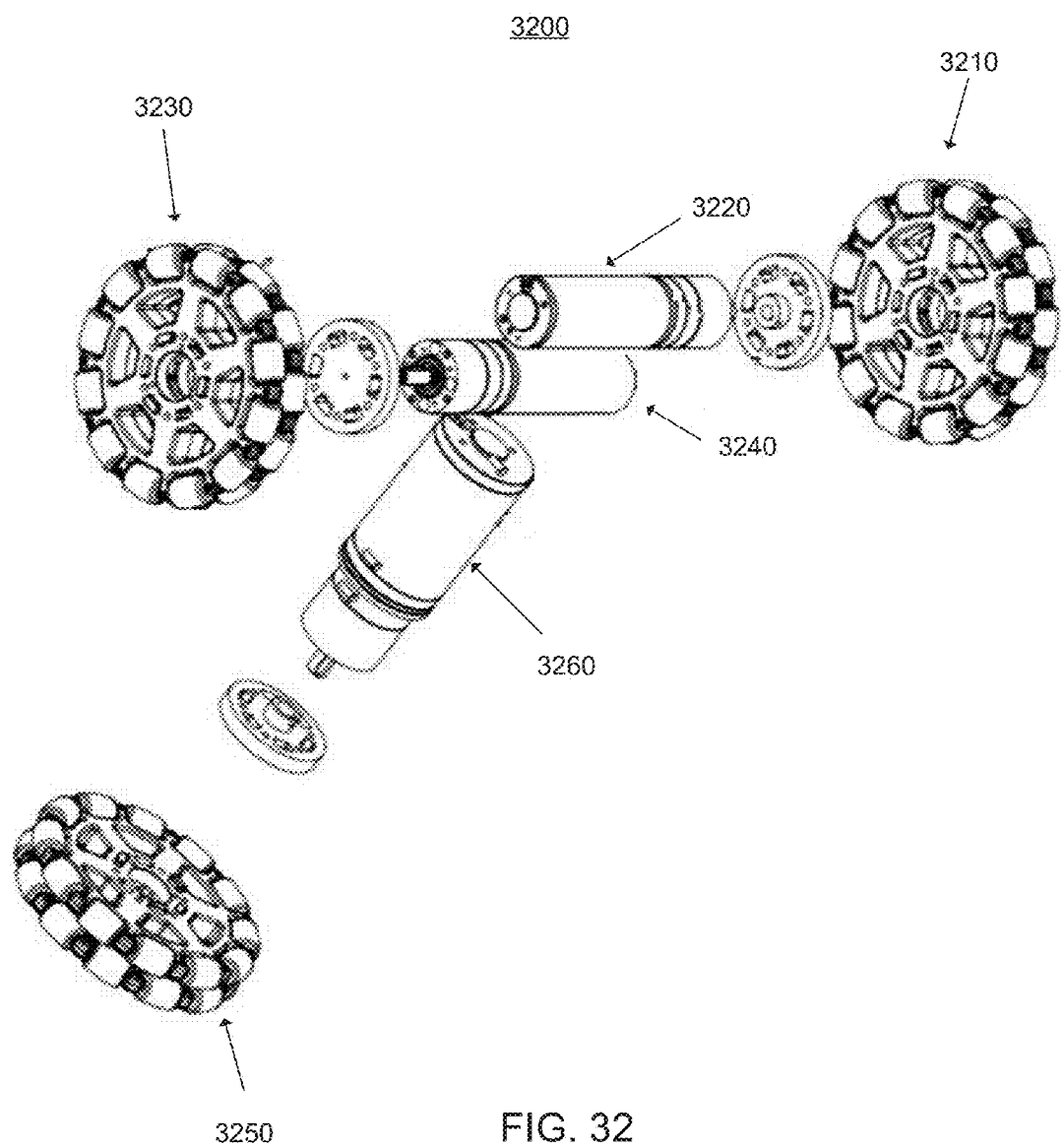
FIG. 32 illustrates motors paired with wheels in accordance with an example.

In one embodiment, each independent motor, such as direct current (DC) motors, of the power assist drive system, can be used to separately drive each wheel of the wheel subsystem. FIG. 32 illustrates three separate motors 3220, 3240, and 3260 that can power three separate wheels 3210, 3230, and 3250 respectively. In one embodiment, the motors and wheels can be paired together, i.e. 3210 with 3220, 3230 with 3240, and 3250 with 3260. Each motor of the motor and wheel pair can control the direction and speed of the wheel of the pair independent of the direction and speed of the other motor and wheel pairs.

Figure 33:
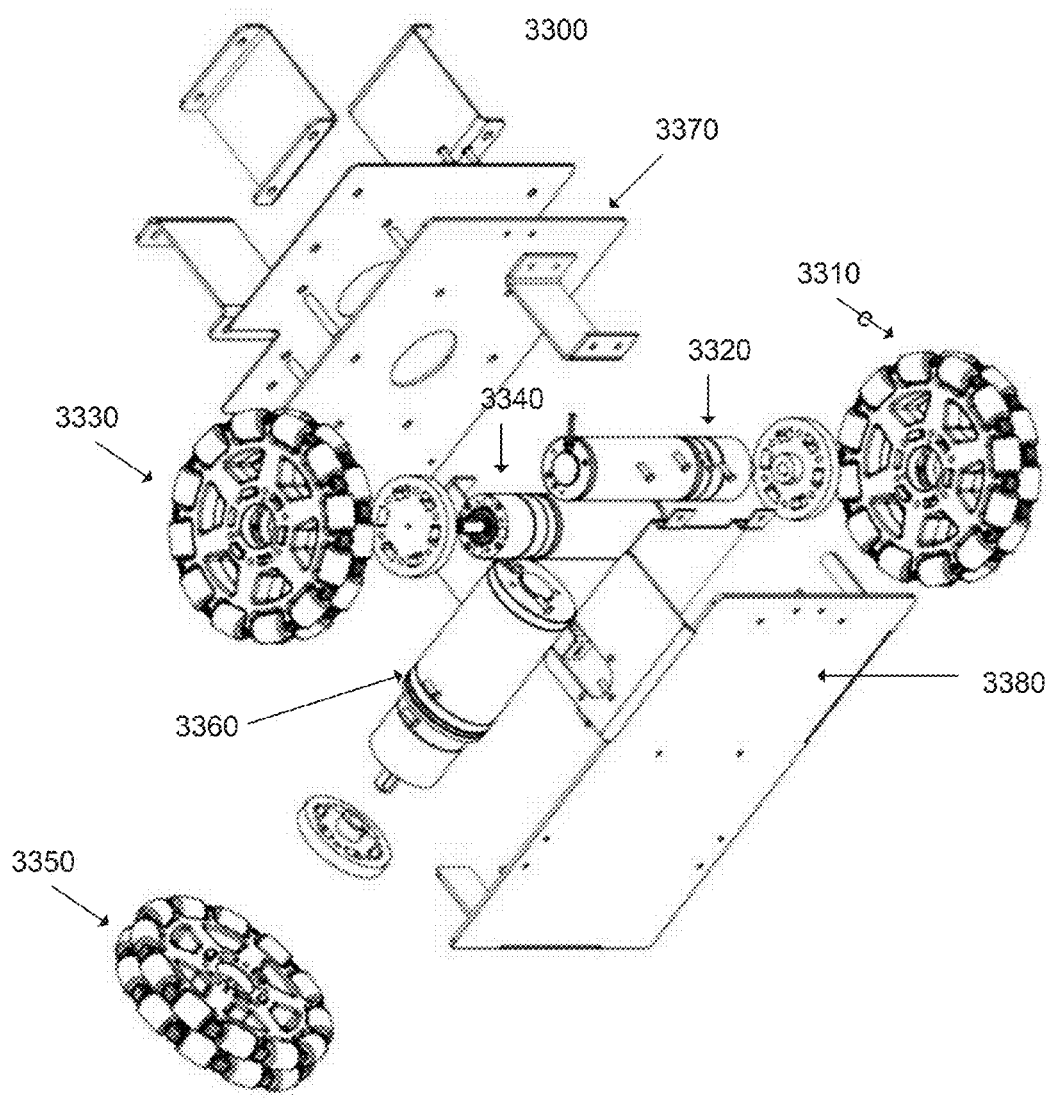
FIG. 33 depicts a power assist drive system housing for wheel and motor pairs in accordance with an example.

FIG. 33 depicts a power assist drive system housing 3300 for the wheels and motor pairs 3310 and 3320, 3330 and 3340, and 3350 and 3360. In one embodiment, the motors, 3320, 3340, and 3360 can each attach to the power assist drive system housing using mounting plates 3370 and 3380. For example, the motors can be attached to the mounting plate 3380, such as attached using fasteners, and mounting plate 3370 can be attached to mounting plate 3380, such as attached using fasteners. In one embodiment, the power assist drive system housing 3300 can enclose the wheels and motor pairs 3310 and 3320, 3330 and 3340, and 3350 and 3360. In one embodiment, the power assist drive system housing of the wheeled pedestal can attach at the covering of the wheeled pedestal. In another embodiment, the power assist drive system housing can attach to the first vertical support. In one embodiment, the motor can include a gear box used to transfer power from the power assist drive system to the wheel subsystem. In another embodiment, the motor can include a drive belt system to transfer power from the power assist drive system to the wheel subsystem.

In another embodiment, the wheel subsystem and/or the power assist drive system can include one or more encoders integrated into the wheels or encoders adjacent to the wheels. The encoders can be used to: collect information, such as position or velocity information; measure the speed or distance a wheel has traveled; determine the direction of movement of the wheel; determine the rotational direction of the wheel; and determine the friction, traction, or slippage of the wheel or smart medical cart. In one embodiment, the velocity of the smart medical cart can be determined by analyzing a change in position versus a change in time. In another embodiment, a motor of the power assist system can be used to determine the direction of movement or rotational direction of the wheels of the smart medical cart. For example, the smart medical cart can determine that the smart medical cart is moving in a forward direction by determining that one or more motors of the power assist drive system are rotating one or more wheels in a clockwise rotation.

Figure 34:
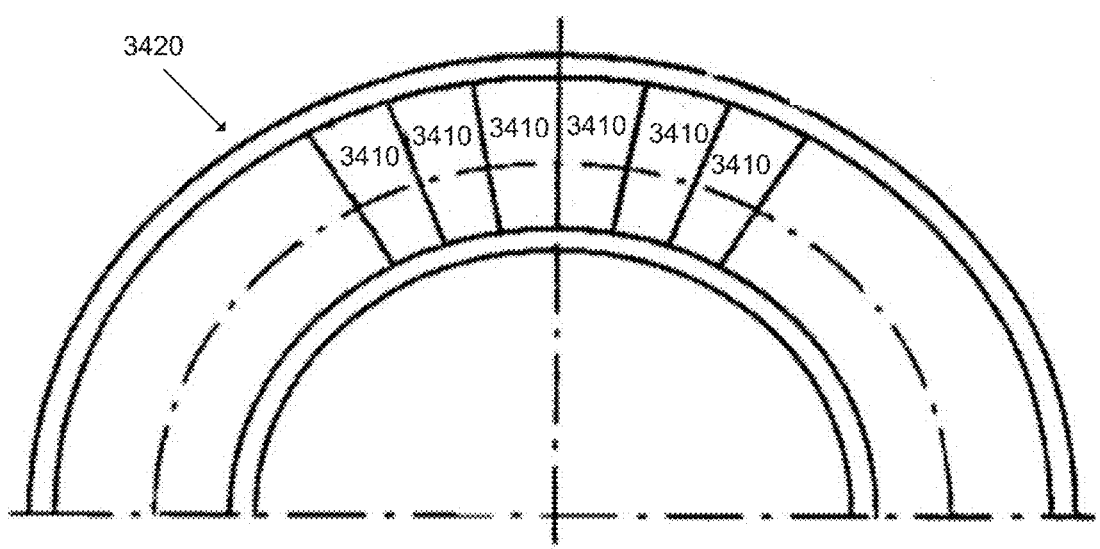
FIG. 34 shows a plurality of encoders integrated into a wheel in accordance with an example.

FIG. 34 shows on exemplary embodiment of a plurality of encoders 3410 integrated into a wheel 3420. In one embodiment, the wheel subsystem or power assist drive system can use the encoders 3410 to detect angular rotation of the wheel by measuring small increments of movement by observing a signal that varies as the wheel rotates. For example, the encoders 3410 can be one or more black and white or colored lines along the side of the wheel 3420 radiating from the center of the wheel. In this example, a line detector can be used to detect the one or more colored line encoders 3410 on the wheel 3420 as it rotates past the detector. The line detector can detect a number of one or more lines and/or a pattern of different colored lines and convert the number of lines or the pattern of colored lines into a digital signal that can be communicated to a digital microcontroller to determine the speed, velocity, and/or direction of the smart medical cart.

In another embodiment, the encoders 3410 can be magnets integrated into the wheel 3420. In this embodiment, a magnetic detector can be used to detect the number of rotations of the magnet as it rotates past the detector. In another embodiment, a receiver or a detector can determine the amount of light that is returned or reflected by an encoder 3410. In one embodiment the detector can located on the wheel 3420. In another embodiment, the detector can be located approximate or adjacent to the wheel 3420. The speed and direction of the wheel 3420 can be determined based on a variation in the amount of light reflected from the wheel 3420 or the encoders 3410. The rotation data gathered from an encoder detector can be used to determine the velocity, acceleration, speed, and/or direction of the smart medical cart. In another embodiment, the smart medical cart can determine speed, velocity, acceleration, and/or direction using a global positioning system (GPS) device, a triangulation device, and so forth.

To engage the power assist drive system, an operator of the smart medical cart, such as a caregiver, can apply a force to a selected location of the smart medical cart where one or more force detectors are located, such as the on the handle of the smart medical cart. For example, in one embodiment, force detectors may be in communication with a handle attached to the smart medical cart. By pushing or pulling the handle, the amount of force can be detected and translated into a direction and speed. While examples of force detectors associated with a handle are provided, they are not intended to be limiting. Force detectors may be located in different or additional locations on the smart medical cart, such as in locations associated with drawers. In this example, applying a force to a drawer may be used to activate the power assist drive system.

In one embodiment, load cells are connected to the handle to measure the load or displacement of the handle from a force applied by the user. The measured load can be converted to digital signals using an analog to digital converter (ND converter) and sent to a control board for processing. After the control board processes the measured load signal then an output signal can applied to one or more individual motor drivers, which then send a current to the motor(s). Each motor can be equipped with an encoder. This encoder can be used to provide positional data, which can be fed back to the power assist drive system. Using the positional data, the motor velocity can be calculated between specified time intervals. This will be described more fully in the proceeding paragraphs.

In one embodiment, the power assisted drive system can include a clutch subsystem. The clutch subsystem can include a clutch that can engage and/or disengage with the power-assisted power assist drive system and the wheel subsystem. The clutch can be a mechanical device that provides for the transmission of power from system or subsystem, such as the power assist drive system, to another system or subsystem, such as the wheel subsystem, when engaged. In one embodiment, the clutch can connect and disconnect two rotating shafts, e.g. drive shafts or line shafts, when engaging and disengaging. The clutch subsystem can be engaged when the power assist drive system is engaged.

Figure 35A:
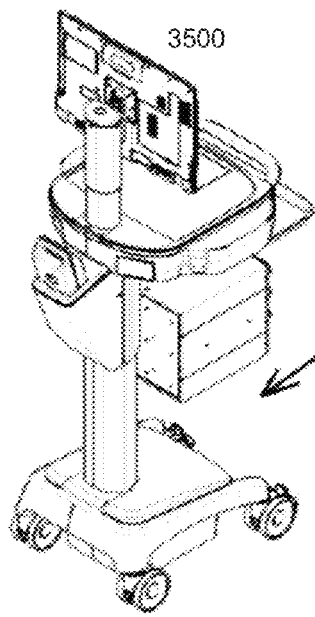
FIG. 35a depicts a perspective view of a smart medical cart moving forward in a diagonally left direction in accordance with an example.
Figure 35B:
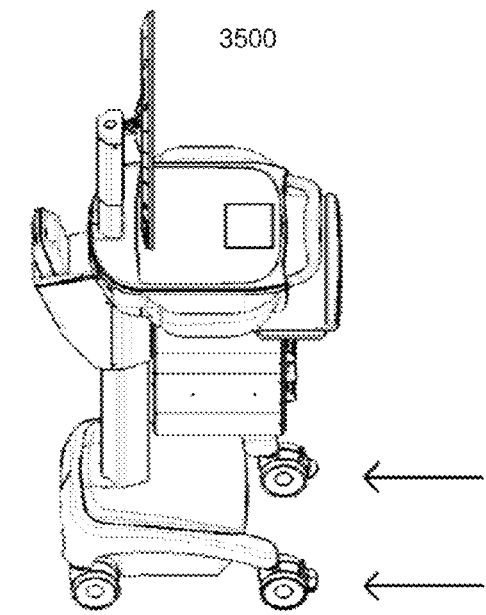
FIG. 35b depicts a side view of a smart medical cart moving forward in a lateral motion in accordance with an example.
Figure 35C:
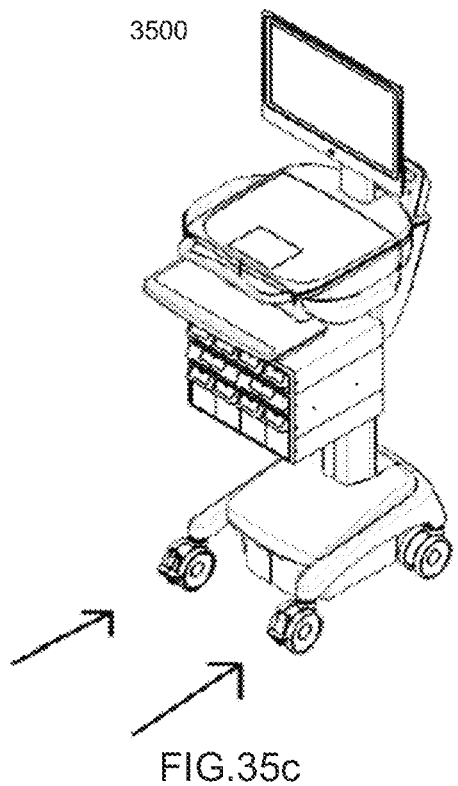
FIG. 35c depicts a perspective view of a smart medical cart moving forward in a diagonally right motion in accordance with an example.

To enable caregivers to more efficiently and easily maneuver the smart medical cart, the power assist drive system can move the smart medical cart in a full degree of motions. The full degree of motions can include: longitudinal motion, e.g. forward and backward motion; latitudinal or lateral motion, e.g. left and right motion; and diagonal motion. FIGS. 35a-c illustrate the smart medical cart 3500 moving in selected degrees of motion. FIG. 35a depicts a perspective view of the smart medical cart moving forward in a diagonally left direction. FIG. 35b depicts a side view of the smart medical cart moving forward in a lateral motion. FIG. 35c depicts a perspective view of the smart medical cart moving forward in a diagonally right motion. The drive system can also provide for rotational movement around a vertical vector or axis, e.g. the smart medical cart can rotate while remaining in a fixed location. For example, the first vertical support, the first work platform, or the second work platform may rotate while the wheeled pedestal remains in substantially the same position. In one embodiment, the first vertical support, the first work platform, or the second work platform can rotate by applying power to a selected wheel at a selected angled that enables the cart to rotate around the vertical axis.

Figure 36:
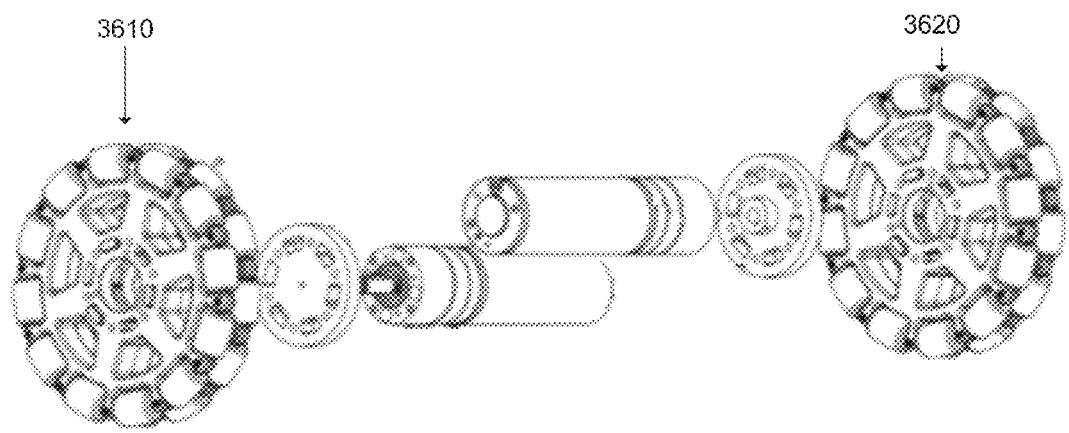
FIG. 36 shows a configuration of a wheel subsystem with two powered wheels located parallel to each other in accordance with an example.

The wheel subsystem can be configured to enable the power assist drive system to provide the full degree of motion. FIG. 36 shows one exemplary embodiment where the wheel subsystem can comprise two powered wheels 3610 and 3620 located adjacent or parallel to each other. In one embodiment, the two parallel wheels 3610 and 3620 can be parallel to the left side of the smart medical cart and the right side of the smart medical cart relative to the front of the medical cart. To provide forward and backward movement, the power assist drive system can rotate the two wheels 3610 and 3620 at the same speed and in the same direction. For example, to move the smart medical cart forward the power assist drive system can rotate the two wheels 3610 and 3620 clockwise at the same speed, and similarly the power assist drive system can rotate the two wheels 3610 and 3620 counterclockwise for backward movement. To provide lateral or diagonal movement, one of the two wheels 3610 or 3620 can rotate clockwise while the other wheel 3610 or 3620 may rotate counter clockwise. To provide rotational movement, the two wheels 3610 and 3620 can be rotated in opposite directions to rotate the smart medical cart about a vertical axis. The speed that the power assist drive system rotates each of the two wheels can be variable and can enable the smart medical cart to be moved at various degrees of longitudinal, lateral, or diagonal movement.

In one embodiment, the power assist drive system can include an orientation sensor to determine the orientation, angle, and/or rate of motion of the smart medical cart. An orientation sensor can measure the rates of rotation and/or motion that the smart medical cart makes around all three physical axes, e.g. the x, y, and z axes. In one embodiment, the power assist drive system can use an orientation sensor to determine an attitude of the smart medical cart, i.e. gyro horizon or artificial horizon, by determining the current direction of the smart medical cart relative to a point of reference. In another embodiment, the power assist drive system can use orientation sensor to determine a heading of the smart medical cart by determining the direction that the smart medical cart is currently pointed.

In one embodiment, the orientation sensor can be one or more accelerometers or gyroscopes. For example, an accelerometer may be located in each of the x, y, and z axes to detect a change in motion. A gyroscope can also be used to measure a change in rotation of the smart medical cart. In another embodiment, a gravity sensor and/or a geomagnetic field sensor can be used to determine the inclination and rotation of the smart medical cart, as discussed in the proceeding paragraphs. In one embodiment, a gravity sensor can give a three dimensional vector for a force of gravity. The force of gravity can be used to determine the direction that the smart medical cart is currently facing. In another embodiment, the geomagnetic field sensors can be used to determine directional outputs relative to a magnetic North.

To provide additional degrees of longitudinal, lateral, or diagonal movement, such as moving the smart medical cart left to right or diagonally without the cart having to be propelled forward, the power assist drive system can rotate the two wheels 3610 and 3620 along a vertical axis. For example, the two wheels may initially be aligned perpendicular to the front of the smart medical cart. To move the smart medical cart left, right, or diagonally, the two wheels 3610 and 3620 can rotate on a vertical axis to selected degrees relative to the front of the medical cart. For example, the power assist drive system can rotate the two wheels 45 degrees clockwise relative to the front of the medical cart and then the power assist drive system can engage the clutch subsystem to provide power to the wheels or the wheel subsystem to move the smart medical cart diagonally right.

Figure 37:
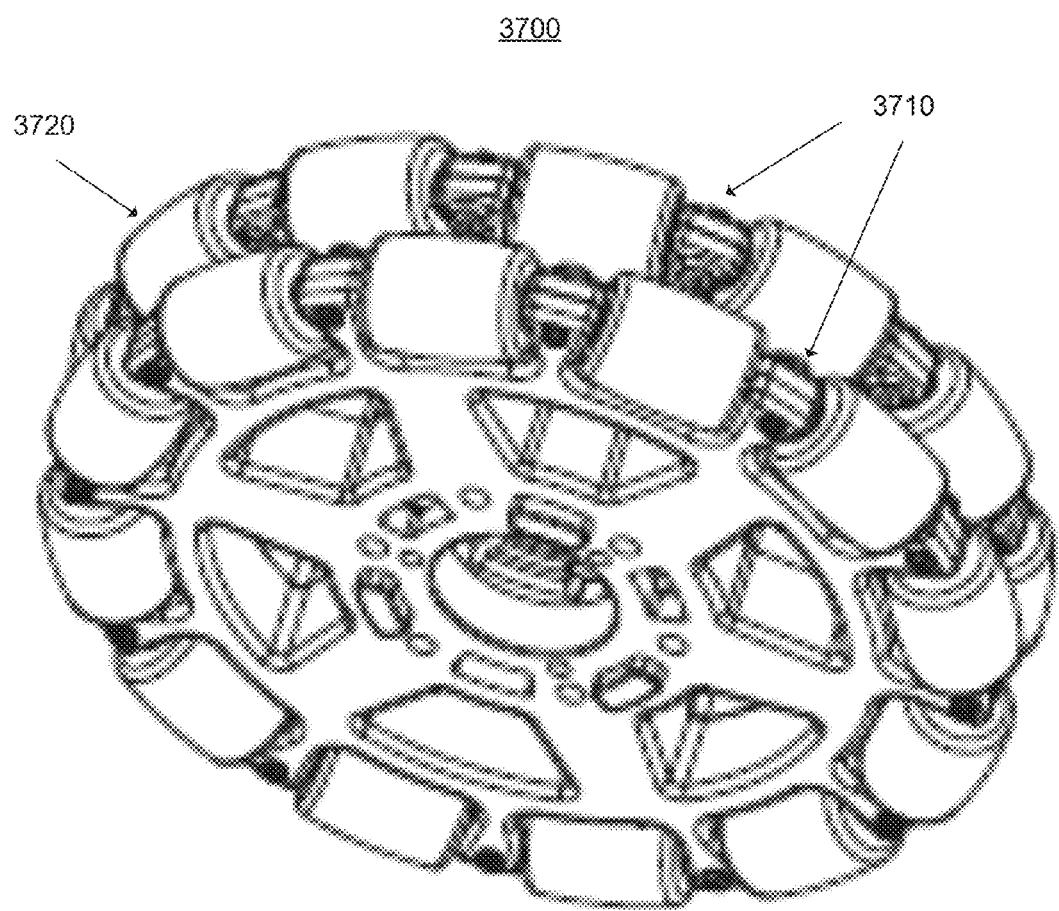
FIG. 37 depicts an omni wheel in accordance with an example.

In another embodiment, the wheel subsystem can include one or more omni wheels or poly wheels to enable the full degrees of movement for the smart medical cart. FIG. 37 illustrates one embodiment of an omni wheel 3700. FIG. 37 depicts that the omni wheel 3700 can have one or more wheels 3710 with small discs 3720 around the circumference of the omni wheel 3700. The small discs 3720 are positioned to be perpendicular to the rolling direction of the one or more wheels 3710. One advantage of the omni wheel 3700 can be that the omni wheel 3700 can roll forward and backward by rolling on the wheel 3710, and can also slide or glide laterally left and right by rolling on the small discs 3720.

In one embodiment, the small discs 3720 or omni discs can enable a user to passively move the smart medical cart in a side-to-side motion without assistance from the power assist drive system. This can be useful in manipulating the smart medical cart in congested locations and positioning the smart medical cart next to a desired location, such as a patient's bed.

In one embodiment, the omni wheel 3700 can be made out of a noise reducing material such as a plastic, a composite material, or rubber to reduce the sound level of the rollers. In another embodiment, the omni discs or small discs 3720 can be made of the noise reducing material and one or more wheels 3710 of the wheel subsystem can be made out of another material, such as a rubber polymer. One advantage of the omni discs 3720 being made out of a noise reducing material and the one or more wheels 3710 being made out of another material is to reduce the noise level of the omni discs 3700 while the one more wheels 3710 maintain a desired level of traction for different surfaces.

Returning to FIG. 32, FIG. 32 further shows an embodiment of a power assist drive system 3200 including a wheel subsystem. FIG. 32 shows the power assist drive system 3200 can comprise electric motors 3220, 3240, and 3260 that drives each omni wheel, 3210, 3230, and 3250 independently. In another embodiment, the power assist drive system 3200 can include one electric motor that drives multiple wheels in the wheel subsystem. In another embodiment, the power assist drive system 3200 can comprise three motors 3220, 3240, and 3260 that are operated by the power assist drive system. Two of the motors, 3220 and 3240, can be used for forward and reverse movement, spin and turn movement, and/or rotational movement. The third motor 3260 can be used to move the smart medical cart left and right.

FIG. 32 further shows a configuration of a wheel subsystem that is configured to enable the full degrees of movement for the smart medical cart. FIG. 32 illustrates a wheel subsystem that has two omni wheels 3210 and 3230 that are on a parallel plain to each other and a third omni wheel 3250 that is perpendicular to the two parallel wheels 3210 and 3230. To provide the forward and backward movement, the two parallel omni wheels 3210 and 3230 can be engaged and rotate clockwise or counterclockwise. To provide left or right movement, only the third omni wheel 3250 will be engaged and rotate while the two parallel omni wheels 3210 and 3230 will not be engaged. To provide diagonal or lateral movement, the two parallel omni wheels 3210 and 3230 and the third omni wheel 3250 can be engaged in combination or sequentially.

Figure 38:
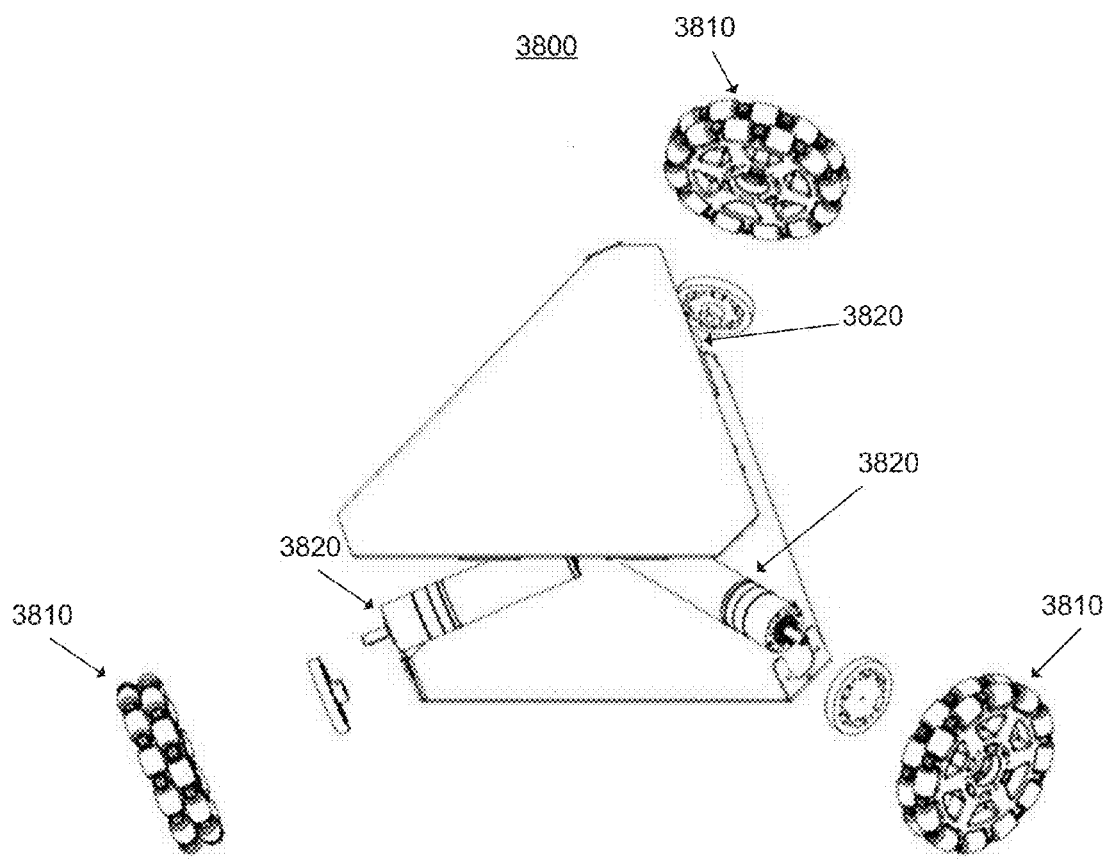
FIG. 38 illustrates a configuration of a wheel subsystem where omni wheels are arranged in an equilateral triangle configuration in accordance with an example.

FIG. 38 illustrates another configuration of the wheel subsystem 3800. FIG. 38 shows three omni wheels 3810 arranged in an equilateral triangle configuration. The motors 3820 of the power assist drive system can drive one or more of the wheels at the same time to achieve a desired motion or direction. For example, two motors 3820 located at the back of the smart medical cart can rotate the wheels 3810 in a clockwise rotation to move the smart medical cart forward or backward. The motors 3820 of the power assist drive system can also drive the three wheels 3810 at the same time and at different rotational directions, e.g. clockwise and counterclockwise, and/or speeds to achieve a desired motion or direction. A vector can be used to represent a direction in which the smart medical cart will move. The vector can be translated to the desired direction and rate of rotation of each of the wheels 3810. The rotational directions and the speed the motors 3820 drive the wheels 3810 can be added and subtracted vectorally to achieve the desired direction of motion and speed of the smart medical cart. The vectorial addition and subtraction of the rotational direction and speed of each of the wheels 3810 can reinforce and/or cancel the directional movement of each of the wheels 3810 to enable the desired movement of the smart medical cart.

Figure 39:
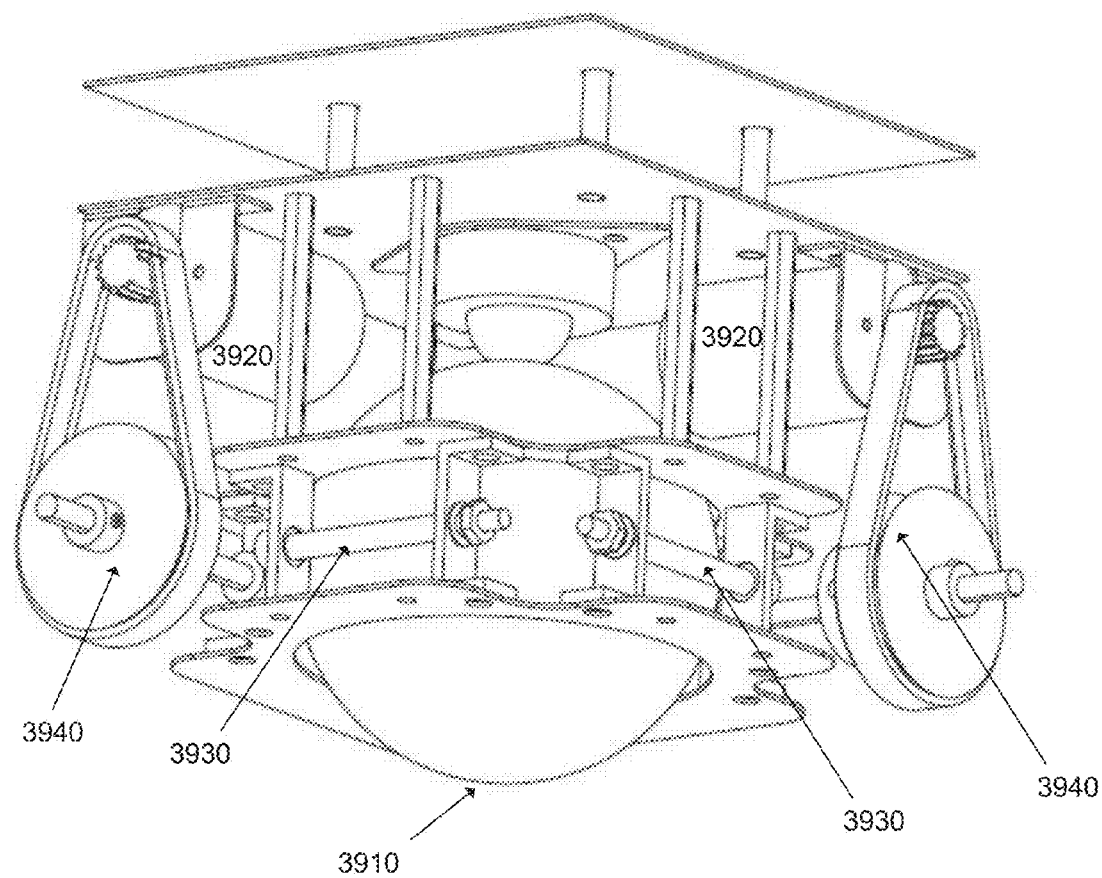
FIG. 39 depicts a configuration of a wheel subsystem with an omni ball in accordance with an example.
Figure 40:
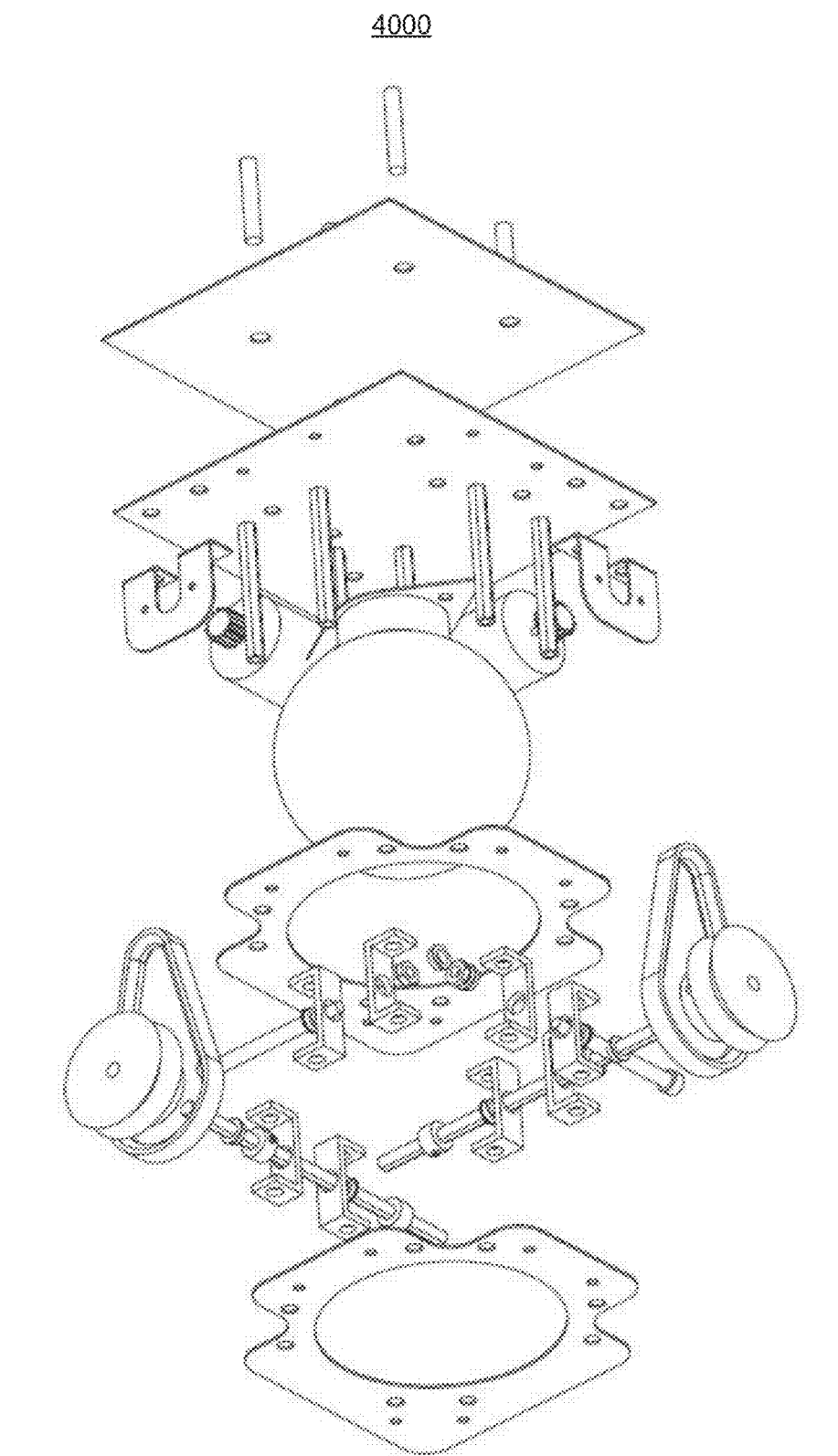
FIG. 40 provides an exploded view of an omni ball wheel subsystem configuration in accordance with an example.

FIG. 39 depicts another configuration of the wheel subsystem, comprising an omni ball 3910 to enable the full degrees of movement for the smart medical cart. In one embodiment, the wheel subsystem can include a plurality of omni balls 3910. In one embodiment, the omni ball 3910 can be a spherical ball located in the center of the wheeled pedestal and attached to the bottom or underside of the wheeled pedestal. The omni ball 3910 can be moved or rotated in 360 degrees of direction using a plurality of motors 3920, such as two motors 3920, to rotate the omni ball 3910 along two axes. In one embodiment, the motors 3920 can use a friction drive system 3940 that can be in contact with the omni ball 3910, such as by using a friction beam or pole 3930. The friction drive system 3940 can directly drive the omni ball 3910 by rotating the friction beams or poles 3930 that can be in contact with the surface of the omni ball. One advantage of using a wheel subsystem configured with an omni ball 3910 can be that the omni ball 3910 can rotate and pivot in all directions, e.g. omni-directional, without the need for complex steering mechanisms. FIG. 40 provides an exploded view of the omni ball wheel subsystem configuration 4000.

Figure 41A:
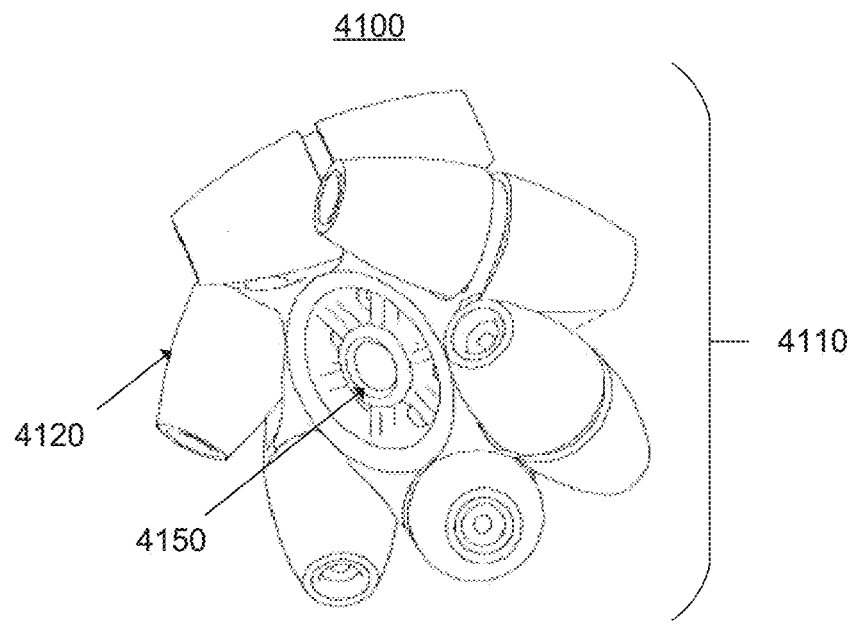
FIG. 41a shows a wheel subsystem that uses a mecanum wheel configuration in accordance with an example.

FIG. 41*a* shows a wheel subsystem that uses mecanum wheel configuration 4100. A mecanum wheel 4110 includes a wheel 4150 at the center or middle in the shape of a conventional wheel shape at the center of the mecanum wheel 4110 with a series of rollers 4120 attached to the circumference of the wheel 4150. The rollers 4120 typically each have an axis of rotation at 45 degrees to the plane of the wheel and at 45 degrees to a line through the center of the roller parallel to the axis of rotation of the wheel 4150.

Figure 41B:
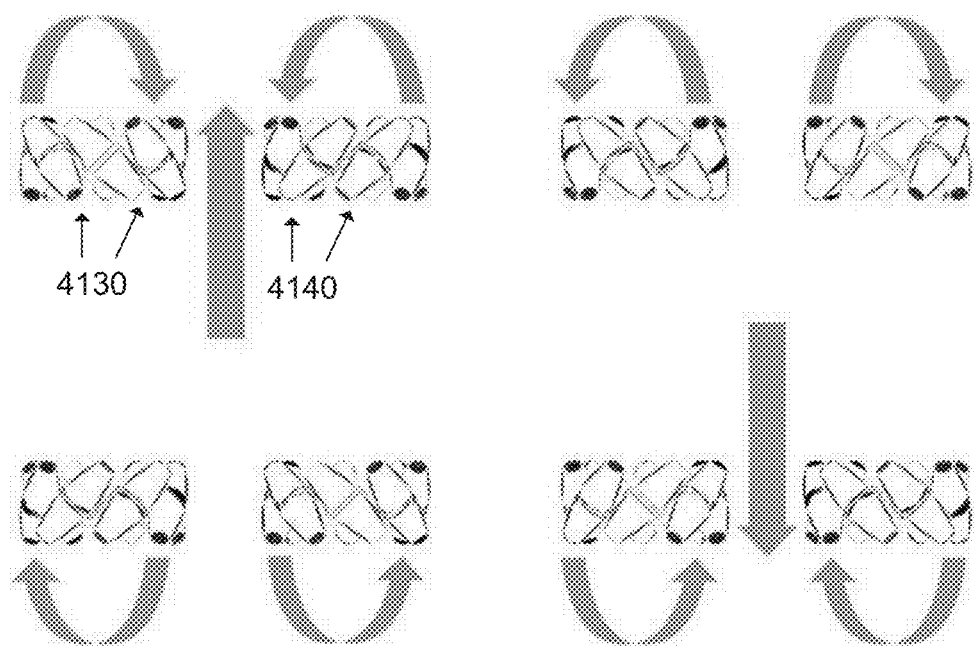
FIG. 41b illustrates mecanum wheels with left-handed rollers and right-handed rollers in accordance with an example.

FIG. 41*b* illustrates alternating wheels with left-handed rollers 4130 and right-handed rollers 4140. In one embodiment, the left-handed rollers 4130 and right-handed rollers 4140 each apply force roughly at right angles to a base, such as a level flooring surface, and at the diagonal that the wheel 4150 is on. One advantage of mecanum wheels 4110 can be that the mecanum wheels 4110 can provide a stable wheeled pedestal for the smart medical cart while enabling the smart medical cart to move in any direction and turn by varying the speed and direction of rotation of each roller 4130 or wheel 4110. In one example, the wheel subsystem of the smart medical cart can comprise four mecanum wheels. When the power assist drive system moves the four wheels in the same direction the smart medical cart moves forward or backward. When the power assist drive system moves two mecanum wheels 4110 on one side, such as the left side of the smart medical cart, in an opposite direction of two mecanum wheels 4110 on the right side of the smart medical cart, the smart medical cart rotates clockwise or counterclockwise. When the power assist drive system moves the two mecanum wheels 4110 in one diagonal in the opposite direction to the two mecanum wheels 4110 in the other diagonal, the smart medical cart moves sideways. One or more combinations of mecanum wheel 4110 movement can enable the smart medical cart to move in any direction with any rotation.

To prevent unwanted movement of the smart medical cart, the power assist drive system can include a braking subsystem, such as in FIG. 19 and described in the preceding paragraphs. In one embodiment, one or more wheels of the wheel subsystem can be locked into place to prevent unwanted movement. In another embodiment, unwanted motion can be prevented by applying a brake to one or more of the wheels of the wheel subsystem. In another embodiment, to prevent unwanted movement the motors of the power assist drive system can be de-energized. In another embodiment, to prevent unwanted movement the clutch of the clutch subsystem can be disengaged.

In one embodiment, the vector analysis can change or be adjusted based on the level of traction or slippage of the wheels. For example, when the wheel subsystem is in a triangular configuration and two of the wheels in the triangular configuration have full traction and the third wheel has zero traction or partial traction, the smart medical cart can adjust the rotational direction and/or the speed of one or more of the wheels to compensate for the change in traction of the third wheel. In one embodiment, the smart medical cart can use encoders integrated into or adjacent to the wheels to determine the rotational direction and/or the speed of each wheel. The power assist drive system can use the rotational direction and/or the speed information of each wheel to compensate for the change in traction of the third wheel. In another embodiment, the caregiver can compensate for the change in traction by adjusting the force applied to the handle of the smart medical cart. When the force applied to the handle is adjusted, the power assist drive system can change the power provided to the wheels based on the change in the force applied to the handle.

In one embodiment, a current draw of the motor can be proportional to the torque output of the motor. For example, a high current draw of the motor can be a high torque output of the motor and a low current draw of the motor can be a low torque output. Torque can be inversely proportional to velocity. In one embodiment, a velocity output of a motor can be converted to torque output of a motor through a gearbox or belt drive system. For example, a low velocity can be converted to a high torque and a high velocity can be converted to a low torque. In one embodiment, encoders can be used on each wheel attached to the motors for positional feedback and/or velocity calculations. In one embodiment, slippage can be determined by comparing a current draw of the motor with encoder information. For example, a slippage can be determined when low current draw and high velocity is detected when the smart medical cart begins moving from a standstill position, when no slippage would show a high current draw and low velocity output.

In the medical care environment, the ambient noise level or environmental noise level can be of concern. Medical patients often need quite environments to aid in their recovery. Additionally, patients are often resting at various times of the day and night. Accordingly, it may be advantageous for the power assist drive system and/or the wheel subsystem of the smart medical cart to operate silently or near silently. In one embodiment, the power assist drive system can operate near silently when it operates below 40 decibels (dB). In one embodiment, to buffer the sound of the power assist drive system, sound absorbent material or noise shielding material can surround or partially enclose at least part of the power assist drive system and/or wheel subsystem. In one embodiment, the motors of the power assist drive system can operate at a maximum noise level of 35 decibels (dB) when operating at full capacity.

In another embodiment, the power assist drive system and/or wheel subsystem can be dynamically and/or automatically adjusted based on defined or selected criteria to operate within a select noise level range. For example, dynamic adjustments can be made to reduce noise when the smart medical cart is operating in an area where patients may be sleeping. For instance, the speed and/or acceleration of the powered wheels of the wheel subsystem may be limited to reduce the noise output of the medical cart. The noise level of the smart medical cart can also be adjusted using shrouding and/or noise reduction materials, such as urethane foam, fiberglass, vinyl, and so forth. In another embodiment, the shrouding and/or noise reduction materials can be used to adjust or alter the frequency of the noise emitted by the smart medical cart. In another embodiment, fluid, such as water, can be used to reduce the noise emitted from the smart medical cart. In one embodiment, the location of the fluid, shrouding, and/or noise reduction materials can be adjusted or moved based on the noise level of the smart medical cart or selected parts of the smart medical cart.

Figure 42:
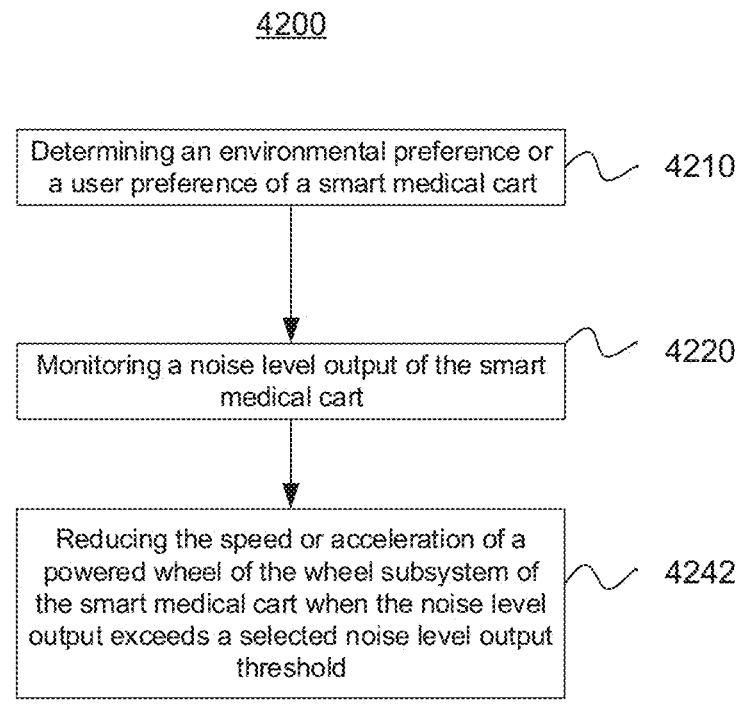
FIG. 42 illustrates a method for adjusting the noise level output of a smart medical cart in accordance with an example.

FIG. 42 provides a flow chart 4200 to illustrate a method for adjusting the noise level output of a smart medical cart. The method can comprise determining an environmental preference or a user preference of a smart medical cart, as in block 4210. The method can further comprise monitoring a noise level output of the smart medical cart, as in block 4220.

The method can also comprise reducing the speed or acceleration of a powered wheel of the wheel subsystem of the smart medical cart when the noise level output exceeds a selected noise level output threshold, as in block 4230. In one embodiment, the selected noise level output threshold can be based on the environmental preference or the user preference of the smart medical cart In one embodiment, the smart medical cart can include a skirt or covering surrounding the outer circumference of the wheels of the wheel subsystem or the wheeled pedestal. The skirt that can be adjusted or changed to alter the noise level output of the smart medical cart. In one embodiment, the height of the skirt or covering can be adjusted relative to the flooring surface. For example, if the smart medical cart identifies that it is operating in a location or at a time when noise is to be reduced, the height of the skirt or covering can be lengthened or lowered so that the skirt or covering is in contact with or approximate the flooring surface. One advantage of a dynamically adjustable skirt or covering is to enable the smart medical cart to reduce the noise level emitted by the smart medical cart and account for other changes in the environment that the smart medical cart is used in, such as a change in the flooring surface and/or slope of the flooring surface.

Figure 43:
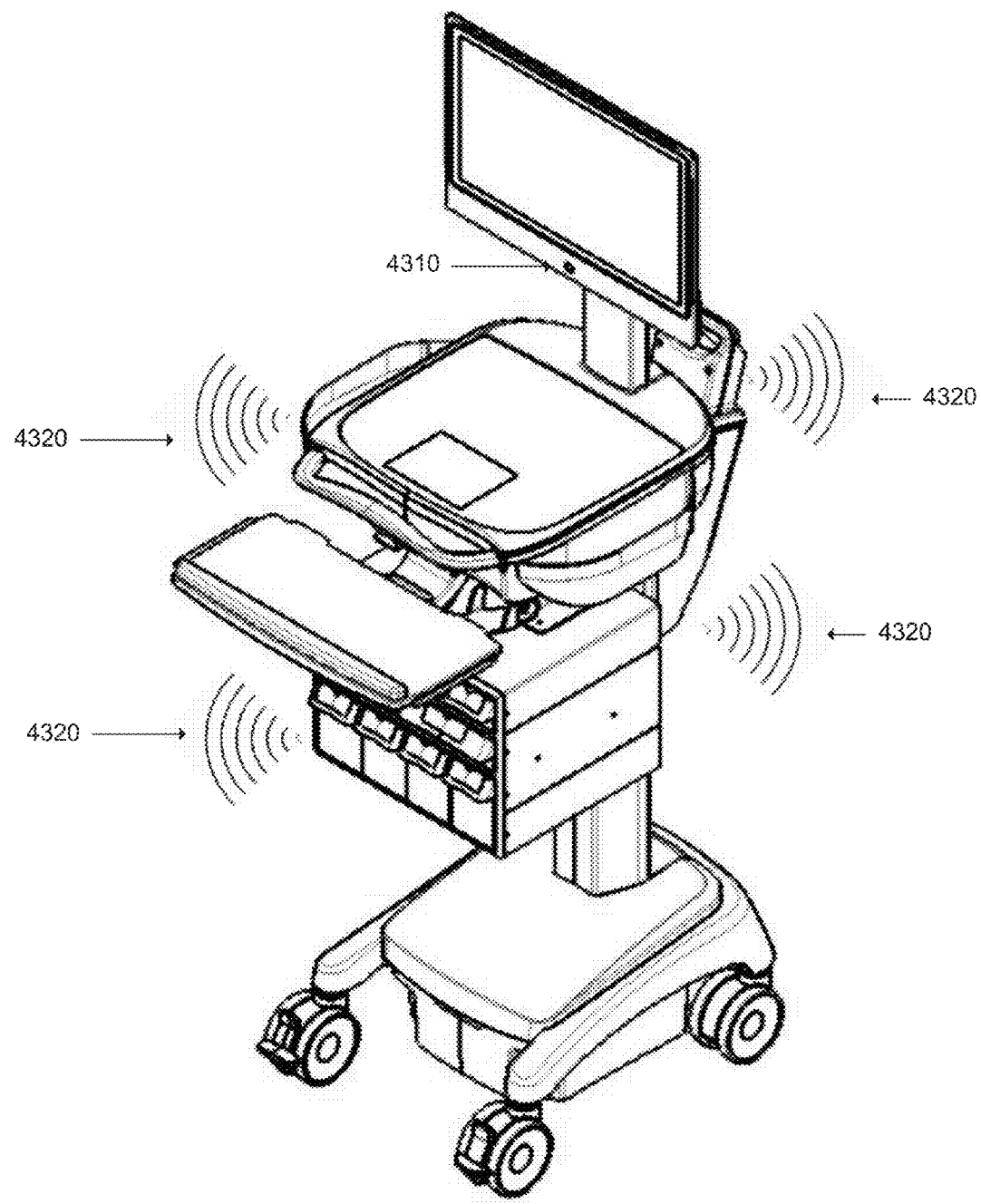
FIG. 43 shows a smart medical cart with an active noise reduction system in accordance with an example.

FIG. 43 shows a smart medical cart with an active noise reduction system. The active noise reduction system can include a noise cancelling subsystem can include a microphone 4310, a noise-canceling module, and one or more speakers 4310. Using the microphone 4310, the noise cancelling subsystem can monitor the ambient noise level, the noise level emitted from the smart medical cart, and/or noise in predetermined frequency ranges approximate the smart medical cart. The noise-canceling module can then be configured to output a signal to one or more speakers 4320 to enable the noise canceling subsystem to emit sound waves that are approximately 180 degrees out of phase with the ambient noise waves or the noise waves emitted from the smart medical cart to cancel or counteract selected noises.

The noise reduction system can include a noise decoupling subsystem to adjust and/or decrease the noise level output of the smart medical cart. Noise decoupling can eliminate vibration transfer of noise in both solid materials and in the air by providing a break between the vibrating solid materials. For example, the smart medical cart can have an inner surface and an outer surface with a gap in between the surfaces for selected areas on the smart medical cart where noise reduction is desired. The gap can reduce or eliminate noise emitted by a part of the smart medical cart, such as the motor, by creating a barrier between the vibrational noise and the outer surface. The barrier between the inner surface and the outer surface can comprise air, fluid, noise reduction materials, and so forth.

Different parts of the smart medical cart can be made from different materials to decouple noise and to adjust and/or decrease the noise level output of the smart medical cart. When a smart medical cart is constructed using all of the same material, such as aluminum, the same material can have a natural frequency that the material vibrates at. When the entire smart medical cart or a large portion of the smart medical cart is constructed using the same material, the natural frequency vibration of each part can reinforce or add to the natural frequency of the other parts made from the same material. In one embodiment, different materials can be used to construct selected parts of the smart medical cart in order to disrupt the natural vibrational frequency of one or more of the materials used on the smart medical cart. In another embodiment, different materials can be used to attach the different parts of the smart medical cart together to disrupt the natural vibrational frequency of one or more of the materials used on the smart medical cart. For example, aluminum can be used for the wheeled pedestal, first and second vertical supports, and the first and second work platforms, while zinc can be used to attach each of the aluminum parts of the smart medical cart together. The aluminum can be used because of its high weight to strength ratio while the zinc can be used for mounting to reduce or eliminate the natural frequency the aluminum can vibrate at during use.

Figure 44A:
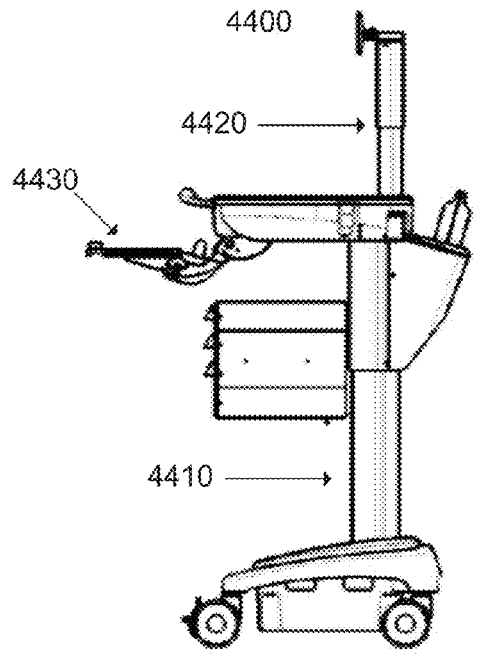
FIG. 44a shows the smart medical cart with a first vertical support adjusted to a maximum height, a second vertical support adjusted to a maximum height, and a second work platform fully extended in accordance with an example.
Figure 44B:
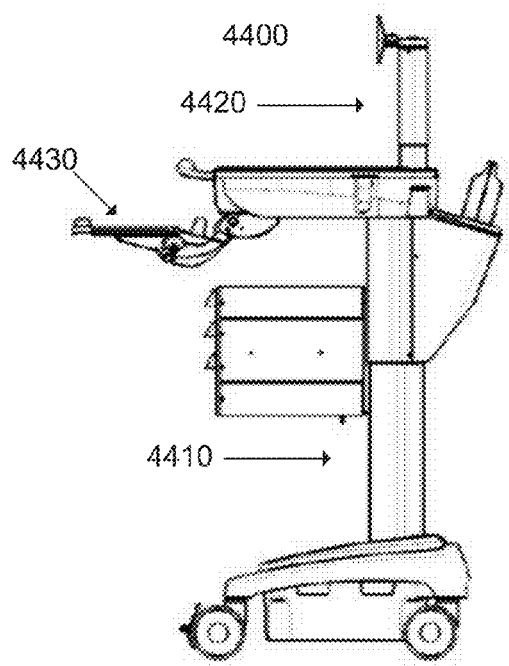
FIG. 44b shows a smart medical cart with a first vertical support adjusted to a maximum height, a second vertical support adjusted to a minimum height, and a second work platform fully extended in accordance with an example.
Figure 44C:
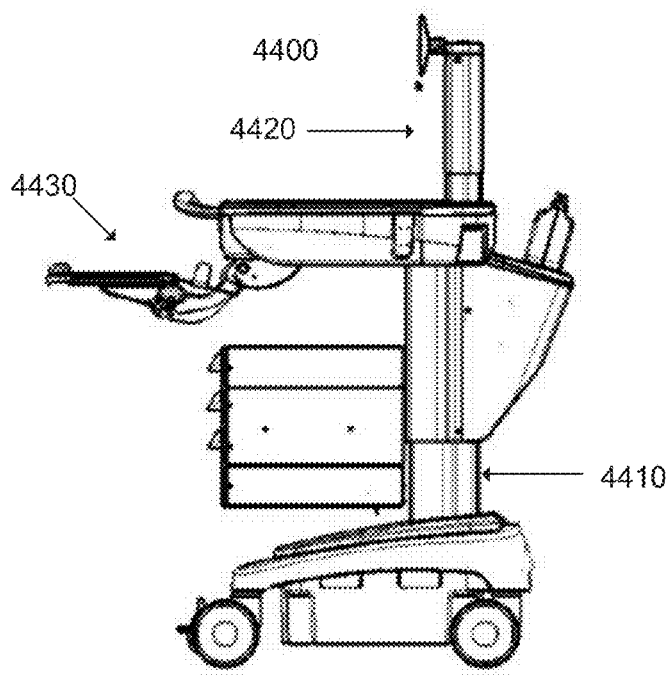
FIG. 44c shows a smart medical cart with a first vertical support adjusted to a minimum height, a second vertical support adjusted to a minimum height, and a second work platform fully extended in accordance with an example.

FIGS. 44*a-c* show that one or more parts of the smart medical cart 4400 can be adjusted. A height of the wheeled pedestal, first vertical support, second vertical support, the first work platform, the second work platform, or the display screen can be adjusted to reduce the vibrational noise level emitted from the smart medical cart. For example, as the height of one or more parts of the smart medical cart is increased, such as the first work platform, the vibration noise emitted from the smart medical cart can also increase. To reduce or decrease the emitted noise, the noise decoupling subsystem can reduce or lower the height or length of one or more selected parts of the smart medical cart to reduce the vibrational noise emitted. FIG. 44*a* shows the smart medical cart 4400 with the first vertical support 4410 adjusted to a maximum height, the second vertical support 4420 adjusted to a maximum height, and the second work platform 4430 fully extended. FIG. 44*b* shows the smart medical cart 4400 with the first vertical support 4410 adjusted to a maximum height, the second vertical support 4420 adjusted to a minimum height, and the second work platform 4430 fully extended. FIG. 44*c* shows the smart medical cart 4400 with the first vertical support 4410 adjusted to a minimum height, the second vertical support 4420 adjusted to a minimum height, and the second work platform 4430 fully extended.

In another embodiment, a noise diffusion module can be used to reduce the noise emitted from the smart medical cart. A noise diffuser can scatter sound in different or in all directions to reduce the overall noise emitted in any given direction. In another embodiment, a white noise module can be used to reduce the noise level emitted by the smart medical cart.

The transfer of vibration or sound from inside of a confined area such as a room to the outside occurs through mechanical connections. The vibrations can pass directly through the brick, woodwork and other solid structural elements. When the vibrations meet with an element such as a wall, ceiling, floor or window, which acts as a sounding board, the vibration can be transmitted or amplified, thereby allowing the vibration to be heard outside the confined area. A mechanical transmission of vibrational energy can be much faster, more efficient and may be more readily amplified than the transmission of vibrations via an airborne transmission of the same initial strength.

The use of acoustic foam and other absorbent means is less effective against this transmitted vibration. To reduce the overall transmission of vibrational energy, an enclosed area can be constructed such that mechanical connections to an area outside the enclosed area are limited.

In one embodiment, the volume or sound level of the computing device or equipment of the smart medical cart may be reduced or silenced based on the environment that the smart medical cart is operating in. The ambient noise level of a typical hospital environment can range from 35 dB during relative quiet periods, such as during the night, to 45 dB during typical operating times, such as during the day. The noise level of the smart medical cart can be measured based on a measurement of the noise level at a given distance from the smart medical cart, such as 1 meter from the smart medical cart. Additionally, the noise level of the smart medical cart can vary logarithmically based on the background noise of the environment in which the smart medical cart is operating in. Also, the frequency spectrum of the ambient noise level can act to reduce, e.g. dull, or increase, e.g. amplify, the noise emitted from the smart medical cart.

Figure 45:
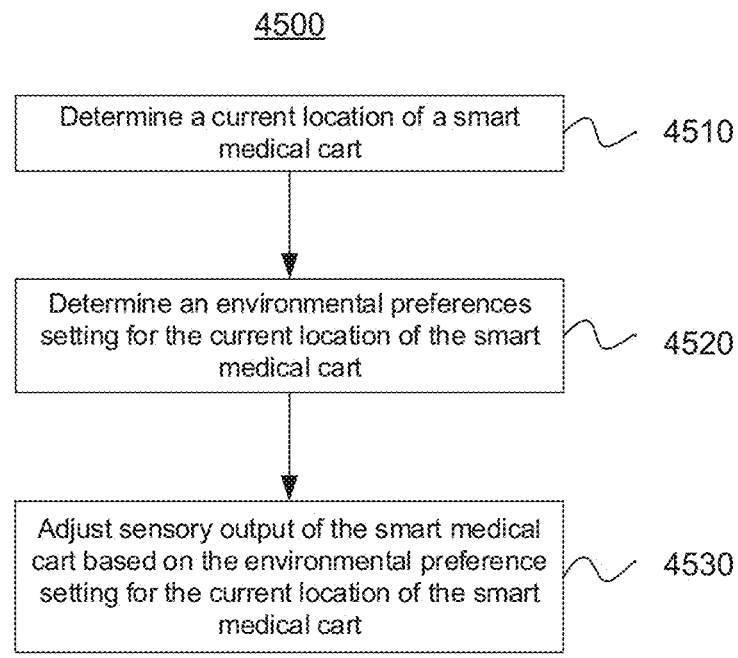
FIG. 45 depicts the functionality of computer circuitry of a user equipment operable to adjust a sensory output of one or more systems, subsystems, or device attached to a smart medical cart in accordance with an example.

FIG. 45 provides a flow chart 4500 to illustrate the functionality of one embodiment of a user equipment, such as a computing device, with computer circuitry operable to adjust a sensory output of one or more systems, subsystems, or device attached to a smart medical cart. The functionality can be implemented as a method or the functionality can be executed as instructions on a machine, where the instructions are included on at least one computer readable medium or one non-transitory machine readable storage medium. The computer circuitry can be configured to determine a current location of a smart medical cart, as in block 4510. The computer circuitry can be further configured to determine an environmental preferences setting for the current location of the smart medical cart, as in block 4520. The computer circuitry can also be configured to adjust a sensory output of the smart medical cart based on the environmental preference setting for the current location of the smart medical cart, as in block 4530. In one embodiment, a sensory output or sensory indication can be an output or indication that relates to one or more of the five sense of an individual, e.g. sight, hearing, taste, smell, and/or touch. For example, a sight indication can be a visual indication, a hearing indication can be auditory indication, a touch indication can be a vibration indication, and so forth.

In one embodiment, the smart medical cart can dynamically and/or automatically adjust the noise level of computing devices and/or medical equipment of the smart medical device. For example, if the smart medical cart is operating in a newborn ward where newborns are often sleeping, then the volume or sound level of the computing device and/or electronic equipment on the medical cart may be reduced or muted. In one embodiment, when the sound or volume level of the computing device and/or equipment is reduced or muted, alternative alerts may be used to inform a caregiver of information. When the smart medical cart is in a location where the volume level is muted, the muted computer device or equipment may vibrate, a light may flash, or an alert or information may be displayed on the computing device or display screen.

As the medical cart is moved in the various medical environments the power assist drive system and/or wheel subsystem can be used to provide power assistance in moving the medical cart. The power, speed, and acceleration of the power assist drive system can be dynamically adjusted to account for various environments and/or the user preferences of different caregivers that may use the smart medical cart. For example, if a large caregiver is using the smart medical cart, the amount of power needed to enable the large caregiver to move the cart at a selected speed may be less than the amount of power needed to assist a smaller caregiver to move the smart medical cart at the same speed. The power assist drive system can adjust the amount of power or assistance provided to aid in moving the smart medical cart based on a user preference of the caregiver. In addition, the speed at which the smart medical cart travels using the power assist drive system can be reduced at selected times or in predetermined locations to reduce noise levels from electric motors, wheels, vibrational noise, or other types of noise caused by movement of the smart medical cart.

In one embodiment, the smart medical cart can make multiple configuration adjustments to customize the smart medical cart to the physique or build of the caregiver. One of the configuration adjustments that can be made to the cart is the height or length of selected parts of the cart, as shown in FIG. 44 and discussed in the preceding paragraphs. In one embodiment, the height of the first work platform and/or the second work platform can be adjusted based on the height of the individual in a standing or sitting position. In another embodiment, the height of the display screen and/or computing device can be adjusted based on the height of the caregiver. In one embodiment, the height of multiple parts of the smart medical cart, such as the height of the work surface, the height of the display screen, and the height of the second work platform can be adjusted based on the physique or build of the caregiver to allow the caregiver to comfortably operate the computing device and other equipment on the smart medical cart. For example, the height of the work surface can be adjusted based on a selected or defined height of the individual, such as a comfortable or optimal height for the user to grab the handle to move the smart medical cart. In addition, the height of the first work platform and/or second work platform relative to the back of the smart medical cart can be adjusted based on the size or physique of the caregiver.

In another embodiment, the height of the display screen can also be adjusted to enable the display screen to be at the eye level of the caregiver. In another embodiment, the distance of the display screen relative to the caregiver can be adjusted to enable the display screen to be at viewable distance for the caregiver. For example, if the caregiver is far or near sighted or has good or bad eyesight, the distance that the display screen is positioned relative to the viewing location of the caregiver can be adjusted. The second work platform height can also be adjusted to provide a comfortable or optimal height for the caregiver to use a peripheral such as a keyboard and mouse.

In one embodiment, height and distance of the first work platform, the second work platform, the handle, and/or the display screen can each be adjusted together to provide an optimal height of each part of the medical cart for the caregiver. For example, if the caregiver has long legs, a short torso, long arms, and is near sighted, the height of a handle used to push the smart medical cart can be increased based on the long leg size, the height of the first work platform can be decreased based on the short torso size, the distance of the second work platform to the caregiver can be increased based on the long arm length, and the height of the display screen and the relative distance of the display screen can be decreased based on the caregiver's short torso and near sight. The height and position of the various components can each be positioned for a selected user. In one embodiment, the positions of these components can be controlled electronically using motors and/or actuators. The positions can be stored electronically for each user. This will be discussed further in the proceeding paragraphs.

In one embodiment, the power source or a power source interface, such as a battery, can be located on the vertical support of the smart medical cart. In one embodiment, the power source can include multiple batteries so that one battery can be exchanged for recharging while the another battery can be used to power the smart medical cart. In one embodiment, the height of the external batteries or the external batteries receptacle can be adjusted. One advantage of adjusting the height of the external batteries or the external batteries receptacle is to enable the caregiver to more efficiently and easily remove or exchange the external batteries. For example, one of the external batteries can weigh several pounds. When the battery is located near the base of a medical cart, the caregiver is required to bend over to remove and replace the battery, which can place undesirable stress and strain on the back of the caregiver. When the height of the battery can be adjusted based on the height of the caregiver, the caregiver can remain upright or nearly upright while exchanging the battery to avoid bending over to lift the external batteries.

In one embodiment, the power, speed, and acceleration of the power assist drive system can be adjusted based on user preferences. In one embodiment, the user preference can be entered manually by the caregiver. In another embodiment, the smart medical cart may use smart algorithms to learn the user preferences of the caregiver and automatically adjust for the user preferences for each caregiver based on the smart algorithms. In another embodiment, the smart medical cart can use a combination of manually input user preferences and smart algorithms to learn user preferences to determine the user preferences of a caregiver. The user preferences can include: the amount of force the user desires to exert to move the smart medical cart at a selected speed or velocity, the rate at which the smart medical cart accelerates, the desired speed at which the smart medical cart will move once it has reached a constant rate of speed, and so forth.

The caregiver can manually input and/or adjust the user preferences by inputting into the smart medical cart the caregiver's desired user preference level for select user preferences. For example, the caregiver can select a user preference of high, medium, or low for selected user preferences. The select user preferences settings can include hardware setting, such as: the height of the first work platform; the height of the second work platform; the height of the display screen or computing device; the sensitivity or responsiveness of the power assist drive system; the amount of force the user desires to exert to move the smart medical cart at a selected speed or velocity; the rate at which the smart medical cart accelerates; the desired speed at which the smart medical cart will move once it has reached a constant rate of speed; and so forth.

The select user preferences can include software settings such as: medication conversion tables; a caregiver's patient list; brightness of the display screen; multiple user operating positions for a selected caregiver, such as a standing or a sitting position; a time of day, such as day and night settings; and so forth. In one embodiment, the user preferences can be stored in an external location, such as a central server of a medical facility in which the smart medical cart is operating. In another embodiment, the user preferences can be stored on the computing device of the smart medical cart.

In another embodiment, the user preferences can be stored on a third party server. In one embodiment, the third party server can be a back-end server. The smart medical cart can communicate to the third party server information collected from the smart medical cart and/or other devices in communication with the smart medical cart. When the third party server receives information from the smart medical cart and/ or other devices in communication with the smart medical cart, the third party server can consolidate or package the information and send the information to a central server or other computing device at the medical facility where the smart medical cart is being used.

In another embodiment, the user preferences can be stored on an external device such as a flash drive or hard drive. The caregiver can log into the smart medical device and the smart medical device can retrieve the user preference information from the computing device, central server, third party server, and/or external device. In one embodiment, the user preferences can be accessed across multiple devices, such as multiple smart medical carts or computing devices. Using the user preference information, the smart medical cart can automatically adjust and customize the smart medical cart's configuration based on the caregiver's preferences.

In another embodiment, the power, speed, and acceleration provided by the power assist drive system can be adjusted for environmental preferences based on the environment in which the smart medical cart is used in. The environmental preference can include: the surface on which the smart medical cart is operating or moving on, such as carpet, tile, concrete or linoleum; the amount of traction that the wheels of the wheel subsystem have for a flooring surface; the time of day; if the medical cart is located a highly populated area or a lower populated area; if the smart medical cart is in a highly congested and/or tight quarters environment or a low congestion and/or open area; and so forth.

Figure 46:
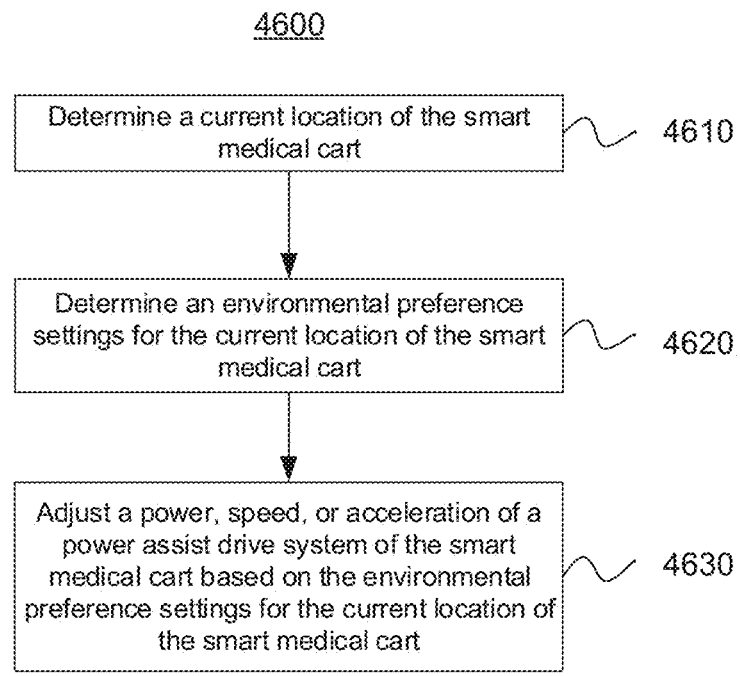
FIG. 46 depicts the functionality of computer circuitry of a user equipment operable to adjust a power, speed, or acceleration output of a power assist drive system of a smart medical cart in accordance with an example.

FIG. 46 provides a flow chart 4600 to illustrate the functionality of one embodiment of a user equipment, such as a computing device, with computer circuitry operable to adjust a power, speed, or acceleration output of a power assist drive system of a smart medical cart. The functionality can be implemented as a method or the functionality can be executed as instructions on a machine, where the instructions are included on at least one computer readable medium or one non-transitory machine readable storage medium. The computer circuitry can be configured to determine the current location of the smart medical cart, as in block 4610. The computer circuitry can be further configured to determine an environmental preference setting for the current location of the smart medical cart, as in block 4620. The computer circuitry can also be configured to adjust a power, speed, or acceleration output of a power assist drive system of the smart medical cart based on the environmental preference setting for the current location of the smart medical cart, as in block 4630.

The velocity, acceleration, and/or speed of the smart medical cart using the power assist drive system can be proportional to the amount of current being drawn by the motors to drive each wheel of the wheel subsystem. The feedback from the encoders, such as positional data, can be combined with the current or voltage being drawn by the drive motors to determine if the wheels are rotating at a predetermined rate for a selected load. The encoder feedback can include current and/or voltage usage measurements from the power assist drive system. The encoder feedback can also be used to determine the traction or slippage of the wheels of the wheel subsystem. For example, when there is a high current output but no movement of the encoders in the wheels, then the smart medical cart is not moving, is stuck, or the braking subsystem may be engaged. In another example, when there is a high current output and the encoders in the wheels are rotating at a higher than expected rate, it can be determined that the wheels of the smart medical cart may be slipping or experiencing low traction. When current output for a selected load and rate of speed is within a desired range, and the encoders in the wheels are rotating at a selected rate for the current sent to the motors, it can be determined that the smart medical cart is likely moving and the wheels have traction on the flooring surface.

Figure 47A:
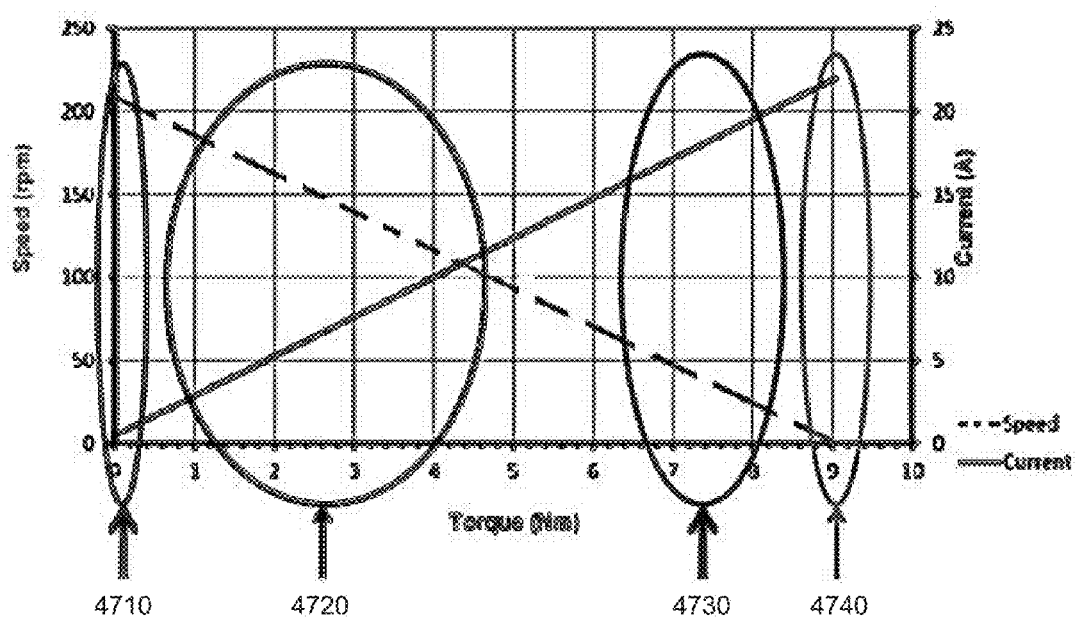
FIG. 47a shows a graph of speed versus torque applied by one or more motors to one or more wheels in accordance with an example.

FIG. 47a shows a graph 4700 of speed versus torque applied by one or more motors to one or more wheels. Circle 4710 shows a very low torque output, very lower current draw, and very high velocity of the motors, indicating that the one or more of the wheels is slipping. Circle 4720 shows a low torque output, lower current draw, and high velocity of the motors, indicating the wheels are operating within normal operational limits. The range or scope of circle 4720 shows that the wheels of the smart medical cart can operate at differently depending on a weight of the smart medical cart and/or a weight of one or more devices attached to the smart medical cart. Circle 4730 shows a high torque output, high current draw, and low velocity of the motors, indicating a normal engagement of the wheels when the smart medical cart is beginning to more from a stopped or standstill position to a moving position. In one embodiment, the smart medical cart can take approximately 1-5 seconds to transition from a standstill position to a moving position. Circle 4740 shows a very high torque output, very high current draw, and very low or zero velocity of the motors, indicating that an object is impeding the movement of the smart medical cart.

Figure 47B:
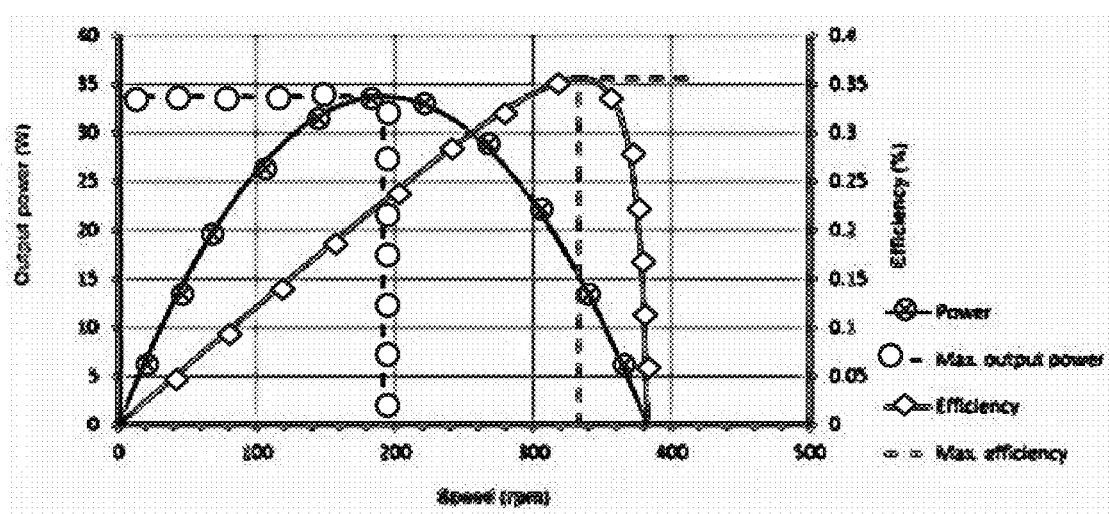
FIG. 47b illustrates a graph of a change in efficiency for different power outputs.

FIG. 47b illustrates a change in efficiency for different power outputs, measured in watts (W), versus different speeds, measured in revolutions per minute (RPM). In one embodiment, a maximum power output can be reached at approximately 200 RPM and a maximum efficiency can be reached at approximately 340 RMP. As the RPMs increase from 0 to 200 RMPs the efficiency and power one or more wheels of the smart medical cart increase. When one or more wheels of the smart medical cart reach approximately 195 RPM a maximum power can be reached, and the power decrease for RPMs exceeding 195 RPM. When one or more wheels of the smart medical cart reach approximately 330 RPM a maximum efficiency can be reached, and the efficiency decrease for RPMs exceeding 330 RPM. At approximately 265 RPM the overall combination maximum of a combined power and efficiency can be reached.

Figure 47C:
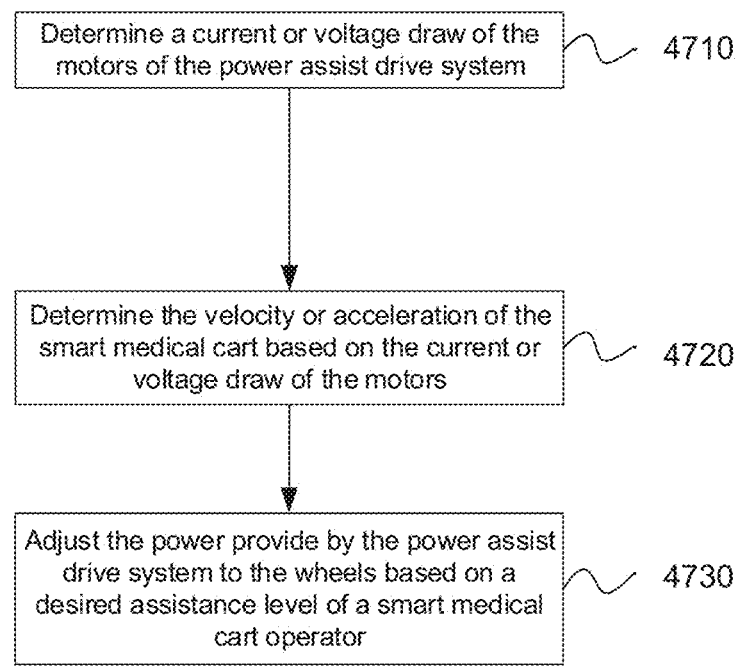
FIG. 47c depicts the functionality of computer circuitry a user equipment operable to adjust a level of power assistance provided to an operator of the smart medical cart in accordance with an example.

FIG. 47c provides a flow chart 4700 to illustrate the functionality of one embodiment of a user equipment, such as a computing device, with computer circuitry operable to adjust a level of power assistance provided to an operator of the smart medical cart. The functionality can be implemented as a method or the functionality can be executed as instructions on a machine, where the instructions are included on at least one computer readable medium or one non-transitory machine readable storage medium. The computer circuitry can be configured to determine a current or voltage draw of one or more motors of a power assist drive system, as in block 4710. The computer circuitry can be further configured to determine a velocity or acceleration of the smart medical cart based on the current or voltage draw of one or more of the motors, as in block 4720. The computer circuitry can also be configured to adjust the power provided by the power assist drive system to the one or more wheels based on a desired assistance level of the operator of the smart medical cart, as in block 4730.

In one embodiment, the smart medical cart can determine the flooring surface that the smart medical cart is moving along by analyzing the coefficient of friction of the flooring surface. When a higher level of current is used to move the smart medical cart, the higher current level can indicate that there is a higher coefficient of friction and the smart medical cart can be on a flooring surface such as carpet. When a lower level of current is used to move the smart medical cart, the lower current level can indicate that there is a lower coefficient of friction and the smart medical cart can be on a flooring surface such as tile or cement. The amount of current sent to the wheels can be reduced, or increased at a relatively slow rate, based on the flooring surface on which the smart medical cart is operating to reduce or eliminate slippage of the wheels on the surface on which they are operating when using the power assist drive system.

The environment preferences can be adjusted based on user preference input. In one embodiment, the smart medical cart can compare the environmental preferences and the user preferences with the current smart medical cart output. For example, the smart medical cart can check encoder and current feedback of the power assist drive system to verify that the smart medical cart is operating within the environmental preference limits.

The amount of traction that the wheels of the wheel subsystem experience can be determined by a traction control sensor or an anti-slip sensor. For example, the smart medical cart may determine there is a decrease in the amount of traction of one or more of the wheels in the wheel subsystem. When the smart medical cart determines a decrease in the traction of a wheel, the smart medical cart may decrease the power, speed, and/or acceleration of the wheel, apply a brake to the wheel, adjust the speed or power to other wheels in the wheel subsystem, or take other actions to allow the wheel to regain traction.

In one embodiment, the smart medical cart can provide warnings or indications to the caregiver for selected situations. The selected situations may include: the loss of traction; the traction control subsystem engagement; change in the center of gravity; the speed the cart is moving; a pedometer; a site map of the location of the smart medical cart; the location of other smart medical carts, patients, caregivers, and other individuals; possible collisions; a tipping over warning; and so forth. The warnings or indications can provide the caregiver with precautionary warnings and/or recommendations. For example, when the caregiver leans on the smart medical cart, increasing the probability that the smart medical cart will tip over, the smart medical cart can provide a warning to the caregiver to indicate to the caregiver to not lean on the smart medical cart or place additional weight on the smart medical cart.

As the environment in which the medical cart operates changes, the smart medical cart can be moved along flat surfaces, inclining surfaces, or declining surfaces. In one embodiment, the smart medical cart can adjust the amount of power, speed, and/or acceleration provided to the wheels of wheel subsystem by the power assist drive system based on the environment that the smart medical cart is located. For example, as the smart medical cart changes from moving along a flat surface to moving along an inclining surface, the power assist drive system can provide additional power to the wheel subsystem in order to maintain the same power, velocity, and/or acceleration that the cart was moving at on the flat surface. In one embodiment, the smart medical cart can use a three dimensional accelerometer and/or a gyroscope to determine when the smart medical cart is moving along an inclining, flat, or declining surface. In another example, when the smart medical cart changes from moving along a flat surface to moving along a declining surface, the power assist drive system can reduce the power to the wheel subsystem in order to maintain the same power, velocity, and/or acceleration that the cart was moving at on the flat surface. In one embodiment, the smart medical cart can apply or release the brakes of a braking subsystem to the wheels of the wheel subsystem in order to reduce or maintain the speed and velocity of the smart medical cart at a desired rate.

Where the smart medical cart can be used in various environments, the flooring surface that the smart medical cart moves on can vary. The flooring surface of the various environments can include carpet, linoleum, granite, cement, tile, and so forth. The various flooring surfaces can have a variety of different flooring surface properties. Each different type of flooring can change the way in which the wheels of the smart medical cart operate. For example, differences can include: different amounts of drag for the wheels of the wheel subsystem, different amounts of traction for the wheels of the wheel subsystem, different levels of depression of the wheels of the wheel subsystem into the different types of flooring surfaces, and so forth. The smart medical cart can dynamically and/or automatically adjust voltage or current outputs from the power assist drive system to one or more of the wheels of the wheel subsystem for the various flooring surface properties.

In one embodiment, the smart medical cart can dynamically and/or automatically adjust one or more of the wheels of the wheel subsystem by raising or lowering the height of each wheel relative to other wheels. In one embodiment, the downward pressure may be dynamically or automatically adjusted using spring loaded coils, hydraulics, gas coils, or other shock systems attached to the wheels of the wheel subsystem. In another embodiment, the downward pressure may be adjusted manually such as by adjusting a jack, using a ratcheting system, and so forth.

Figure 48A:
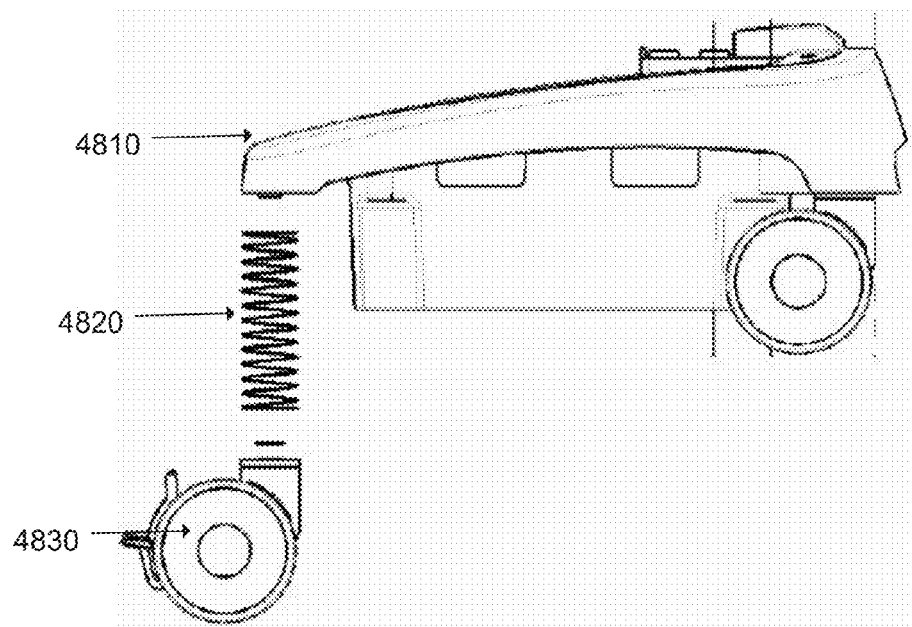
FIG. 48a shows spring loaded coils for dynamically adjusting a height of a wheel of the wheeled pedestal in accordance with an example.
Figure 48B:
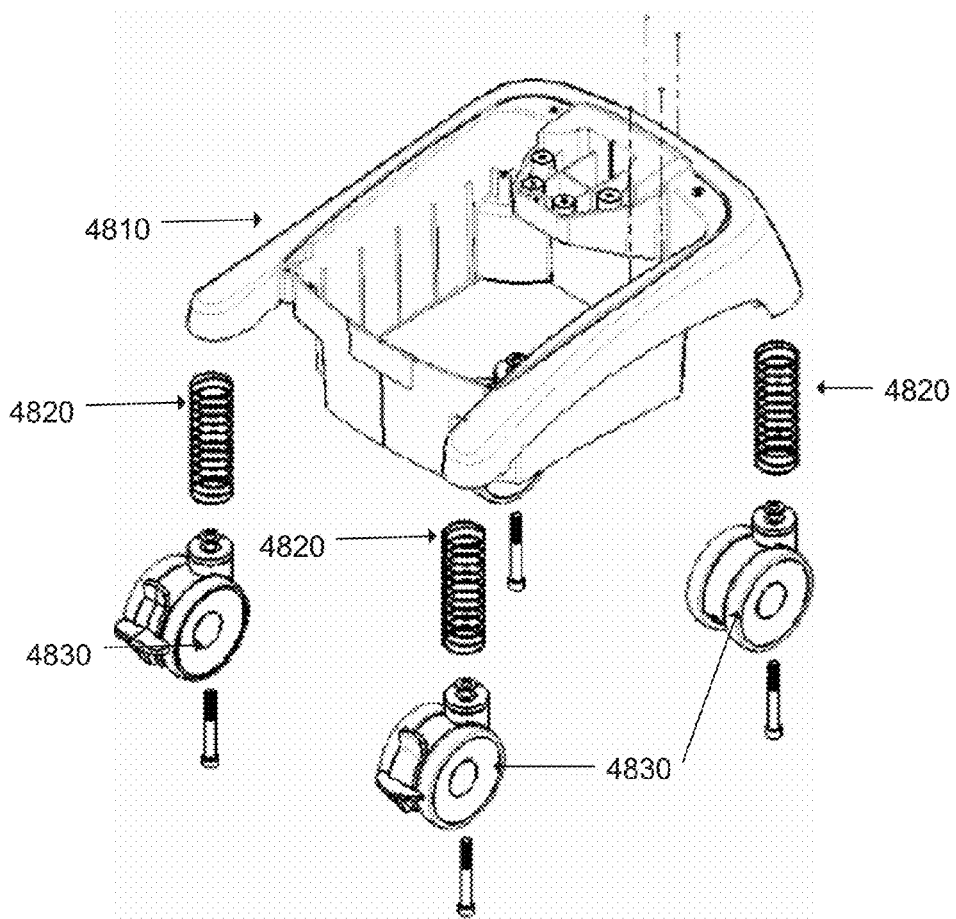
FIG. 48b depicts a perspective view of adjusting a plurality of wheels of a wheeled pedestal in accordance with an example.
Figure 49A:
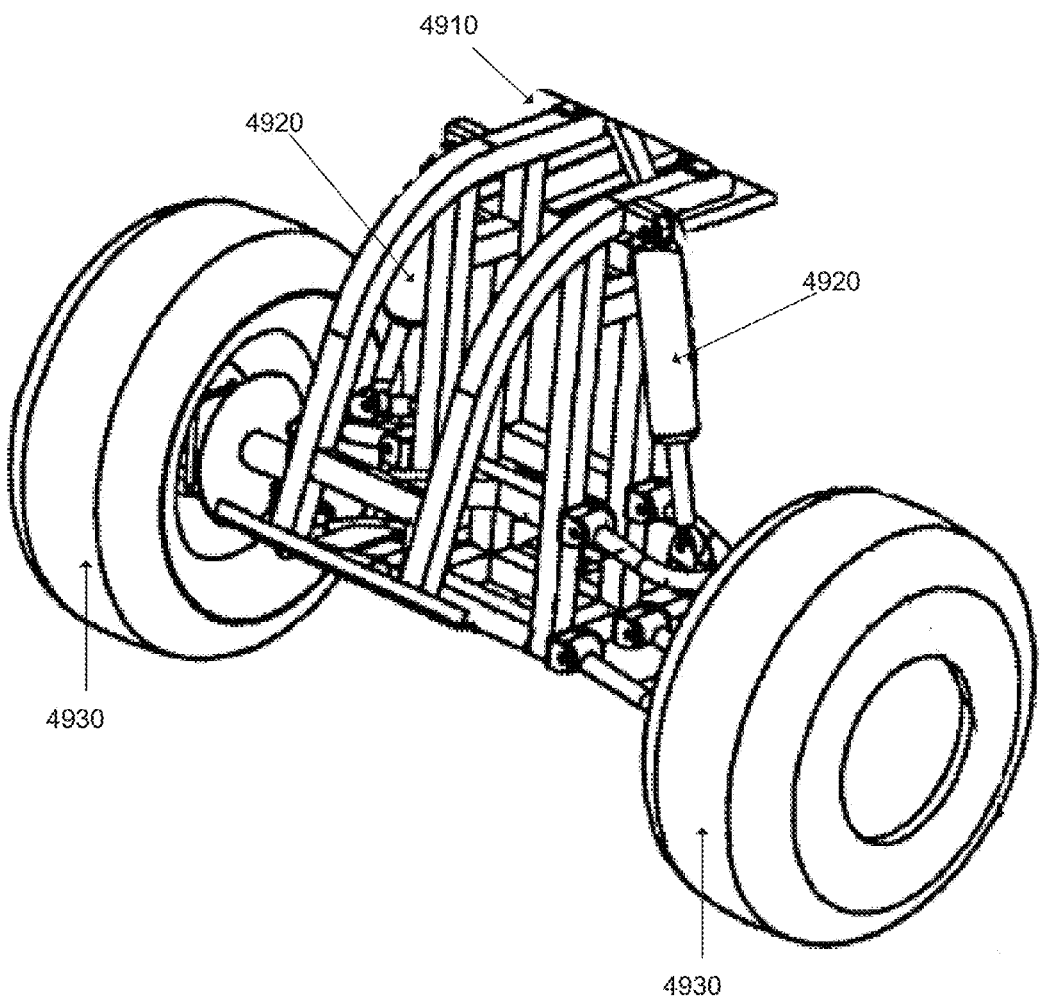
FIG. 49a shows shocks for dynamically adjusting a height of the wheels of the wheeled pedestal in accordance with an example.

FIGS. 48a and 48b depict a side view of adjusting a wheel 4830 of the wheeled pedestal 4810. FIG. 48a shows using spring loaded coils 4820 to dynamically adjust the height of the wheel 4830 of the wheeled pedestal 4810. FIG. 48b depicts a perspective view of adjusting a plurality of wheels 4830 of the wheeled pedestal 4810. FIG. 48b shows using spring loaded coils 4820 to dynamically adjust the height of the wheels 4830 of the wheeled pedestal 4810. FIG. 49 depicts a side view of adjusting the wheels 4930 of the wheeled pedestal 4910. FIG. 49a shows using shocks 4920a to dynamically adjust the height of the wheels 4930a of the wheeled pedestal 4910a.

In another embodiment, the smart medical cart can dynamically and/or automatically adjust one or more of the wheels of the wheel subsystem by increasing or decreasing the power provided by the power assist drive system to each of the wheels. In another embodiment, the smart medical cart can dynamically and/or automatically adjust one or more of the wheels of the wheel subsystem by increasing or decreasing the weight distribution or downward pressure on each of the wheels.

The smart medical cart can dynamically and/or automatically adjust one or more of the wheels of the wheel subsystem for surface level changes in the flooring surface. In one embodiment, the downward pressure of one or more of the wheels of the wheel subsystem may be adjusted when the smart medical cart is moved from a first flooring surface level to a second flooring surface level. For example, the downward pressure of one or more of the wheels of the wheel subsystem may be adjusted when the smart medical cart is moved from a ground floor flooring surface level to an elevator flooring surface level. When the flooring surface level of the first flooring changes to the second flooring surface level, there can be a gap in the flooring surface level and/or a difference in elevation between the first flooring surface level and the second flooring surface level. When the smart medical cart moves from the first flooring surface level to the second flooring surface level, the vertical wheel positions of the one or more wheels of the wheel subsystem can be adjusted upward or downward to compensate for the difference in elevations of the flooring surface levels. In one embodiment, the vertical wheel positions of the one or more wheels of the wheel subsystem can be adjusted upward or downward to force contact between the wheels of the wheel subsystem and the flooring surface.

In one embodiment, the one or more motors of the power assist drive system can each be mounted on a different shock or housing of a shock subsystem. The different shock or housing for each of the motors can enable elevation changes of the motors that correlate with the different elevations of the wheels. The shock subsystem can be connected to the wheeled pedestal, covering, storage area, vertical support, and so forth. In one embodiment, a shock subsystem can include a shock plate attached one or more of the motors.

Figure 49B:
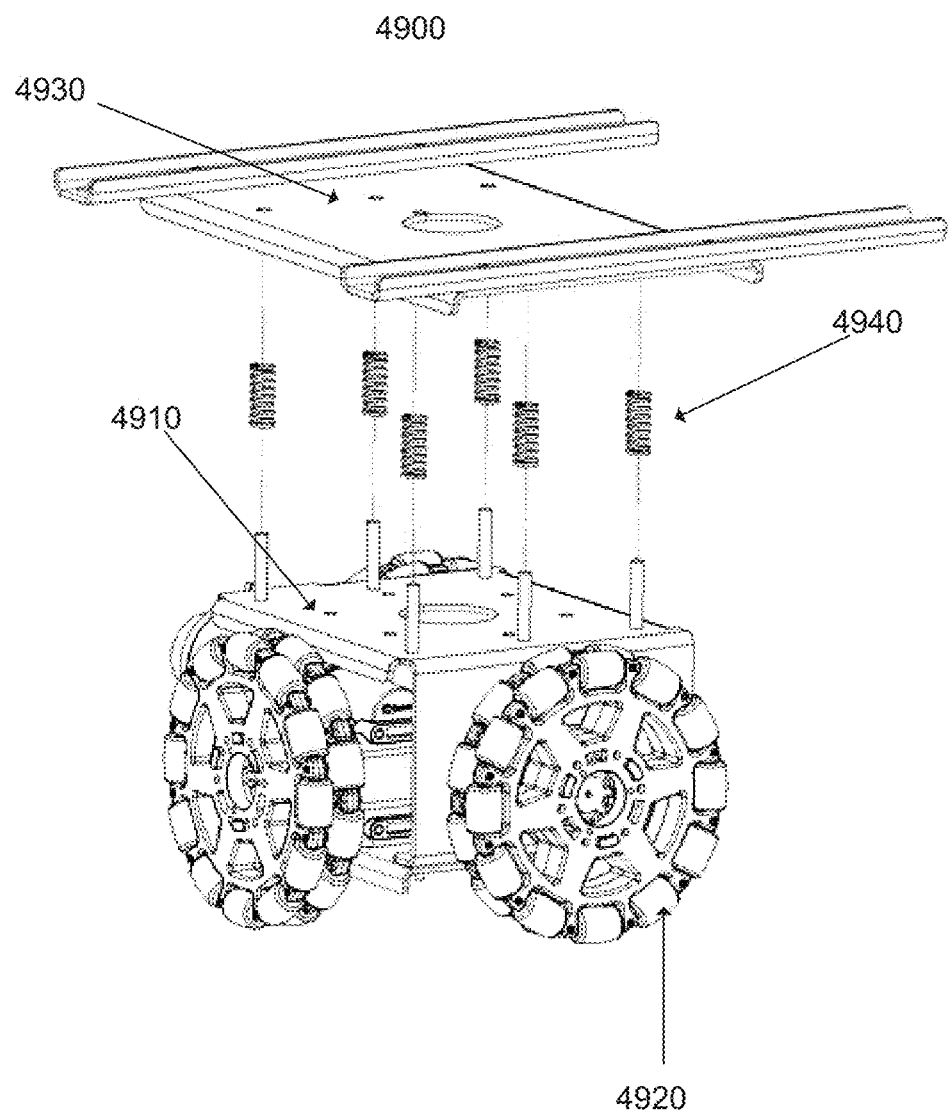
FIG. 49b depicts a power assist drive system with a motor housing and a shock plate in accordance with an example.

In another embodiment, one or more motors of the power assist drive system can be mounted in a motor housing. FIG. 49b depicts a power assist drive system 4900 with a motor housing 4910, a plurality of wheels 4920, a shock plate 4930, and shocks or coils 4940. FIG. 49b shows the motor housing 4910 attached to the bottom side of the shock plate 4930 with shocks or coils 4940 located between the motor housing 4910 and the shock plate 4930. The wheels 4920 of the wheel subsystem can be mounted to one or more motors of the motor housing 4910.

As the wheels 4920 move along different flooring surfaces and/or encounter different elevations of flooring surfaces, the wheels 4920 can place upward or downward pressure on the motor housing 4910. The motor housing 4910 can transfer the upward or downward pressure from the wheels to the shock plate 4930 using one or more shocks or coils 4940. Based on the upward or downward pressure of the motor housing 4910 on the shock plate 4930, the shocks or coils 4940 can move upward or downward to compensate for the wheels 4920 of a smart medical cart moving along different flooring surfaces and/or encountering different elevations of flooring. In another embodiment, the shocks or coils 4940 can be hydraulics shocks, gas loaded shocks, or spring loaded shocks.

For example, the smart medical cart can be moved from a carpeted flooring surface to a cement flooring surface. The carpeted flooring surface can allow the wheels to extend further into the flooring surface because the carpet can be a less rigid flooring surface. As the smart medical cart moves to the cement flooring surface, the cement flooring surface can be a more rigid flooring surface and can cause upward pressure on the wheels. The upward pressure on the wheels will be transferred to the shocks of the shock plate for each motor and the shocks can compress to compensate for the different flooring surface. The shocks of the shock plate can be adjusted based on the environment that the smart medical cart is used in. In one embodiment, load sensors can be attached to the motors or the shock plate to measure the force or deflection by the wheels as the move along various flooring surfaces or change in the flooring surface elevation.

When the smart medical cart moves along different flooring surfaces, such as flat flooring surfaces, inclining flooring surfaces, or declining flooring surfaces, the center of gravity of the smart medical cart may change or shift. For example, as the smart medical cart is moved along a declining surface, the center of gravity of the smart medical cart may shift from a lower location on the smart medical cart to higher location on the smart medical cart. Additionally, as equipment, supplies, and containers are attached or added to the smart medical cart, the center of gravity of the smart medical cart may also change or shift.

Figure 50A:
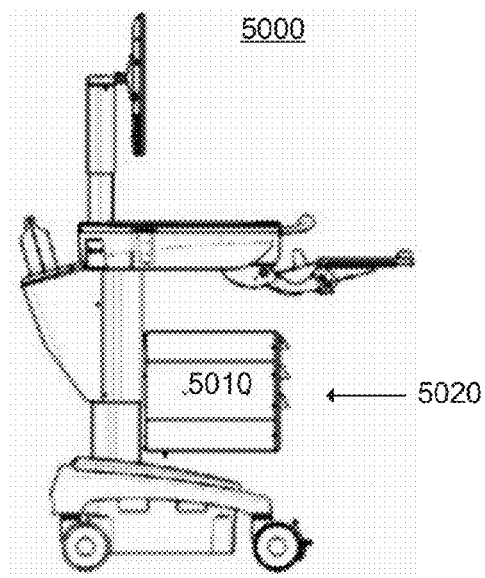
FIG. 50a depicts a side view of a smart medical cart with medication drawers of a medication storage container in the closed position in accordance with an example.
Figure 50B:
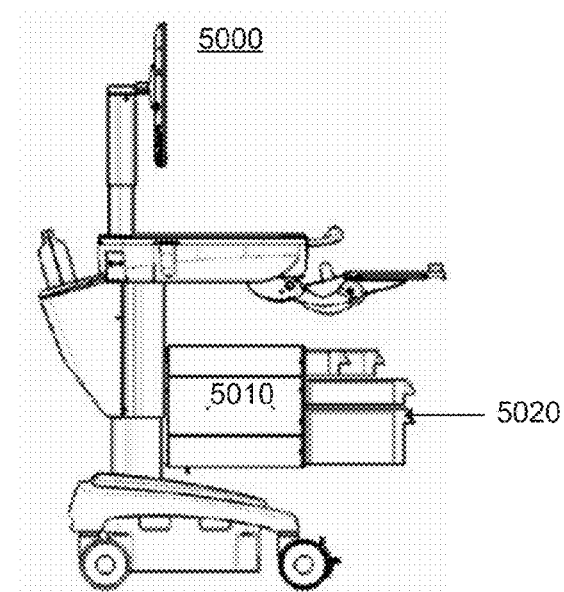
FIG. 50b depicts a side view of a smart medical cart with medication drawers of a medication storage container in an open position in accordance with an example.
Figure 50C:
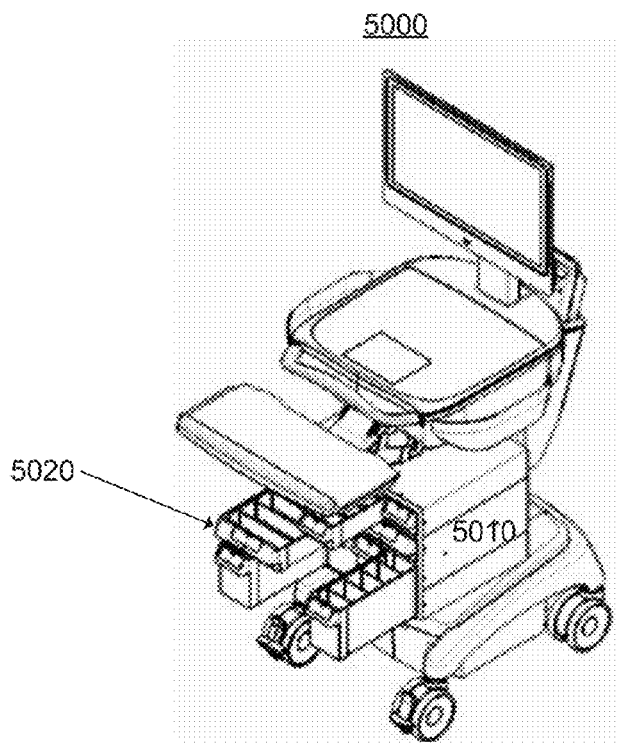
FIG. 50c depicts a perspective view of a smart medical cart with medication drawers of a medication storage container in an open position in accordance with an example.

FIGS. 50a-50c illustrate a smart medical cart 5000 with a medication storage container 5010 that has medication drawers 5020. FIG. 50a depicts a side view of the smart medical cart 5000 wherein the medication drawers 5020 of the medication storage container 5010 are in the closed position. FIG. 50b depicts a side view of the smart medical cart 5000 wherein the medication drawers 5020 of the medication storage container 5010 are in the open position. FIG. 50c depicts a perspective view of the smart medical cart 5000 wherein the medication drawers 5020 of the medication storage container 5010 are in the open position. In one embodiment, when a container, such as the medication storage container 5010, is added to the smart medical cart 5000 to store medication or medical supplies the center of gravity of the smart medical cart will shift as more or less medication or supplies are stored in the medication drawer 5020 of the medication storage container 5010. In another embodiment, when the medication drawers 5020 of the medication storage container 5010 change from a closed to an open position or vice versa, the center of gravity of the smart medical cart 5000 can change.

In one embodiment, the smart medical cart can determine the height and/or location of one or more parts or sensors of the smart medical cart relative to another object, such as the flooring surface. When the height and/or location of one or more parts or sensors of the smart medical cart relative to another object changes, the smart medical cart can use the height change to determine a change in the center of gravity and/or a change in the probability of the smart medical cart tipping over at a selected speed. In another embodiment, the smart medical cart can include a cord or clip that is worn by the caregiver and attaches to the smart medical cart, such as the handle of the smart medical cart. In one embodiment, when the cord or clip is disconnected from the smart medical cart, the smart medical cart can slow and stop the smart medical cart until the cord or clip is reattached. In another embodiment, the smart medical cart can determine a change in the center of gravity and/or a change in the probability of the smart medical cart tipping over at selected speed by determining the tension between the where the cord or clip is attached to the smart medical cart and the caregiver.

In one embodiment, the smart medical cart can use one or more accelerometers to measure acceleration forces, such as meters per second squared (m/s2), or gravitational forces (g-forces) that are applied to one or more locations on the smart medical cart. In one embodiment, the one or more accelerometers can measure the acceleration forces or g-forces on three physical axes, e.g. the x axis, y axis, and z axis. In one embodiment, the accelerometer can measure the inertial acceleration due to external forces. In another embodiment, an accelerometer can sum all forces applied to the smart medical cart.

In another embodiment, the smart medical cart can use gravity sensors to determine a change in the center of gravity of the smart medical cart. A gravity sensor can measure the force of gravity or gravity acceleration in cm/s2 that is applied to a device on three physical axes, e.g. the x axis, the y axis, and the z axis. A gravity sensor can measure the gravitational field and can measure minor changes in gravity, such as 1 gravimeter. In one embodiment, a gravity sensor can be used in combination with an accelerometer to more accurately measure forces applied to the smart medical cart.

In another embodiment, the smart medical cart can use a gyroscope to determine a change in the center of gravity of the smart medical cart. A gyroscope can measure rate of rotation of the smart medical cart in rad/s around each of the three physical axes.

In another embodiment, the smart medical cart can use pressure sensors to determine a change in the center of gravity of the smart medical cart. The pressure sensors can measure mechanical stress (e.g. pressure) at mounting points where pressure sensors are located. Changes in mechanical stress can be used to indicate a potential for the smart medical cart to tip over. For example, for different heights and mechanical configurations of the medical cart, a threshold pressure value can be set for each sensor for a selected range of velocities and accelerations in a selected direction. If the threshold pressure value is exceeded, predetermined changes can be made to the acceleration, velocity, direction, and/or the physical configuration of the smart medical cart. For example, the center of gravity of the smart medical cart can be reduced by reducing a height of components on the smart medical cart relative to the ground. The velocity can be momentarily reduced or accelerated to reduce the risk of tipping for the smart medical cart.

In another embodiment, in order to keep the smart medical cart upright and avoid the smart medical cart tipping over, a center of gravity or center of mass of the smart medical cart can be dynamically and/or automatically adjusted. In one embodiment, the smart medical cart can detect a change in the center of gravity and/or the smart medical cart reaching a tipping point using a gyroscope, an accelerometer, a 3 dimensional (3D) or 3-axis accelerometer, a pressure sensor, and so forth. In one embodiment, to adjust the center of gravity of the smart medical cart, a mass that is located at or near a bottom of the smart medical cart can be dynamically changed or redistributed.

Figure 51A:
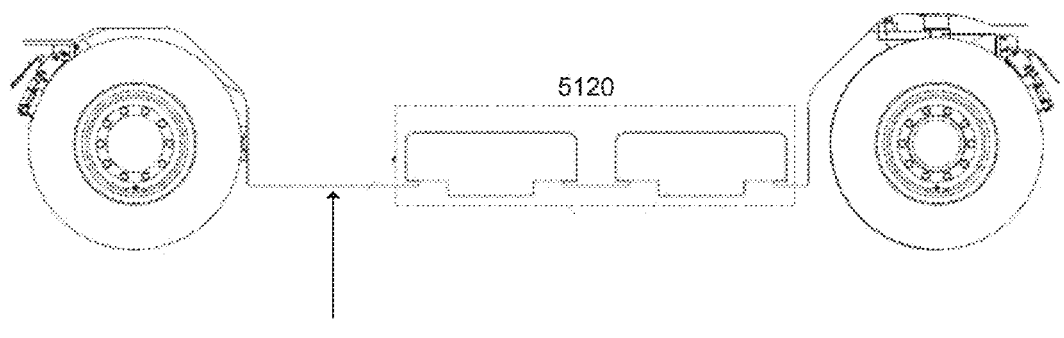
FIG. 51a shows weights that can be moved to different locations to redistribute the weight of the wheeled pedestal in accordance with an example.
Figure 51B:
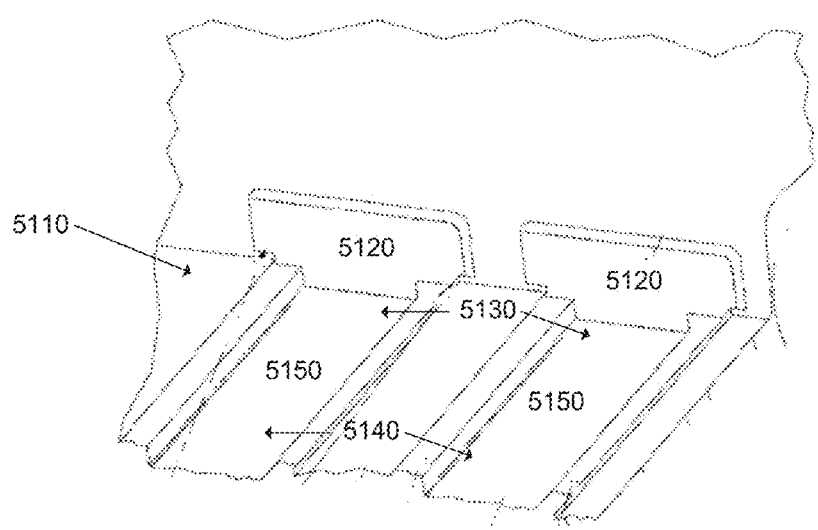
FIG. 51b shows an exposed view of weights attached to the wheeled pedestal in accordance with an example.

In one embodiment, a weight distribution on the smart medical cart can be changed by shifting or moving masses, which are referred to as weights, to different locations on the smart medical cart, such as different locations in storage area of the cover or in the wheeled pedestal of the smart medical cart. FIG. 51*a* shows an exemplary embodiment of weights 5120 that can be moved to different locations to redistribute the weight of the wheeled pedestal 5110 to adjust the center of gravity of a smart medical cart. FIG. 51*a* shows an exposed side view of weights 5120 attached to the wheeled pedestal 5110. FIG. 51*b* shows an exposed view of the weights 5120 attached to the wheeled pedestal 5110. In FIG. 51*b*, the weights 5120 can initially be located at a selected location 5130. The location of the weights 5120 can be adjusted by moving the weights, such as using an electric motor and/or and actuator, along a channel 5150 to a second selected location 5140. When the location of the weights 5120 is changed from the initial selected location 5130 to the second selected location 5140, the center of gravity of the smart medical cart can be adjusted, such as to avoid the smart medical cart tipping over.

In one embodiment, the weights 5120 can be shifted or moved using a pneumatic arm or electric motor. In one embodiment, linear actuators can be used in conjunction with a motor to move the weights 5120. In another embodiment, the mass can comprise a liquid that is contained in one or more compartmentalized fluid containers. The fluid containers can be positioned at selected locations of the smart medical cart, such as the wheeled pedestal and/or storage area of the covering. The liquid can be shifted or moved between the one or more fluid containers to maintain or adjust the center of gravity of the smart medical cart, thereby reducing a risk of the smart medical cart tipping over. In one embodiment, a pump or bellow can be used to transfer or move the fluid from one location on the smart medical cart to another location on the smart medical cart.

In another embodiment, the center of gravity of the smart medical cart can be maintained by adjusting the amount of power, speed, and/or acceleration of one or more of the wheels in the wheel subsystem. In another embodiment, the height of the first work platform and/or second work platform may be lowered or raised to adjust the center of gravity of the smart medical cart. For example, if the smart medical cart is moving along an inclining surface and the center of gravity shifts toward the top of the smart medical cart and increases the probability that the smart medical cart may tip over, the smart medical cart can decrease the height of the first work platform or the second work platform in order to lower the center of gravity to an acceptable level or below a selected probability of tipping over threshold.

In another embodiment, the location of the power source, such as one or more of the external batteries, can be changed to adjust the center of gravity. For example, the one or more external batteries can usually be located near the upper portion of the vertical support, where the vertical support attaches to the first work platform. In this example, when the center of gravity moves to a location that would increase the probability of the smart medical cart tipping over, the one or more external batteries can be dynamically, manually, or automatically adjusted to be moved to a different location, such as lower along the vertical support near where the vertical support attaches to the wheeled pedestal. One advantage of adjusting the height of the first work platform, second work platform, and/or the location of the power source to adjust the center of gravity of the smart medical cart can be to reduce the probability of the smart medical cart tipping over.

In another embodiment, the smart medical cart may include a gyroscope to adjust or move the center of gravity of the smart medical cart. The gyroscope can be one or more spinning wheels or discs that can freely move along one or more axles and assume any orientation. When the smart medical cart determines that the probability of tipping over has exceed a selected threshold or the center of gravity has shifted, the smart medical cart can change or adjust one or more axis or directions that the discs or wheels of the gyroscope can spin. The change in rotation of the gyroscope can be used to offset a change in the center of mass of the smart medical cart to reduce the probability of the smart medical cart tipping.

In another embodiment, the radius of the wheeled pedestal can be increased or decreased to adjust the center of gravity in the cart or to enable a higher center of gravity without increasing a probability of tipping over the smart medical cart. In one embodiment, the wheeled pedestal includes telescoping legs or arms to which the wheels of the wheel subsystem can be attached. The radius of the wheeled pedestal may be increased or decreased using telescoping legs or arms. For example, when the center of gravity approaches a selected tipping over probability threshold the smart medical cart, the radius of the wheeled pedestal may be increased to lower the center of gravity and provide additional stability to the smart medical cart. In another embodiment, a rotary motion could be used to generate a gyroscopic motion to enable a dynamic change of the center of gravity of the smart medical cart.

Figure 51C:
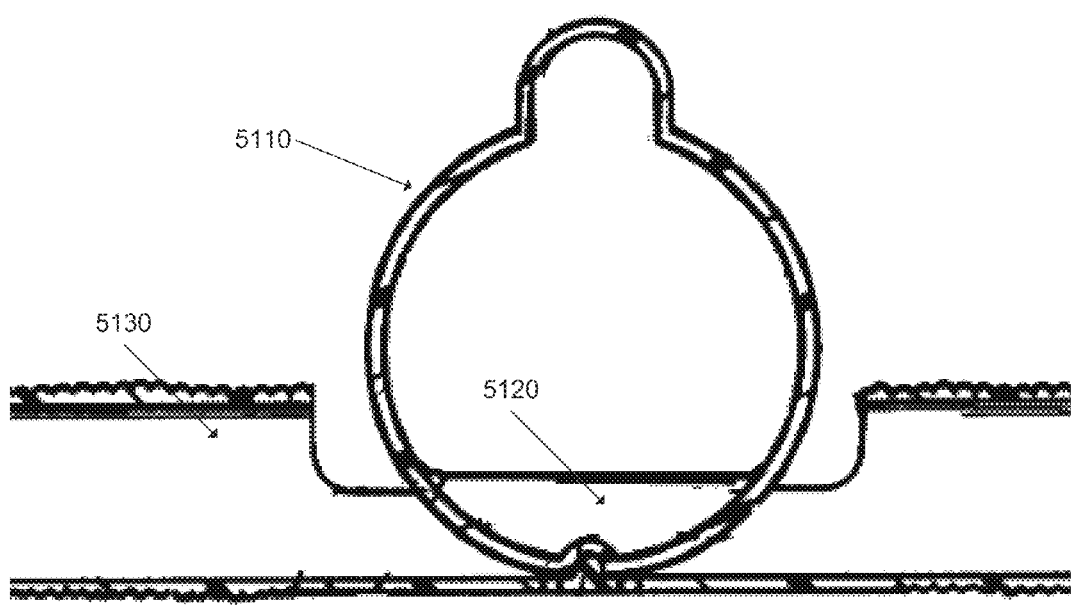
FIG. 51c illustrates a ballast weight in accordance with an example.

In one embodiment, the center of gravity can be adjusted using a ballast or weight pendulum. The ballast or weight pendulum can be a device used to provide stability to the smart medical cart. The ballast can include a ballast weight, such as water or a heavy material, that can shift or move locations on the smart medical cart to adjust the center of gravity and/or readjust the weight distribution of the smart medical cart. FIG. 51*c* illustrates an exemplary embodiment of the ballast weight 5110. FIG. 51 shows the ballast weight 5110 is a vessel containing a fluid 5120, such as water. The fluid 5120 of the ballast weight 5110 can be redistributed to counterbalance or compensate for a shift in the center of gravity or the movement of the smart medical cart. In one embodiment, the ballast weight 5110 can be located in the storage area 5130 of the covering. In one example, the ballast weight 5110 can be used when the center of gravity of the smart medical cart changes and increases the probability of the smart medical cart tipping over. In this example, the fluid 5120 in the interior of the ballast weight 5110 can shift to counterbalance the change in center of gravity. In another embodiment, the ballast or the ballast weight 5110 can be dynamically repositioned for changing the load distribution of the smart medical cart. In another embodiment, a rotary motion or gyroscope can change the inertial direction of the smart medical cart.

In one embodiment, a change in the center of gravity can cause the smart medical cart to move in an undesired direction, such as pulling to the right or left of a defined course. To compensate, the smart medical cart can adjust the center of gravity and/or the speed, velocity, acceleration, or direction of one or more of the wheels to adjust for the non-normal movement. In one embodiment, directional sensors in a sensor array of the smart medical cart, such as an accelerometer or gyroscope, can be used to determine selected measurements or information, such as when the smart medical cart is moving in an undesired direction.

As discussed in the preceding paragraphs, one or more sensors can be attached and/or integrated into the smart medical cart. The one or more sensors can be integrated into a sensor array. The sensors in the sensor array can include: encoders, such as wheel encoders or motor encoders to measure position or velocity information; proximity sensors, which can be used to measure and determine a location of potential obstacles relative to the smart medical cart; load cell sensors, for use in measuring current force loads and stresses exerted on the smart medical cart; accelerometers, for use in measuring applied forces and accelerations at the smart medical cart; angular position sensors, for use in determining a position of the smart medical cart relative to another location; location sensors, such as a GPS or triangulation module for measuring positional data of the smart medical cart; cameras, for use in taking facial recognition measurements; and battery level sensors, for use in measuring the current power level and/or predicted power level of a power source of the smart medical cart.

Figure 52:
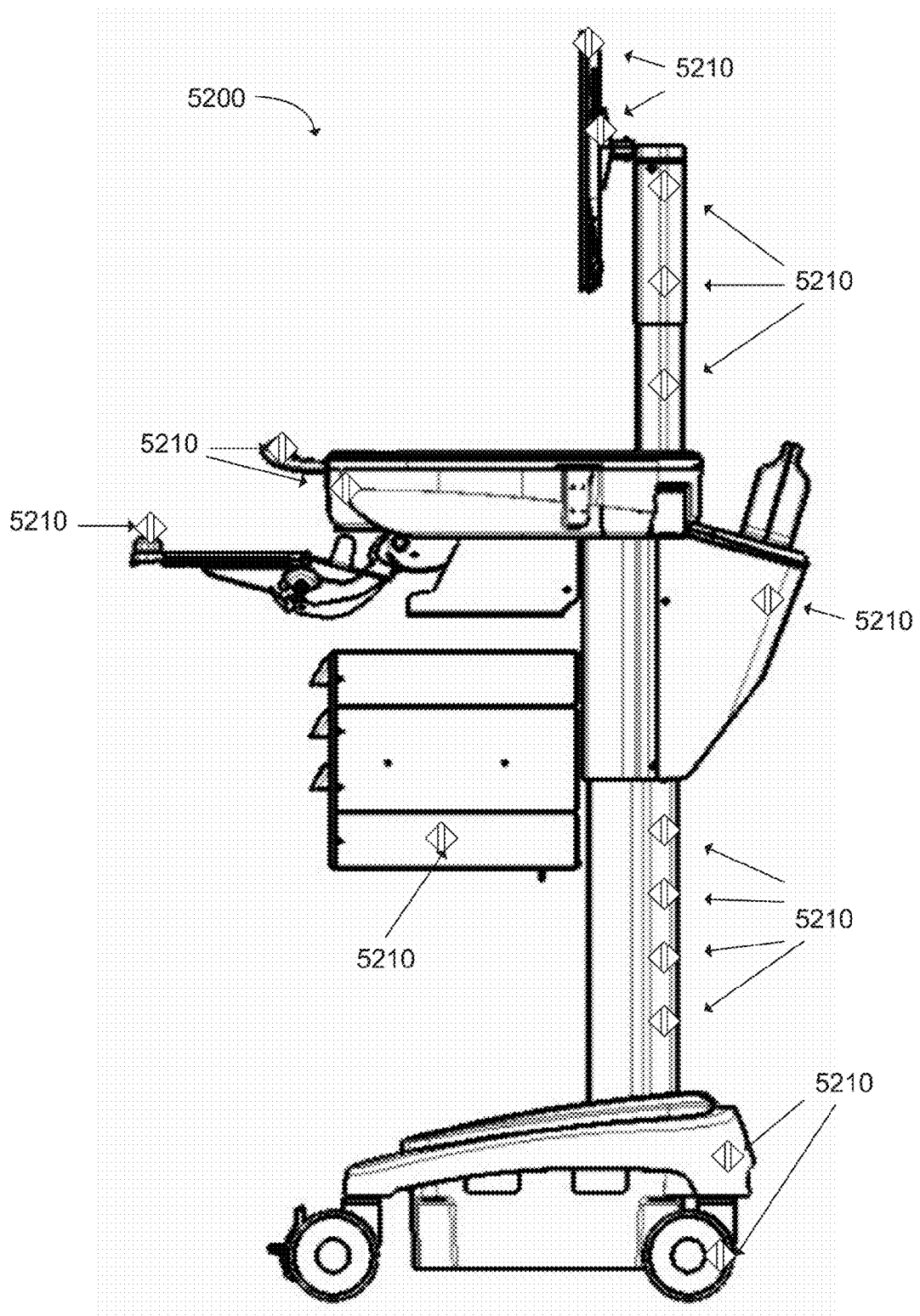
FIG. 52 illustrates a location of one or more sensor locations for sensors or sensor arrays on a smart medical cart in accordance with an example.

FIG. 52 illustrates an exemplary embodiment of the location of one or more sensor locations 5210 for the sensors or sensor arrays on the smart medical cart 5200. The sensor locations 5210 can be locations as shown in FIG. 1, including: the handle, the first work platform, the second work platform, the frame, the first vertical support, the second vertical support, the wheeled pedestal, the covering, the wheels, the mounting bracket of the second vertical support, the computing device, the power source, the medication storage container, and other desirable location on the smart medical cart 5200. For example, one sensor array can be located at the covering of the smart medical cart and another sensor array can be located at the first work platform of the smart medical cart.

In one embodiment, the sensor array can be attached to or integrated into the covering of the wheeled pedestal. For example, a plurality of collision avoidance or obstacle avoidance sensors can be incorporated into the covering of the wheeled pedestal to provide a broader or fuller sensing area for collision or obstacle avoidance. In another embodiment, one or more sensors can be located on the second vertical support, such as where a display screen attaches.

One advantage of a sensor being located on the second vertical support is that the second vertical support can be the highest point of the smart medical cart. The highest point of the smart medical cart can be an optimal sensor location to determine if the smart medical cart is going to collide into an object or if the smart medical cart is beginning to tip over because the highest point provides the greatest vantage point for sensors. For example, if a tipping sensor to located at the on the second vertical support at the highest point on the smart medical cart, the tipping sensor can optimally detect if there is a change in angle between the tipping sensor and the flooring surface because the highest point can be the location where the tipping sensor can detect a change in distance or angle between the highest point and the flooring surface the earliest. By detecting a change in distance or angle between the highest point and the flooring surface the earliest, a tipping sensor located at the highest point on the smart medical cart can enable the smart medical cart to more efficiently adjust the smart medical cart to avoid the smart medical cart tipping over.

In another embodiment, one or more collision avoidance sensors in the sensor array can be located along the vertical support. One advantage of locating one or more of the collision avoidance sensors in the sensor array along the vertical support is to enable the smart medical cart to detect obstacles that are at various heights. For example, a shelf can be located along the wall at a height of 5 feet. Collision avoidance sensors located at the wheeled pedestal may not detect the shelf because of the difference in height between the shelf and the wheeled pedestal.

When sensors are located along the vertical support, the collision avoidance sensors can detect obstacles of various heights, including a 5 foot shelf, as the collision avoidance sensors along the vertical support can vary in height. Another advantage of locating one of more collision avoidance sensors along the vertical support can be that when the length of the vertical support changes, such as to adjust the height of the first work platform, the height of the collision avoidance sensors can also be adjusted. For example, if the height of the first work platform is adjusted from 3 feet to six feet, obstacles of various heights can still be detected using a plurality of collision avoidance sensors along the vertical support.

In one embodiment, the smart medical cart sensor array can include a thermal coupling sensor. The thermal coupling sensor can be attached to the smart medical cart at defined locations where heat emanates and/or is emitted. The defined locations can include locations such as the power source, the motors, the computing device, and so forth. For example, a thermal coupling sensor can be located near an external battery to determine the temperature of the external battery. When the battery temperature exceeds a defined threshold temperature, the smart medical cart can shut down one or more systems and/or subsystems to decrease the battery temperature. In another example, a thermal coupling sensor can be located at the wheeled pedestal adjacent the motors of the power assist drive system. When a motor temperature exceeds a defined threshold temperature, the smart medical cart can determine that one or more motors may not be functioning properly. When a motor may not be functioning properly, the smart medical cart can adjust the power of the motor, shut down the motor, and/or adjust the power or drive of the other motors.

Positioning the plurality of sensor arrays in different locations can enable the smart medical cart to more broadly or fully sense the environment the smart medical cart can be used in. For example, one of the sensor arrays can be located at or near where the vertical support attaches to the wheeled pedestal and another sensor array can be located at the first work platform. In this example, one sensor array located at or near where the vertical support attaches to the wheeled pedestal can be used to determine the weight of the smart medical cart and another sensor array located at the first work platform can be used to determine the height of the smart medical cart. The data or measurements taken from each sensor array can be aggregated or analyzed in combination. For example, data obtained from multiple sensors that are located at multiple locations can be used to determine the center of gravity of the smart medical cart or the probability of the smart medical cart tipping over at a selected angle or change of velocity.

The sensor array can also include environmental sensors such as ambient air temperature sensors, air pressure sensors, illumination sensors, light sensors, humidity sensors, and so forth. In one embodiment, an ambient air temperature sensor and an air pressure sensor can be a thermometer and a barometer, respectively. The illumination sensors and/or the light sensors can be photometers. In one embodiment, the light sensor can determine the ambient light adjacent the smart medical cart and the illumination sensor can determine the light emitted from the smart medical cart.

The smart medical cart can also be aware of its surrounding environment and the user preferences of the caregiver using the smart medical cart. The environmental and/or user preference awareness can enable the smart medical cart to adapt to its surrounding environment and/or the caregiver that is using the smart medical cart. In one embodiment, a sensor array can be integrated or attached at or near the power assist drive system or the wheel subsystem. In one embodiment, the one or more sensors of a sensor array located at or near the power assist drive system or the wheel subsystem can be a velocity or acceleration sensor. In one embodiment, a velocity or acceleration sensor can monitor the number of rotations and/or a change in the rate of the number of rotations of the wheels of the wheel subsystem to determine the velocity and/or acceleration of the smart medical cart. In another embodiment, the velocity or acceleration sensor can determine the speed and/or velocity of the smart medical cart by using a GPS device and/or triangulation device. The velocity or acceleration sensor can determine the speed or a change in speed of the smart medical cart with respect to time by measuring periodic changes in location.

In one embodiment, the velocity or acceleration sensor can be used to determine if a caregiver needs more or less aid in moving or repositioning the smart medical cart. For example, when a caregiver is pushing the smart medical cart up an incline and the velocity or acceleration sensor determines that the smart medical cart is beginning to slow down while being pushed up the incline, the smart medical cart can provide additional power assistance from the power assist drive system to the wheel subsystem to maintain a selected velocity. When the smart medical cart determines that additional power assistance is desired by the caregiver, by detecting an additional force on the handle, the power assist drive system can provide additional power to the wheeled subsystem to increase the speed of the smart medical cart as it continues up the incline. In one embodiment, the smart medical cart can determine that additional power assistance is needed when the speed that the smart medical cart is moving decreases below a selected threshold.

In one embodiment, the velocity or acceleration sensor can be used as a safety measure to determine when the smart medical cart is accelerating above a selected threshold, e.g. too quickly. In another embodiment, the velocity or acceleration sensor can be used as a safety measure to determine when a user has lost control of, or is not in control of, the smart medical cart. For example, the smart medical cart may be operated on a declining slope. An increase in speed or momentum of the smart medical cart may occur and the user can lose control of the smart medical cart. In this example, it can be determined from a sensor configured to measure speed that the smart medical cart may need to slow down while moving along the declining slope to operate at a safe speed for a given environment, a determined center of gravity, or for a given user. The smart medical cart can decrease the power to the wheel subsystem or apply a brake of the brake subsystem.

Figure 53:
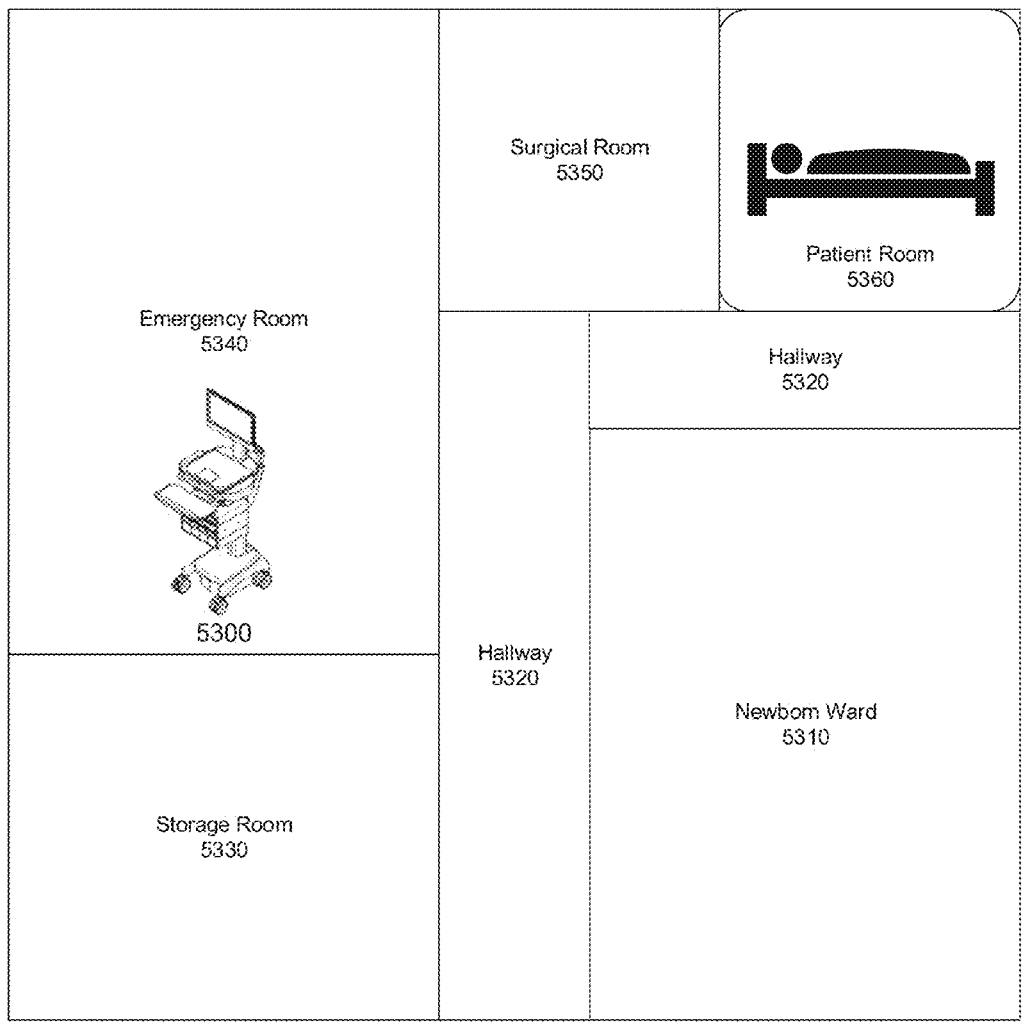
FIG. 53 illustrates a medical facility environment where a user of a smart medical cart can operate the smart medical cart in accordance with an example.

The smart medical cart can have a location sensor to detect the location of the smart medical cart. FIG. 53 illustrates a medical facility environment where a user of a smart medical cart 5300 can operate the smart medical cart 5300. The smart medical cart 5300 can be used in a plurality of different environments, such as a newborn ward 5310, a hallway 5320, a storage room 5330, an emergency room 5340, a surgical room 5350, a patient room 5360, and so forth. In one example, the location sensor can detect that the smart medical cart 5300 is located in the emergency room 5340. In one embodiment, the smart medical cart can be adjusted or dynamically changed based on the location that the smart medical cart is used in by the caregiver.

In one embodiment, the location sensor can be a global positioning system (GPS). In another embodiment, the location sensor can include a transceiver, transmitter, and/or receiver that sends or receives a beacon signal that the smart medical cart can use to determine the location of smart medical cart. The beacon signal can be transmitted or received using a wireless communication network, a cellular network, or a radio network. In one embodiment, the beacon signal can include location information. In another embodiment, the smart medical cart can use multiple beacon signals to triangulate the location of the smart medical cart. In another embodiment, a magnetic field sensor can be used to determine the location of the smart medical cart.

Figure 54:
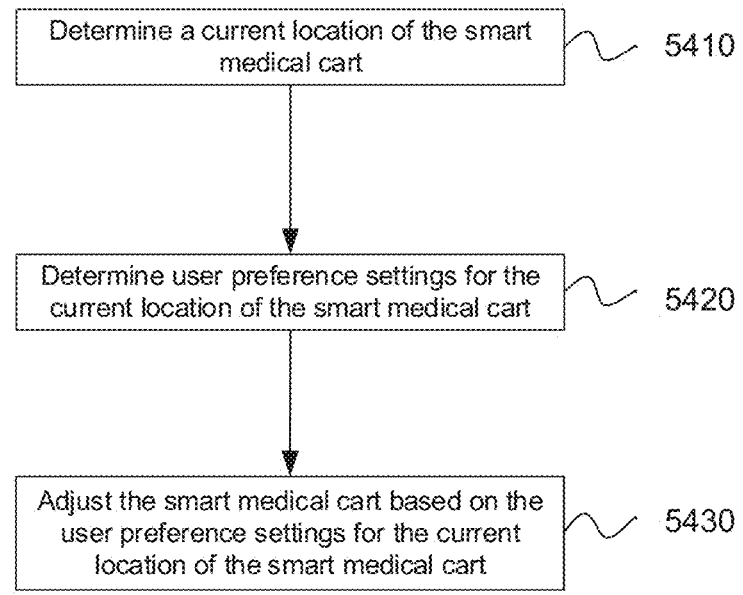
FIG. 54 depicts the functionality of computer circuitry of a user equipment with computer circuitry operable to adjust a smart medical cart in accordance with an example.

FIG. 54 provides a flow chart 5400 to illustrate the functionality of one embodiment of a user equipment, such as a computing device, with computer circuitry operable to adjust a smart medical cart. The functionality can be implemented as a method or the functionality can be executed as instructions on a machine, where the instructions are included on at least one computer readable medium or one non-transitory machine readable storage medium. The computer circuitry can be configured to determine the current location of the smart medical cart, as in block 5410. The computer circuitry can be further configured to determine a user preference setting for the current location of the smart medical cart, as in block 5420. The computer circuitry can also be configured to adjust the smart medical cart based on the user preference setting for the current location of the smart medical cart, as in block 5430. In one embodiment, the adjustment to the smart medical cart can a hardware setting or a software setting as discussed in the preceding paragraphs.

The magnetic field sensor can measure the ambient geomagnetic field for up to three physical axes, e.g. the x axis, the y axis, and the z axis. An ambient geomagnetic field inside a building, such as a medical facility, can be non-uniform and vary for different locations inside the building. The non-uniformity of an ambient geomagnetic field inside a building can be caused by a plurality of sources, from both natural and man-made sources, such as steel and reinforced concrete structures, electric power systems, electric and electronic appliances, and industrial devices. The non-uniform ambient geomagnetic field inside a building can remain approximately static and each unique ambient geomagnetic field can be mapped to the approximate location of the ambient geomagnetic field in the building. In one embodiment, the location sensor can include an ambient geomagnetic field sensor and a smart medical cart can determine the location of the smart medical cart by comparing an ambient geomagnetic field at the location of the smart medical cart with the mapping of the ambient geomagnetic fields.

In one embodiment, the smart medical cart can use a plurality of location sensors, such as a plurality of ambient geomagnetic field sensors to determine the location of the smart medical cart. In another embodiment, the smart medical cart can use a plurality of different types of location sensors, such as a GPS sensor and a beacon signal to determine the location of the smart medical cart. In one embodiment, the smart medical cart can record the location of the smart medical cart for a selected period of time using one or more location sensors.

Inertial navigation can be used for location sensing and/or navigation of the smart medical cart. In one embodiment, the smart medical cart can use inertial navigation by using measurements provided by accelerometer sensors and gyroscope sensors to track the position and orientation of the smart medical cart relative to a known starting point, orientation, and/or velocity. In one embodiment, the smart medical cart can use three orthogonal gyroscopes and three orthogonal accelerometers to measure the angular velocity and linear acceleration of the smart medical cart. The smart medical cart can use the angular velocity and linear acceleration information to determine the position and orientation of a smart medical cart relative to the known starting point.

In another embodiment the smart medical cart can use a geomagnetic field sensor in combination with an accelerometer to determine the location of the smart medical cart relative to a defined location, such as the magnetic north pole. The smart medical cart can also use orientation information to determine the position or orientation of the smart medical cart relative to the defined location. For example, the geomagnetic field sensor can provide geomagnetic field strength values for each of the three coordinate axes and the orientation information can provide yaw, pitch, and/or roll values. The smart medical cart can use the geomagnetic field information and orientation information to determine the location and orientation of the smart medical cart as it moves in selected directions measured by the geomagnetic field sensor.

The location sensor can be used to assist a user in determining the location of the smart medical cart. In one embodiment, the smart medical cart can alert the user and/or medical facility personnel when the smart medical cart has been moved to a different location without the user's knowledge. In another embodiment, the location sensor can be used in adapting the smart medical cart to different environments. For example, the smart medical cart can use a location sensor to determine that the smart medical cart is in a patient's room. When the smart medical cart determines it is in a patient's room, the smart medical cart can adapt to moving in tight quarters or adjust the volume level or light levels of computing devices, medical equipment, and other types of electronic devices operating on the smart medical cart. For example, the location sensor can determine that the smart medical cart is located in a newborn ward and decrease the noise level output of the electronic equipment.

The smart medical cart can be configured to store, record, and/or track the movement of the smart medical cart based on information from sensors located on the medical cart. In one embodiment, a location sensor can record the previous route(s) that the smart medical cart has moved along and provide the caregiver with directions for following the same route in the future. In another embodiment, one or more routes may be entered or programmed into the smart medical cart. For example, if a user is unfamiliar with a medical facility location or is a newly hired employee, the smart medical cart can automatically provide route information to the user. The user can follow route information to perform his or her duties with the smart medical cart.

One advantage of the smart medical cart recording previous routes or having one or more routes programmed into the smart medical cart is for a user, such as a caregiver, that habitually takes the same route each time when they are making rounds to care for patients. Where the smart medical cart records the previous route of a caregiver or has a programmed route, the smart medical cart can ensure that the caregiver visits selected patients along the previous or programmed route during the work period of the caregiver. In one embodiment, the smart medical cart can receive patient visiting information. The patient visiting information can be communicated from a central server or input by a caregiver. The patient visiting information can include when a patient should be checked up on, when the patient should receive medication, the last time the patient was visited, and so forth. In one embodiment, the smart medical cart can provide the caregiver with reminders to visit a patient at a selected time. In another embodiment, the smart medical cart can provide the caregiver and/or a third party with an indication or alert if a patient has not been visited at a selected time.

Another advantage of the smart medical cart recording previous routes of the caregiver or having a programmed route is that the smart medical cart can learn or record the location of obstacles in order to avoid the obstacles in the future. For example, when a caregiver takes a selected route for the first time, the smart medical cart can use one or more sensors and/or a sensor array to determine obstacles along the route of the smart medical cart, such as stationary or fixed obstacles. When the smart medical cart moves along the same route in the future, the smart medical cart can recall the previous location of the obstacles and anticipate or avoid the obstacles as the smart medical cart moves along the same route.

The location sensor may be used to assist a caregiver in determining an optimal or standardized workflow path for the caregiver to follow. In one embodiment, the smart medical cart can use the location sensor to guide and/or assist a caregiver in following optimal or standardized workflow path. For example, the smart medical cart can monitor the workflow path of a caregiver over a period of time, such as for days or weeks. Determining the workflow path can enable the caregiver to navigate the workflow path in the shortest amount of time, for the shortest distance, avoid congestion, visit critical patients first, and so forth. In another embodiment, the optimal workflow path can be predetermined and the smart medical cart can provide promptings or indications to the caregiver as to what workflow path to follow.

The smart medical cart can communicate with other smart medical carts, location sensors, other devices, other caregivers, and so forth. In one embodiment, the smart medical cart can communicate with other smart medical carts, location sensors, other devices, and/or other caregivers using a wireless communication network, a cellular network, or a radio network. In one embodiment, the smart medical cart can communicate location information with other smart medical carts, location sensors, other devices, and/or other caregivers to determine the optimal path based on the communicated location information. For example, the smart medical cart may have a predetermined path that the caregiver normally takes. However, the smart medical cart can analyze location information communicated by other devices and determine that the predetermined path that the caregiver normally takes is congested or blocked. When the predetermined path that the caregiver normally takes is congested or blocked, the smart medical cart can reroute or provide an alternate workflow path for the caregiver to follow, such as a path to avoid the congested or blocked areas. In another embodiment, the smart medical cart can provide a different optimal workflow path depending on the time of day or the location of the smart medical cart.

The location sensor can collect location information to be used in training a new user of the smart medical cart, such as a new employee. The smart medical cart can be programmed or have predetermined paths and provide the new user with direction information or guidance information. For example, if a new employee is unfamiliar with the medical care facilities, the location of each patient room that the caregiver is scheduled to visit can be entered into the smart medical cart and the smart medical cart can then provide directions to each patient's room. In another example, if a new employee becomes lost, disoriented, or is in a location other than the location designated for that employee, the smart medical cart can provide assistance or information to the new employee to enable the new employee to return to the correct location. The location information can also be used to alert hospital security when a caregiver or smart medical cart is located in a location not designated for the smart medical cart or employee, such as a restricted or secured area.

In one embodiment, the smart medical cart may use collected or recorded location information to learn the environment that the smart medical cart is used in. For example, the smart medical cart can learn that when the smart medical cart is located in a patient's room that the speed and acceleration at which the cart moves should be reduced. The smart medical cart can also learn that when the smart medical cart is in a hallway, the smart medical cart can learn that the speed, acceleration, and sensitivity of collision avoidance sensors at which the cart moves should be increased.

The smart medical cart may have an obstacle or collision avoidance subsystem. In one embodiment, obstacle or collision avoidance subsystem can determine if there is an obstacle in the path of the smart medical cart or a probability that a moving object will be in a current path of the smart medical cart. In one embodiment, the obstacle or collision avoidance subsystem can comprise obstacle or collision avoidance sensors. The obstacle or collision avoidance sensors can include an ultrasonic sensor, a motion detection sensor, a laser sensor, an infrared sensor, a thermal heat sensor, a thermal imaging sensor, a video sensor, a photo LED, an imaging sensor, a sonar sensor, and/or a microphone. The smart medical cart can use an obstacle or collision avoidance sensor or a combination of obstacle or collision avoidance sensors to determine obstacle avoidance information including the distance, location, speed, acceleration, velocity, size, and/or directional movement of one or more obstacles. In one embodiment, the obstacle or collision avoidance sensor can be used to detect obstacles in a direction of movement of the smart medical cart. In another embodiment, obstacles within a selected field of view, such as 90, 120, 150, 180, 210, 240, 270, 300, 330, or 360 degrees can be monitored to enable the smart medical cart to avoid potential obstacles.

Obstacle avoidance information can be correlated to the motion path of the smart medical cart, using distance, location, speed, acceleration, velocity, size, and/or directional movement information of the smart medical cart to determine an avoidance procedure for the smart medical cart. For example, the smart medical cart can use the closing distance of the smart medical cart and an obstacle at a current velocity of the smart medical cart and the obstacle to determine the probability of a collision and notify the caregiver of the approaching object. In another embodiment, the obstacle or collision avoidance subsystem can determine that an object is on a collision course or headed in a direction that will intersect with the smart medical cart's path. For example, the smart medical cart may determine that a patient is walking down a hallway on a path that intersects with the path of the smart medical cart and that at the current speed that the smart medical cart and the patient are moving at, the smart medical cart and the patient are likely to collide.

In one embodiment, a predictive feedback controller can be utilized to update the motion path of the smart medical cart and/or an obstacle. The predictive feedback controller can be used to prevent a collision through comparison of the motor velocity and calculated direction of the smart medical cart versus the distance, velocity, current location, and/or calculated direction of the object to be avoided. The predictive feedback controller comparing the current smart medical cart velocity and motion path against the current distance and location of the obstacle can yield an avoidance value, such as a time and/or distance value to the obstacle. In one embodiment, the predictive feedback controller can determine the current position or location, direction of motion, velocity, and the acceleration or deceleration of the smart medical cart from the sensor array and/or encoder feedback and collect the current position or location, direction of motion, velocity, and the acceleration or deceleration of the object to be avoided. The smart medical cart can calculate the predicted paths of the smart medical cart and the obstacle to be avoided. When the predicted paths of the smart medical cart and the obstacle are calculated to intersect, then there can be a probability of collision. In one embodiment, the predicted paths of the smart medical cart and/or the obstacle to be avoided can be update on a continuous, a semi-continuous, or a periodic basis.

In one embodiment, the smart medical cart can use the predictive feedback controller to alter a preset path of the smart medical cart to avoid an obstacle. In another embodiment, the smart medical cart can use the predictive feedback controller to indicate to the caregiver an alternative path to the current calculated path of the smart medical cart to avoid the obstacle. In another embodiment, when the probability of a collision exceeds a selected threshold, the smart medical cart can decrease the speed of the smart medical cart or stop the movement of the smart medical cart. In one embodiment, when the avoidance value is below a selected or defined threshold limit, the smart medical cart can continue the calculated path of the smart medical cart. In one embodiment, information from the obstacle or collision avoidance sensors can enable early detection of an obstacle. Early detection can enable the smart medical cart to monitor the avoidance value before the avoidance value exceeds a selected or defined threshold limit and indicate to the caregiver as the probability of a collision is increasing.

The obstacle or collision avoidance subsystem can include a predictive feedback controller to update the motion path of the smart medical cart. In one embodiment, the smart medical cart can uses the predictive feedback controller to determine when there is an obstacle in the path of the smart medical cart and the smart medical cart can assist the caregiver in moving the smart medical cart to avoid the obstacle. The predictive feedback controller can determine the current course of the smart medical cart based on the location information and/or velocity, acceleration, and speed information of the smart medical cart, determine the current location and/or path of the obstacle, and determine the optimal avoidance path of the obstacle. In one embodiment, the smart medical cart can use a video camera to analyze the surrounding environment and determine the optimal path of avoidance.

In one embodiment, the smart medical cart can notify the caregiver of an approaching object using visual, auditory, and/or sensory notifications. In another embodiment, the smart medical cart can provide the caregiver with directions or indications on how to avoid the obstacles.

In one embodiment, the smart medical cart can use an obstacle avoidance sensor to determine the identity of an obstacle, such as a door, hallway, person, desk, other smart medical cart, and so forth. In one embodiment, the obstacle avoidance sensor used to determine the identity of the obstacle can be an imaging device, such as video camera, 3d laser sensor, and so forth.

As discussed above, the smart medical cart can be used and maneuvered in tight quarter locations, such as a patient's room. In one embodiment, the smart medical cart can include one or more proximity sensors. In one embodiment, the smart medical cart can adjust one or more parts of the smart medical cart, such as the height of the first work platform, the second work platform, the display screen, the computing device, the wheels, and so forth when a proximity sensor determines that the smart medical cart is operating in a tight quarter environment.

Figure 55:
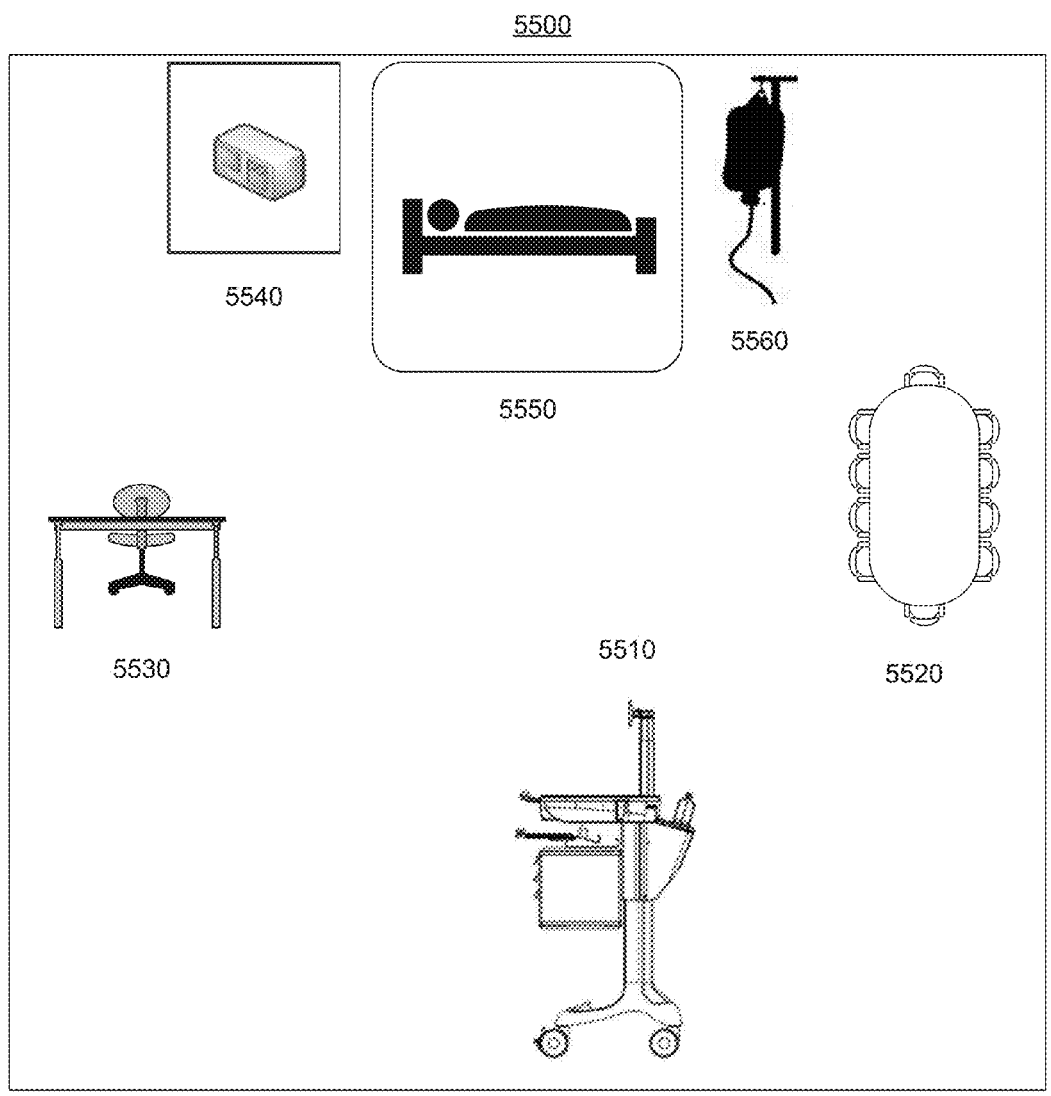
FIG. 55 depicts a smart medical cart located in a location with tight quarters in accordance with an example.

FIG. 55 depicts the smart medical cart 5510 located in a location with tight quarters 5500, such as a patient's room. The smart medical cart 5510 can operate in a location with tight quarters 5500, such as a patient's room, that has a plurality of objects, including: a table 5520, a desk 5530, a medical device 5540, a patient's bed 5550, an infusion pump or IV pump 5560, and so forth. When the smart medical cart 5510 uses the proximity sensor to detect that the smart medical cart 5510 is in a tight quarter location 5500, the smart medical cart 5510 can decrease the distance of the second work platform relative to the first vertical support in order to decrease the overall area the smart medical cart is taking up.

In one embodiment, the proximity sensor can detect the presence of nearby objects, such as objects 5520-5560, and/or the distance from the sensor to the objects without any physical contact. In one embodiment, the proximity sensor can emit an electromagnetic field or a beam of electromagnetic radiation, such as an infrared beam, to detect the proximity of the smart medical cart and an object. The proximity sensor can detect changes in the electromagnetic field or electromagnetic radiation beam and/or detect objects based on returned or reflected signals of the field or beam.

In one embodiment, the smart medical cart can use different proximity sensor to detect different objects. For example, a capacitive photoelectric sensor can be used to detect plastic objects and an inductive proximity sensor can be used to detect metal objects. In another embodiment, the distance, scope, and/or range that a proximately sensor can detect objects can be changed or adjusted. In another embodiment, the proximity sensors can detect a graduated distance of an object from the sensor.

In one embodiment, the smart medical cart can use the proximity sensor to determine if the smart medical cart is approaching an object that should be avoided. The smart medical cart may also use the proximity sensor to detect an alternate course for the smart medical cart to use to avoid collision with the object. In another embodiment, the smart medical cart can use the proximity sensor in tight quarters to get near an object without colliding with the object. In one embodiment, a threshold distance can be set for a maximum or minimum distance between the smart medical cart and an object in tight quarters. For example, if a caregiver desires to move the smart medical cart alongside or in close proximity with a patient's bed without colliding or contacting the bed, the smart medical cart can use the proximity sensors to provide the caregiver with the distance that the medical cart is in relation to the bed. The smart medical cart can also be configured to stay a selected distance away from an object, such as a bed. If a user, such as a caregiver, moves the smart medical cart closer than the selected distance, the power assist drive system can be activated to move the smart medical cart away from the object by approximately the selected distance.

The smart medical cart can use the proximity sensors to dynamically and/or automatically adjust the speed and/or acceleration of the smart medical cart based on the congestion level of a location or how tight the quarters the smart medical cart is operating in. In one embodiment, one or more threshold speed or acceleration limits can be set based on the location of the smart medical cart or the congestion level of the area the smart medical cart is operating in. For example, if the smart medical cart is being used in a patient's room, which can be highly congested, the smart medical cart can limit the speed and/or acceleration of the medical cart to avoid colliding with objects in the patient's room.

The power assist drive system can be used to provide power to the wheel subsystem and provide assistance in moving and/or maneuvering the smart medical cart. In one embodiment, an activity or movement sensor can be used to engage the power assist drive system and detect the desired movement that the caregiver would like the smart medical cart to make. In one embodiment, the activity sensor can comprise a plurality of load cell sensors. A load cell sensor can be a transducer configured to convert a force into an electrical signal, such as a piezoelectric sensor. A load cell can include a hydraulic load cell, a pneumatic load cell, and/or a strain gauge load cell.

A load cell sensor can take load measurements that include force measurements, pressure measurements, tension measurements, weight measurements, stress measurements, strain measurements, and other load measurements. A load cell sensor can be a sensor whose resistance varies with applied force. The load cell sensor can convert force, pressure, tension, weight, etc., into a change in electrical resistance which can then be digitally measured. For example, when an external force is applied to an object, stress and strain can result. Stress can be an object's internal resisting forces and strain can be the displacement and deformation that occur to the object. A load cell sensor can measure tensile strain and/or compressive strain, e.g. expansion and contraction respectively. In one embodiment, the load cell sensor can associate a tensile strain with a positive sign and a compressive strain with a negative sign, or vice versa. In one embodiment, the load cell sensor can measure strain caused by force, pressure, moment, heat, acceleration, displacement, vibration, and/or structural change applied to the smart medical cart and/or the load cell sensor.

One or more load cell sensors can be integrated into the smart medical cart and/or attached to the smart medical cart at one or more locations on the smart medical cart. In one embodiment, one or more load cell sensors can be integrated into where the handle attached to the smart medical cart, such as where the handle attached to the first work platform as shown in FIG. 1 or a handle attached to the second work platform of the smart medical cart.

Figure 56A:
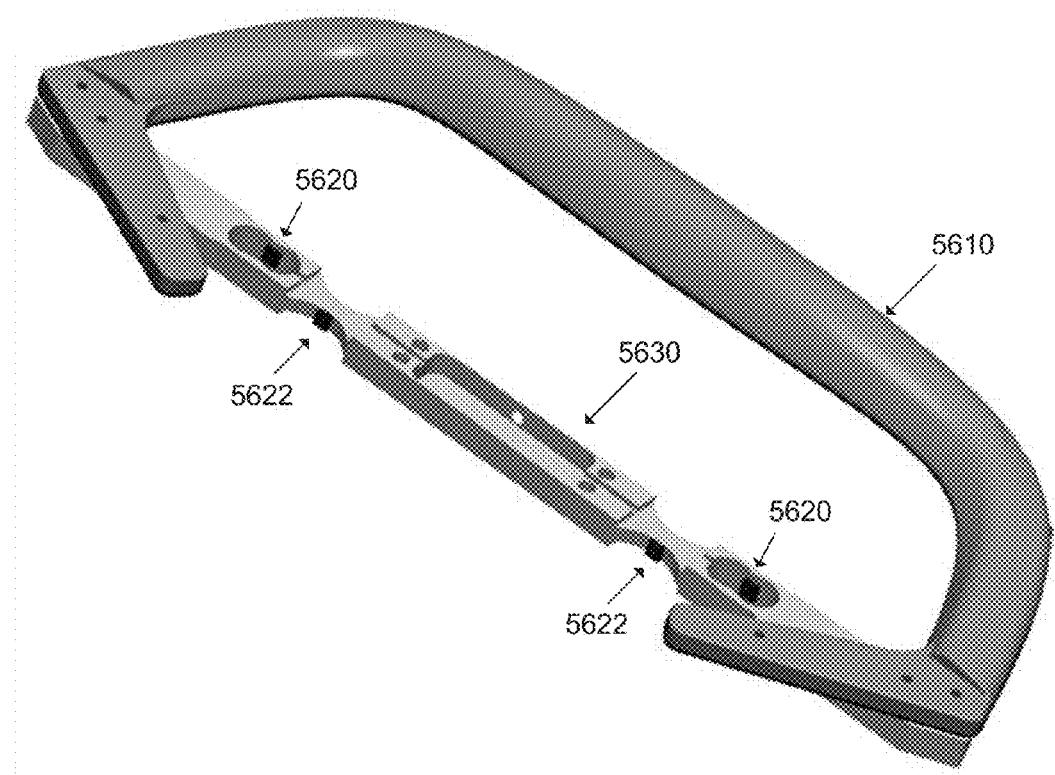
FIG. 56*a* illustrates one or more load cell sensors integrated in a mounting bracket that attaches to a handle in accordance with an example.

FIG. 56a illustrates one exemplary embodiment of one or more load cell sensors 5620 and 5622 integrated into a mounting bracket 5630 that attaches to the handle 5610. In FIG. 56a, the one or more load cell sensors 5620 and 5622 can be located at various locations along the mounting bracket 5630. The mounting bracket 5630 can be attached to the handle 5610 using an epoxy, fastener, snapping the mounting bracket 5630 onto the handle 5610, a clasp, and so forth. FIG. 56a further shows one exemplary embodiment, where load cell sensors 5620 measure the strain created in the x axis direction. In one embodiment, the mounting bracket 5630 can bend or flex to enable the load cell sensors 5620 to measure load in the x axis directions and/or y axis direction. For example, the shape of the mounting bracket 5630 enables a stretching load to be measured by the strain gauges 5620 when a lateral left or lateral right motion is applied to the handle. In one embodiment, load cell sensors 5622 can measure the shear strain, torsion, or load created by moving the handle in upward and downward motions, i.e. a load in the z axis direction.

Figure 56B:
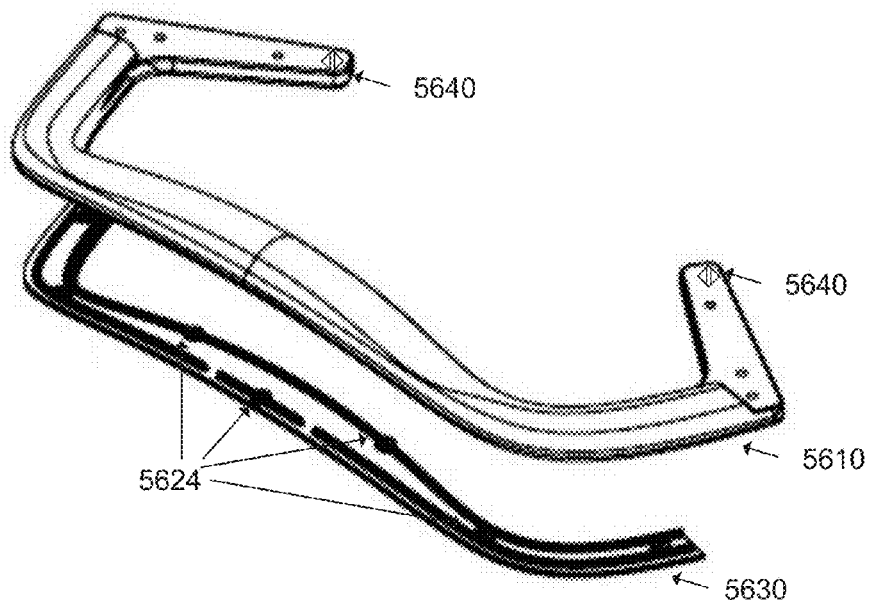
FIG. 56*b* illustrates one or more load cell sensors located at each end of a handle in accordance with an example.

FIG. 56b illustrates another exemplary embodiment of one or more load cell sensors 5640 located at each end of the handle 5610 where the handle 5610 attaches to a smart medical cart, as shown in FIG. 1. FIG. 56b further illustrates that the one or more load cell sensors 5640 can be located at each end of the handle 5610 where the handle 5610 attaches to the smart medical cart and a plurality of load cell sensors 5624 can be located at various locations along the mounting bracket 5630.

Figure 57A:
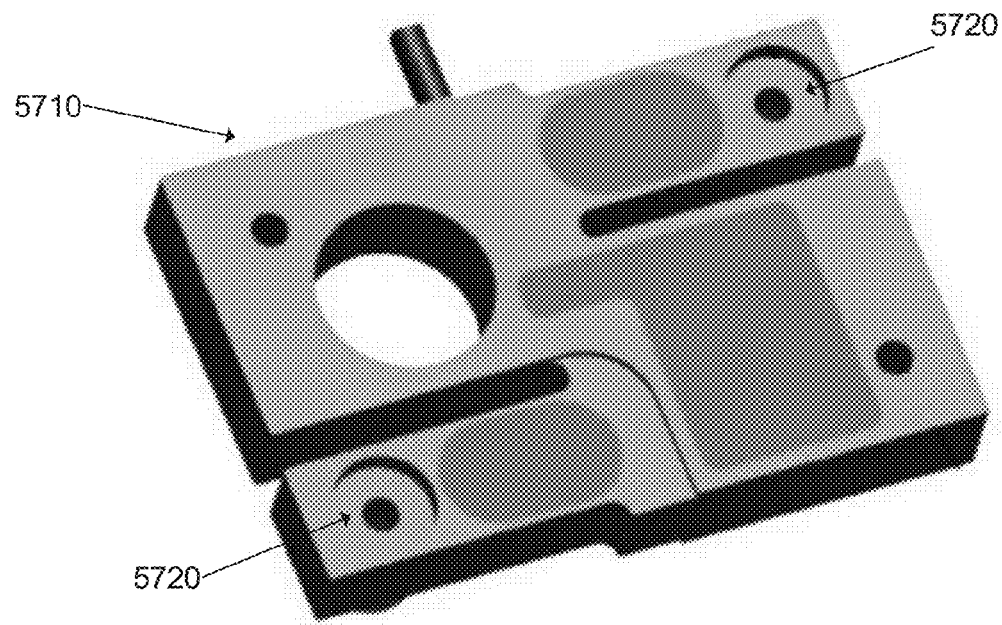
FIG. 57*a* shows a perspective view of a single mounting element with a variety of attachment locations for load cell sensors in accordance with an example.
Figure 57B:
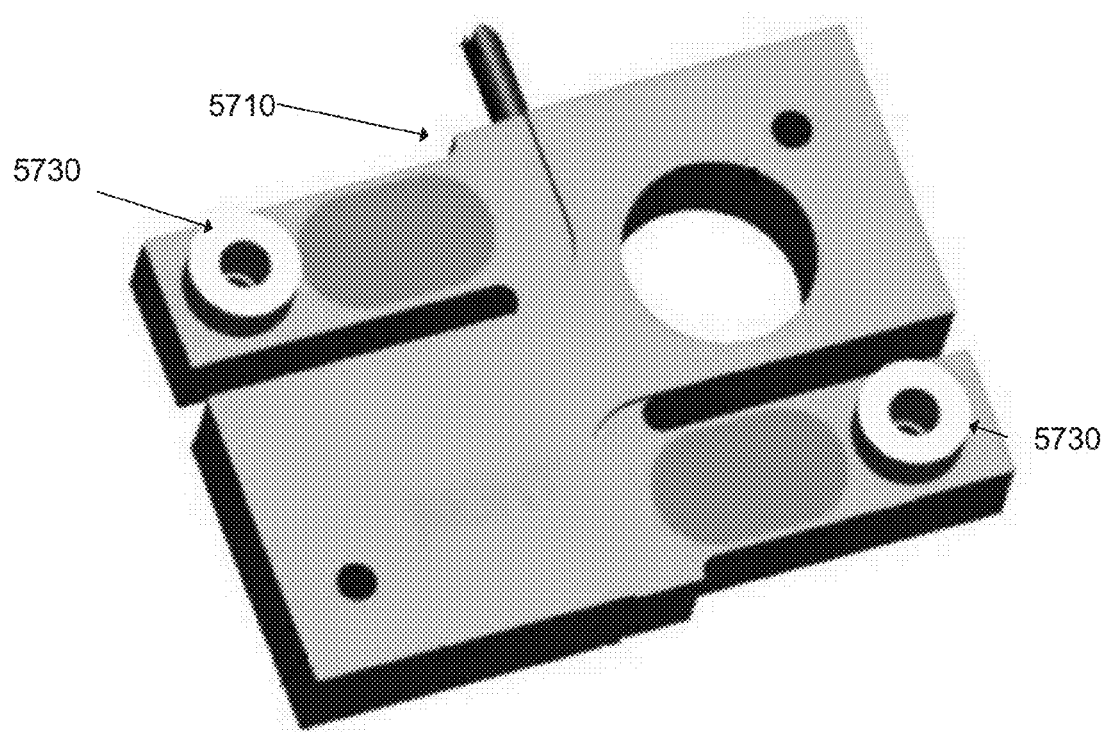
FIG. 57*b* shows a perspective view of a single mounting element with a plurality of load cell sensors attached to the single mounting element in accordance with an example.

In one embodiment, a plurality of load cell sensors can be attached on a single element. FIGS. 57a and 57b illustrate an exemplary embodiment of a single attachment element 5710 for a plurality of load cell sensors 5730. FIG. 57a shows a perspective view of the single mounting element 5710 with load cell sensor attachment locations 5720 to attach a plurality of load cell sensors. The single attachment element 5710 can be attached to a plurality of locations on a smart medical cart, such as each side of the handle as shown in FIG. 56b. FIG. 57b shows a perspective view of the single mounting element 5710 with a plurality of load cell sensors 5730 attached to the single mounting element 5710.

Figure 58A:
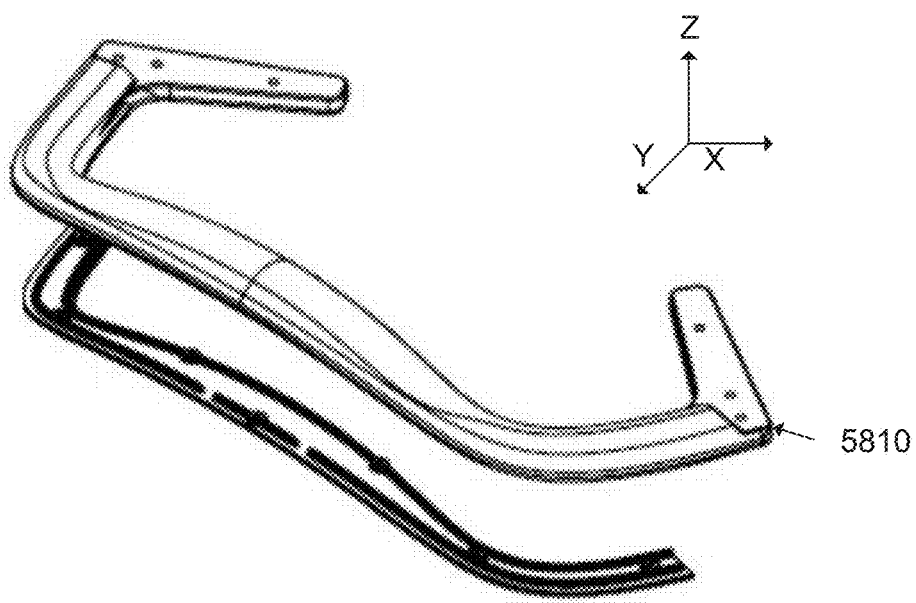
FIG. 58*a* shows directional information that a handle can measure in accordance with an example.
Figure 58B:
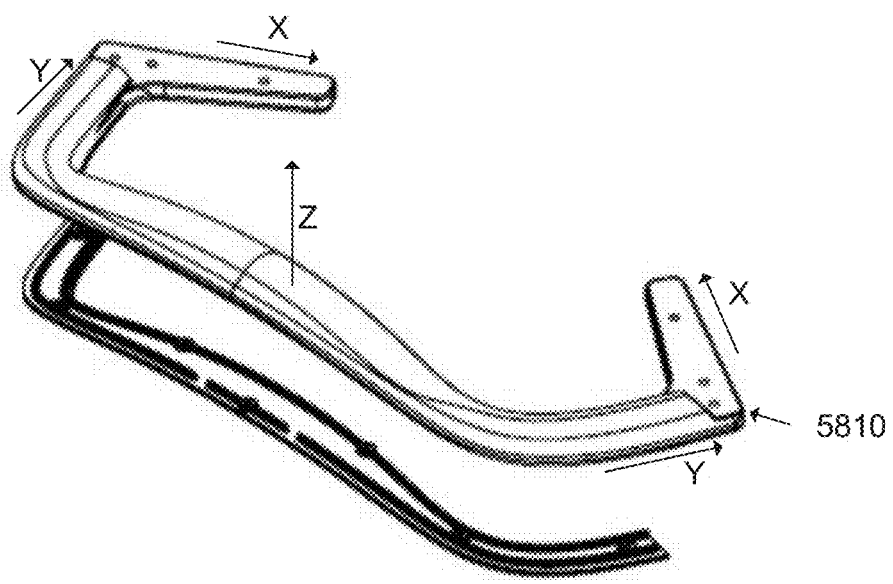
FIG. 58*b* illustrates a load in x, y, and z axis directions in accordance with an example.

In one embodiment, three load cell sensors can be mounted orthogonally on a single attachment element where one load cell sensor can measure a load in the x axis direction, one load cell sensor can measure a load in the y axis direction, and one load cell sensor can measure a load in the z axis direction. FIG. 58a shows the directional information that the handle 5810 can measure. The handle 5810 can collect axis directional information in the x axis direction, the y axis direction, and the z axis direction using one or more load cell sensors, as shown in FIGS. 56a, 56b, 57a, and 57b. FIG. 58b illustrates one exemplary embodiment where the load in the x axis direction, the load in the y axis direction, and the load in the z axis direction can be determined by using trigonometry of the movement of the handle 5810. In one embodiment, a smart medical cart can use an orientation of one or more load cell sensors relative to the handle to determine a load applied in the x axis direction, y axis direction, and/or z axis direction.

In one embodiment, three orthogonally mounted load cell sensors measuring the load on the x, y, and z axis can be attached to each side of the handle 5810 where the handle 5810 attaches to the smart medical cart, as shown in FIGS. 56a, 56b, 57a, and 57b. FIG. 58b further depicts direction information received from the load cell sensors of the handle 5810. Each load cell sensor for the x, y, and z axes on one side of the handle can be mounted orthogonally to the load cell sensors for the same axis mounted on the other side of the handle.

When the load cell sensors on each axis on one side of the handle can be mounted orthogonally to the load cell sensors on the same axis on the other side of the handle, each load cell sensor can receive unique load information from the load on each side of the handle. For example, when a first load cell sensor and a second load cell sensor are parallel with each other on a same axis, such as when a load cell sensor is mounted on each side of the handle 5810 of the smart medical cart, as loads are applied to the first load cell sensor and the second load cell sensor on the same axis the same load is registered for both of the load cell sensors. When the same load is registered for both of the load cell sensors on the same axis, the second load cell sensor provides no load information or minimal load information in addition to the load information already collected by the first load cell sensor. When the first load cell sensor and the second load cell sensor on the same axis are orthogonal to each other, the first load cell sensor provides unique or different information from the information provided by the second load cell sensor.

In one embodiment, when one or more of the load cell sensors are disoriented, such as not oriented along the x, y, or z axis, the information received from the load cell sensor can be calibrated to get the proper alignment.

In one embodiment, the load cell information from each load cell sensor can be analyzed individually. In another embodiment, the load cell information from each load cell sensor on the same axis can be vectorially summed together. In one embodiment the load cell information can be modified or adjusted based on other information, such as wheel orientation, velocity, or acceleration of a smart medical cart. For example, the load cell information on each of the x, y, and z axes can be summed together for each axis, respectively, and produce a single x vector value, a single y vector value, and a single z vector value. In this example, a resultant vector length is the square root of $(x^2+y^2+z^2)$, where the x is the single x vector value, y is the single y vector value, and z is the single z vector value. In one embodiment, the direction of the resultant vector can be the arctan(y/x). In another embodiment, the load cell information on all the x, y, and z axes can be summed together to produce a single vector value. The direction and length of the vector is dependent on the load cell information in the x axis direction, the y axis direction, and the z axis direction.

In one embodiment, the load cell sensor measurements can be converted into velocity, acceleration, and direction movement inputs for a smart medical cart using vector mathematics. The smart medical cart can then convert the movement inputs into individual commands for each motor of a power assist drive system.

In one embodiment, the load in the x axis direction and the load in the y axis direction can be converted into a directional movement by using:

$$\theta = \tan^{-1}\left(\frac{BY}{X} - C\right) \quad (1)$$

$$\frac{Xw(\theta)}{Yw(\theta)} = \begin{bmatrix} \cos(\theta) & -\sin(\theta) \\ \sin(\theta) & \cos(\theta) \end{bmatrix} \begin{bmatrix} SX \\ SY \end{bmatrix} \quad (2)$$

where SX and SY can represent the X and Y outputs from the load cell sensors on the x and y axes before a load is applied to the load cell sensors, such as before a caregiver applies a load to the handle. $Xw(\theta)$ and $Yw(\theta)$ represent the load after the caregiver applies a load to the load cell sensors, such as after the caregiver applies a load to the handle. B can represent a sensitivity scale value, such as a caregiver's desired load cell sensitivity. In one embodiment, to avoid dividing BY by an X equal to 0, when no load is placed on a load cell sensor, X can be set equal to a selected value greater than zero, such as 0.01. To enable $\theta$ to be zero when X and Y are equal to each other, a value C can be subtracted from BY/X.

In one embodiment, load measurements are taken for the x axis and the y axis directions using the load cell sensors at selected periods of time, such as ten measurements per second. The power assist drive system can calculate the X and Y outputs for each load cell sensor measurement. In another embodiment, load measurements are taken for the x axis and the y axis directions using the load cell sensors on a continuous or semi-continuous basis and the power assist drive system can calculate the X and Y inputs on a continuous or semi-continuous basis. At the end of each calculation, the X and Y inputs can be translated into power inputs for each of the wheels of the wheel subsystem to rotate the wheels at selected rates or amounts. In one embodiment, wheel rotation stops when a load is not applied.

In one embodiment, the load in the x axis direction and the load in the y axis direction can be converted into an acceleration value by determining an amplitude or load value using the equation $A=\sqrt{X^2+Y^2}$, where A is the load value, X is the load measured on the x axis using one or more load cell sensors, and Y is the load measured on the y axis using one or more load cell sensors. For example, a stronger load on the handle can indicate the desire for a faster acceleration. In one embodiment, the acceleration and angle can be correlated together to smooth the movement or acceleration of the smart medical cart.

The power assist drive system can provide power to the wheel subsystem differently based on the speed at which the smart medical cart is moving. For example, the power assist drive system can provide a different amount of power to one or more of the wheels of the wheel subsystem when the smart medical cart is moving versus at a stopped position, such as when the smart medical cart is parked in a designated location. The smart medical cart can determine desired movement of the smart medical cart based on the current state of motion, e.g. the speed of the smart medical cart, as well as the load values from the load cell sensors. The smart medical cart can determine the movement of the smart medical cart based on a current state of motion and the load values using the following equation:

$$\frac{Xw(\theta)}{Yw(\theta)} = \begin{bmatrix} \cos(\theta) & -\sin(\theta) \\ \sin(\theta) & \cos(\theta) \end{bmatrix} \begin{bmatrix} Vx & Vxy \\ Vyx & Vy \end{bmatrix} \begin{bmatrix} Ax & Axy \\ Ayx & Ay \end{bmatrix} \cdots \begin{bmatrix} Gx & Gxy \\ Gyx & Gy \end{bmatrix} \begin{bmatrix} SX \\ SY \end{bmatrix} \quad (3)$$

In the above equation, V represents velocity information, A represents acceleration information, SX represents a load value on the x axis, and SY represent a load value on the y axis. The smart medical cart can also determine the desired movement of the smart medical cart based on additional parameters, such as differences between cart operators, center of gravity shifts, incline, wall proximity, etc. G represents a succession of general matrices used to adjust the desired movement of the smart medical cart based on the additional parameters. In one embodiment, the cross terms, such as Gxy or Gyx, can be zero so that the matrix is diagonal and independently scales the x value and y value. The coefficients for each matrix can be found from a look-up table. In one embodiment, the look-up table can include predetermined values. The other variables of equation (3) are the same as described in the preceding paragraphs for equation (1) and equation (2).

In one embodiment, the look-up table can be populated by mapping predetermined reaction information to different movements of a caregiver and/or using the smart medical cart in different environments. In one embodiment, reaction information can be collected from a selected caregiver. For example, when the caregiver first uses the smart medical cart, the caregiver can perform a selected number of different tasks such as moving the smart medical cart in selected directions and in selected environments and the smart medical cart can record the information into the look-up table for each selected direction and/or environment.

In another embodiment, the look-up table can be pre-populated based on reaction information from selected individuals. For example, a group of individuals of various or selected characteristics, such as gender, height, weight, physical fitness, or other characteristics, can perform a selected number of different tasks such as moving the smart medical cart in selected directions and in selected environments and the smart medical cart can record the information into a pre-population look-up table for each selected direction and/or environment. In one embodiment, when the caregiver first uses the smart medical cart, the caregiver can input selected preference information and/or user information into the smart medical cart or a device in communication with the smart medical cart and the smart medical cart can map the selected preference information and/or user information of the caregiver with selected preference information and/or user information from one of more individuals from the pre-populated group or an average of a selected number of individuals from the pre-populated group. The smart medical cart can correlate the movement information of the caregiver with the pre-populated information from the pre-population group.

Sensor data can be translated to matrix coefficients. Values from one or more look-up tables can be used to modify the matrix coefficients. The modification can be done by multiplying a formed matrix by another matrix chosen from a table of possibilities. The chosen table can be selected based on the position, velocity, and acceleration of the smart medical cart at a selected instance or period of time.

Figure 59:
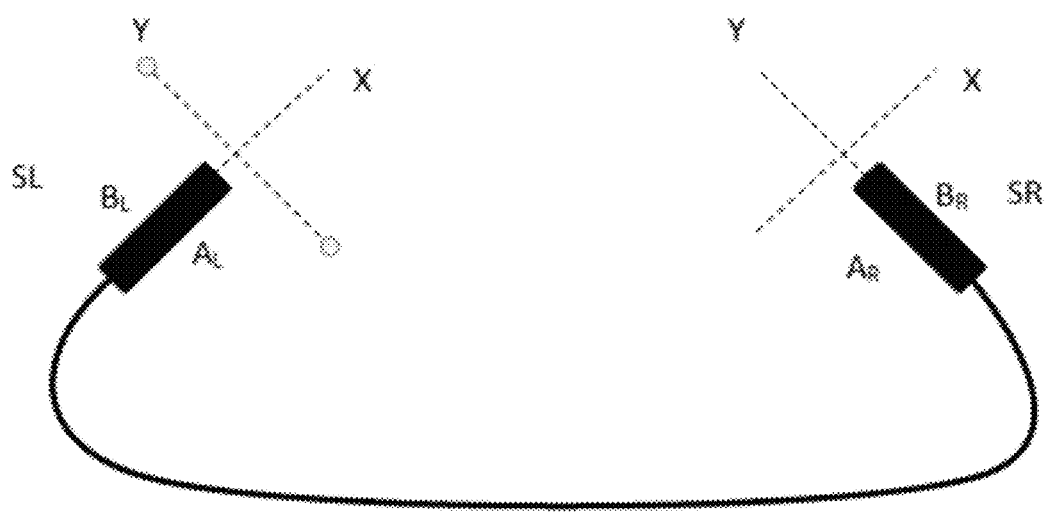
FIG. 59 illustrates strain gauges that can detect a load in x, y, and z axis directions in accordance with an example.

In another embodiment, the load in the x axis direction and the load in the y axis direction can be converted into a directional movement by using a linear algebra analysis. In the linear algebra analysis, the load in the x axis direction and the load in the y axis direction, such as loads gathered using strain gauges, can be converted into inputs for the linear algebra analysis and the output of the linear algebra analysis can be converted into a power output, such as voltage, supplied to one or more motors from the power source. FIG. 59 illustrates the configuration of the handle. FIG. 59 shows that the x axis and the y axis of the strain gauges on each side of the handle can have the same orientation for both sides.

FIG. 59 illustrates that strain gauges can detect a load in an x axis direction, a load in a y axis direction, or a combination of loads in the x axis direction and the y axis direction. $A_L$ and $A_R$ can represent loads applied to the interior portion of the handle approximate to where the handle connects to the left and right sides of a first work platform. $B_L$ and $B_R$ can represent loads applied to the exterior portion of the handle approximate to where the handle connects to the left and right sides of the first work platform. In one embodiment, when a compressing load is applied one or more strain gauges, the compressing load can represent a positive signal. In another embodiment, when a stretching load is applied one or more strain gauges, the compressing load can represent a negative signal. In another embodiment, when a compressing load is applied one or more strain gauges, the compressing load can represent a negative signal. In another embodiment, when a stretching load is applied one or more strain gauges, the compressing load can represent a positive signal.

The compressing loads and stretching loads on strain gauges on each side of the handle can be converted into strain values in the x axis and y axis directions and can be represented as $SR_X$ (the x-axis strain value the right side of the handle), $SR_Y$ (the y-axis strain value the right side of the handle), $SL_X$ (the x-axis strain value the left side of the handle), and $SL_Y$ (the y-axis strain value the left side of the handle). The compressing loads and stretching loads of $SR_X$, $SR_Y$, $SL_X$, and $SL_Y$ can be determined using the following equations: $SR_X=B_R-A_R$; $SR_Y=A_R+B_R$; $SL_X=A_L+B_L$; and $SL_Y=B_L-A_L$.

In one embodiment, each wheel connected to a motor of the power assist drive system can be fixed and in contact with the ground and the direction of motion of the wheel can be determined by monitoring a rate of rotation of each of the wheels. An axis of the smart medical cart or the location that the handle attaches to the smart medical cart, such as the first work platform, can be offset by −45 degrees from the axis of the strain gauges. The inputs from the strain gauges can be rotated to offset reference frame via the relationship:

$$\begin{bmatrix} Xw(\theta) \\ Yw(\theta) \end{bmatrix} = \begin{bmatrix} \cos(\theta) & -\sin(\theta) \\ \sin(\theta) & \cos(\theta) \end{bmatrix} \begin{bmatrix} SX \\ SY \end{bmatrix} \quad (4)$$

The variable SX and SY represent the strain gauge readings, such as a strain gauge reading from strain gauges mounted on the left or right of the handle, for X and Y components of the strain gauge readings. The variables $Xw(\theta)$ and $Yw(\theta)$ are new components after rotation of the wheels. To prevent division by 0, e.g. when no pressure is applied to a strain gauge, the base value that the strain gauge readings are set at when no pressure is applied to the strain gauges can be set to a minimal or negligible value, such as 0.01.

Figure 60:
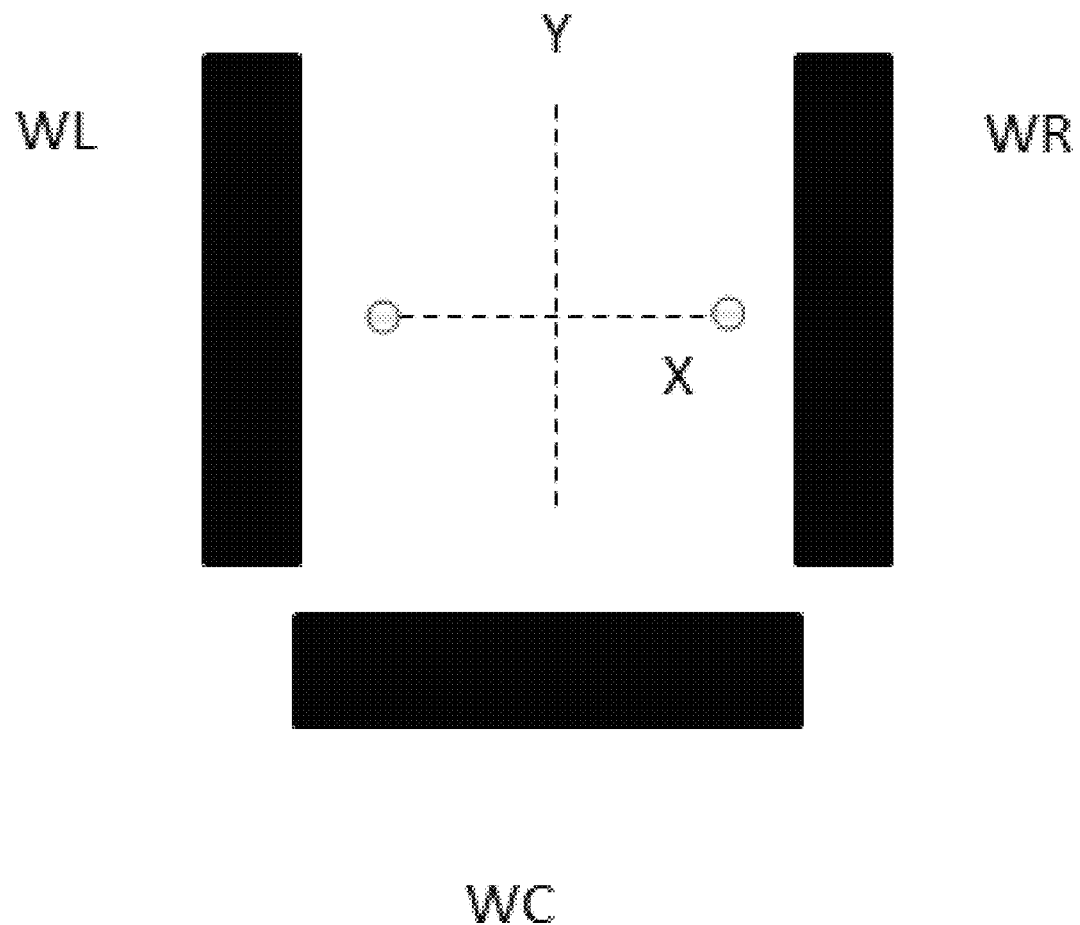
FIG. 60 illustrates force inputs received from a strain gauge and converted into inputs to one or more wheels of a power assist drive system in accordance with an example.

FIG. 60 illustrates force inputs received from a strain gauge and converted into inputs to one or more wheels of the power assist drive system. The inputs to the wheels are calculated from the strain gauge inputs in accordance with the above formula as follows:

$$W_R = SR_X * \cos(-45) - SR_Y * \sin(-45) \text{(similar to the preceding } Xw(\theta)) \quad (5)$$

$$W_L = SL_X * \cos(-45) - SL_Y * \sin(-45) \text{(similar to the preceding } Xw(\theta)) \quad (6)$$

$$W_C = -((SR_X + SL_X)/2) * \sin(-45) + ((SR_Y + SL_Y)/2) * \cos(-45) \text{(similar to the preceding } Yw(\theta)) \quad (7)$$

The power to be provided to each wheel connected to a motor is represented by W. The W variable correlate with the $Xw(\theta)$ and $Yw(\theta)$ variables of equation (2), e.g. $W_R$ correlates with the load values on the right side of the handle as discussed in preceding paragraphs and $W_L$ correlates with the load values on the left side of the handle as discussed in preceding paragraphs. $W_C$ correlates with an average of load values on the left side and right side of the handle. In one embodiment, a power assist drive system can have three motors connected to three wheels, as seen in FIG. 32. The power provide to each wheel is represented as $W_L$, $W_R$, and $W_C$, where $W_L$ is the power to a left wheel, $W_R$ is the power to a right wheel, and $W_C$ is the power to the center wheel.

In one embodiment, a rotation matrix can be used to determine the power provided to each wheel, e.g. a rate that each wheel rotates. The rate of rotation of the left wheel can be based on the left strain gauge input ($W_L$), the rate of rotation of the right wheel can be based on the right strain gauge input ($W_R$), and the rate of rotation of the center wheel can be based on the average of the left and right strain gauge inputs ($W_C$). In one embodiment, the rate of rotation or power of the left and right wheels can be based on x axis components of one or more strain gauges and rate of rotation or power of the center wheel can be based on y axis components of one or more strain gauges.

FIG. 60 further shows the spatial relation between the wheels and the strain gauges as described in the preceding paragraphs. FIG. 60 also shows the coordinate axes are offset by 45 degrees.

The rotation matrix can be expanded to allow for other inputs such as a collision avoidance sensor and the velocity data. The rotation matrix in the preceding paragraphs can be expanded to be:

$$\begin{pmatrix} WR(t) \\ WL(t) \\ WC(t) \end{pmatrix} = \begin{pmatrix} \cos(\theta) & -\sin(\theta) & \text{other inputs}\ldots \\ \cos(\theta) & -\sin(\theta) & \text{other inputs}\ldots \\ \sin(\theta) & \cos(\theta) & \text{other inputs}\ldots \end{pmatrix} \begin{pmatrix} SX(t) \\ SY(t) \\ \text{velocity, etc} \end{pmatrix} \quad (8)$$

The right matrix can have the same number of rows as the number of columns of the middle matrix.

FIG. 61 provides an exemplary table of the strain gauge values converted to signals for the power assist drive system to be used to determine the amount of power to apply to one or more wheels of the wheel subsystem. The cart angle and tilted angle columns represent a 45 degree rotation between a handle of the smart medical cart, as shown in FIG. 1, and a titled strain gauge coordination system. Columns AR, BR, AL, and BL represent inputs from strain gauges, as shown in FIG. 59, for 10 units of force at the selected values in the tilted angle column. Columns SRX, SRY, SLX, and SLY are the x and y values from each of the strain gauges, as shown in FIG. 59. The Sum X is the addition of the values for SRX with the values for SLX. The Sum Y is the addition of the values for SRY with the values for SLY. The WR, WL, and WC columns are voltage values for each of wheel of a wheel subsystem of a smart medical cart, e.g. WR can be a right wheel, WL can be a left wheel, and WC can be a center wheel. The voltage values for each wheel are the voltages supplied to a motor of each wheel to direct the smart medical cart in a direction based on the strain gauge inputs AR, BR, AL, and BL. The Rotation column and the Calculated column are voltage values calculated from the strain gauge inputs AR, BR, AL, and BL after a negative 45 degree rotation. The example values shown in FIG. 61 are not intended to be limiting. The values can depend on the strain applied to one or more strain gauges of the smart medical cart, such as strain gauges in FIGS. 56a and 56b.

Figure 62:
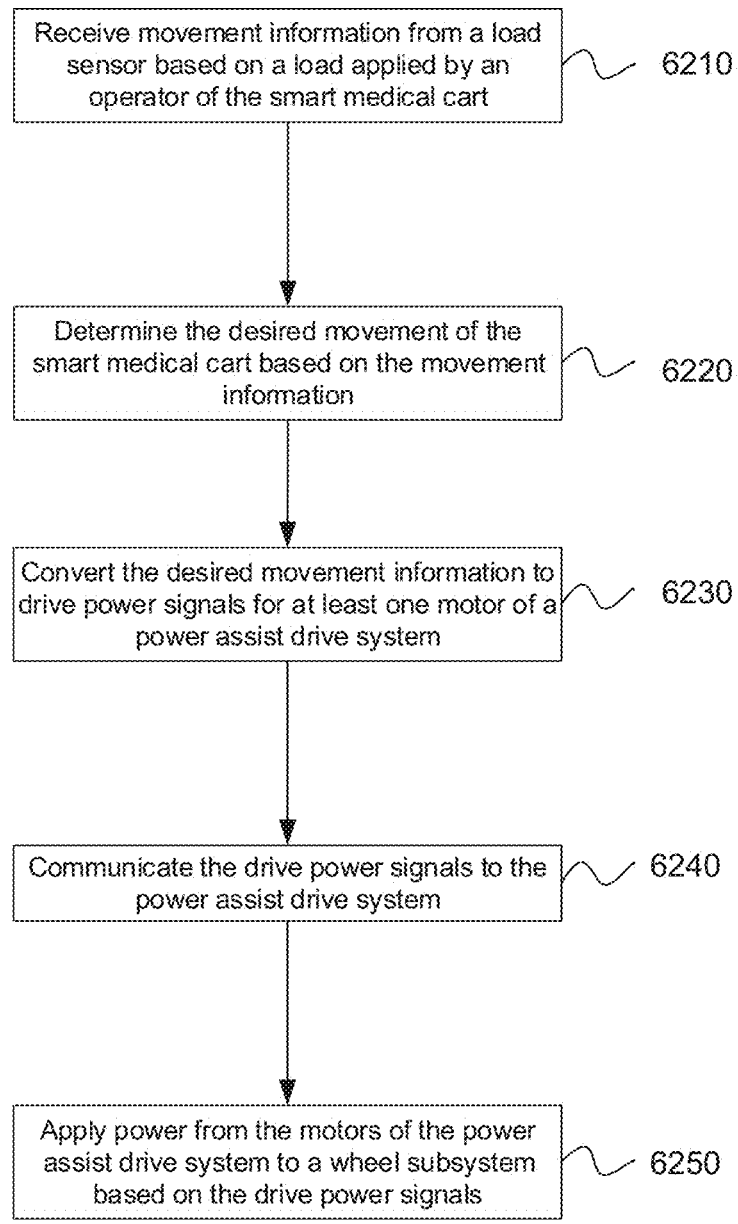
FIG. 62 depicts the functionality of computer circuitry of a user equipment operable to control a power assist drive system of a smart medical cart in accordance with an example.

FIG. 62 provides a flow chart 6200 to illustrate the functionality of one embodiment of a user equipment, such as a computing device, with computer circuitry operable to control a power assist drive system of a smart medical cart. The functionality can be implemented as a method or the functionality can be executed as instructions on a machine, where the instructions are included on at least one computer readable medium or one non-transitory machine readable storage medium. The computer circuitry can be configured to receive load information or movement information from a load sensor based on a load applied by an operator of the smart medical cart, as in block 6210. The computer circuitry can be further configured to determine desired movement of the smart medical cart based on the movement information, as in block 6220. The computer circuitry can also be configured to convert the desired movement information to drive power signals for at least one motor of a power assist drive system of the smart medical cart, as in block 6230. The computer circuitry can also be configured to communicate the drive power signals to the power assist drive system, as in block 6240. The computer circuitry can also be configured to apply power from the motors of the power assist drive system to a wheel subsystem of the smart medical cart based on the drive power signals, as in block 6240.

In one embodiment, the smart medical cart can distinguish a desire by the caregiver to move the smart medical cart diagonally from a desire by the caregiver to move the smart medical cart in a rotational direction, e.g. rotate the smart medical cart along the z axis. The smart medical cart can distinguish the input for a diagonal movement from a rotation movement by analyzing the forces applied to the load cell sensors in the x and y directions. When the load on the x axis and the load on the y axis are opposite in sign (e.g. positive and negative values), the magnitude of the load on the x axis and the magnitude of the load on the y axis are equal, and the smart medical cart is stationary (e.g. not moving), the smart medical cart can rotate about the z axis. To move in a diagonal direction the load applied on the load cell sensors of the handle of the smart medical cart can be on the same axis and the load on the x axis and the load on the y axis are the same in sign. For example, to rotate about the z axis there can be a pulling back force on one load cell sensor and a pushing force on another load cell sensor. In another example, to move the smart medical cart in a diagonal direction there is a pushing force on both of the load cell sensors.

The smart medical cart can determine an acceleration rate from a stopped position by monitoring for a constant force in a selected direction that is applied to the load cell sensors for a defined period of time. For example, when the caregiver applies a forward force to the handle for one second, the smart medical cart can determine that the caregiver desires that the smart medical cart to accelerate forward. In one embodiment, the smart medical cart can determine the rate of acceleration based on the amount of constant force applied to the strain gauges for the defined period of time. When the amount of constant force applied to the load cell sensors for the defined period of time is within a selected range, such as a relatively minimal value, the smart medical cart can determine that the caregiver desires the smart medical cart to accelerate at a relatively slow rate. When the amount of constant force applied to the load cell sensors for the defined period of time is within a different selected range, such as a relatively large value, the smart medical cart can determine that the caregiver desires the smart medical cart to accelerate at a relatively fast rate.

In one embodiment, the smart medical cart can determine if the caregiver desires to slow down the forward movement of the smart medical cart by pulling back on the handle or desires the smart medical cart to move in reverse by pulling back on the handle. When the smart medical cart is moving in a forward direction and a caregiver pulls back on the handle of the smart medical cart, the smart medical cart can begin to decelerate. When the smart medical cart is in a stopped position and/or has nearly or completely decelerated and a caregiver pulls back on the handle of the smart medical cart, the smart medical cart can move in a reverse direction.

In one embodiment, the smart medical cart can require the caregiver to apply a selected or threshold load to the handle of the smart medical cart when the smart medical cart is moving. For example, when the smart medical cart is moving at a constant rate of 5 MPH, the smart medical cart can require that the caregiver apply a selected minimum or threshold amount load, such as force or pressure, to the handle of the smart medical cart for the smart medical cart to continue to mover at the constant rate of 5 MPH. In one embodiment, when the caregiver does not apply the minimum threshold load to the handle of the smart medical cart, the smart medical cart can decelerate and/or stop the smart medical cart. In one embodiment, the smart medical cart can provide a selected level of power assistance for the caregiver and require the caregiver to provide a selected level of force to move the smart medical cart. For example, the caregiver can desire that the smart medical cart move at a constant speed of 5 MPH. The smart medical cart can provide power assistance equivalent to 4.5 MPH, e.g. a 90% level of power assistance, and require that the caregiver apply 0.5 MPH of force to the handle of the smart medical cart, e.g. 10% level of force, for the smart medical cart to move at the desired 5 MPH constant speed. In one embodiment, the zero point for where the smart medical cart is moving at a constant speed, velocity, and/or acceleration can have an additional selected load that the caregiver can apply to the smart medical cart. The zero point with the additional selected load can be associated with the speed, velocity, and/or acceleration of the smart medical cart.

In one embodiment, the smart medical cart can have a limit or maximum threshold value for the speed, velocity, and/or acceleration level of the smart medical cart. For example, when the caregiver applies a load that the smart medical cart translates into a defined speed, such as 20 MPH, the smart medical cart can limit the speed of the smart medical cart to a maximum speed of 6 MPH. In one embodiment, when the limit or maximum threshold value for the speed, velocity, and/or acceleration level of the smart medical cart is approaching or is reached, the smart medical cart can provide an indication, such as a sensory indication, to the caregiver that the smart medical cart is reaching or has reached the maximum threshold value. In another embodiment, when the limit or maximum threshold value for the speed, velocity, and/or acceleration level of the smart medical cart is approaching or is reached, the smart medical cart can apply one or more brakes of the brake subsystem to one or more wheels of the wheel subsystem.

The handle of the smart medical cart can be ergonomically shaped and/or have a selected tactile feel to guide the hands of the caregiver to the optimal locations of the handle to direct the smart medical cart. In one embodiment, the caregiver can place their hands at multiple locations on the handle to direct the smart medical cart. When the hands of the caregiver are placed at the optimal locations of the handle to direct the smart medical cart, the smart medical cart can define a pivot point of the handle. The pivot point of the handle can be a point at which the handle of the smart medical cart turns or rotates. When the caregiver places their hands at suboptimal locations on the handle, the smart medical cart can adjust or calibrate load information based on a different pivot point from the optimal pivot point. In one embodiment, the smart medical cart can detect the location of one or more hands of the caregiver on the handle of the smart medical cart. In one embodiment, the handle of the smart medical cart can include a capacitive or resistive touch sensor to determine the location of the one or more hands of the caregiver on the handle of the smart medical cart.

In one embodiment, the caregiver can direct the smart medical cart by placing two hands on the handle of the smart medical cart. In another embodiment, the caregiver can direct the smart medical cart by placing one hand on the handle of the smart medical cart. The number and location of one or more hands of the caregiver on the handle when directing the smart medical cart can change the load information from the load cells of the handle. In one embodiment, the smart medical cart can compensate or calibrate the load information based on the number and location of one or more hands of the caregiver on the handle when directing the smart medical cart. In another embodiment, the smart medical cart can define a fixed pivot point of the handle regardless of the number and location of one or more hands of the caregiver on the handle when directing the smart medical cart.

When the pivot point of the handle is fixed, the smart medical cart can analyze load information the same regardless of the number and location of one or more hands of the caregiver on the handle when directing the smart medical cart. In one embodiment, when the pivot point of the handle is fixed, to direct the smart medical cart in a desired location and/or direction, the caregiver can adjust the location and/or orientation of the handle to a desired location and/or orientation to obtain a desired or optimal response for directing the smart medical cart when the caregiver places a load on the load cell sensors. In another embodiment, when the pivot point of the handle is fixed, the caregiver can self-adjust the load the caregiver applies to one or more load cell sensors of the handle to obtain a desired or optimal response for directing the smart medical cart when the caregiver places a load on the load cell sensors. For example, when the caregiver uses one hand to direct the smart medical cart and the caregiver desires that the smart medical cart move forward, the caregiver can apply both a forward load on the handle and twist the wrist of the caregiver to apply a diagonal force to compensate for using one hand to direct the smart medical cart.

The load information received from the load cell sensors can be filtered and/or smoothed. In one embodiment, a box car average or moving average can be used to smooth the load information. A moving average can be used to analyze data points by creating a series of averages of different subsets of the full data set. In one embodiment, the moving average can include a series of numbers and a fixed subset size (N), the first element of the moving average is obtained by taking the average of the initial fixed subset of the number series. Then the subset is modified by shifting forward, e.g. excluding the first number of the series and including the next number following the original subset in the series. This creates a new subset of numbers, which is averaged. The moving average of each subset can be repeated over the entire data series. The moving average can be a set of numbers, each of which is the average of the corresponding subset of a larger set of datum points.

In one embodiment, a moving average can use unequal weights for each data value in the subset to emphasize particular values in the subset. In another embodiment, the number of subsets, the subset size, and/or the weights for each data value can vary based on the caregiver using the smart medical cart. In one embodiment, each subset can be the load information collected from the handle of the smart medical cart during 0.2 seconds. In another embodiment, the number of subsets, N, can be adjusted to larger values for increased smoothing of the load information and smaller values for decreased smoothing of the load information.

The smart medical cart can be used in environments with varying degrees of traction. When the flooring surface that the smart medical cart is moving along changes to a flooring surface with reduced traction, the caregiver can push harder to indicate that the smart medical cart is not providing the desired amount of assistance for the flooring surface. When the caregiver pushes harder on the handle of the smart medical cart, the smart medical cart can increase the amount of power the power assist drive system provides to one or more wheels of the wheel subsystem to move the smart medical cart at a higher velocity.

In one embodiment, the smart medical cart can lose traction to one or more wheels while maintaining traction to the other wheels of the wheel subsystem. In one embodiment, the smart medical cart can lose traction to all the wheels of the wheel subsystem. The smart medical cart can use the look-up table to determine the optimal adjustment in power to each of the wheels for the reduced traction level based on each wheel's current velocity and acceleration. Similarly, the smart medical cart can determine the optimal adjustment in power to each of the wheels in other situations, such as changes in flooring surfaces, inclining or declining flooring surfaces, increasing or decreasing downward pressure on the wheels, and so forth.

In one embodiment, noise from the load cell sensor measurements can be filtered out and then the load cell sensor measurements can be used to adjust the smart medical cart and/or direct the path of the smart medical cart.

Returning to FIG. 58, illustrates a handle of the smart medical cart that can control the three axial directional movements, e.g. the x, y, and z axes, that the load cell sensors can control. In one embodiment, the load cell sensors that measure the load in the x axis direction and the load in the y axis direction can be used to determine the forward motion, backward motion, lateral motion, and diagonal motion. In another embodiment, one or more load cell sensors that measure a load in the z axis direction. The load information in the z axis direction can be used to adjust, e.g. lower or raise, the height of the first work platform, second work platform, computing device, display screen, first vertical support, second vertical support, and so forth.

In one embodiment, the load cell sensors that measure the load in the z axis can be engaged when the smart medical cart is in a stationary or substantially stationary position and can be disengaged while the smart medical cart is moving. For example, a medical caregiver can adjust the height of various parts of the smart medical cart when the smart medical cart is stationary or not moving and when the smart medical cart is moving the caregiver will not be able to adjust the height of the various parts of the smart medical cart. In another embodiment, the load cell sensors that measure the load in the z axis can be continuously engaged and the mechanisms to adjust the height of selected parts of the smart medical cart can be engaged when the smart medical cart is stationary and disengaged when the smart medical cart is moving The smart medical cart can include one or more activity sensors. In another embodiment, the activity sensors can be integrated or embedded at multiple locations along the handle. In another embodiment, the activity sensors can include a touch sensor, a pressure sensor, and so forth.

In one example, the smart medical cart may use an activity sensor to determine if the caregiver controlling the smart medical cart desires that the smart medical cart move forward, laterally, speed up, slow down, rotate, etc.

The activity sensor can be adapted or customized to the caregiver who is currently using the medical cart. In one embodiment, a baseline value can be set for the activity for the amount of force to apply to the handle of the smart medical cart to indicate a desire to move the smart medical cart forward, laterally, speed up, slow down, rotate, and so forth. In one embodiment, the baseline values can be preset or defined values. For example, an average caregiver can apply a defined load on the handle of the smart medical cart to direct the smart medical cart to a desired location at a desired speed. The loads that the average caregiver applies to the handle of the smart medical cart can be set as the preset or defined baseline values for different loads that the average caregiver applies for selected directions and speed of the smart medical cart.

To adapt or customize the activity sensor for each unique caregiver, the baseline value can be adjusted based on user preferences of each caregiver. The user preferences of each caregiver can include the amount of assistance provided to the move the smart medical cart, the maximum speed of the smart medical cart, the acceleration rate of the smart medical cart, the braking or deceleration rate of the smart medical cart, and so forth. In one embodiment, the caregiver can initially input the caregiver's user preferences to adjust the baseline value by increasing or decreasing the baseline value using a gain value based on user preference of the caregiver. For example, the user can input a preference of low, medium, or high for each user preference and the smart medical cart will increase or decrease the gain value accordingly. In another embodiment, the caregiver can perform selected activities to adjust the baseline value for the caregiver. For example, the caregiver can apply a load to the smart medical cart to move the smart medical cart forward, backward, diagonally, at selected walking speeds, accelerate from a stop to walking speed, and so forth and the smart medical cart can adjust the baseline value based on the load the caregiver applies for the selected activities.

The caregiver can input into the smart medical cart selected physical information of the caregiver, such as the gender, height, weight, physical fitness, and so forth of the caregiver. The smart medical cart can adjust one or more baseline values based on the physical information of the caregiver. For example, when the caregiver is a relatively tall individual, the stride of the individual can be longer than the stride of a relatively shorter individual. The smart medical cart can adjust the speed, velocity, and/or acceleration baseline values to account for the stride of the caregiver. In another embodiment, if the caregiver is relatively physically fit, the caregiver may move at a faster speed than a caregiver that is relatively less physically fit. The smart medical cart can adjust the speed, velocity, and/or acceleration baseline values to account for the physical fitness level of the caregiver. In another example, when the weight level of the caregiver is relatively high, the caregiver may apply a larger load to the handle of the smart medical cart than the load applied by a caregiver with a weight level that is relatively low. The smart medical cart can adjust the sensitivity baseline values of one or more of the load cell sensors to account for the weight level of the caregiver.

The baseline values and/or adjusted baseline values can be stored in a matrix or lookup table. The smart medical cart can continuously, semi-continuously, or periodically update and/or adjust the baseline values and/or adjusted baseline values based on the smart medical cart adapting or customizing input from one or more sensors of the smart medical cart. In one embodiment, gross baseline values can be stored in a matrix or lookup table. The gross values can be iteratively refined to adjust for the adapting or customizing input of one or more sensors of sensor information of the smart medical cart.

In one embodiment, the smart medical cart can update and/or adjust the baseline values and/or adjusted baseline values by multiplying one or more of the baseline values and/or adjusted baseline values of a lookup table by a selected gain value. The smart medical cart can update and/or adjust the baseline values and/or adjusted baseline values by multiplying one or more of the baseline values and/or adjusted baseline values of a matrix by a selected gain value. In one embodiment, the smart medical cart can use eigenvectors and eigenvalues to update and/or adjust the baseline values and/or adjusted baseline values of the lookup table and/or matrix. Eigenvectors can be vectors, such as characteristic vectors, proper vectors, or latent vectors, associated with a linear system of equations, such as the preceding matrix equations. Each eigenvector can be paired with a corresponding eigenvalue. In one embodiment, the eigenvectors and eigenvalues can be equivalent to matrix diagonalization. The eigenvectors and eigenvalues can be used to enable stability analysis of data from one or more sensors of the smart medical cart and/or to determine oscillations of data from one or more sensors of the smart medical cart.

The smart medical cart can also be configured to learn or adapt the baseline value with a gain value using a smart algorithm. In one embodiment, the smart medical cart can monitor and/or record the activity sensor information during periods when a selected caregiver is using the cart. The smart medical cart can then analyze the activity sensor information to determine trends or patterns in the activity sensor information and adapt or adjust the user preference gain values based on the trends or patterns. For example, if each time a selected caregiver uses the smart medical cart the caregiver has a firm grip or a soft grip, the activity sensor can record that user preference information.

The smart medical cart can analyze data from one or more sensors to determine a constant or regular recursive values or sequences in the sensor data. For example, when a caregiver applies a relatively large load to the handle of the smart medical cart each time the caregiver desires that the smart medical cart move forward from a stopped position and a relatively small load each time the caregiver desires that the smart medical cart stop, the smart medical cart can adjust the baseline values for acceleration from a stopped position and deceleration to a stopped position based on determined recursive values. In another embodiment, the smart medical cart can determine when input from one or more sensors is underdamped or overdamped to obtain a desired response for the smart medical cart. For example, when an acceleration value from a caregiver is consistently overdamped, the smart medical cart can adjust the sensor input and/or adjust the input data to adapt to the consistently overdamped acceleration value.

The smart medical cart can analyze the data from one or more sensors to determine when there may be oscillation on the input data from the sensors. In one embodiment, oscillation in the input data from the sensors can indicate that the smart medical cart may be fluctuating between providing too much and too little assistance to the caregiver, such as when the caregiver desires assistance to move the smart medical cart. In one embodiment, oscillation in the input data from the sensors can indicate that the smart medical cart may be providing assistance for too much of a period of time and the caregiver is overcorrecting to account for too much assistance.

The smart medical cart can analyze oscillation in the input data from the sensors to determine when the caregiver has to overcorrect and adjust the baseline value from the one or more sensors of the smart medical cart to compensate or correct for the overcorrecting of the caregiver. For example, the caregiver may desire to move the smart medical cart forward. When applying a load to the handle of the smart medical cart, the caregiver may initially apply a greater load to the left side of the handle than the right side of the handle, indicating to the smart medical cart that the caregiver desires to go right. To compensate for the rightward movement the caregiver may apply a greater load to the right side of the handle to correct for the rightward movement. The smart medical cart can determine the oscillation between loads on the right and left side of the handle can adjust the input value to avoid overcorrecting by the caregiver and direct the smart medical cart in the direction the caregiver desires. In one embodiment, the smart medical cart can adjust the input values by increasing or decreasing the sensitivity of one or more of the sensors of the smart medical cart. In another embodiment, the smart medical cart can smooth or filter the input data from one or more of the sensors of the smart medical cart to eliminate or reduce oscillation of in the input data of the sensors.

The smart medical cart can adjust one or more sensors, sensor data, systems, subsystems, and/or devices of the smart medical cart based on one or more other sensors, sensor data, systems, subsystems, and/or devices of the smart medical cart. For example, the smart medical cart can adjust the amount of power provided to each wheel of the wheel subsystem by the power assist drive system based on sensor data from a center of gravity sensor, and ambient noise level sensor, and a flex point sensor.

The smart medical cart can analyze the user preference information using the smart algorithm to determine the user preference and adjust the gain value of the user grip to be automatically calibrated for the caregiver. In one example, when the caregiver prefers a relatively more sensitive control or a relatively less sensitive control, the smart medical cart can automatically calibrate the gain value of the user sensitivity preference to account for the difference in user preferences between different caregivers. In one embodiment, when the caregiver desires more sensitive steering, e.g. a lower force input, a larger gain will be applied to the baseline value. In another embodiment, when the caregiver desires less sensitive steering, e.g. a high force input, a lower gain will be applied to the baseline value.

In one embodiment, the smart medical cart can collect data or information from the activity sensor and perform a vector analysis on the data or information to determine a desired smart medical cart movement by the caregiver. For example, the smart medical cart may analyze the data or information collected from the activity sensor and determine that the activity sensor information indicates the caregiver desires to move the cart forward. In another example, the smart medical cart may analyze the activity sensor information and determine that the activity sensor information indicates the caregiver desires to rotate the medical cart 90 degrees clockwise from its current position. In another embodiment, the smart medical cart may use an activity sensor to determine a desired responsiveness and/or sensitivity of the smart medical cart to sensor or data input.

An activity sensor and/or a load cell sensor can be located at one or more flex points on the smart medical cart. The flex point location on the smart medical cart can include: where the motor attaches to the wheeled pedestal; where the vertical support attaches to the wheeled pedestal; where the vertical support attaches to the first work platform and/or second work platform; along the vertical support; and so forth.

In one embodiment, the activity sensor or load cell sensor can be used in combination or in the aggregate with a three dimensional (3D) accelerometer or 3D level. For example, when the smart medical cart is moving along a declining surface, the caregiver may pull back on the handle of the cart to slow the cart down but still desire that the cart move forward. In this example, if the activity sensor was used independent of the 3D accelerometer, the smart medical cart may determine that the caregiver desires that the medical cart move backwards and begin moving the smart medical cart in a backwards movement. If the activity sensor was used in combination with the 3D accelerometer, the smart medical cart can determine that the smart medical cart is moving along a declining surface and that the caregiver desires that the smart medical cart continue to move forward at a reduced or decelerated speed.

The smart medical cart can include a flex point sensor. In one embodiment, the flex point sensor can be used to determine if an angle of one location of the smart medical cart has changed relative to another location. An increase or decrease in the angle of one location of the smart medical cart relative to another location can indicate a change in the probability of the smart medical cart tipping over.

A flex point sensor can be used to determine if there are one or more areas or locations on the smart medical cart that are sagging or bending. For example, if the caregiver loads the cart with too much weight, such as medical supplies and equipment, the smart medical cart can use one or more flex point sensors to determine that the wheeled pedestal is beginning to sag or bend. In another embodiment, the smart medical cart can adjust the height of the smart medical cart based information received from the flex point sensors. For example, if a caregiver places a large amount of medication in a container of the smart medical cart, the smart medical cart can adjust the maximum height of the smart medical cart based on the weight distribution of the smart medical cart.

In another embodiment, the smart medical cart can use the flex point sensors to determine when the cart has been modified to void a manufacturer warranty. For example, when the maximum display screen weight that can be mounted or attached to the second vertical support is 2 pounds (lbs) and a user installs a 5 pound display screen, the smart medical cart can have a flex point sensor at or approximate to a location where the display screen attaches to the second vertical support to determine when that the display screen is too heavy for the vertical support and the manufacturer warranty is voided.

In another embodiment, a load cell sensor or weight gauge can be located at or near where the vertical support attaches to the wheeled pedestal. The load cell sensor or weight gauge can be used to determine the weight of the medication storage area. In one embodiment, the weight of the medication storage area can be used to determine if the predetermined amount of medication is present on the smart medical cart or if medication has been dispensed to a medical patient. For example, as a nurse begins his or her patient visits to check up on the patients and dispense medication, the smart medical cart may be loaded with a desired amount of medication. In one embodiment, the weight of the medication may be predetermined, and the smart medical cart can determine if the actual weight of the medication in the medication storage containers of the smart medical cart matches the predetermined weight of the medication using a load cell sensor and/or a weight gauge. In another example, the smart medical cart can measure the weight of the empty medication storage containers and the weight of the medication storage containers of the smart medical cart to determine the amount of medication placed in the medication storage containers.

The load cell sensor or weight gauge can be used to determine if the proper amount of medication has been dispensed. For example the strain gauge or weight gauge can measure the weight of the medication storage area before the medication is taken out to be dispensed and the weight after the medication has been taken out to be dispensed. The smart medical cart can determine the difference between the weights and compare it to the predetermined weight of the medication or the weight of the empty medication storage container to determine if the correct amount of medication has been dispensed.

As a smart medical cart can have a considerable amount of weight at selected locations, such as locations other than the wheeled pedestal of the smart medical cart, it may be advantageous to determine where the center of gravity of the smart medical cart is located and/or be able to adjust the center of gravity to avoid the smart medical cart tipping over or the caregiver losing control of the smart medical cart as the smart medical cart is moved. In one embodiment, a center of gravity sensor can be used to calculate where the center of gravity is located on the smart medical cart. In another embodiment, the center of gravity sensor can be used to determine if the center of gravity has shifted or moved. In one embodiment, the center of gravity sensor can be an accelerometer, angular position sensor, load cell sensor, flex point sensor, and so forth. The smart medical cart can use one center of gravity sensor or a combination of center of gravity sensors to more accurately determine the center of gravity. In one embodiment, determining the center of gravity of the smart medical cart can include measuring the angle of various parts of the smart medical cart in relation to the flooring surface.

In one example, the smart medical cart may use the center of gravity sensor to determine the probability or likelihood of the smart medical cart tipping over. A load cell sensor can determine the current mass/stress at certain locations on the smart medical cart. The measurements from the load cell sensor can be taken in combination with an accelerometer (or motor encoders) to determine the changes in the relative location of the center of gravity due to motion. For each calculated center of gravity, a speed threshold can be set for movement of the smart medical cart on a flat surface, and at various angles of surfaces. The smart medical cart can be configured to be limited to a top speed below the speed threshold when using the power assist drive system based on an identified center of gravity.

In one embodiment, one or more load cell sensors can be located in the vertical support, the wheel pedestal, the first work platform, the second work platform, the second vertical support, and/or other defined locations on the smart medical cart. The load cell sensors can be used to detect the angle of the smart medical cart relative to a defined location, such as the angle of the vertical support relative to the wheeled pedestal. The load cell sensors can also be used to calculate the mass of each section. The mass of each section may change due to the placement of equipment or medicines on the smart medical cart. The angle, mass, and height of each portion of the smart medical cart can be used to calculate the center of gravity.

In one embodiment, the smart medical cart can determine when the smart medical cart is starting to tilt in an undesirable direction. When the smart medical cart starts to tilt in an undesirable direction, the smart medical cart can adjust the height or location of the wheels relative to the first or second vertical support, the height or location first work platform, the height or location of the second work platform, the height or location of the first vertical support, the height or location of the second vertical support, and so forth. In one embodiment, the smart medical cart can adjust the height of one or more of the wheels of the wheel subsystem and maintain the height of the other wheels in the wheel subsystem to tip the cart in a selected direction to compensate for tipping.

In one embodiment, an angular position sensor of a rotary sensor can be used in combination with a load cell sensor and/or an accelerometer to determine the probability of the smart medical cart tipping over. The angular position sensor or the rotary sensor can measure the relation between a defined position and another selected position. The angular position sensor calculates the orientation of an object with respect to a specified reference position as expressed by the amount of rotation necessary to change from one orientation to another orientation about a selected axis. The angular position sensor can be an absolute position sensor or a relative position sensor, such as a displacement sensor. The angular position sensor can be a linear, angular, or multi-axis sensor. In one embodiment, one or more angular position sensors can be located in the first support column, the wheel pedestal, first work platform, second work platform, the second support column, and/or other defined locations on the smart medical cart.

When the smart medical cart determines that the center of gravity of the smart medical cart has changed or shifted to increase the probability beyond a selected threshold or likelihood of the smart medical cart tipping, the smart medical cart can adjust the center of gravity of the smart medical cart to avoid the smart medical cart tipping over. When the angular position sensor measures a change in the position of the smart medical cart relative to a defined location, such as the flooring surface, the smart medical cart can adjust the center of gravity to compensate for the change in position to avoid the smart medical cart tipping over. In one embodiment, the smart medical cart can adjust the center of gravity of the smart medical cart by redistributing one or more masses located on the smart medical cart. In addition, the height of selected portions of the smart medical cart can be reduced to lower the center of gravity, as previously discussed. In another embodiment, the power provided by a motor to one or more of the wheels can be adjusted to return the smart medical cart to an acceptable position to prevent tipping.

In one embodiment, to determine the probability of the smart medical cart tipping over, the smart medical cart can determine the current smart cart velocity and use a load cell sensor to determine the location of the current center of gravity. The load cell sensor can measure the flex points at selected locations on the smart medical cart to determine a direction the center of gravity can be shifted to compensate for the increase probability of the smart medical cart tipping over.

In another embodiment, the smart medical cart can determine the relative velocity of one location of the smart medical cart in relation to another location of the smart medical cart. When the one location of the smart medical cart changes velocity or speed in relation to another location of the smart medical cart, the change in velocity or speed can indicate an increase or decrease in the probability of the smart medical cart tipping over. In another embodiment, the smart medical cart can determine an increase or a decrease in the probability of the smart medical cart tipping over using one or more load cell sensors or weight gauges to determine a shift or change in weight or load distribution and/or the direction the weight is moving.

Figure 63:
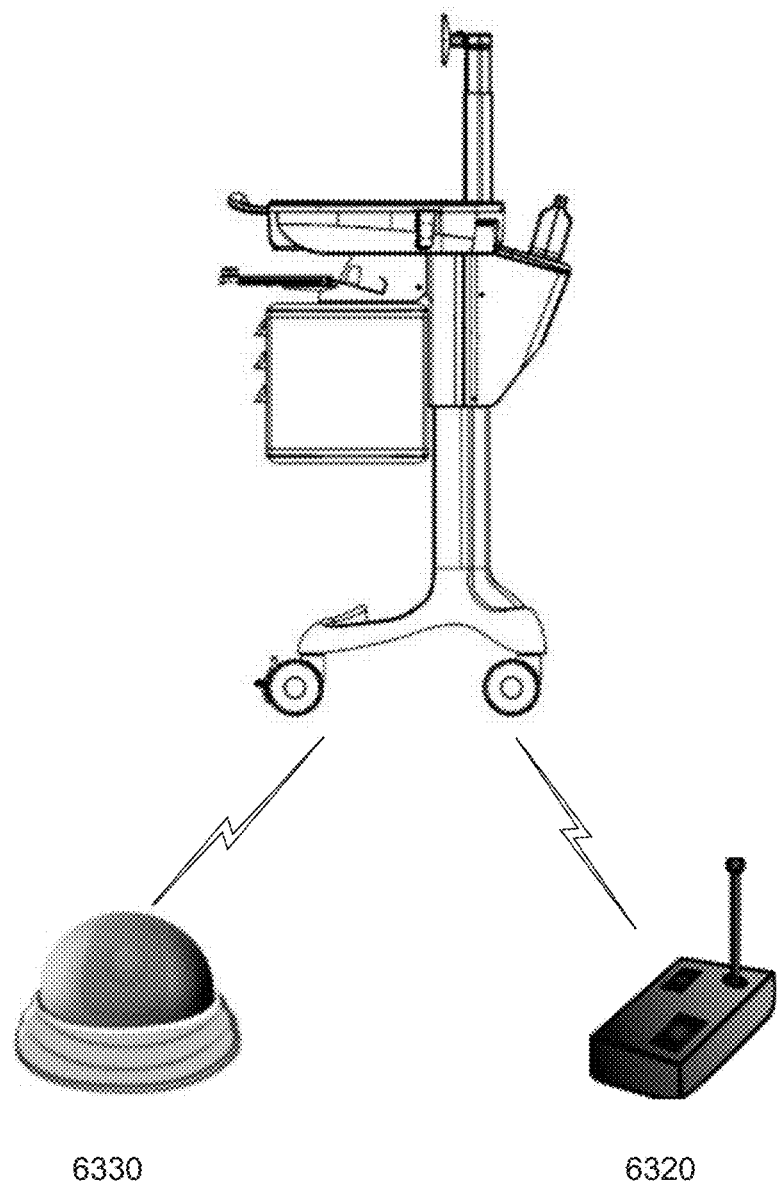
FIG. 63 shows a smart medical cart communicating with sensors external to the smart medical cart in accordance with an example.

FIG. 63 shows the smart medical cart 6310 communicating with sensors external to the smart medical cart (external sensors) 6320 and 6330. The smart medical cart 6310 can communicate with one or more with sensors external 6320 and 6330. For example, a medical facility can have external motion sensors 6320 and 6330 located at selected locations around the medical facility. The smart medical cart 6310 can communicate with the external motion sensor 6330 or external location sensor 6320 and use the information from the external sensors 6320 and 6330 in combination with the sensors integrated or attached to the smart medical cart 6310 to get a more detailed or optimal picture of the environment surrounding the smart medical cart 6310. In one embodiment, the smart medical cart 6310 can aggregate the data communicated from the external sensors 6320 and 6330 with the data from the sensors integrated or attached to the smart medical cart 6310.

In one embodiment, the smart medical cart can determine the power level for the power source of the smart medical cart, such as the power level of one or more of the external batteries or internal batteries powering the smart medical cart. In another embodiment, the smart medical cart can determine the rate at which the smart medical cart is consuming power from the power source of the smart medical cart. The smart medical cart can determine the power level or the rate that the power is being consumed by using a power gauge, battery gauge, a voltage meter, or a current meter. In one embodiment, the smart medical cart can determine when the power level has dropped below a selected threshold or the smart medical cart is consuming power above a selected power consumption rate. When the power level drops below a selected threshold or the consuming power exceeds a selected power consumption rate the smart medical cart can switch to a power saving mode or reduce the power consumption mode of the smart medical cart. The power saving mode can include decreasing the brightness of a display screen, decreasing the processing power of a computing device, decreasing the power provided to the power assist drive system, turning off the power provided to the power assist drive system, and so forth.

In another embodiment, a camera can be used to determine if a user such as a caregiver is located at the smart medical cart or proximate to the smart medical cart. When a caregiver is not located at the smart medical cart or proximate to the smart medical cart for a selected period of time, the smart medical cart can enter into the power savings mode. In one embodiment, when a user such as a caregiver returns to the smart medical cart, the smart medical cart can determine the caregivers presence and exit the power saving mode and return to a normal usage mode. The presence of the caregiver may be determined using motion sensors or more complex detection means, such as facial recognition or other remote biometric identification means such as retinal scanning.

In one embodiment, the smart medical cart can disengage the power assist drive system when the power source decreases below a selected threshold, such as 25 percent of power remaining. One advantage of disengaging the power assist drive system at a selected threshold is to save the remaining power to enable the smart medical cart to provide power the computing device and/or medical devices. Another advantage of disengaging the power assist drive system at a selected threshold is to motivate the user to recharge the power source and/or exchange the power source, such as a depleted battery, for another power source such as a recharged battery.

The smart medical cart can include a mobile power source, such as a battery, to power the systems, subsystems, devices, and/or equipment of the smart medical cart. When the mobile power source is fully discharged, e.g. the batteries are empty, the smart medical cart can switch to a manual operation mode. In one embodiment, the manual operation mode can disengage the power assistance system, wheels, drive motors, and so forth to enable the caregiver to continue to maneuver the smart medical cart.

The smart medical cart can automatically save selected data, information, user preferences, and so forth before the mobile power source is fully discharged. In one embodiment, when the smart medical cart reaches a power level of 5 percent power remaining for an external battery, the smart medical cart will automatically save all or selected information and data of the computing device to the computing device. In one embodiment, when the smart medical cart reaches a power level of 5 percent power remaining for an external battery, the smart medical cart can communicate all or selected information and data of the computing device to a central server and/or a third party. In another embodiment, the smart medical cart can indicate to the caregiver that the smart medical cart may lose power if the power source is not recharged or exchanged. In another embodiment, the smart medical cart can indicate to the caregiver to save information and data to the computing device before the mobile power source if fully depleted.

The smart medical cart can have an integrated or external power source, such as a backup battery, to provide the smart medical cart with power while the main power source is exchanged or recharged. In one embodiment, the backup battery can provide power when the smart medical cart communicates information to a third party or central server and/or saves information to the computing device.

The smart medical cart can determine when the smart medical cart is moving or transporting between locations and switch the smart medical cart into a transportation mode. In one embodiment, when the smart medical cart is in a transportation mode, the smart medical cart can adjust a height of one or more parts of the smart medical cart, such as the first work platform, second work platform, first vertical support, second vertical support, computing device, display screen, and so forth. For example, when the smart medical cart is being transported or moved between locations of use, the display screen height can be reduced to enable the caregiver to be able to see over the display screen to steer the smart medical cart. The height of the parts of the smart medical cart may be reduced based on a height of the user. A shorter user can have the height further reduced to enable the shorter user to see over the display screen or other components on the smart medical cart. The height of the user can be entered and stored as a user preference, as previously discussed.

In another embodiment, transportation mode can comprise adjusting the location and/or orientation of the one or more parts of the smart medical cart, such as the first work platform, second work platform, computing device, display screen, and so forth. For example, when the smart medical cart is being transported or moved between locations of use, the second work platform can be retracted to a location under the first work platform. In another example, when the smart medical cart is being transported or moved between using locations of use the display screen can be reoriented from an orientation where a plane of the display screen is facing the caregiver to an orientation where the plane of the display screen is facing away from the caregiver. In another example, when the smart medical cart is being transported or moved between use locations, the display screen plane can be moved to face the caregiver and can be moved to the left or right side of the cart relative to the caregiver while still facing the caregiver. One advantage of reorienting and/or moving the display screen plane is to provide a substantially clear field of view for the caregiver to navigate or direct the smart medical cart while the smart medical cart is being transported between use locations.

The smart medical cart can enter or switch to a transportation mode when the smart medical cart triggers a selected preference. In one embodiment, the selected preference can include the speed of the smart medical cart, the velocity of the smart medical cart, the location of the smart medical cart, and so forth. In one embodiment, when the speed that the smart medical cart is moving at is equal to or exceeds a selected or defined threshold, the smart medical cart can switch into a transportation mode. For example, when the speed of the smart medical cart exceeds 2 miles per hour (mph), the medical cart can enter into a transportation mode. In another example, when the smart medical cart is located in the hallway of a medical facility, the smart medical cart can switch to the transportation mode. In another embodiment, the user can manually switch the smart medical cart into a transportation mode.

In another embodiment, when the smart medical cart enters or switches to the transportation mode, the smart medical cart will also enter other defined or selected modes, such as a power saving mode. For example, when the smart medical cart exceeds 2 mph, the smart medical cart can enter a transportation mode and reduce the height of the display screen and at substantially the same time the smart medical cart can also enter a power saving mode and enable the brightness of the display screen or the processing power of the computing to be reduced, and other electronic devices operating on the smart medical device to be operated in a power saving mode when available.

The smart medical cart can reenter or resume a normal usage mode when the speed of the smart medical cart decreases below a selected speed level and/or when the smart medical cart arrives at a selected location.

Figure 64:
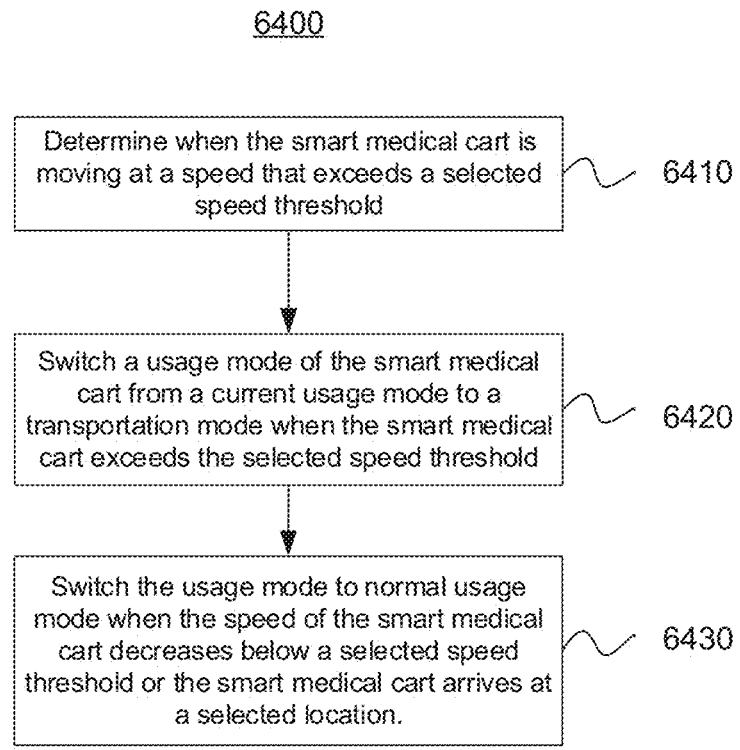
FIG. 64 depicts the functionality of computer circuitry of a user equipment operable to control a usage mode of a smart medical cart in accordance with an example.

FIG. 64 provides a flow chart 6400 to illustrate the functionality of one embodiment of a user equipment, such as a computing device, with computer circuitry operable to control a usage mode of a smart medical cart. The functionality can be implemented as a method or the functionality can be executed as instructions on a machine, where the instructions are included on at least one computer readable medium or one non-transitory machine readable storage medium. The computer circuitry can be configured to determine when the smart medical cart is moving at a speed that exceeds a selected speed threshold, as in block 6410. The computer circuitry can be further configured to switch a usage mode from a current usage mode of the smart medical cart to a transportation mode when the smart medical cart exceeds the selected speed threshold, as in block 6420. In one embodiment, the smart medical cart can adjust one or more setting, such as hardware settings or software settings, when the smart medical cart enters a transportation mode. The computer circuitry can also be configured to switch the usage mode to a normal usage mode when the speed of the smart medical cart decreases below a selected speed threshold or the smart medical cart arrives at a selected location, as in block 6430.

The smart medical cart can be used in a location where a plurality of individuals are located and/or an individual's privacy level is lower. In one embodiment, the smart medical cart can determine that individuals other than the caregiver are located in proximity to the smart medical cart and can enter a privacy mode. In another embodiment, the caregiver can switch the smart medical cart into a privacy mode. When the smart medical cart is in a privacy mode, the smart medical cart can adjust the viewing angle of the display screen to enable the caregiver to view the display screen and disable or hinder other individuals from viewing the display screen. In one embodiment, the smart medical cart can rotate or reorient the display screen along the vertical axis or z axis to change the viewing angle of the display screen. In another embodiment, the smart medical cart or the caregiver can adjust the illumination level of the display screen based on the level of privacy approximate the smart medical cart. For example, when the smart medical cart is in a private area the smart medical cart can be fully illuminated and when the smart medical cart is in an area with lower privacy levels the illumination level of the display screen can be decreased. One advantage of rotating or reorienting the display screen plane is to protect critical information, such as patient information, from being viewed by unauthorized individuals.

In one embodiment, the smart medical cart can include a security access system. The security access system can include a biometric identification (ID) module to determine the ID of an individual, such as when an individual is in proximity to the smart medical cart. In one embodiment, the biometric ID module can determine the ID of an individual by using biometric sensors, such as an imaging device or scanner, to perform: facial recognition of the individual, fingerprint scanning of the individual, palm print scanning of the individual, iris recognition scanning, retina scanning, voice recognition, vein pattern recognition, and other biometric measurements. In one embodiment, the biometric sensors can take at a biometric measurement of a biometric characteristic of the individual that is internal to the individual or not visible from outside the individual's body, such as a biometric measurement at a subdermal layer, muscular layer, vascular layer, or other internal layer of the human body. In one embodiment, the biometric sensors can take at a biometric measurement of a biometric characteristic of the individual that is externally visible, such as a biometric measurement at a dermal layer.

In one embodiment, the smart medical cart can communicate with a central server to determine the identification information and/or security information of the individual desiring to be a user. For example, the central server can maintain an active directory of the staff, employees, patients, third party contractors, guest, and so forth. In determining the identification information and/or security information of the individual desiring to use the smart medical cart, the smart medical cart can collect the user's identification information and/or security information and compare the collected identification information and/or security information with the identification information and/or security information stored on the central server. When the smart medical cart or the central server determines the identification information and/or security information of the individual substantially matches the identification information and/or security information stored on the central server, the individual can be given access to selected systems, subsystems, devices, equipment, or information on or attached to the smart medical cart based on the user's authentication information and the security level granted by the central server and/or the computing device operating on the smart medical cart.

One advantage of the smart medical cart using the identification information and/or security information of the central server can be when the security or access status or level of an individual changes. For example, if a nurse previously had security access to a smart medical cart that contained medication, but the nurse recently changed employers or was fired, the information can be changed at the central server and the security access information can be automatically updated for all of the smart medical carts. With the up-to-date identification information and/or security information, the nurse could not gain access to the medication in the smart medical carts.

The security access system can restrict access to selected parts, systems, subsystems, devices, or equipment of the smart medical cart. In one embodiment, the smart medical cart can restrict access to the medication drawers of the smart medical cart. The medication drawers can have actuators that are locked at all times until the smart medical cart provides security access to the user. The security access system of the smart medical cart can include a security access manual override, such as a security key. In one embodiment, when the smart medical cart loses power, a security access manual override can provide the user with access to the medication drawers.

In another embodiment, the smart medical cart can perform biometric ID of selected individuals or all users within a scanning or measuring range or radius of one or more biometric sensors of the biometric ID system. For example, when the smart medical cart is located in a secured area of a medical facility, such as an infant ward, where only medical personnel, the infant's parents, and authorized guest are allowed in secured area, the smart medical cart can use a facial recognition sensor to monitor the ID of individuals within the scanning range of the facial recognition sensor. When the biometric ID system detects an individual that does not match the ID of individuals authorized to be in secured area, the smart medical cart can alert the caregiver and/or a third party.

In one embodiment, the smart medical cart can determine the location of the smart medical cart when an individual attempts to access medication in one or more medication storage compartments. In one embodiment, selected locations of an area, such as a medical facility, can be designated as locations for medication dispensing or medication storage compartment access locations. In one embodiment, when the smart medical cart is located at a location not designated for medication dispensing or medication storage compartment access, such as a non-patient location, the smart medical cart can lockout the individual from using or controlling the smart medical cart. In another embodiment, when the smart medical cart is located at a location not designated for medication dispensing or medication storage compartment access, such as a non-patient location, the smart medical cart can provide a sensory indication to the individual, such as a warning message that the individual is not at a medication dispensing location. In another embodiment, when the smart medical cart is located at a location not designated for medication dispensing or medication storage compartment access, such as a non-patient location, the smart medical cart can alert or warn a third part of the attempted access to the medication storage compartment.

The security access system can include a multimodal security access subsystem. In one embodiment, the smart medical cart can use a plurality of biometric measurements or biometric sensors of the biometric ID module to identify an individual. In one embodiment, the security access system can use the biometric ID module in combination with another source of identification, such as an ID badge, swipe card, personnel ID, RFID card, personal identification number (PIN), and so forth. For example, a caregiver may initially identify himself using an ID badge to gain access to the smart medical cart and then the smart medical cart can authenticate the biometric ID of the individual using the biometric ID module, or vice versa.

When the security access system authenticates the biometric ID of the individual, the authenticated can determine if the individual is authorized to access or control the smart medical cart and/or view or edit information available to the smart medical cart. If the individual is privileged to have access or control the smart medical cart and/or view information or data available to the smart medical cart, the smart medical cart can then unlock or enable access or control of the smart medical cart to the individual. In one embodiment, an individual can be granted partial or limited privileges or access to access or control the smart medical cart and/or view or edit information available to the smart medical cart. For example, the smart medical cart can enable the individual to move the medical cart and restrict access to information available to the smart medical cart. In another example, the smart medical cart can provide the individual access to selected information available to the smart medical cart and restrict access to other information available to the smart medical cart. In one embodiment, when the individual does not have authorization to access or control the smart medical cart, the smart medical cart can indicate to another person or third party that an unprivileged person is attempting to access or control the smart medical cart, such as by sounding an alarm.

In one embodiment, an individual with access or control of the smart medical cart can gain access to one or more secure networks that the smart medical cart is in communication with. For example, when an individual gains access or control of a smart medical cart, the individual can use the smart medical cart to access a network, a server, a nearby device, a communications device, or other computing devices. In one embodiment, the smart medical cart can provide the user of the smart medical cart with access to medical and/or billing records of a medical facility, such as a hospital medical or billing information database. For example, the smart medical cart can provide a caregiver with access to the medical and/or billing records of a patient that the caregiver is attending to.

In one embodiment, the network can be a communications network, such as a central hospital local area network (LAN) or wide area network (WAN), a third party LAN or WAN, or a localized wireless secure network with nearby devices using the localized wireless secure network. In another embodiment, the nearby devices can communicated directly with the smart medical cart or communicate with the smart medical cart through the network using wireless fidelity (WiFi) communications, cellular network communications, Bluetooth communications, Zigbee communications, wireless induction communications, wireless resonance communications, or other communication types.

In one embodiment, the smart medical cart can operate as a communications hub or data hub of one or more devices attached to the smart medical cart or in communications with the smart medical cart. In one embodiment, the smart medical cart can be a relay hub, where the smart medical cart transfers information from one or more devices attached to the smart medical cart or in communications with the smart medical cart to a server, such as a central server or database of a medical facility. In another embodiment, the smart medical cart can be a central hub, where the smart medical cart receive data or information from one or more devices attached to the smart medical cart or in communications with the smart medical cart and stores the information and/or displays the information to an operator of the smart medical cart using a computing device.

In one embodiment, when the privilege level of an individual has been determined, the smart medical cart can customize the smart medical cart's user interface for the identified individual. The customization of the smart medical cart may include: adjusting the height of the first work platform to the individual's preference, adapting a user interface setup for the computing device and/or display screen based on the caregiver's security access privileges, adjusting the sensitivity of the various sensor of the smart medical cart, unlocking selected information available to the smart medical cart, and so forth.

The smart medical cart can be instructed or automatically determine that the caregiver accessing the smart medical cart is a new user. For example, if it is the first time a user has logged in to a smart medical cart, the user can be considered a new user. When the smart medical cart determines that the caregiver is a new user, the smart medical cart can provide special assistance to the new caregiver. The special assistance can include: smart medical cart user training, user tips, troubleshooting information, a different user interface, a learning program, tutorial videos, first-time user preference selection, a customer service hotline program, a user manual, and so forth.

In one embodiment, a selected individual, such as a security administrator or caregiver supervisor can select a security authentication procedure for a caregiver to access or control the smart medical cart. For example, the caregiver supervisor can select the minimum number of digits for the security code or PIN code that a caregiver can use to access a smart medical cart. In one embodiment, the security authentication procedure can change or vary based on the location or use of the smart medical cart. For example, when the smart medical cart is located in an emergency room, the security authentication procedure can be changed to enable quicker access or control to the smart medical cart, such as only requiring facial recognition to access or control the smart medical cart.

In one embodiment, the smart medical cart can use the security access system, such as the biometric security module, to determine the security rights of a selected caregiver. In one embodiment, the security access system of the smart medical cart can use a non-contact identification sensor, such as a facial recognition and/or voice recognition, to authenticate the ID of an individual and determine access or control to security rights and access levels of the caregiver to control or access the smart medical cart.

One advantage of using a non-contact identification sensor, such as a facial recognition and/or voice recognition security system, can be to enable a caregiver to access or control the smart medical cart without having to touch a surface of the smart medical cart. When the medical environment the smart medical cart is being used in is a sterile environment, such as a surgery room, the caregiver may avoid or minimize touching non-sterilized surfaces. Other security measures such as a PIN or a fingerprint scan can cause the caregiver to come in contact with a non-sterilized surface of the smart medical cart. A non-contact identification subsystem can enable the caregiver to gain access or control to the smart medical cart while avoiding non-sterilized surfaces.

The security access system can be activated or enabled when the non-contact identification subsystem determines that an individual desires to control or access the smart medical cart. In one embodiment, the security access system can determine when an individual attempts to control or access the smart medical cart based on the proximity of the individual to the smart medical cart. In one embodiment, the smart medical cart can determine that an individual is approximate to the smart medical cart by detecting an RFID badge. In another embodiment, the smart medical cart can determine that an individual is approximate to the smart medical cart by using facial recognition to determine the distance the individual is relative to the smart medical cart and/or the location of the individual relative to the smart medical cart. In another embodiment, the security access system can determine when an individual attempts to control or access the smart medical cart based on an audible or visual signal provided by the individual, such as waving or saying a command.

When a caregiver does not attempt to control or access the smart medical cart, the smart medical cart can be disabled and/or enter the power saving mode. When a caregiver or other type of user does not attempt to control or access the smart medical cart, the smart medical cart can be enabled and/or enter a normal operation mode. For example, when an individual is within a selected proximity of the smart medical cart, the non-contact identification subsystem can determine the ID of the individual to determine the security rights and access level of the individual and provide the individual control or access to the smart medical cart. In one embodiment, when the smart medical cart is disabled or is in power saving mode, the smart medical cart can still enable or provide power to the non-contact identification subsystem so the smart medical cart can detect when a caregiver desires to access the smart medical cart. One advantage of the smart medical cart being disabled or in power saving mode when a caregiver is not present is to ensure individuals that do not have security rights or access rights to the smart medical cart cannot use the smart medical cart when the smart medical cart is left unattended.

The security access system, including the non-contact identification subsystem, can require active participation by the individual desiring to access or control the smart medical cart to authenticate the ID of an individual. In one embodiment, the smart medical cart can indicate an activity for the individual to perform for the active participation. The activity can be blinking a selected number of times, holding up a selected number of fingers to a camera, reading a sentence displayed on the display screen, and so forth. One advantage of requiring active participation by the individual to authenticate the ID of an individual can be to ensure that the individual is living and actually present. For example, without an active participation requirement, an individual could hold up a picture of another individual for facial recognition access. By requiring the individual to blink, the non-contact identification subsystem can determine the actual presence of the individual desiring access to the smart medical cart.

Figure 65:
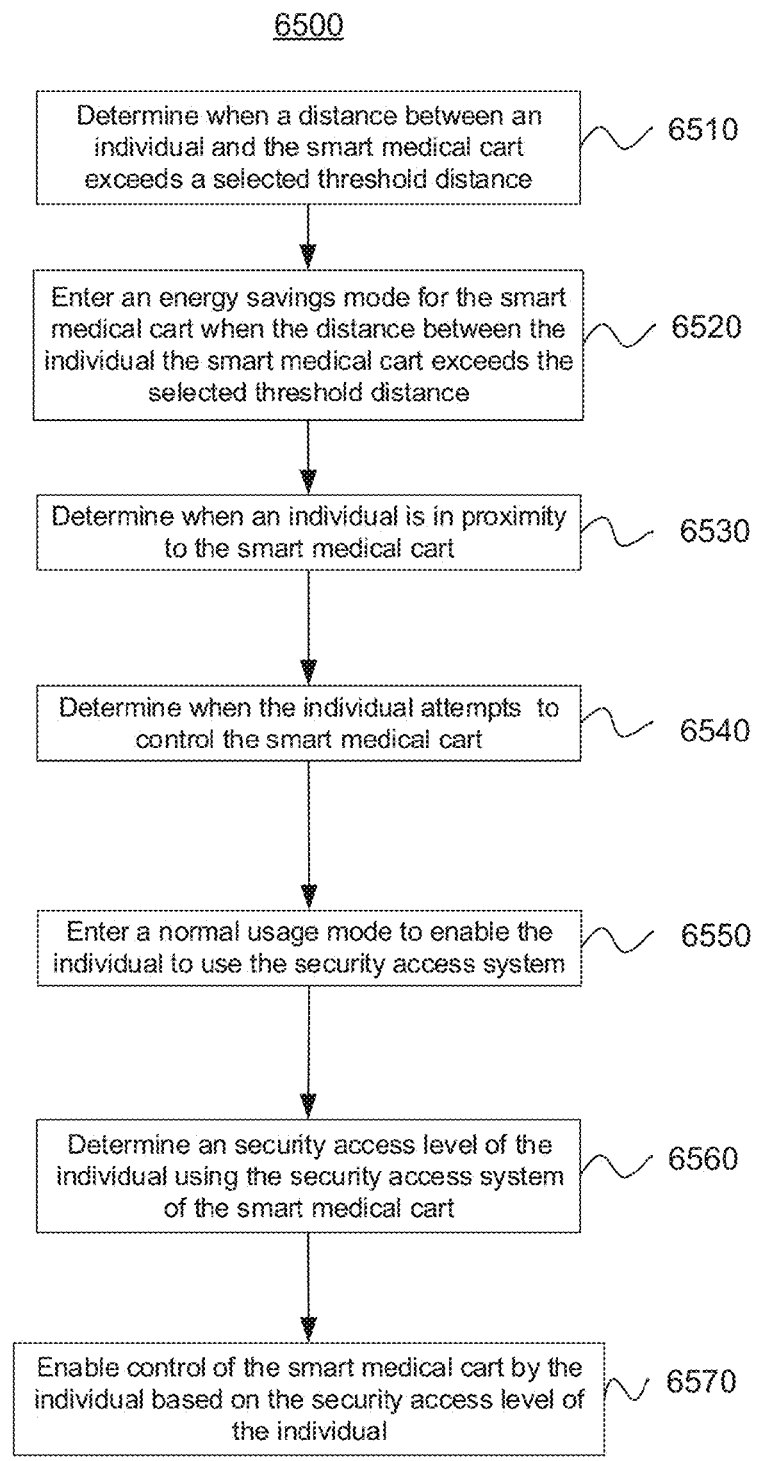
FIG. 65 depicts the functionality of computer circuitry of a user equipment operable to enable control of the smart medical cart in accordance with an example.

FIG. 65 provides a flow chart 6500 to illustrate the functionality of one embodiment of a user equipment, such as a computing device, with computer circuitry operable to enable control of the smart medical cart. The functionality can be implemented as a method or the functionality can be executed as instructions on a machine, where the instructions are included on at least one computer readable medium or one non-transitory machine readable storage medium. The computer circuitry can be configured to determine when a distance between an individual and the smart medical cart exceeds a selected threshold distance, as in block 6510. The computer circuitry can be further configured to enter an energy saving or power saving mode for the smart medical cart when the distance between the individual and the smart medical cart exceeds the selected threshold distance, as in block 6520. The computer circuitry can also be configured to determine when an individual is in proximity or within a selected threshold distance of the smart medical cart, as in block 6530. The computer circuitry can also be configured to determine when the individual attempts to control the smart medical cart, as in block 6540. The computer circuitry can also be configured to enter a normal usage mode to enable the individual to use a security access system of the smart medical cart, as in block 6550. The computer circuitry can also be configured to determine an access level of the individual using the security access system of the smart medical cart, as in block 6560. The computer circuitry can also be configured to enable control of the smart medical cart by the individual based on the security access level of the individual, as in block 6570.

The smart medical cart or parts on the smart medical cart can be repaired, maintained, exchanged, replaced, and/or upgraded. In another embodiment, the smart medical cart can validate or authenticate repaired, maintained, exchanged, replaced, and/or upgraded parts on the smart medical cart. One advantage of validating or authenticating repaired, maintained, exchanged, replaced, and/or upgraded parts can be to ensure optimal performance of the smart medical cart and decrease malfunctions of the smart medical cart. For example, when the smart medical cart is repaired, a technician or repairman can replace a part with a third party part or unauthorized part. The third party part or unauthorized part may not be fully compatible with the other systems, subsystems, or devices of the smart medical cart. By authenticating a repaired, maintained, exchanged, replaced, and/or upgraded part, the smart medical cart can ensure full compatibility.

The container of the smart medical cart can be a medication storage container. The medication storage container can include medication drawers for storage and dispensing of various medications and/or medical supplies. In one embodiment, the medication drawers can be categorized to store different types of medication in different drawers, such as narcotics in one drawer and antibiotics in another drawer. In another embodiment, the medication drawers can be categorized based on the patients on the caregiver's route. For example, the caregiver can have 20 patients to visit on a route during a given period and each of 20 drawers can be separately loaded with the medication for each patient. In one embodiment, the number of drawers can be based on a maximum height of the smart medical cart. For example, a smart medical cart that has a maximum height of 6 feet can have up to 32 drawers while a smart medical cart with a maximum height of 7 feet can have up to 64 drawers. In another embodiment, the number of drawers can be based on a minimum height level limitation of the smart medical cart. For example, a smart medical cart that can be lowered to where the minimum distance between the first work platform and the wheeled pedestal, as shown in FIG. 1, is 1 foot can have up to 15 drawers while a smart medical cart that can be lowered to where the minimum distance between the first work platform and the wheeled pedestal, as shown in FIG. 1, is 2 feet can have up to 30 drawers. The number of drawers can vary based on the maximum height and minimum height ability of the smart medical cart.

Many of the medications given to patients can be controlled substances. To ensure the safety and security of controlled substances in the medication storage container, the smart medical cart can have several security measures. One security measure for the medication storage container can be to limit or restrict the access of a caregiver to selected medication drawers. For example, a nurse can be provided security access by a supervisor to have access to medication drawers containing antibiotics and denied access to medication drawers containing narcotics. One or more medication locations in one or more of the medication drawers can be selected or categorized based on the type of medication, such as a defined drawer for narcotic medications. In another embodiment, the ID of two or more caregivers can be verified for the smart medical cart or the security access system to enable access to selected or defined medication drawers. For example, to access a narcotic medication drawer, the security access system can authenticate the ID of each of two caregivers before access is granted to the narcotic medication drawer.

In another embodiment, the smart medical cart can determine and/or store medication inventory information. The medication inventory information can include the amount of medication located in one or more of the medication drawers, the type of medication located in one or more of the medication drawers, the amount and/or type of medication dispensed to a patient, and so forth. In one embodiment, the smart medical cart can use a medication feedback device to determine the amount of medication located in one or more drawers of the medication drawers. In one embodiment, the medication feedback device can be a weight measuring device, such as a strain gauge or weight scale. In another embodiment, the smart medical device can monitor or store information for the amount of medication located in one or more of the medication drawers before the medication is dispensed and monitor or store information for the amount of medication located in one or more of the medication drawers after the medication is dispensed. The smart medical cart can compare the weight of the medication or the amount of medication located in one or more of the medication drawers before the medication is dispensed and the weight of the medication or the amount of medication located in one or more of the medication drawers after the medication is dispensed to determine the amount of medication a caregiver removed from the one or more medication drawers. In another embodiment, the smart medical cart can store the time and/or location of the smart medical cart and the amount of medication or weight of a medication drawer. One advantage of tracking the amount of medication or the medication drawer weight can be to track the amount of medication at different times and/or locations to determine when medication is removed and/or the location where the medication was removed. Tracking the amount of medication or the medication drawer weight can enable medication dispensing security, such as a hospital ensuring that an individual does not distribute medication that is not prescribed or intended for that individual. In one embodiment medication inventory information can be tracked from the original location of the medication, such as a pharmacy, to the end user, such as a patient.

The medication inventory information can be tracked by inputting medication information, such as the amount and type of medication, into a computing device of the smart medical cart and/or central server when the medication is removed from the original location of the medication and put into the medication drawers. The smart medical cart can include a scanning device to input the medication information into the computing device of the smart medical cart. In one embodiment, the scanning device can be: an imaging device, such as a bar code scanner; a camera; a radio frequency identification (RFID) scanner; and so forth. In one embodiment, the medication inventory information can be input by communicating the medication information to a computing device operating on the smart medical cart as the medication is put in a medication drawer. For example, the medication information may be scanned or transmitted. In another embodiment, the medication inventory information can be input by an individual, such as a caregiver or pharmacist, entering the medication information as the medication is dispensed from the original location of the medication. In one embodiment the medication drawers of the smart medical cart can be locked when the medication has been placed in the medication drawer. When the caregiver has arrived at the location to distribute or dispense the medication, such as at a patient's bedside, the smart medical cart can verify the ID information of the caregiver before providing access to one or more medication drawers. In one embodiment, the ID of the individual, such as the patient, receiving the medication can be verified before the medication can be distributed. For example, the identification of the caregiver and/or individual receiving the medication can be verified by: the security access system; inputting the signature of the caregiver and/or receiving individual, such as by using a signature pad or touch screen of a computing device; scanning a security wristband on the caregiver and/or receiving individual, and so forth. When the ID of the caregiver and/or the individual receiving the medication has been verified, the smart medical cart can provide the caregiver access to the medication drawer, such as unlocking the medication drawers, where the medication is located for the individual receiving the medication.

In one embodiment, the caregiver can communicate the medication and/or the medication container before distributing the medication to the selected individual receiving the medication. The smart medical cart can verify that the individual has received the medication and/or consumed the medication. In one embodiment, when the individual receiving the medication refuses to receive and/or consume the medication, the caregiver can input the refusal by the individual into the smart medical cart. In one embodiment, the caregiver can put the medication back into the medication drawer. In another embodiment, the individual receiving the medication can verify receipt, consumption, or refusal of the medication. The individual can verify receipt, consumption, or refusal of the medication by: inputting the signature of the individual, such as by using a signature pad or touch screen of a computing device; scanning a security wristband on the receiving individual; and so forth. In another embodiment, the smart medical cart can disable or restrict control or access to the smart medical cart until the status of the medication distribution is input.

In caring for patients in the hospital setting, there are likely multiple caregivers that will care for a patient over a given hospital stay. As a first caregiver finishes a work period, a second caregiver may begin a work period. Additionally, the first caregiver can begin another work period at a later time. With the constant changing of caregivers, the data and information collected and/or stored on the smart medical cart can be transferred between the smart medical cart and other devices.

Figure 66:
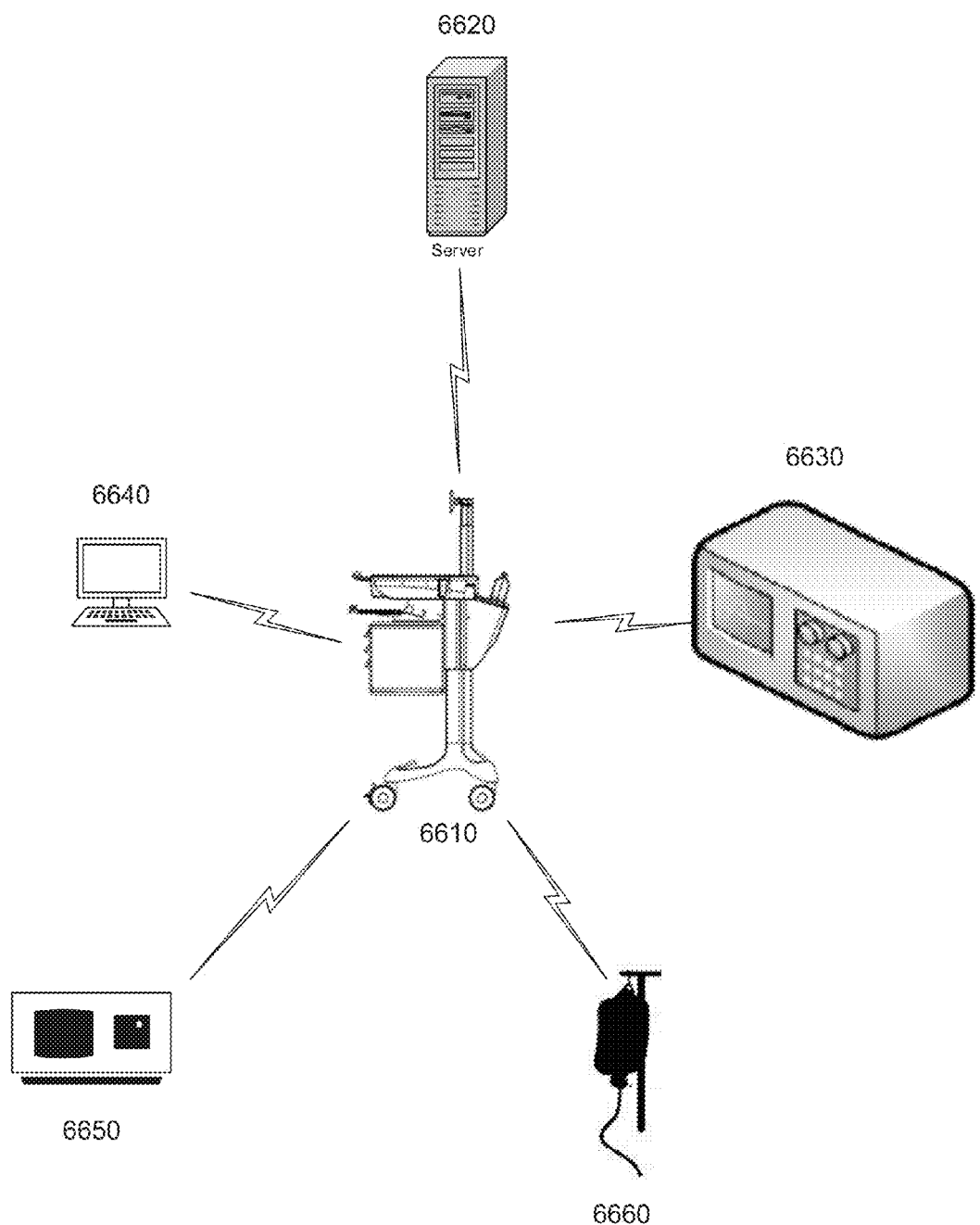
FIG. 66 illustrates a smart medical cart communicating with other devices in accordance with an example.

In one embodiment, the data and information collected and/or stored on the smart medical cart can be periodically communicated to the central server. FIG. 66 illustrates the smart medical cart 6610 communicating with other devices. In one embodiment, the smart medical cart 6610 can communicate with devices 6630-6660. The smart medical cart 6610 can receive external device information, such as medical information, monitoring information, treatment information, status information, and so forth. When the smart medical cart 6610 receives the external device information, the smart medical cart can communicate the external device information to a server 6620. In one embodiment, the smart medical cart 6610 communicates internal information of the smart medical cart to the server 6620. In another embodiment, the smart medical cart 6610 can aggregate the external device information from other devices 6630-6660 and the internal information of the smart medical cart 6620 and communicate the aggregated information to the server 6620. In one embodiment, the server 6620 can be a third party server located external to the medical facility. In another embodiment the server 6620 can be a central server or server internal to the medical facility.

The smart medical cart 6610 can communicate using a wired communication means with other devices or servers, such as with an input/output (I/O) port, universal serial bus (USB) port, Ethernet port, and so forth. In another embodiment, the smart medical cart 6610 can wirelessly communicate with the other devices 6630-6660 and/or server 6620. The smart medical cart 6610 can wirelessly communicate with other devices using an optical connection such as an infrared connection, or via a radio frequency connection, such as a wireless fidelity (WiFi) network, WiFi direct, a Bluetooth connection, a cellular communications system such as a third generation partnership project (3GPP) long term evolution (LTE) connection, device to device (D2D) communication, a machine type communication, or via another type of proprietary wireless connection. The cellular communications system can comprise one or more cellular network nodes and one or more Institute of Electrical and Electronics Engineers (IEEE) 802.11-2012 configured access points. In one embodiment, the one or more cellular networks may be 3rd generation partnership project (3GPP) long term evolution (LTE) Rel. 8, 9, 10, or 11 networks and/or IEEE 802.16p, 802.16n, 802.16m-2011, 802.16h-2010, 802.16j-2009, 802.16-2009 networks.

Figure 67:
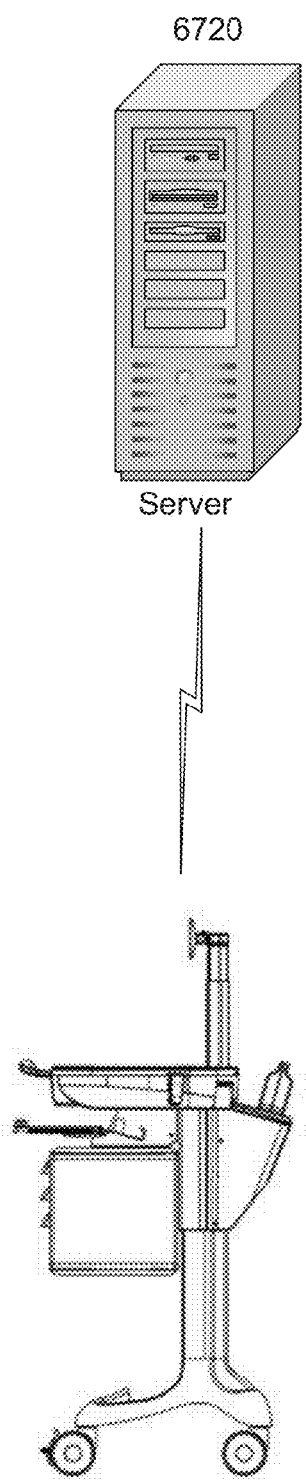
FIG. 67 depicts a smart medical cart communicating with a third party or central server in accordance with an example.

FIG. 67 depicts the smart medical cart 6710 communicating with the third party or central server 6720. In one embodiment, the smart medical cart 6710 can be in direct communication with the third party or central server 6720. The smart medical cart 6710 can communicate information such as user preferences, medical information, information for external devices, internal information, and so forth.

The central server or third party server 6720 can be a hub where the data and information collected and/or stored on one or more smart medical carts can be stored in a central location. The central server may be located at the same location as the smart medical carts. Alternatively, the central server may be located remotely. The central server may be controlled and operated by the owner of the smart medical carts. Alternatively, a third party can control operate the central server.

The data and information stored on the central server can be accessible to one or more smart medical carts, equipment, and/or devices. In one embodiment, selected information can be communicated to a smart medical cart from a remote device, such as the central server, when a caregiver logs into the smart medical cart. For example, when the caregiver begins their work shift, the caregiver can be assigned or select a smart medical cart to use during the work shift. When the caregiver logs into the assigned or selected smart medical cart, the user preferences of the caregiver are communicated from the remote computing device, such as a central server, to the assigned or selected smart medical cart. Additionally, when the caregiver logs into the smart medical cart, care information such as patient status, medication charts, treatment notes, and so forth can be communicated to the assigned or selected smart medical cart.

In another embodiment, selected information can be communicated from a smart medical cart to a remote computing device, such as the central server, when a caregiver logs out from smart medical cart. For example, when the caregiver's work period ends and the caregiver completes their work, the caregiver can log out of the smart medical cart and the user preference information and/or selected care information can be communicated to another device, such as the central server.

In another embodiment, the user preference information and/or the care information can be transferred to device remote computing device when the power source level of the smart medical cart decreases below a defined threshold. For example, when an external battery level of the smart medical cart decreases below 10%, the smart medical cart can communicate selected information to the remote computing device, such as the central server, to back up the information in case the smart medical device loses power.

In another embodiment, the smart medical cart can communicate user preference information and/or care information to the remote computing device on a periodic basis to synchronize information between the smart medical cart and the remote computing device to enable the smart medical cart and/or the remote computing device to both have relatively up-to-date information. For example, the smart medical cart can communicate user preference information and/or care information every 10 minutes to the central server to enable backup of the user preference information and/or care information for when there is a problem with the smart medical cart.

In another example, multiple caregivers can provide care to a patient and each caregiver can use a different smart medical cart. In this example, when a first caregiver provides care to the patient, such as giving the patient medication or taking their vital signs, the care information from the smart medical cart of the first caregiver can be communicated to the smart medical cart of a second caregiver to enable the first caregiver and second caregiver to have synchronized and up-to-date care information. In one embodiment, one or more smart medical carts can detect when another smart medical cart and/or other device or equipment is located within a selected distance of the smart medical cart. When the one or more smart medical carts detect another smart medical cart and/or other device or equipment, the smart medical carts can begin communicating and/or synchronizing information with the other smart medical cart and/or other device or equipment. The smart medical cart can use Bluetooth, WiFi, WiFi direct, a cellular network, a wireless charging system, and so forth to communicate information with other devices.

The smart medical cart can mirror information displayed on one device attached to the smart medical cart, such as the computing device and/or display screen, with other devices attached to the smart medical cart or external to the smart medical cart. For example, the smart medical cart can have a first computing device, such as a tablet, integrated into the first work platform of the smart medical cart and a second computing device mounted or attached to the second vertical support as a display screen. In another example, the smart medical cart can have a first computing device, such as a tablet, below the conductive touch screen work surface, as shown in FIGS. 5a and 5b, and a second computing device mounted or attached to the second vertical support as a display screen. The second computing device can be detached from the smart medical cart and used throughout the patient's room while the caregiver provides care to the patient. As the caregiver provides care to the patient, the caregiver can record care information to the second computing device and that care information can be mirrored and/or communicated to the first computing device.

Figure 68:
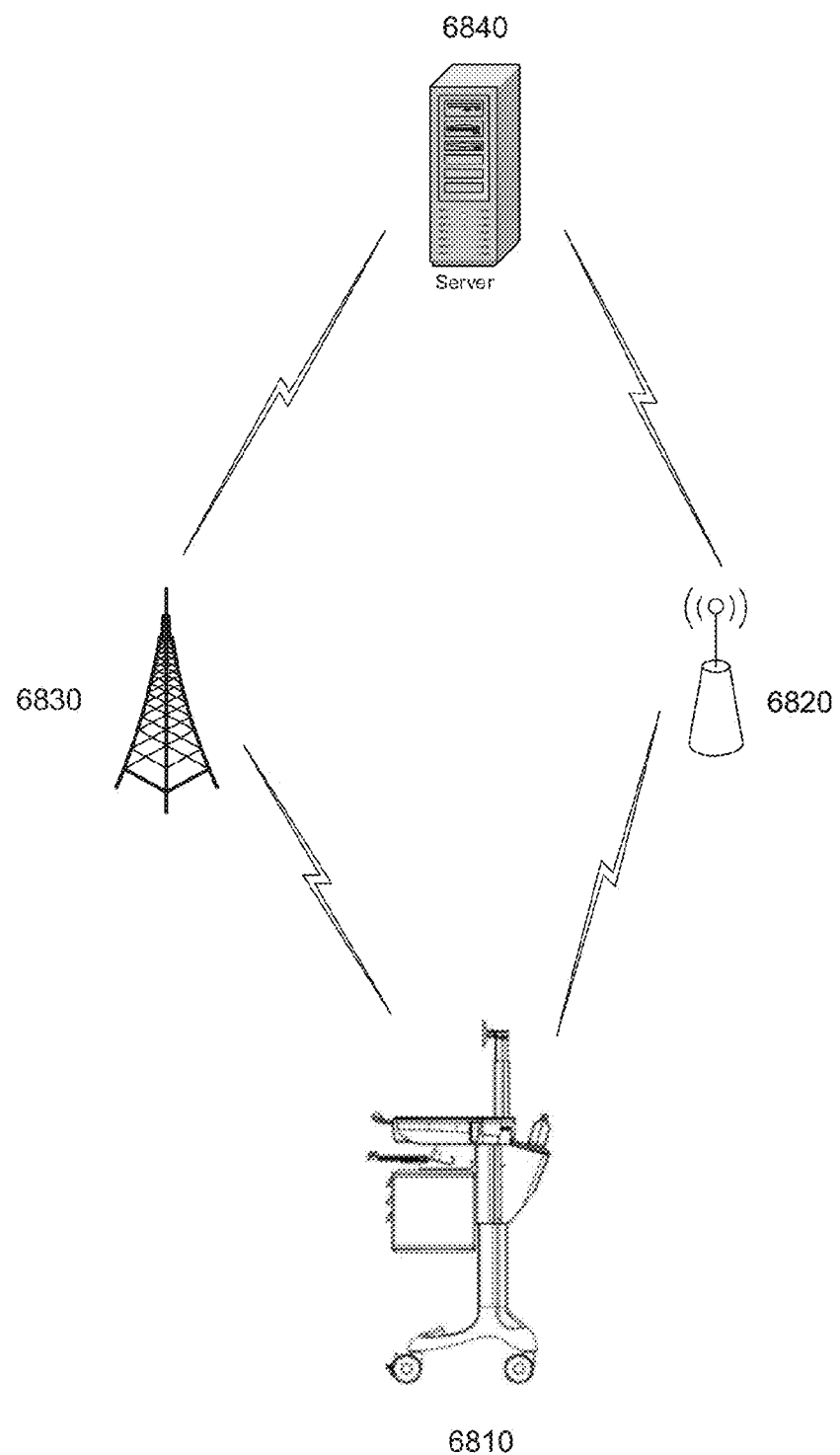
FIG. 68 depicts a smart medical cart in communication with a third party server or central server in accordance with an example.

FIG. 68 depicts the smart medical cart 6810 indirectly communicating with the third party server or central server 6840 using a wireless communication network 6820 and/or a cellular communication network 6830. In one embodiment, the smart medical cart 6810 can communicate using the wireless communication network 6820 when the smart medical cart 6810 is within range of a wireless node. In another embodiment, the smart medical cart 6810 can communicate using the cellular communication network 6830 when the smart medical cart 6810 is not within range of a wireless node. In another embodiment, the caregiver can select whether the smart medical cart 6810 can select the communication procedure of the smart medical cart 6810, such as wired communication or wireless communication, wireless network communication, cellular network communication, and so forth.

Figure 69:
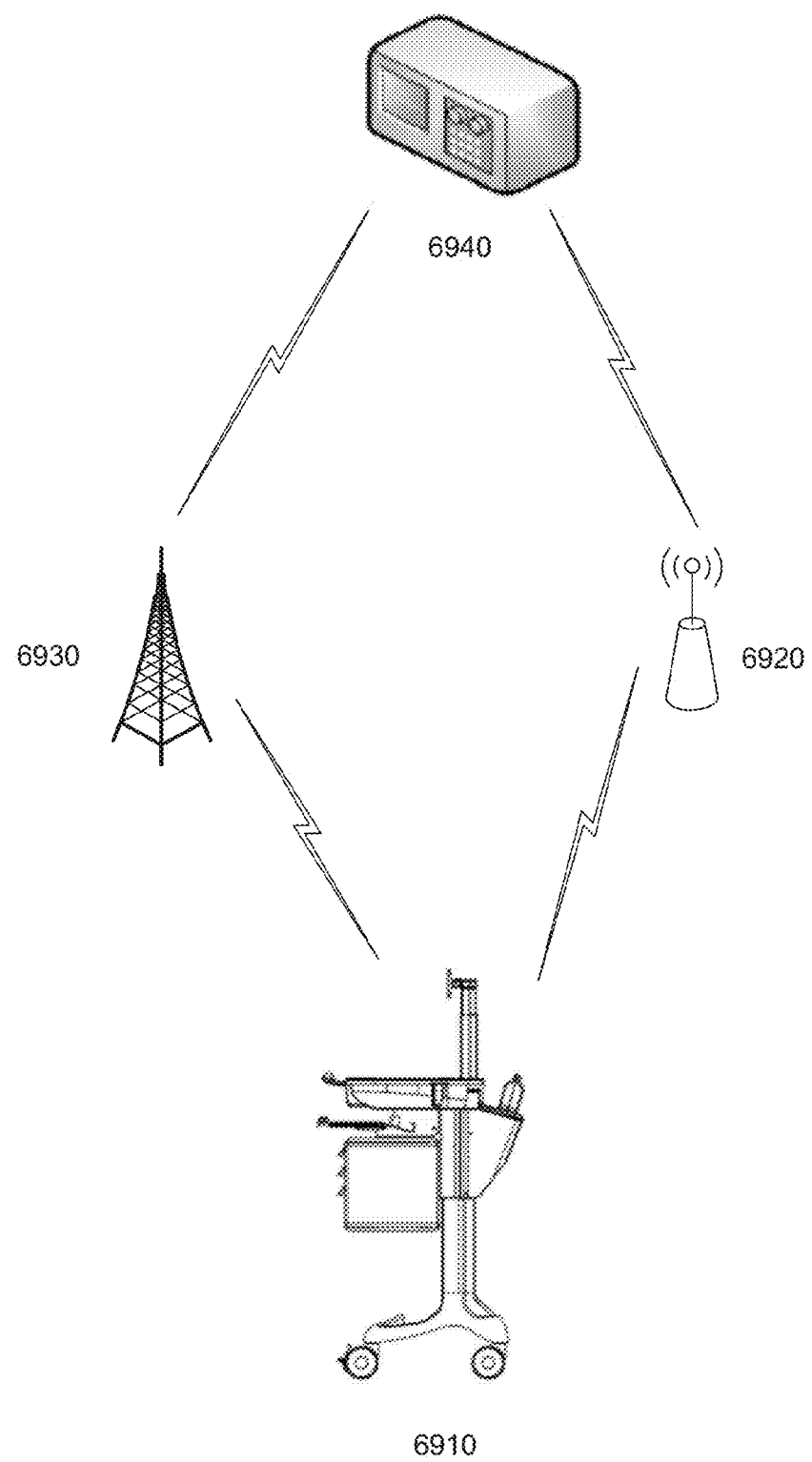
FIG. 69 depicts a smart medical cart in communication with an external device in accordance with an example.

FIG. 69 depicts a smart medical cart 6910 communicating with an external device 6940 indirectly using a wireless communication network 6920 and/or a cellular network 6930.

Figure 70:
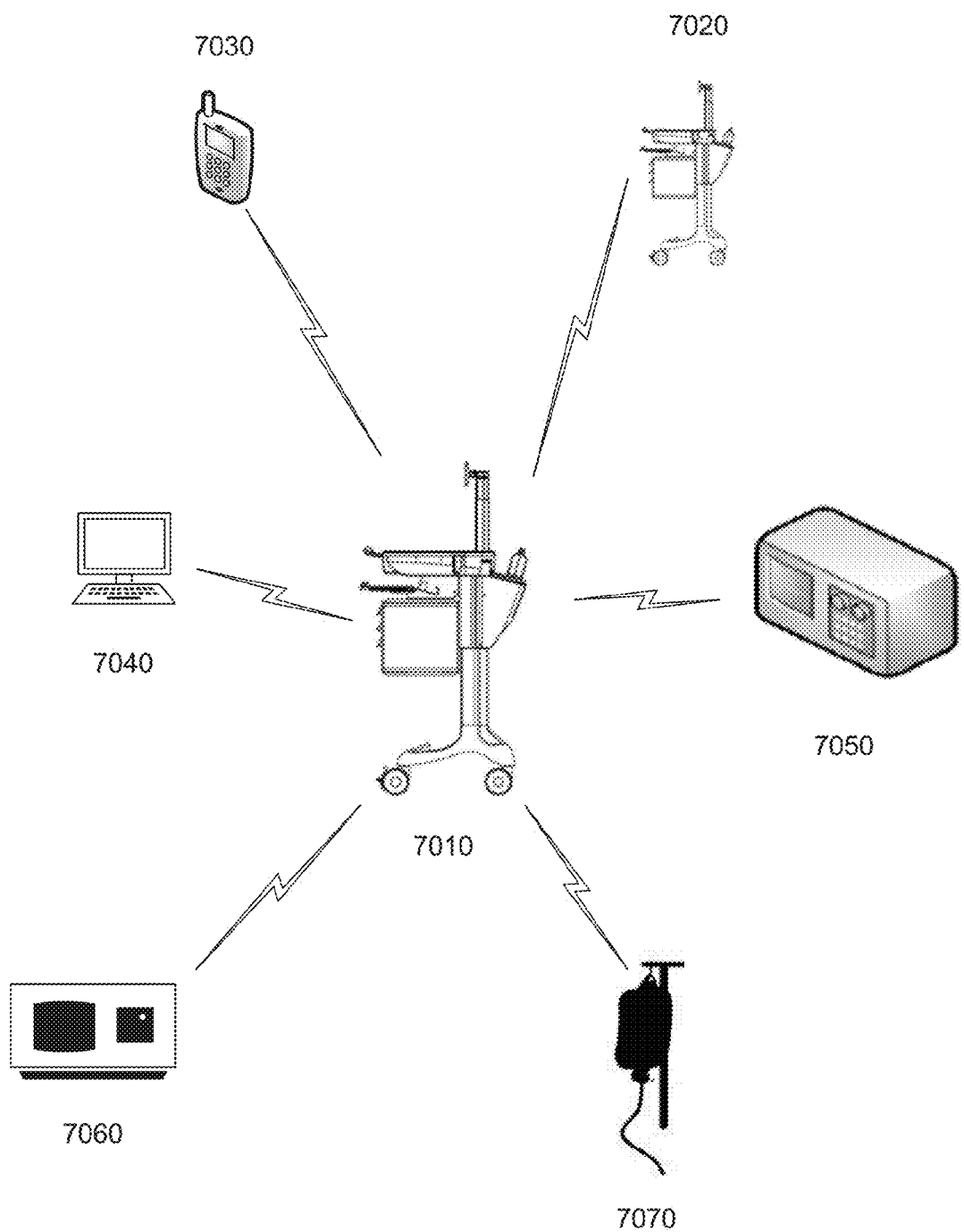
FIG. 70 illustrates a smart medical cart communicating with other external devices in accordance with an example.

FIG. 70 illustrates the smart medical cart communicating with other external devices. The external devices can include: another smart medical cart 7020; a smartphone or tablet 7030; a computing device 7040; a medical monitoring device 7050; a medical analysis or medical diagnosis device 7060; an infusion pump or IV pump 7070; medical devices; and other external devices. In one embodiment, the smart medical device 7010 can receive information from the external devices 7020-7070. In one embodiment, the smart medical cart 7010 can receive information from external devices 7020-7070 when the smart medical cart 7010 is within communication range of the external devices 7020-7070. For example, when the smart medical cart 7010 is moved into a patient's room, the smart medical cart can come within the communication range of external devices while in the patient's room, such as an intravenous (IV) pump, an electro-cardiogram (EKG) machine, a pulse oximeter, and so forth. The external devices, such as external devices 7020-7070, can communicate selected information to the smart medical cart 7010.

In another embodiment, the smart medical cart can send a beacon signal other medical devices and/or other devices signaling to the medical devices and/or other devices to communicate selected information. One advantage of the smart medical cart receiving information from medical devices and/or other devices can be to enable the caregiver to have selected information about the patient in a central or consolidated location. For example, the smart medical cart can receive information from all the medical devices and equipment in a patient's room and provide the caregiver with a consolidated location to view all of the patient's information. In one embodiment, the smart medical cart can receive information from other medical devices and/or other equipment verifying that the medical devices and/or other devices are functioning properly. In another embodiment, the smart medical cart can receive treatment and/or medication information about the treatment or medication that has been given to the patient and/or the medical status of the patient from other medical devices and/or other devices. One advantage of the smart medical cart receiving treatment and/or medication information is to enable the caregiver to check the treatment or medication that has been given to the patient and/or the medical status of the patient and avoid giving the patient additional medication or treatment that could have adverse effects on the patient.

One advantage of the smart medical cart receiving information from medical devices and/or other devices can be to reduce miscommunications or errors caused by a lack of information sharing between multiple caregivers. For example, if a first caregiver, such as a doctor, gives a patient a selected dosage of medication but has poor handwriting, the type of medication or the dosage can be miscommunicated to a second caregiver. When the information is input into a smart medical cart or other device, such as by scanning the medication before dispensing it to the patient, the miscommunication due to poor handwriting between the first caregiver and the second caregiver can be avoided.

The smart medical cart can anticipate when medical devices and/or other devices should be refilled, changed, adjusted, and so forth. For example, an IV pump provides the patient with fluids or medication at a selected rate for a defined period. When the fluids or medications remaining in the IV pump decrease below a selected level, the IV pump can communicate with the smart medical cart that the fluids or medications should be replaced with additional fluids or medications.

In one embodiment, the smart medical cart can control other medical devices and/or other devices. For example the smart medical cart can control the dispensing of pain medication from an IV pump by communicating with the IV pump to increase or decrease a dosage. In another embodiment, another device can control the smart medical cart. For example, a caregiver's smartphone can access and/or control the smart medical cart, such as by accessing the smart medical cart using a smartphone application.

The smart medical cart can validate or check that the correct medication is given to a patient. In one embodiment, the smart medical cart can check what medication and/or treatments have previously been given to a patient and verify that there may be minimal interference or no interference between the medication or treatment which the current caregiver desires to give the patient and the previous medication or treatment given to the patient.

In one embodiment, when the caregiver desires to give the patient medication, the smart medical cart can check the medication with medication previously given to the patient before enabling the caregiver to access the medication storage container. In another embodiment, when the caregiver desires to give the patient multiple medications and/or treatments, the smart medical cart can check that there are no conflicts or minimal conflicts or interference between the multiple medications and/or treatments.

A computing device operating on the smart medical cart can be configured to run one or more medical applications or medical cart applications. In one embodiment, the smart medical cart can receive medical application or medical cart applications from a third party and/or the medical facility, such as a medical cart application database, in which the smart medical cart is operating. In one embodiment, the smart medical cart can communicate payment information to the third party. In one embodiment, a third party can authorize and/or restrict what applications a caregiver can view, purchase, download, and/or access. For example, a nurse supervisor can limit or restrict what application an attending nurse can use on the computing device of the smart medical cart.

The applications available on the smart medical cart can include: biometric authentication, finger scanner, facial recognition, dosage meters, dosage calculators, drug interaction calculators, medication trackers, medical information tracking, medical device controller applications or device drivers, and so forth. In one embodiment, the caregiver can view, purchase, download, and/or access applications without touching or contacting the smart medical cart or computing device, e.g. a non-contact interface. In one embodiment, a caregiver can view, purchase, download, and/or access applications using a facial recognition sensor or voice recognition sensor of the security access system.

The smart medical cart or a third party can limit the applications that can be purchased, downloaded, and/or accessed based on the equipment integrated into the smart medical cart or attached to the smart medical cart. In one embodiment, the smart medical cart can limit the applications that can be purchased, downloaded, and/or accessed based on the model type of the smart medical cart, device attached to the smart medical cart, and/or devices in communication with the smart medical cart. For example, when the caregiver is using a smart medical cart that does not have a medication drawer attached to the smart medical cart, the smart medical cart can restrict or disallow purchasing, downloading, and/or accessing an application on the computing device for medication dispensing. In one embodiment, the smart medical cart can verify other devices that the smart medical cart can communicate with and restrict or disallow purchasing, downloading, and/or accessing application on the computing device for medical devices that have not been authenticated by the smart medical cart, medical facility, and/or third party.

A third party can control what medical cart applications a smart medical cart, caregiver, or medical facility can view, purchase, download, and/or access applications for a smart medical cart. In one embodiment, the third party can authenticate the configuration of a smart medical cart and the applications, such as medical cart applications, available to the smart medical cart. For example, the third party can determine that a medical cart is configured with selected load sensors and provide access for the smart medical cart, caregiver, or medical facility to access applications used for the selected load sensors. In another example, the third party can determine that prohibited equipment has been attached or installed to the smart medical cart and restrict or limit access to applications to be used with the prohibited equipment.

The smart medical cart or a third party can provide different applications for the caregiver based on the other devices the caregiver and/or medical facility are using. For example, if the caregiver is using a selected type of fusion pump, the smart medical cart can provide selected applications such as device drivers that are compatible with the selected type of fusion pump. In one embodiment, the smart medical cart or the third party can provide selected applications based on the type of device the caregiver and/or medical facility is using, wherein the communication or data format between the smart medical cart and the other device are configured to be compatible.

In another embodiment, the smart medical cart or the third party can provide selected applications based on the type of device the caregiver and/or medical facility is using or a device that is attached to the smart medical cart or in communication with the smart medical cart, wherein the commands or instructions communicated between the smart medical cart and the selected device can be compatible. For example, when a medical facility uses a selected type of fusion pump, the functionality and data communication format can be different from another type of fusion pump. When the third party provides applications for the smart medical cart, caregiver, and/or medical facilities to use with a smart medical cart in communication with the another device, the third party can determine the functionality and data communication structure of selected devices and limit the applications available for the caregiver and/or medical facilities to view, view, purchase, download, and/or access to the applications that are compatible with the selected type of device.

Figure 71:
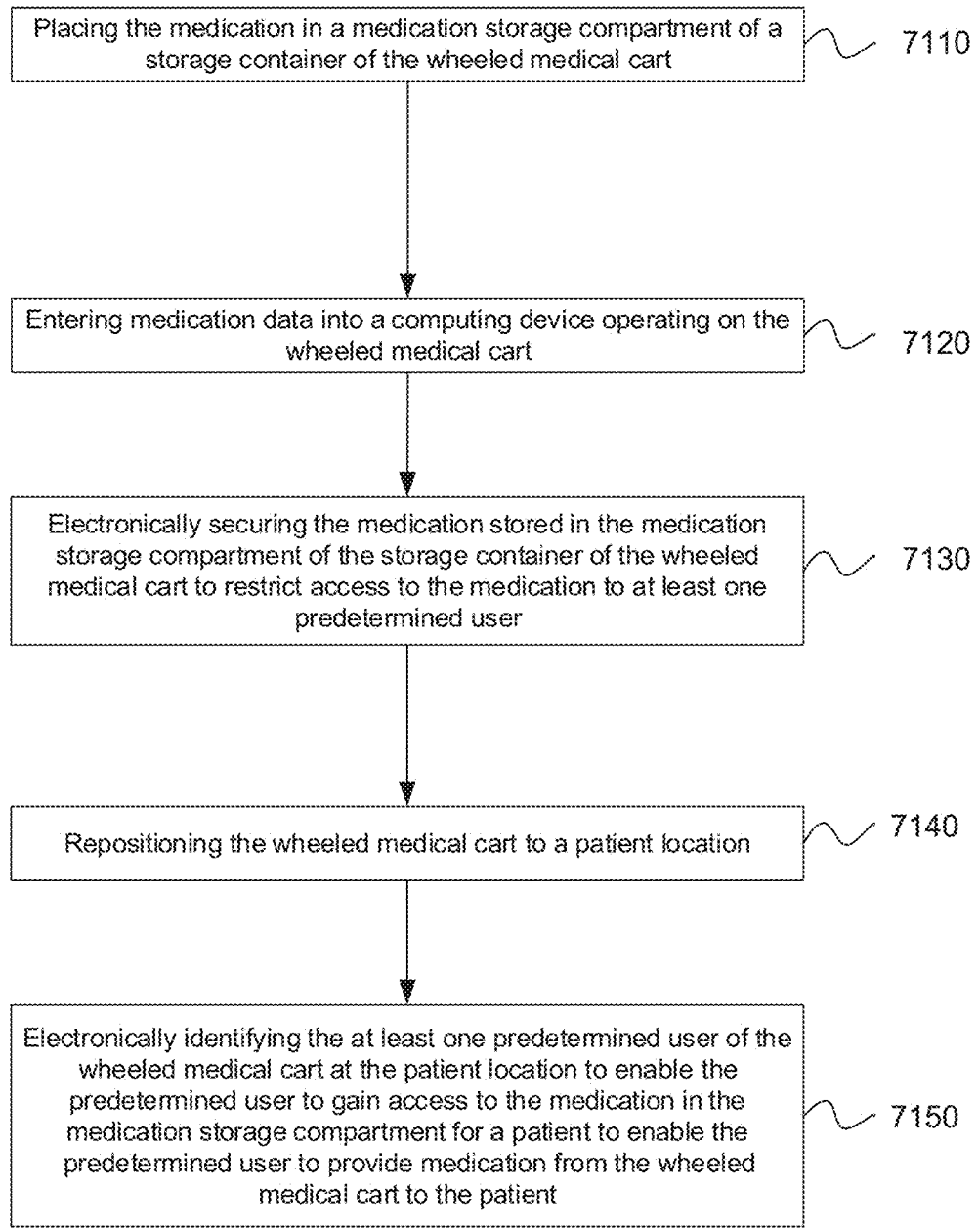
FIG. 71 illustrates a method for dispensing medication from a wheeled medical cart in accordance with an example.

Another example provides a method 7100 for dispensing medication from a wheeled medical cart, as shown in the flow chart in FIG. 71. The method may be executed as instructions on a machine or computer circuitry, where the instructions are included on at least one computer readable medium or one non-transitory machine readable storage medium. The method includes the operation of placing the medication in a medication storage compartment of a storage container of the wheeled medical cart, as in block 7110. Another operation of the method includes entering medication data into a computing device operating on the wheeled medical cart, as in block 7120. In one embodiment, the medication data can identify each type or amount of medication stored in the wheeled medical cart. Another operation of the method can be electronically securing the medication stored in the medication storage compartment of the storage container of the wheeled medical cart to restrict access to the medication to at least one predetermined user, as in block 7130. Another operation of the method can be repositioning the wheeled medical cart to a patient location, as in block 7140. Another operation of the method can be electronically identifying the at least one predetermined user of the wheeled medical cart at the patient location to enable the predetermined user to gain access to the medication in the medication storage compartment for a patient to enable the predetermined user to provide medication from the wheeled medical cart to the patient, as in block 7150.

In one embodiment, the method can further comprise electronically identifying the patient receiving the medication from the wheeled medical cart. In another embodiment, the method can further comprise electronically identifying the patient receiving the medication or the at least one predetermined user using a biometric identification device operating on the wheeled medical cart. In one embodiment, the method can further comprise electronically verifying a status of the medication when the at least one predetermined user gains access to the medication, wherein the status of the medication can comprise: a receipt of the medication provided to the patient by the at least one predetermined user; a consumption of the medication provided to the patient by the at least one predetermined user; or a refusal of the patient to receive the medication provided to the patient by the at least one predetermined user.

In one embodiment, the method can further comprise identifying when the patient refuses to receive the medication from the predetermined user and/or electronically verifying a disposal of the medication. In another embodiment, the method can further comprise disabling control of the wheeled medical cart until the status of the medication is electronically verified when the at least one predetermined user gains access to the medication. In another embodiment, the method can further comprise providing access to the medication in the medication storage compartment when the at least one predetermined user of the wheeled medical cart has been electronically identified.

Figure 72:
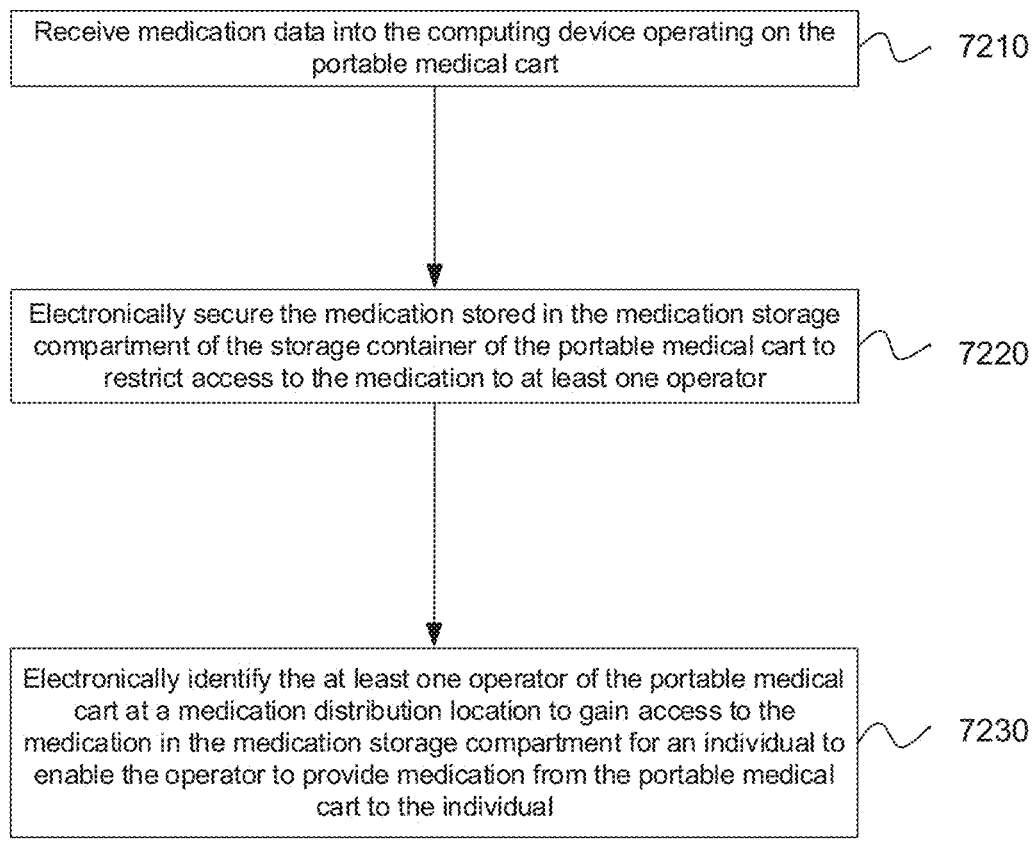
FIG. 72 depicts the functionality of computer circuitry of a portable medical cart in accordance with an example.

FIG. 72 uses a flow chart 7200 to illustrate the functionality of one embodiment of a portable medical cart having a computing device with computer circuitry. The functionality can be implemented as a method or the functionality can be executed as instructions on a machine, where the instructions are included on at least one computer readable medium or one non-transitory machine readable storage medium. The computer circuitry can be configured to receive medication data into the computing device operating on the portable medical cart, as in block 7210. In one embodiment, the medication data can identify each type of medication stored in a medication storage compartment of a storage container of the portable medical cart. The computer circuitry can further be configured to electronically secure the medication stored in the medication storage compartment of the storage container of the portable medical cart to restrict access to the medication to at least one operator, as in block 7220. The computer circuitry can also be configured to electronically identify the at least one operator of the portable medical cart at a medication distribution location to gain access to the medication in the medication storage compartment for an individual to enable the operator to provide medication from the portable medical cart to the individual, as in block 7230.

In one embodiment, the computer circuitry can be further configured to verify the identity of the operator of the portable medical cart at a time approximate to a time the operator provides the medication from the portable medical cart to the individual. In another embodiment, the computer circuitry can be further configured to electronically identify the at least one operator of the portable medical cart when the portable medical cart is located in proximity to a location of the individual and/or provide access to at least one medication storage compartment of a storage container when the identity of the at least one operator of the portable medical cart is verified at the location in proximity to the individual. In another embodiment, the computer circuitry can be further configured to electronically identify the individual receiving the medication from the medication storage compartment of the medication drawer and/or limit access of the at least one operator of the portable medical cart to medication drawers containing medication for the electronically identified individual.

In one embodiment, the computer circuitry can be further configured to: electronically identifying the individual receiving the medication from the medication storage compartment of the medication drawer; determine when the medication stored in the medication storage compartment will interfere with other medications that the electronically identified individual is using; and/or provide a sensory indication to the at least one operator when the medication will interfere with the other medications. In another embodiment, the computer circuitry can be further configured to map at least one medication storage compartment to at least one selected type of medication. In another embodiment, the computer circuitry can be further configured to electronically restrict access to selected medication storage compartments to require electronic identification of at least two operators of the medical cart to access the selected medication storage compartments. In another embodiment, the selected medication storage compartment can contain a narcotic medication or another restricted medication type. In one embodiment, the computer circuitry can be configured to determine the time period that the wheeled medical cart is located at a selected location for dispensing medication. In another embodiment, the computer circuitry can be configured to enable access to the medication storage compartment when the wheeled medical cart is located at the selected location for dispensing medication.

Figure 73:
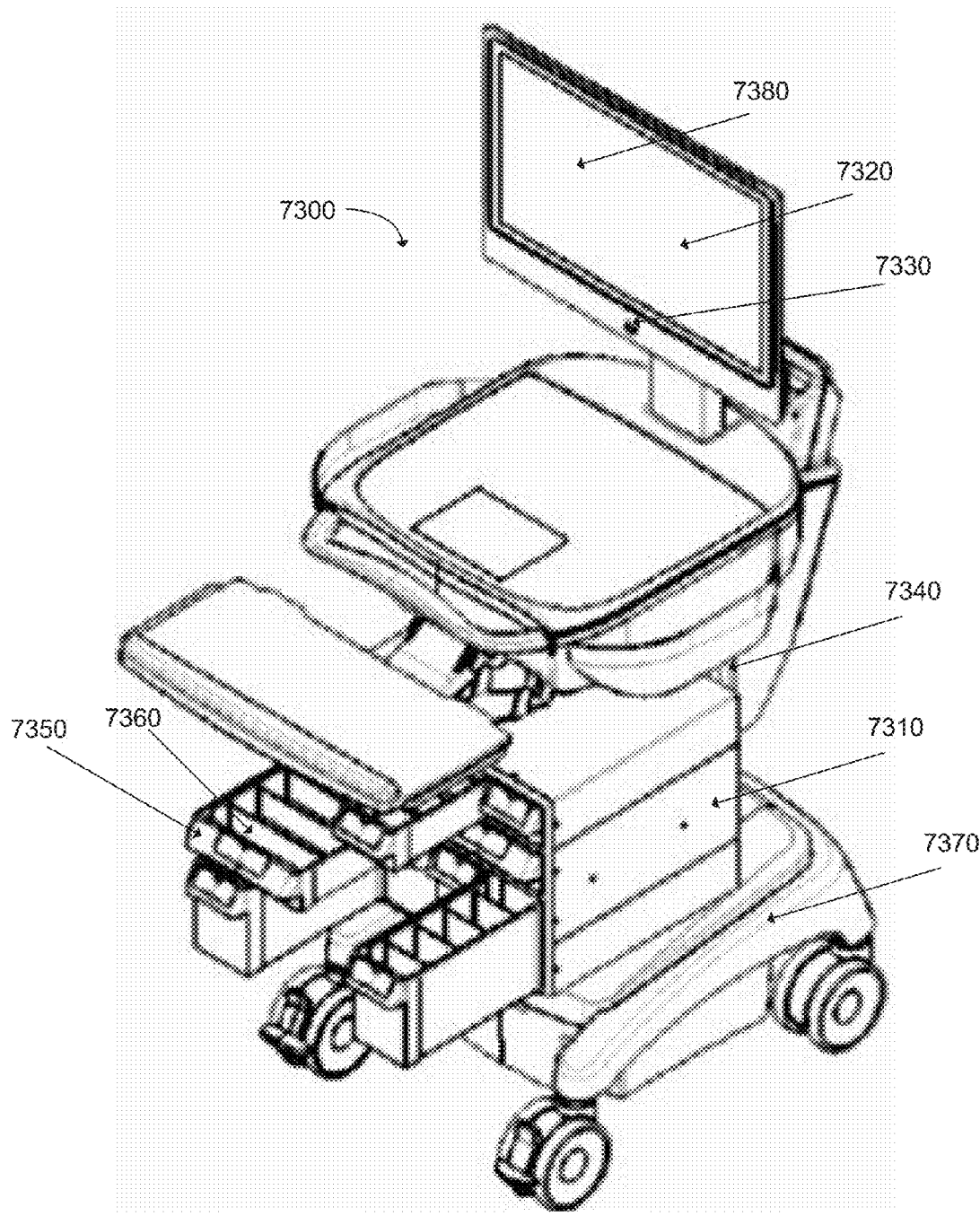

FIG. 73 shows a wheeled medical cart 7300 for the dispensing of medication. The wheeled medical cart 7300 can include a storage container 7310, a computing device 7320 operating on the wheeled medical cart 7300, an electronic identification device 7330, and a structure 7340 connecting the storage container 7310 to a wheeled pedestal 7370 of the wheeled medical cart 7300. FIG. 73 further shows that the storage container 7310 can have at least one medication storage compartment 7350 with an interior space 7360 for storing at least one medication or at least one medical supply. In one embodiment, the computing device 7320 can receive medication data that identifies each type or amount of medication or medical supply stored in the at least on medication storage compartment 7350. In one embodiment, the electronic identification device 7330 can electronically identify at least one operator of the wheeled medical cart 7300 at a patient location to enable the at least one operator to gain access to medication in the medication storage compartment 7350 for distribution to a patient.

Figure 74:
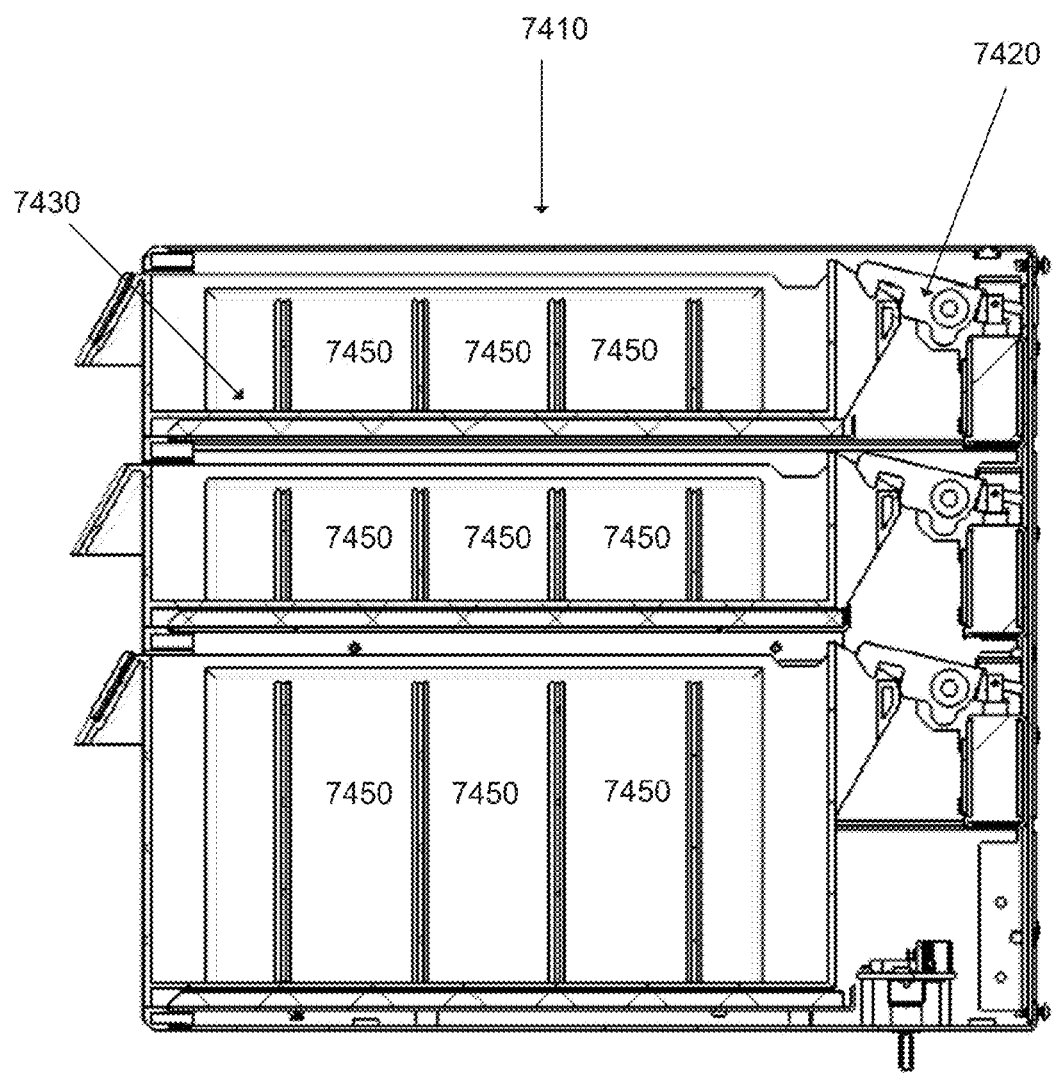

FIG. 74 shows a storage container 7410 of a wheeled medical cart, such as in FIG. 73. The storage container 7410 can include an electronic locking device 7420 that can electronically secure medication or medical supplies stored in a medication storage compartment 7450 of the storage container 7410 of a wheeled medical cart, as shown in FIG. 73, to restrict access to the medication storage compartment 7450 to at least one operator. In one embodiment, the wheeled medical cart or the storage container 7410 of the wheeled medical cart can further comprise a medication storage compartment measurement device 7430 to determine an amount of medication in a selected medical storage compartment 7450. In one embodiment, a computing device, such as in FIG. 73, can be configured to display or record the amount of medication in the selected medical storage compartment 7450. In another embodiment, the medication storage compartment measurement device 7430 can determine the amount of medication remaining after the medication has been dispensed. In one embodiment, the medication storage compartment measurement device 7430 can use a load cell, such as strain gauge or weight scale, to determine the amount of medication remaining after the medication has been dispensed.

Returning to FIG. 73, the wheeled medical cart 7300 can further include a medication dispensing recordation device 7380, such as computing device 7320, that can record the location and/or time that the operator accesses the medication storage compartment 7350 to provide medication from the wheeled medical cart 7300 to a patient.

Various techniques, or certain aspects or portions thereof, may take the form of program code (i.e., instructions) embodied in tangible media, such as floppy diskettes, CD-ROMs, hard drives, non-transitory computer readable storage medium, or any other machine-readable storage medium wherein, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, EPROM, flash drive, optical drive, magnetic hard drive, or other medium for storing electronic data. The base station and mobile device may also include a transceiver module, a counter module, a processing module, and/or a clock module or timer module. One or more programs that may implement or utilize the various techniques described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations.

It should be understood that many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as defacto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of materials, fasteners, sizes, lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A method for dispensing medication from a wheeled medical cart, comprising:
    placing the medication in a medication storage compartment of a storage container of the wheeled medical cart;
    entering medication data into a computing device operating on the wheeled medical cart, wherein the medication data identifies each type or amount of medication stored in the wheeled medical cart;
    electronically securing the medication stored in the medication storage compartment of the storage container of the wheeled medical cart to restrict access to the medication to at least one predetermined user;
    repositioning the wheeled medical cart to a patient location; and
    electronically identifying the at least one predetermined user of the wheeled medical cart at the patient location to enable the predetermined user to gain access to the medication in the medication storage compartment for a patient to enable the predetermined user to provide medication from the wheeled medical cart to the patient;
    electronically verifying a status of the medication when the at least one predetermined user gains access to the medication, wherein the status of the medication comprises:
        a receipt of the medication provided to the patient by the at least one predetermined user;
        a consumption of the medication provided to the patient by the at least one predetermined user; or
        a refusal of the patient to receive the medication provided to the patient by the at least one predetermined user; and
        disabling control of the wheeled medical cart until the status of the medication is electronically verified when the at least one predetermined user gains access to the medication.

2. The method of claim 1, further comprising electronically identifying the patient receiving the medication from the wheeled medical cart.

3. The method of claim 2, further comprising electronically identifying the patient receiving the medication or the at least one predetermined user using a biometric identification device operating on the wheeled medical cart.

4. The method of claim 1, further comprising:
    identifying when the patient refuses to receive the medication from the predetermined user; and
    electronically verifying a disposal of the medication.

5. The method of claim 1, further comprising providing access to the medication in the medication storage compartment when the at least one predetermined user of the wheeled medical cart has been electronically identified.

6. A portable medical cart having a computing device with computer circuitry configured to:
    receive medication data into the computing device operating on the portable medical cart, wherein the medication data identifies each type of medication stored in a medication storage compartment of a storage container of the portable medical cart;
    electronically secure the medication stored in the medication storage compartment of the storage container of the portable medical cart to restrict access to the medication to at least one operator; and
    electronically identify the at least one operator of the portable medical cart at a medication distribution location to gain access to the medication in the medication storage compartment for an individual to enable the operator to provide medication from the portable medical cart to the individual;
    electronically restrict access to selected medication storage compartments to require electronic identification of at least two operators of the medical cart to access the selected medication storage compartments; and
    determine a time period that the wheeled medical cart is located at a selected location for dispensing medication.

7. The portable medical cart of claim 6, wherein the computer circuitry is further configured to verify the identity of the operator of the portable medical cart at a time approximate to a time the operator provides the medication from the portable medical cart to the individual.

8. The portable medical cart of claim 6, wherein the computer circuitry is further configured to:
    determine a proximity of the individual using a proximity sensor;
    electronically identify the at least one operator of the portable medical cart when the portable medical cart is located in proximity to a location of the individual; and
    provide access to at least one medication storage compartment of a storage container when the identity of the at least one operator of the portable medical cart is verified at the location in proximity to the individual.

9. The portable medical cart of claim 6, wherein the computer circuitry is further configured to:
    electronically identify the individual receiving the medication from the medication storage compartment of the storage container; and
    limit access of the at least one operator of the portable medical cart to medication storage compartment containing medication for the electronically identified individual.

10. The portable medical cart of claim 6, wherein the computer circuitry is further configured to:
    electronically identifying the individual receiving the medication from the medication storage compartment of the storage container;
    determine when the medication stored in the medication storage compartment will interfere with other medications that the electronically identified individual is using; and provide a sensory indication to the at least one operator when the medication will interfere with the other medications.

11. The portable medical cart of claim 6, wherein the computer circuitry is further configured to map at least one medication storage compartment to at least one selected type of medication.

12. The portable medical cart of claim 6, wherein the selected medication storage compartment contains a narcotic medication or another restricted medication type.

13. The portable medical cart for the dispensing of medication of claim 6, wherein the computer circuitry is further configured to enable access to the medication storage compartment when the portable medical cart is located at the selected location for dispensing medication.

14. A wheeled medical cart for a dispensing of medication, comprising:
- a storage container, wherein the storage container has at least one medication storage compartment with an interior space for storing at least one medication or at least one medical supply;
- a computing device operating on the wheeled medical cart, wherein the computing device can receive medication data that identifies each type or amount of medication or medical supply stored in the at least on medication storage compartment;
- an electronic locking device that electronically secures the medication or medical supply stored in the medication storage compartment of the storage container of the wheeled medical cart to restrict access to the medication storage compartment to at least one operator;
- an electronic identification device to:
  - electronically identify the at least one operator of the wheeled medical cart at a patient location to enable the at least one operator to gain access to the medication in the medication storage compartment for distribution to a patient;
  - electronically restrict access to selected medication storage compartments to require electronic identification of at least two operators of the medical cart to access the selected medication storage compartments; and
  - determine a time period that the wheeled medical cart is located at a selected location for dispensing medication; and
- a structure connecting the storage container to a wheeled pedestal of the wheeled medical cart.

15. The wheeled medical cart for the dispensing of medication of claim 14, further comprising a medication storage compartment measurement device to determine an amount of medication in a selected medical storage compartment.

16. The wheeled medical cart for the dispensing of medication of claim 15, wherein the medication storage compartment measurement device can use a strain gauge or weight scale to determine an amount of medication in a selected medical storage compartment.

17. The wheeled medical cart for the dispensing of medication of claim 15, wherein the computing device is configured to display or record the amount of medication in the selected medical storage compartment.

18. The wheeled medical cart for the dispensing of medication of claim 15, wherein the medication storage compartment measurement device determines the amount of medication remaining after the medication has been dispensed.

19. The wheeled medical cart for the dispensing of medication of claim 14, further comprising a medication dispensing recordation device that records a location of the wheeled medical cart or a time that the operator accesses the medication storage compartment.

* * * * *